United States Patent
Grace et al.

(10) Patent No.: US 11,058,492 B2
(45) Date of Patent: Jul. 13, 2021

(54) LASER-INDUCED PRESSURE WAVE EMITTING CATHETER SHEATH

(71) Applicant: The Spectranetics Corporation, Colorado Springs, CO (US)

(72) Inventors: Kenneth P. Grace, Woodland Park, CO (US); Thomas Triffo, Colorado Springs, CO (US); James Cezo, Colorado Springs, CO (US)

(73) Assignee: THE SPECTRANETICS CORPORATION, Colorado Springs, CO (US)

(*) Notice: Subject to any disclaimer, the term of this patent is extended or adjusted under 35 U.S.C. 154(b) by 613 days.

(21) Appl. No.: 15/659,064

(22) Filed: Jul. 25, 2017

(65) Prior Publication Data
US 2017/0333132 A1 Nov. 23, 2017

Related U.S. Application Data

(63) Continuation-in-part of application No. 14/984,308, filed on Dec. 30, 2015, now abandoned.

(60) Provisional application No. 62/441,021, filed on Dec. 30, 2016, provisional application No. 62/366,409, filed on Jul. 25, 2016, provisional application No.
(Continued)

(51) Int. Cl.
*A61B 18/24* (2006.01)
*A61B 18/26* (2006.01)
*A61B 18/00* (2006.01)
*A61B 18/22* (2006.01)
(Continued)

(52) U.S. Cl.
CPC ............ *A61B 18/245* (2013.01); *A61B 18/26* (2013.01); *A61B 2017/00867* (2013.01); *A61B 2017/00907* (2013.01); *A61B 2018/00386* (2013.01); *A61B 2018/00577* (2013.01); *A61B 2018/2211* (2013.01); *A61B 2018/2255* (2013.01); *A61B 2018/2272* (2013.01); *A61B 2018/263* (2013.01); *A61B 2018/266* (2013.01); *A61M 25/005* (2013.01); *A61M 25/0026* (2013.01); *A61M 25/0045* (2013.01); *A61M 2025/0039* (2013.01)

(58) Field of Classification Search
CPC .............................. A61B 18/245; A61B 18/26
USPC ....................................................... 606/2.5
See application file for complete search history.

(56) References Cited

U.S. PATENT DOCUMENTS

| 4,732,448 A * | 3/1988 | Goldenberg ......... A61B 18/245 385/117 |
| 4,770,653 A | 9/1988 | Shturman |

(Continued)

FOREIGN PATENT DOCUMENTS

| CN | 103462688 A | 12/2013 |
| DE | 2517019 A | 10/1976 |

(Continued)

OTHER PUBLICATIONS

International Preliminary Report on Patentability issued in PCT/US2014/019268, dated Sep. 24, 2015, 9 pages.
(Continued)

*Primary Examiner* — John R Downey

(57) ABSTRACT

The present disclosure relates generally to the use of medical devices for the treatment of vascular conditions. In particular, the present disclosure provides devices and methods for
(Continued)

using laser-induced pressure waves created within a sheath to disrupt intimal and medial calcium within the vasculature.

14 Claims, 58 Drawing Sheets

Related U.S. Application Data

62/268,797, filed on Dec. 17, 2015, provisional application No. 62/264,725, filed on Dec. 8, 2015, provisional application No. 62/248,753, filed on Oct. 30, 2015, provisional application No. 62/248,936, filed on Oct. 30, 2015, provisional application No. 62/212,242, filed on Aug. 31, 2015, provisional application No. 62/209,691, filed on Aug. 25, 2015, provisional application No. 62/098,242, filed on Dec. 30, 2014.

(51) Int. Cl.
*A61B 17/00* (2006.01)
*A61M 25/00* (2006.01)

(56) References Cited

U.S. PATENT DOCUMENTS

| | | | |
|---|---|---|---|
| 4,785,806 A | 11/1988 | Deckelbaum | |
| 4,793,359 A | 12/1988 | Sharrow | |
| 4,832,023 A | 5/1989 | Murphy-Chutorian et al. | |
| 4,862,886 A | 9/1989 | Clarke et al. | |
| 4,878,492 A | 11/1989 | Sinofsky et al. | |
| 4,960,108 A * | 10/1990 | Reichel | A61K 33/14 606/2.5 |
| 4,966,596 A | 10/1990 | Kuntz et al. | |
| 4,968,314 A * | 11/1990 | Michaels | A61B 18/245 606/15 |
| 4,993,412 A | 2/1991 | Murphy-Chutorian | |
| 5,010,886 A | 4/1991 | Passafaro et al. | |
| 5,026,366 A | 6/1991 | Leckrone | |
| 5,026,367 A | 6/1991 | Leckrone et al. | |
| 5,029,588 A | 7/1991 | Yock et al. | |
| 5,041,108 A | 8/1991 | Fox et al. | |
| 5,041,121 A * | 8/1991 | Wondrazek | A61B 18/26 606/15 |
| 5,053,033 A | 10/1991 | Clarke | |
| 5,055,109 A | 10/1991 | Gould et al. | |
| 5,176,674 A | 1/1993 | Hofmann | |
| 5,192,278 A | 3/1993 | Hayes et al. | |
| 5,192,286 A * | 3/1993 | Phan | A61B 17/02 604/264 |
| 5,242,454 A * | 9/1993 | Gundlach | A61B 18/26 128/898 |
| 5,246,447 A * | 9/1993 | Rosen | A61B 17/22022 601/24 |
| 5,281,212 A | 1/1994 | Savage et al. | |
| 5,304,171 A | 4/1994 | Gregory et al. | |
| 5,334,207 A | 8/1994 | Gay et al. | |
| 5,350,375 A | 9/1994 | Deckelbaum et al. | |
| 5,354,324 A | 10/1994 | Gregory | |
| 5,395,361 A | 3/1995 | Fox et al. | |
| 5,423,805 A | 6/1995 | Brucker et al. | |
| 5,443,443 A * | 8/1995 | Shiber | A61B 17/22012 604/22 |
| 5,468,239 A | 11/1995 | Tanner et al. | |
| 5,470,330 A * | 11/1995 | Goldenberg | A61B 1/00165 606/10 |
| 5,505,725 A * | 4/1996 | Samson | A61B 18/245 600/108 |
| 5,573,531 A | 11/1996 | Gregory | |
| 5,620,438 A * | 4/1997 | Amplatz | A61B 18/245 606/10 |
| 5,649,923 A | 7/1997 | Gregory et al. | |
| 5,722,972 A | 3/1998 | Power et al. | |
| 5,722,979 A | 3/1998 | Kusleika | |
| 5,733,301 A | 3/1998 | Forman | |
| 5,741,246 A | 4/1998 | Prescott | |
| 5,741,247 A * | 4/1998 | Rizoiu | A61B 18/26 606/10 |
| 5,769,843 A | 6/1998 | Abela et al. | |
| 5,876,373 A | 3/1999 | Giba et al. | |
| 5,876,397 A | 3/1999 | Edelman et al. | |
| 5,944,687 A * | 8/1999 | Benett | A61B 18/26 604/22 |
| 6,022,309 A | 2/2000 | Celliers et al. | |
| 6,024,738 A | 2/2000 | Daikuzono et al. | |
| 6,123,718 A | 9/2000 | Tu et al. | |
| 6,132,423 A | 10/2000 | Aita et al. | |
| 6,152,909 A * | 11/2000 | Bagaoisan | A61B 17/22 604/173 |
| 6,210,395 B1 * | 4/2001 | Fleischhacker | A61B 17/3207 604/523 |
| 6,210,404 B1 | 4/2001 | Shadduck | |
| 6,254,597 B1 * | 7/2001 | Rizoiu | A61C 1/0046 606/13 |
| 6,283,958 B1 | 9/2001 | Vogl et al. | |
| 6,368,318 B1 * | 4/2002 | Visuri | A61B 18/26 606/12 |
| 6,379,325 B1 | 4/2002 | Benett et al. | |
| 6,551,302 B1 | 4/2003 | Rosinko et al. | |
| 6,561,998 B1 | 5/2003 | Roth et al. | |
| 6,592,612 B1 | 7/2003 | Samson et al. | |
| 6,660,001 B2 | 12/2003 | Gregory | |
| 6,752,800 B1 | 6/2004 | Winston et al. | |
| 7,125,404 B2 | 10/2006 | Levatter | |
| 7,144,248 B2 | 12/2006 | Irwin | |
| 7,226,470 B2 | 6/2007 | Kemény et al. | |
| 7,238,178 B2 | 7/2007 | Maschke | |
| 7,306,585 B2 | 12/2007 | Ross | |
| 7,818,053 B2 | 10/2010 | Kassab | |
| 7,891,361 B2 | 2/2011 | Irwin | |
| 8,104,483 B2 | 1/2012 | Taylor | |
| 8,162,964 B2 | 4/2012 | Piippo et al. | |
| 8,167,810 B2 | 5/2012 | Maschke | |
| 8,396,548 B2 | 3/2013 | Perry | |
| 8,454,669 B2 | 6/2013 | Irwin | |
| 8,465,452 B2 | 6/2013 | Kassab | |
| 8,551,096 B2 | 10/2013 | Perry et al. | |
| 8,574,247 B2 | 11/2013 | Adams et al. | |
| 8,684,970 B1 | 4/2014 | Koyfman et al. | |
| 8,702,773 B2 | 4/2014 | Keeler | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,790,386 B2 | 7/2014 | Dwork | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,138,249 B2 | 9/2015 | Adams et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,320,530 B2 | 4/2016 | Grace | |
| 2001/0027310 A1 | 10/2001 | Parisi et al. | |
| 2002/0058890 A1 * | 5/2002 | Visuri | A61B 18/26 601/4 |
| 2002/0133111 A1 * | 9/2002 | Shadduck | A61B 17/22 604/19 |
| 2002/0151924 A1 * | 10/2002 | Shiber | A61B 8/12 606/194 |
| 2003/0009157 A1 | 1/2003 | Levine | |
| 2003/0181938 A1 | 9/2003 | Roth et al. | |
| 2003/0229370 A1 | 12/2003 | Miller | |
| 2004/0006333 A1 * | 1/2004 | Arnold | A61B 18/24 606/15 |
| 2004/0143287 A1 | 7/2004 | Konstantino | |

(56) References Cited

U.S. PATENT DOCUMENTS

| | | |
|---|---|---|
| 2005/0021071 A1 | 1/2005 | Konstantino |
| 2005/0143678 A1* | 6/2005 | Schwarz .......... A61B 17/12022 |
| | | 601/4 |
| 2005/0216044 A1 | 9/2005 | Hong |
| 2005/0240212 A1 | 10/2005 | McAuley |
| 2005/0251116 A1 | 11/2005 | Steinke et al. |
| 2006/0189930 A1 | 8/2006 | Lary et al. |
| 2006/0190022 A1 | 8/2006 | Beyar et al. |
| 2007/0078500 A1 | 4/2007 | Ryan et al. |
| 2007/0093745 A1 | 4/2007 | Steward et al. |
| 2007/0198047 A1 | 8/2007 | Schon et al. |
| 2008/0103575 A1 | 5/2008 | Gerber |
| 2008/0249515 A1 | 10/2008 | Taylor |
| 2009/0112198 A1 | 4/2009 | Khanna et al. |
| 2009/0112239 A1 | 4/2009 | To |
| 2009/0270846 A1 | 10/2009 | Okada et al. |
| 2009/0270850 A1 | 10/2009 | Zhou et al. |
| 2010/0016862 A1 | 1/2010 | Hawkins et al. |
| 2010/0049182 A1 | 2/2010 | Ryan et al. |
| 2010/0137847 A1* | 6/2010 | Cecchetti ................ A61B 18/26 |
| | | 606/2.5 |
| 2010/0152720 A1 | 6/2010 | Sauro et al. |
| 2010/0222786 A1 | 9/2010 | Kassab |
| 2010/0286709 A1* | 11/2010 | Diamant .......... A61B 17/22012 |
| | | 606/128 |
| 2011/0034832 A1* | 2/2011 | Cioanta ............ A61B 17/22004 |
| | | 601/1 |
| 2011/0152683 A1 | 6/2011 | Gerrans et al. |
| 2011/0208185 A1* | 8/2011 | Diamant ............ A61B 18/1492 |
| | | 606/42 |
| 2012/0116289 A1 | 5/2012 | Hawkins et al. |
| 2012/0203255 A1 | 8/2012 | Hawkins et al. |
| 2012/0221013 A1 | 8/2012 | Hawkins |
| 2012/0303011 A1 | 11/2012 | Schaeffer |
| 2013/0030431 A1 | 1/2013 | Adams |
| 2013/0030447 A1 | 1/2013 | Adams |
| 2013/0046293 A1 | 2/2013 | Arai et al. |
| 2013/0096545 A1* | 4/2013 | Laudenslager ......... A61B 18/24 |
| | | 606/7 |
| 2013/0197555 A1 | 8/2013 | Schaer |
| 2014/0005576 A1 | 1/2014 | Adams et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052114 A1 | 2/2014 | Ben-Oren et al. |
| 2014/0052145 A1 | 2/2014 | Adams et al. |
| 2014/0074113 A1 | 3/2014 | Hakala et al. |
| 2014/0121458 A1* | 5/2014 | St. George ............. A61B 1/018 |
| | | 600/107 |
| 2014/0133814 A1 | 5/2014 | Stevens |
| 2014/0163592 A1 | 6/2014 | Hawkins et al. |
| 2014/0214061 A1 | 7/2014 | Adams |
| 2014/0276682 A1 | 9/2014 | Hendrick et al. |
| 2014/0288570 A1 | 9/2014 | Adams |
| 2015/0039002 A1 | 2/2015 | Hawkins |
| 2015/0073430 A1 | 3/2015 | Hakala et al. |
| 2015/0105714 A1 | 4/2015 | Laudenslager et al. |
| 2015/0238208 A1 | 8/2015 | Adams et al. |
| 2015/0238209 A1 | 8/2015 | Hawkins et al. |
| 2015/0320432 A1 | 11/2015 | Adams |
| 2015/0359557 A1* | 12/2015 | Shimokawa ........... A61B 18/26 |
| | | 601/2 |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2017/0265942 A1 | 9/2017 | Grace et al. |
| 2018/0008348 A1 | 1/2018 | Grace et al. |

FOREIGN PATENT DOCUMENTS

| | | |
|---|---|---|
| DE | 4240182 C2 | 6/1994 |
| DE | 4437578 A1 | 5/1996 |
| EP | 0182689 B1 | 5/1986 |
| EP | 0189329 A3 | 7/1986 |
| EP | 0355200 A1 | 2/1990 |
| EP | 0820786 A2 | 1/1998 |
| EP | 0902654 B1 | 3/1999 |
| EP | 1200002 B1 | 5/2002 |
| EP | 2300091 A2 | 3/2011 |
| EP | 2362798 B1 | 9/2011 |
| EP | 2866689 A1 | 5/2015 |
| EP | 2879597 A1 | 6/2015 |
| EP | 2879607 A1 | 6/2015 |
| EP | 2882357 A1 | 6/2015 |
| EP | 2884911 A1 | 6/2015 |
| EP | 2895086 A1 | 7/2015 |
| JP | H01148278 A | 6/1989 |
| JP | 2004215862 A | 8/2004 |
| JP | 2009061083 A | 3/2009 |
| KR | 100996733 B1 | 11/2010 |
| WO | WO199006087 A | 6/1990 |
| WO | 1991010403 A1 | 7/1991 |
| WO | WO199745157 A | 12/1997 |
| WO | WO2000012168 A1 | 3/2000 |
| WO | 2003057060 A1 | 7/2003 |
| WO | WO2004060460 A2 | 7/2004 |
| WO | 2006006169 A2 | 1/2006 |
| WO | 2010054048 A2 | 5/2010 |
| WO | 2009152352 A8 | 12/2010 |
| WO | 2011006017 A1 | 1/2011 |
| WO | 2013070750 A1 | 5/2013 |
| WO | 2013169807 A1 | 11/2013 |
| WO | 2014004887 A1 | 1/2014 |
| WO | 2014025397 A1 | 2/2014 |
| WO | 2014025620 A1 | 2/2014 |
| WO | 2014025981 A1 | 2/2014 |
| WO | 2014028885 A1 | 2/2014 |
| WO | 2014043400 A1 | 3/2014 |
| WO | 2014163955 A1 | 10/2014 |
| WO | 2015017499 A1 | 2/2015 |
| WO | 2015034840 A8 | 5/2015 |
| WO | 2015171515 A1 | 11/2015 |

OTHER PUBLICATIONS

International Preliminary Report on Patentability issued in PCT/US2015/068161, dated Jul. 13, 2017, 15 pages.
International Search Report and Written Opinion issued in International Application No. PCT/US13/25147, dated Jun. 13, 2013, 11 pages.
International Search Report and Written Opinion issued in PCT/US2014/019268 dated Jun. 13, 2014, 13 pages.
International Search Report and Written Opinion issued in PCT/US2015/068161, dated May 4, 2016, 19 pages.
International Search Report and Written Opinion issued in PCT/US2015/068169, dated Jul. 13, 2017, 21 pages.
International Search Report and Written Opinion issued in PCT/US2015/068169, dated May 13, 2016, 28 pages.
International Search Report and Written Opinion issued in PCT/US2015/068170, dated May 13, 2016, 13 pages.
International Search Report and Written Opinion issued in PCT/US2015/068173, dated Apr. 19, 2016, 16 pages.
International Search Report and Written Opinion issued in PCT/US2017/043680, dated Oct. 31, 2017, 14 pages.
International Search Report and Written Opinion issued in PCT/US2017/043762, dated Oct. 31, 2017, 14 pages.
Supplemental European Search Report issued in EP Application 14778867, dated Aug. 10, 2016, 7 pages.
U.S. Appl. No. 14/984,050 entitled Laser-Induced Fluid Filled Balloon Catheter, filed Dec. 30, 2015.
U.S. Appl. No. 14/984,294 entitled Electrically-Induced Fluid Filled Balloon Catheter, filed Dec. 30, 2015.
U.S. Appl. No. 14/984,308 entitled Laser-Induced Pressure Wave Emitting Catheter Sheath, filed Dec. 30, 2015.
U.S. Appl. No. 14/984,710 entitled Electrically-Induced Pressure Wave Emitting Catheter Sheath, filed Dec. 30, 2015.

(56) References Cited

OTHER PUBLICATIONS

U.S. Appl. No. 15/090,736 entitled "Apparatus and Method for Balloon Angioplasty," filed Apr. 5, 2016.

* cited by examiner

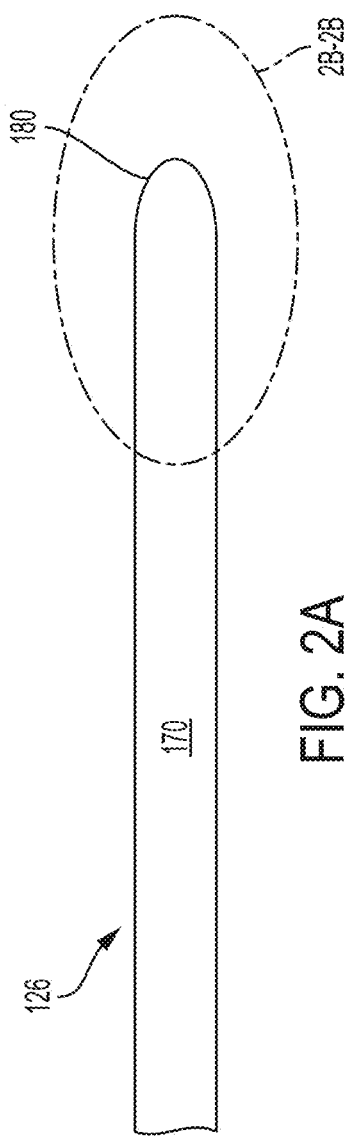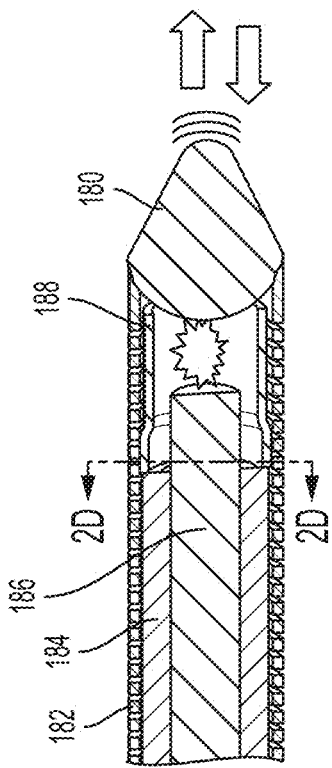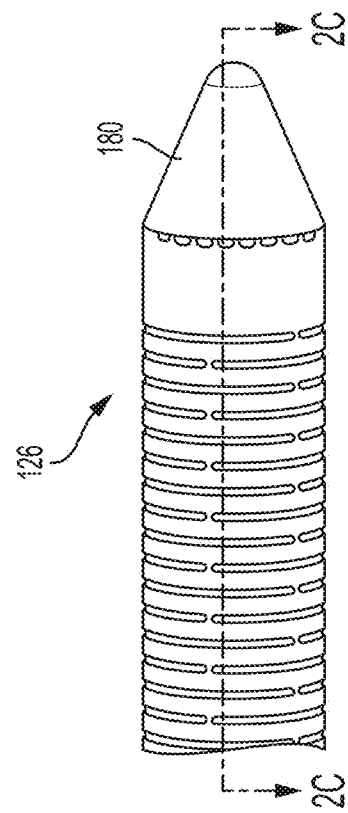

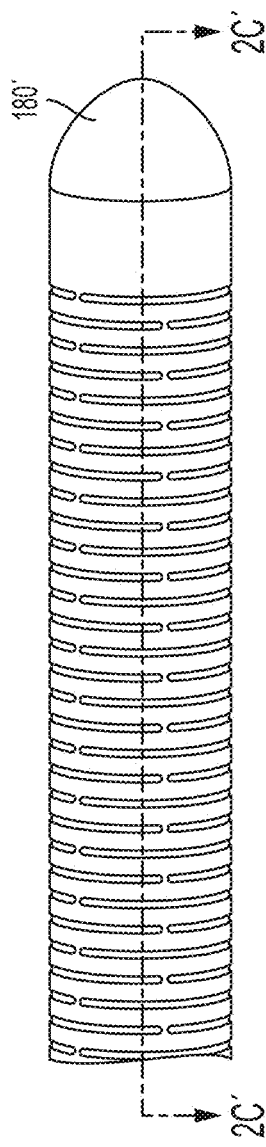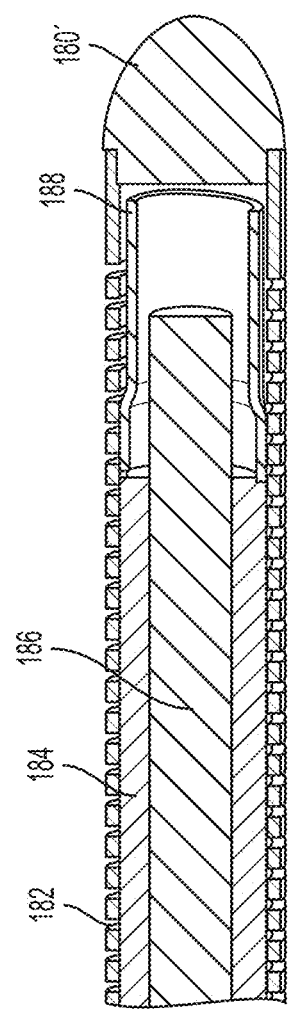
FIG. 2B'
FIG. 2C'

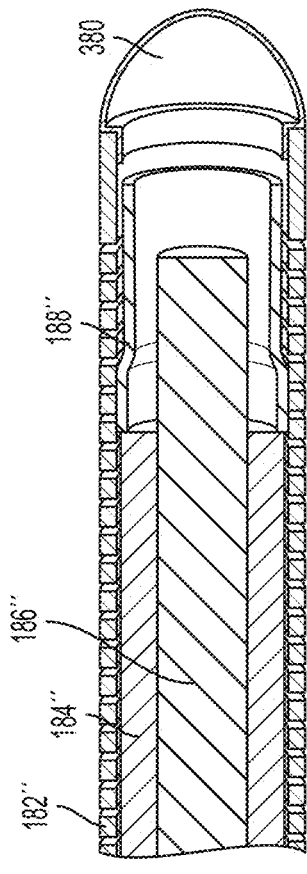
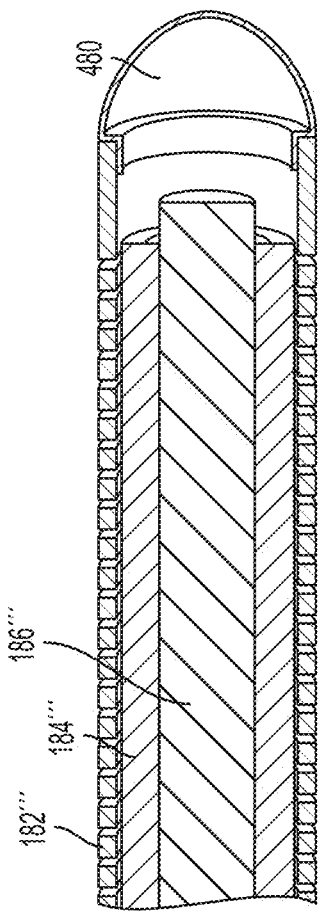
FIG. 3
FIG. 4

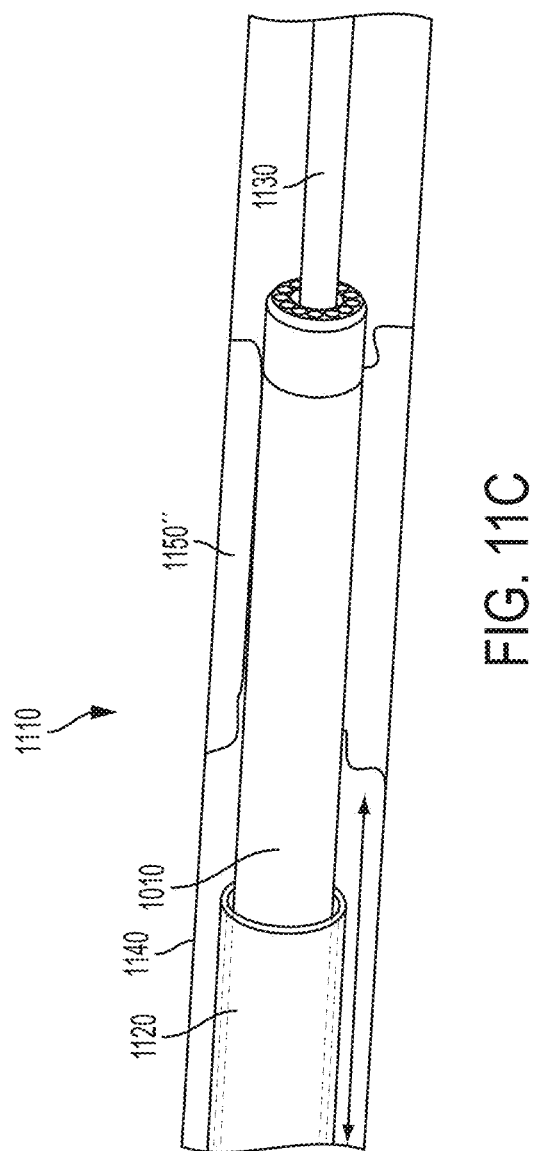

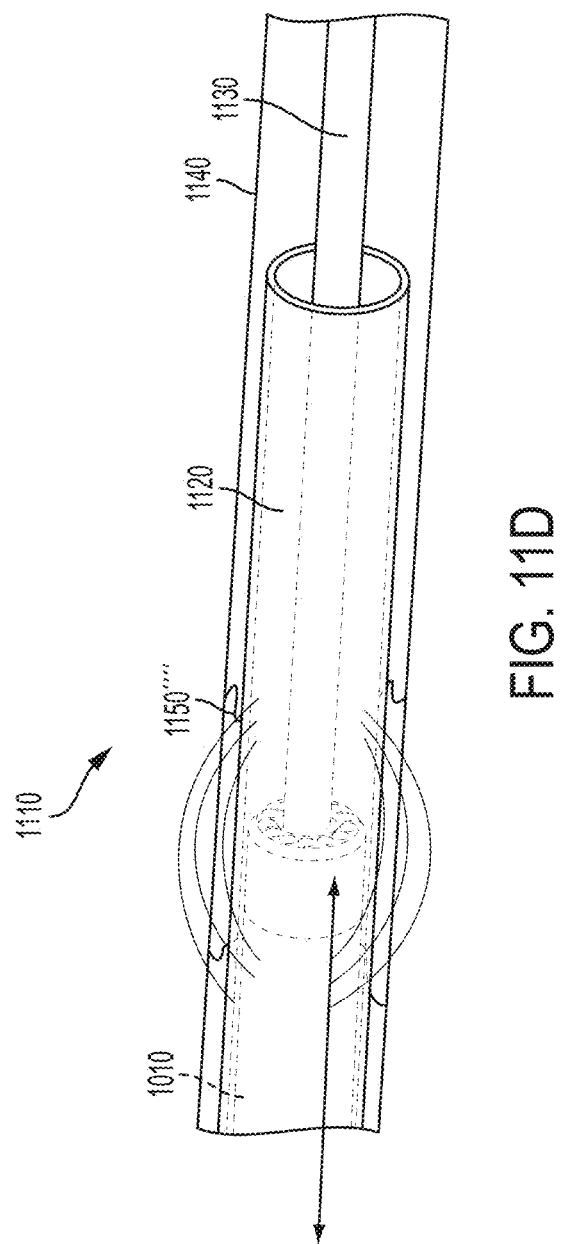

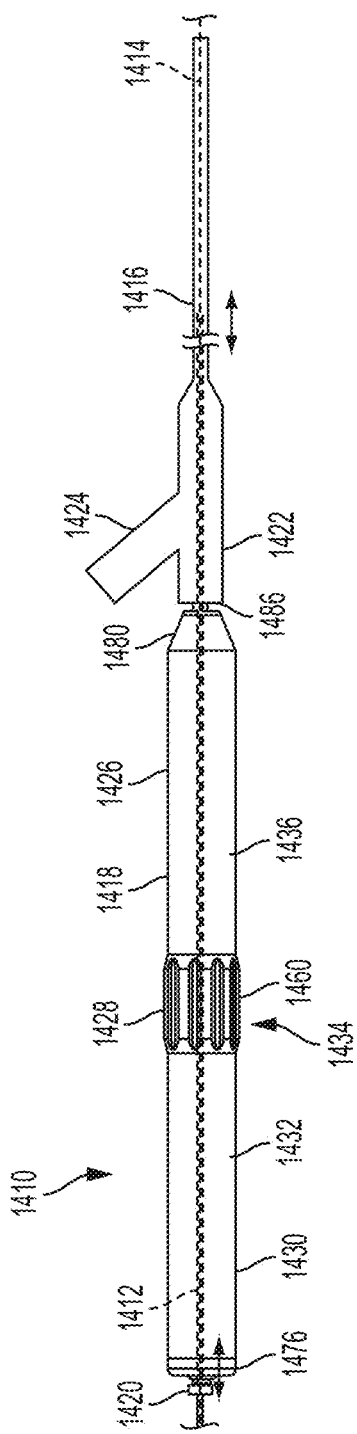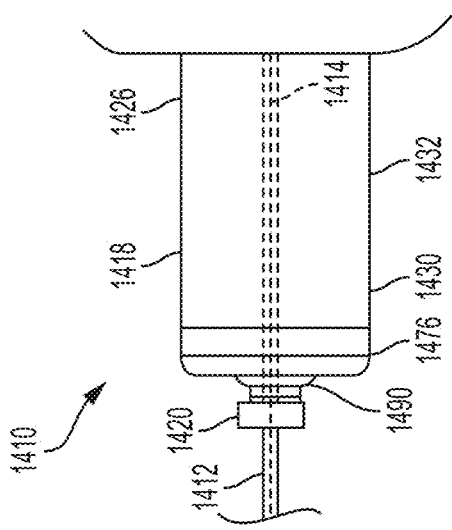
FIG. 14A
FIG. 14B

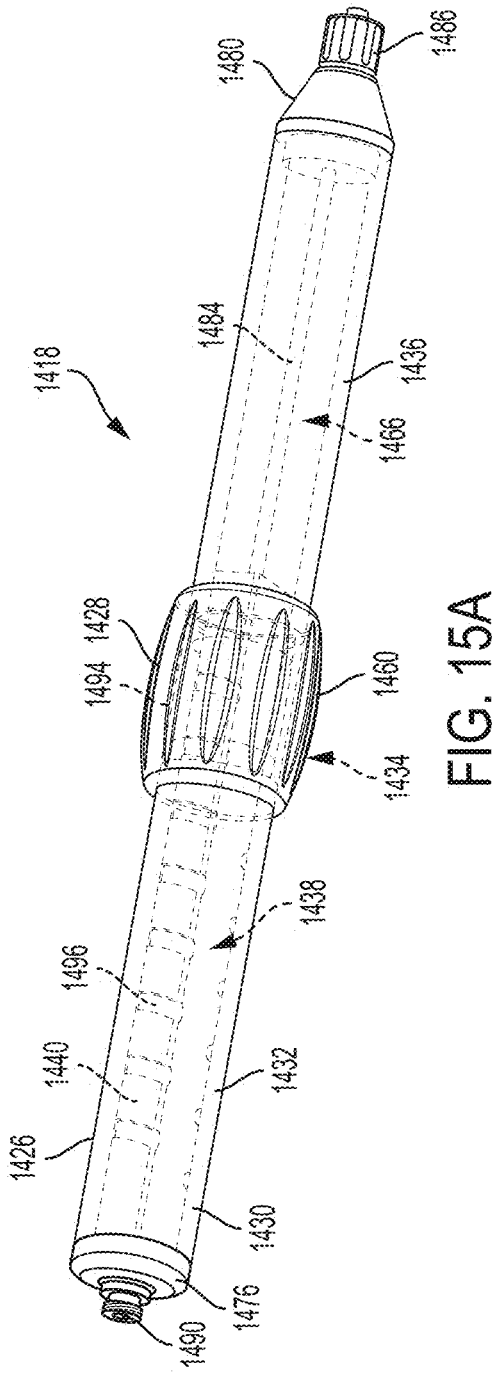
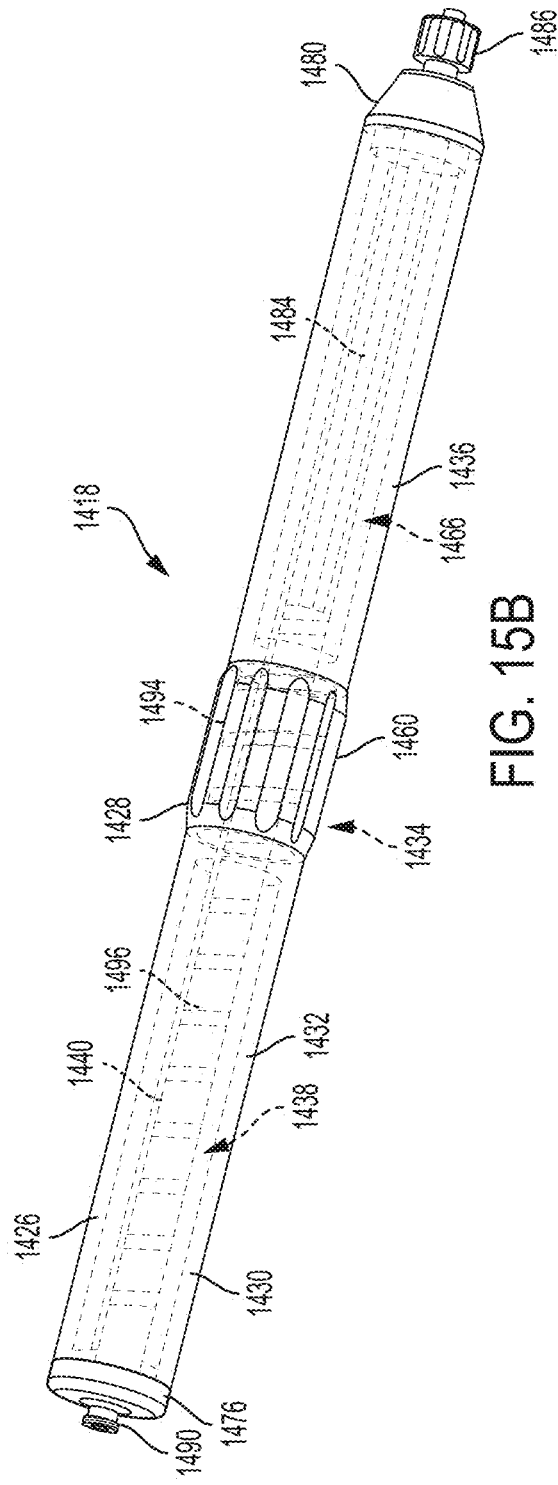
FIG. 15A
FIG. 15B

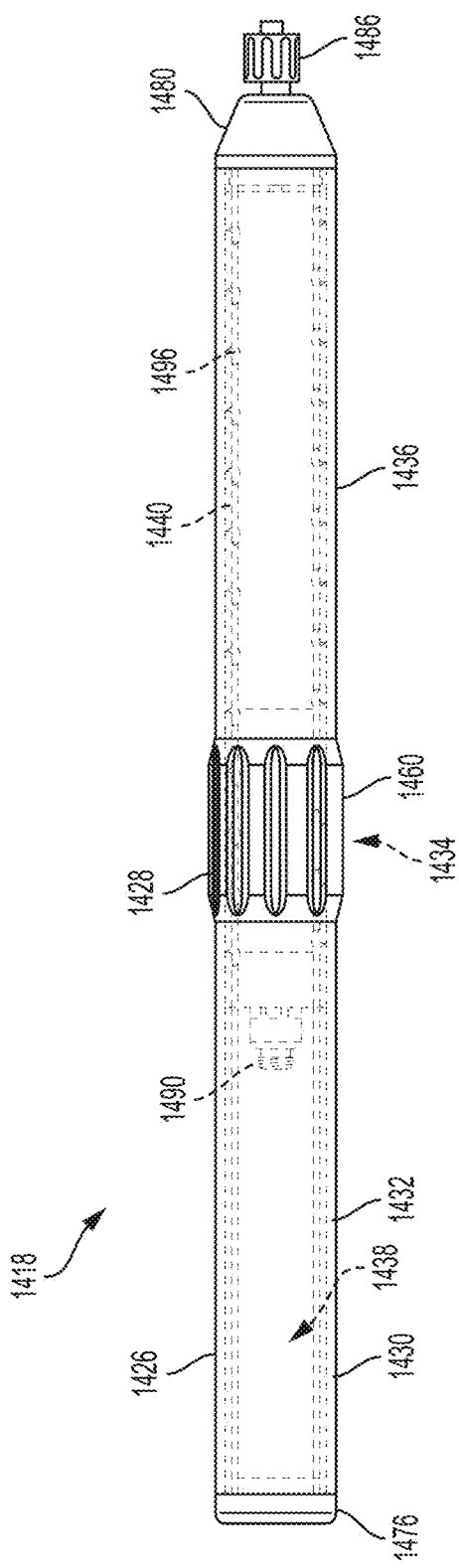
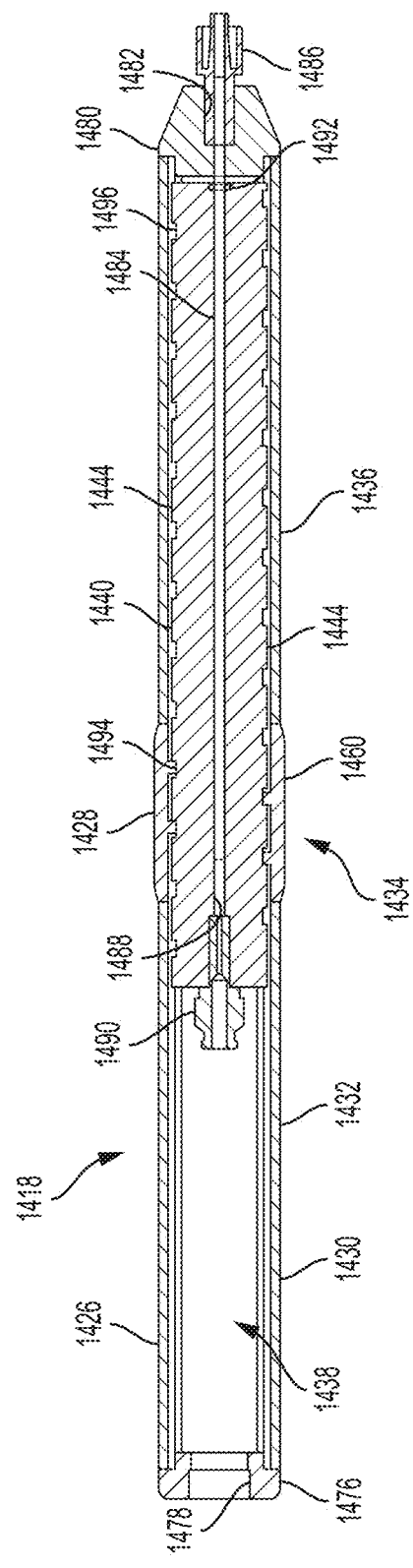
FIG. 15E
FIG. 15F

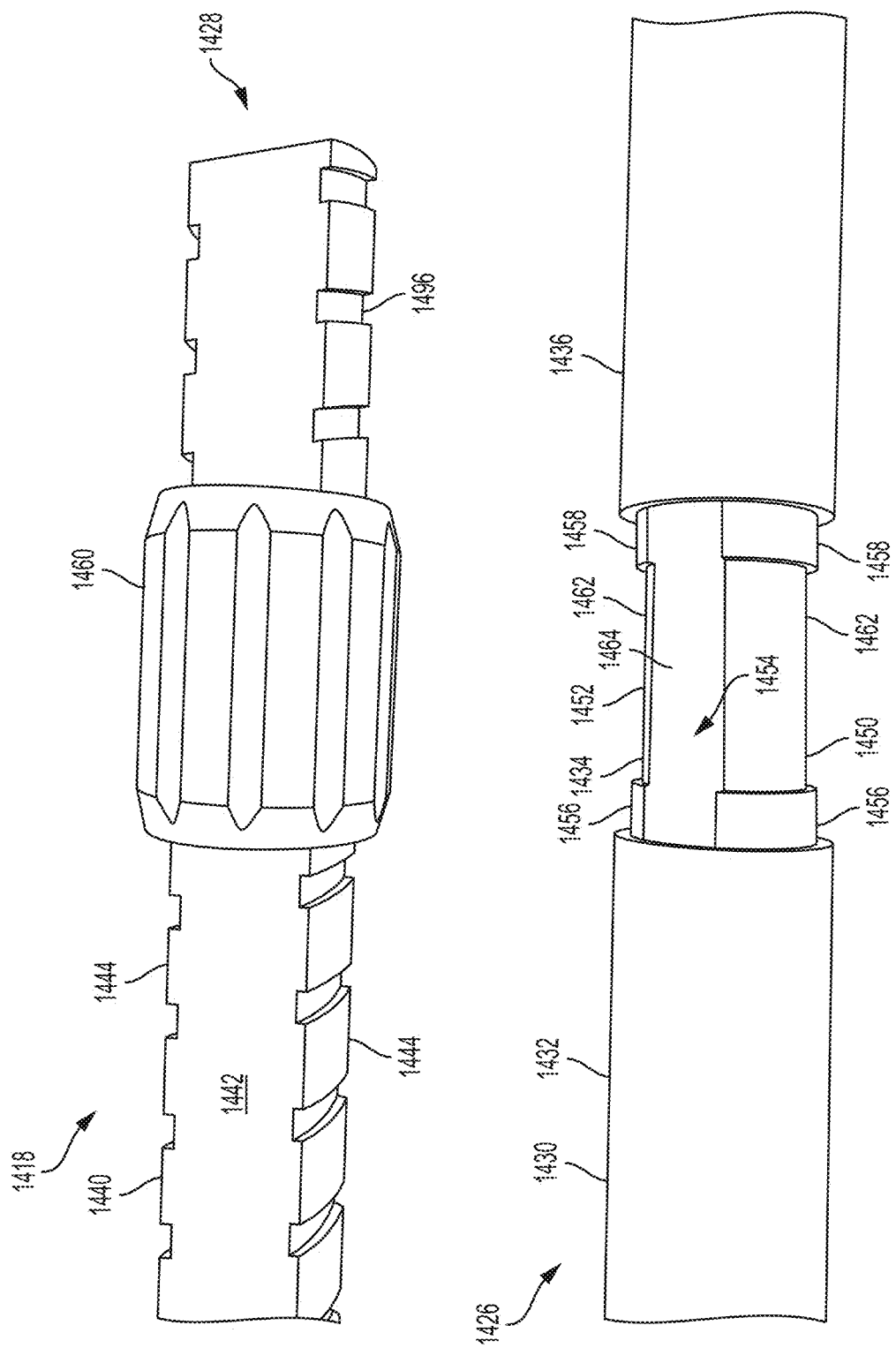

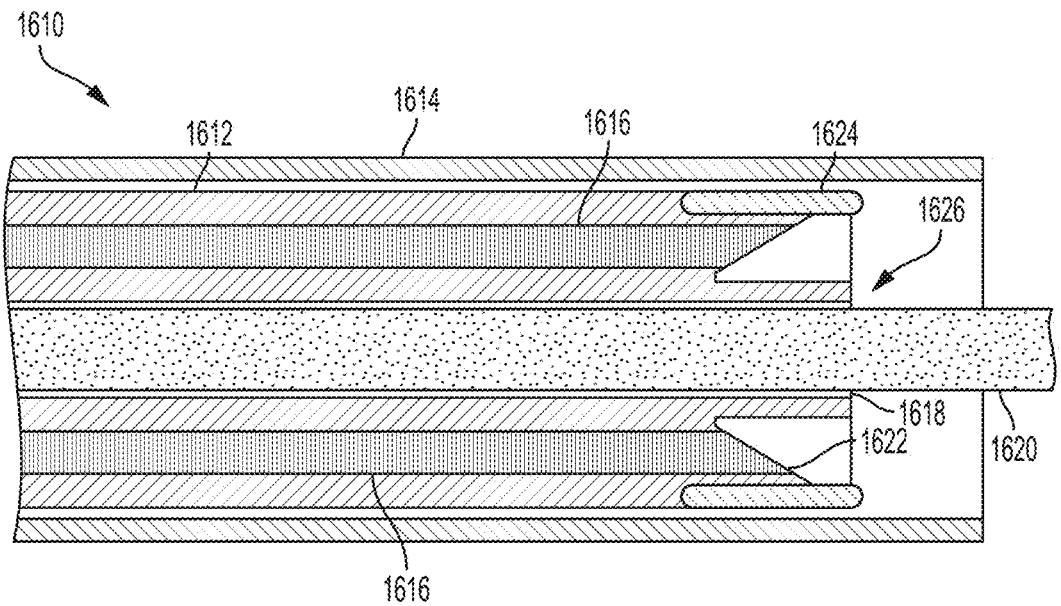
FIG. 20
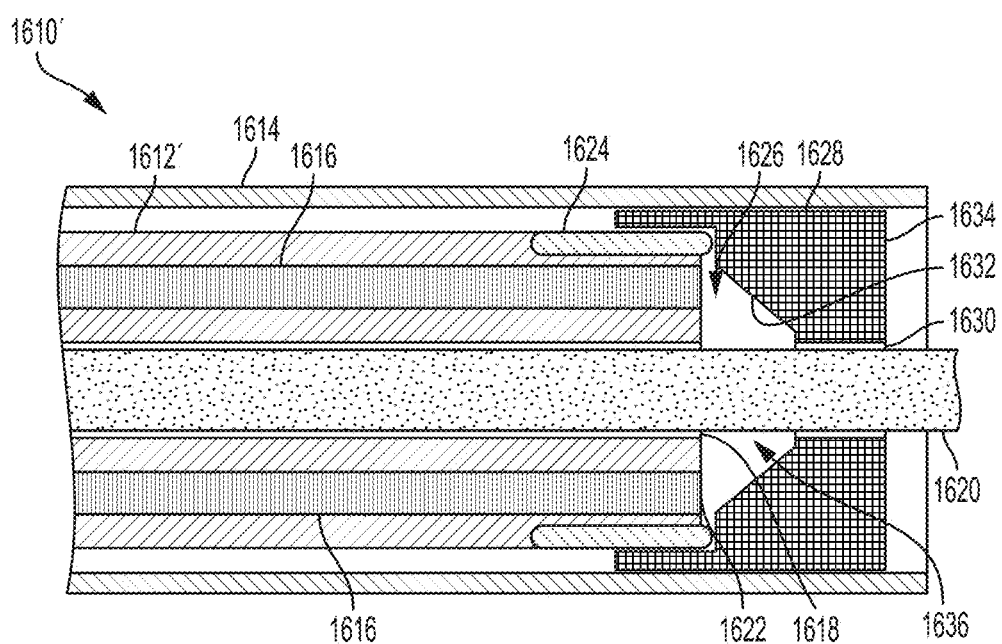
FIG. 20´

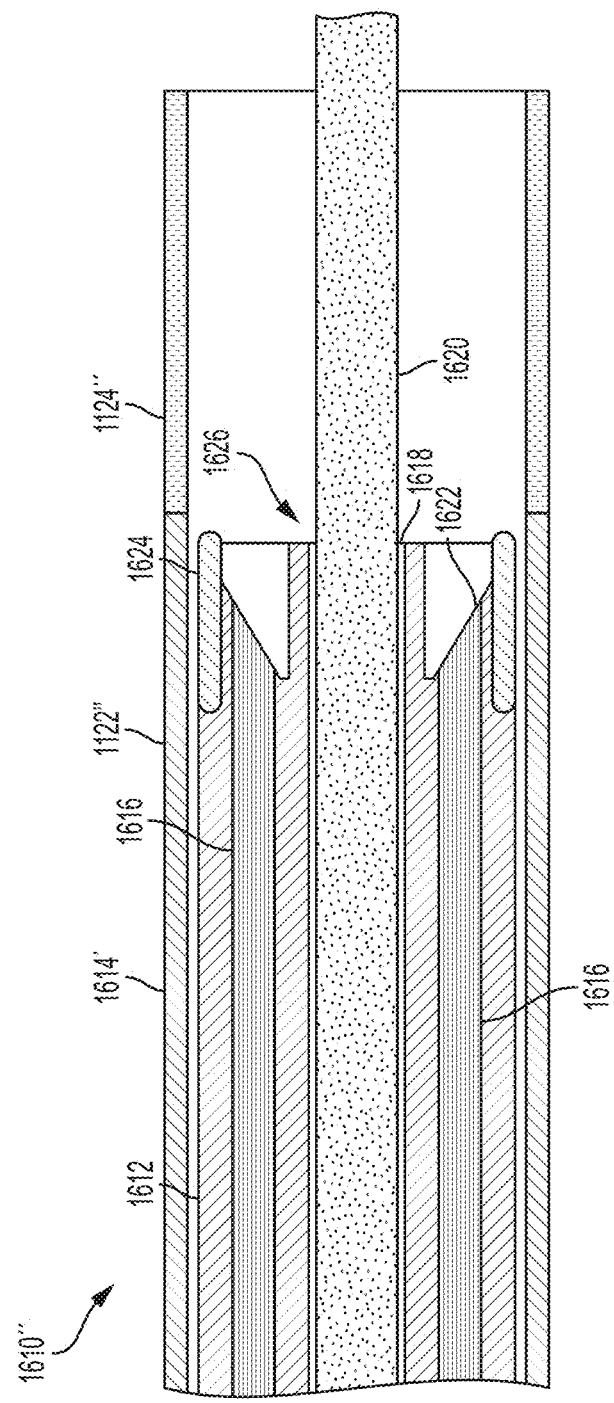

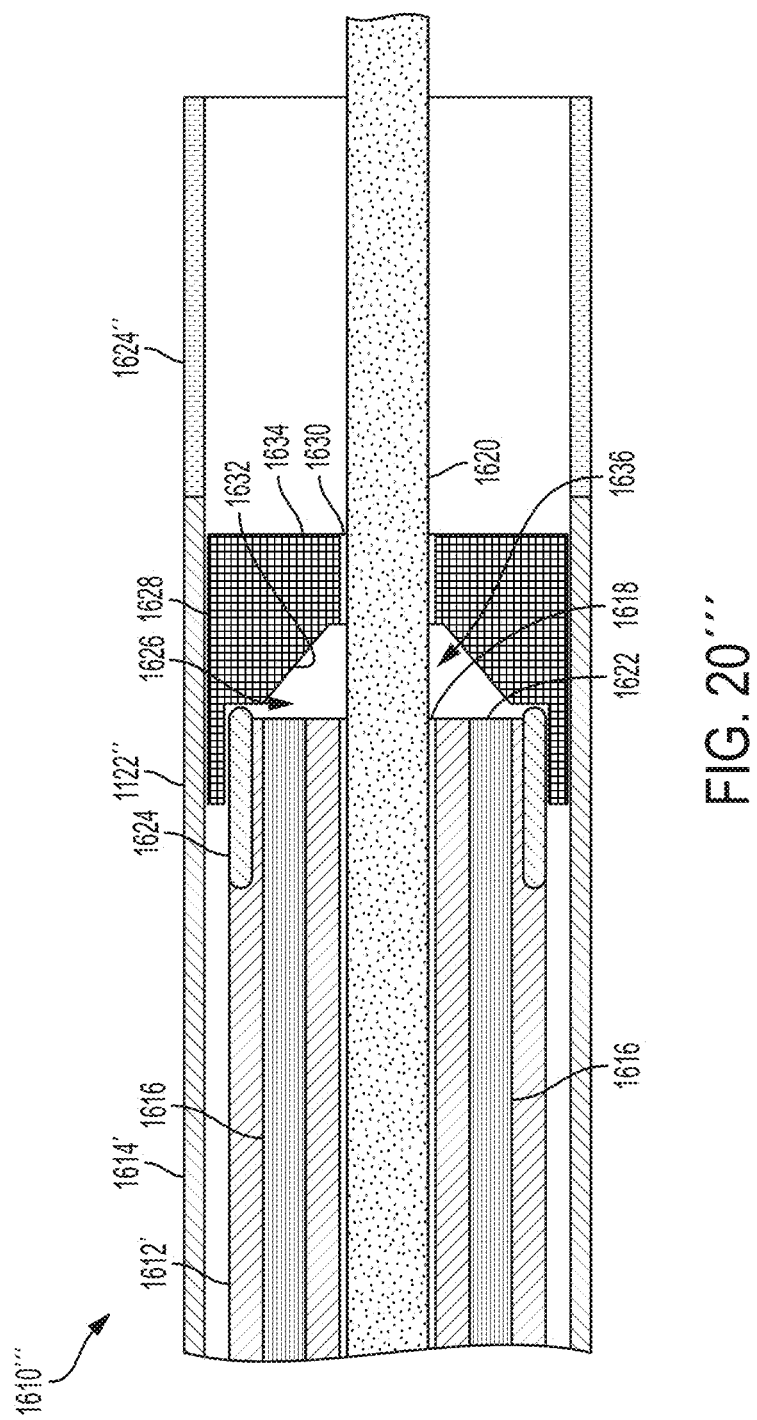

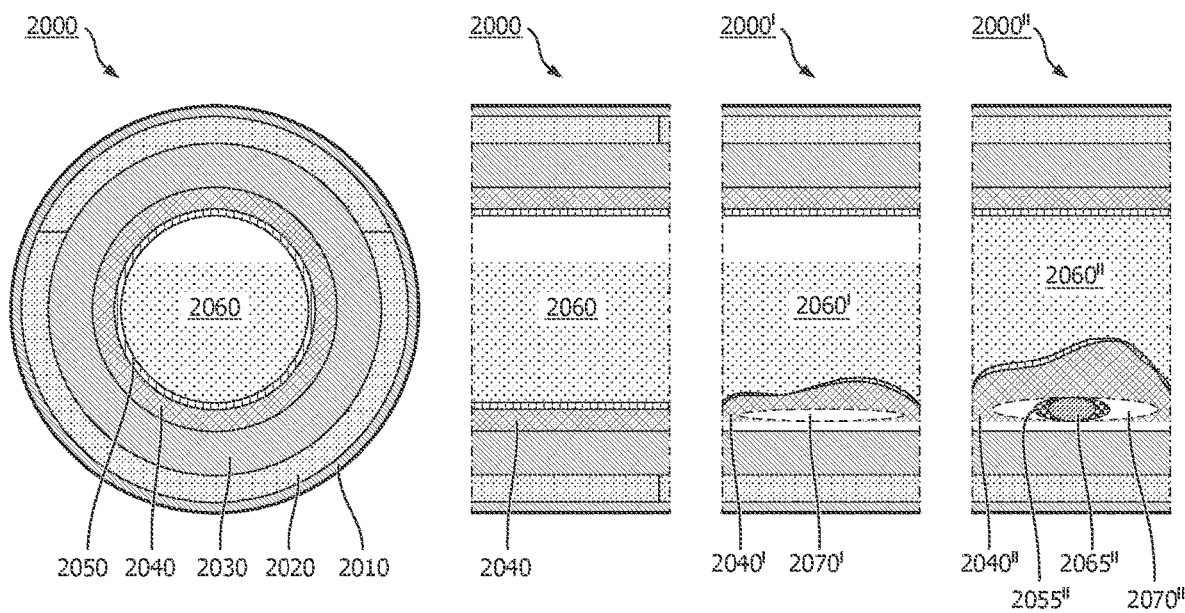

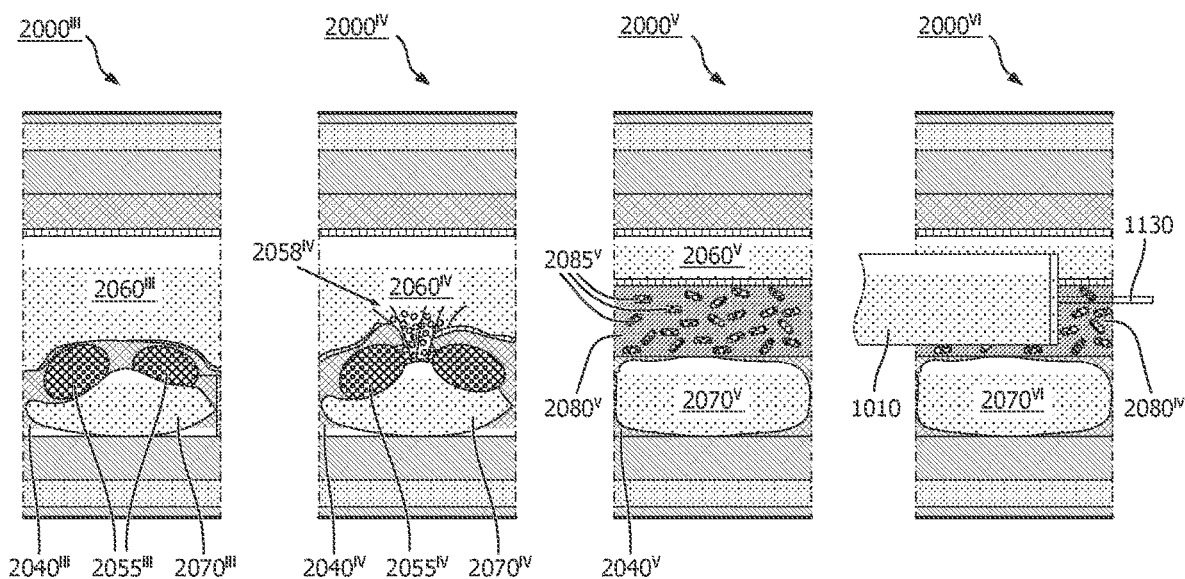

```
2700
```

LOCATE A VASCULAR OBSTRUCTION OR RESTRICTION IN THE VASCULATURE OF A SUBJECT
2705

POSITIONING A GUIDEWIRE WITHIN VASCULATURE OF A SUBJECT
2710

PERFORM AN ATHERECTOMY PROCEDURE ON THE VASCULAR OBSTRUCTION
2715

POSITIONING A SHEATH OVER A LASER CATHETER WITHIN VASCULATURE OF A SUBJECT
2720

POSITIONING THE SHEATH AND LASER CATHETER (AND OPTIONALLY THE GUIDEWIRE) SUCH THAT A PRESSURE WAVE REFLECTIVE ELEMENT WITHIN THE SHEATH IS ADJACENT AN OCCLUSION WITHIN VASCULATURE OF A SUBJECT AND THE DISTAL END OF THE LASER CATHETER IS DISPOSED WITHIN THE PRESSURE WAVE REFLECTIVE ELEMENT
2725

INTRODUCING LIQUID MEDIUM HAVING LIGHT ABSORBING MATERIAL TO THE DISTAL END OF THE LASER CATHETER
2730

ACTIVATE THE EMITTER AND DISRUPT A PORTION OF THE VASCULAR OBSTRUCTION
2735

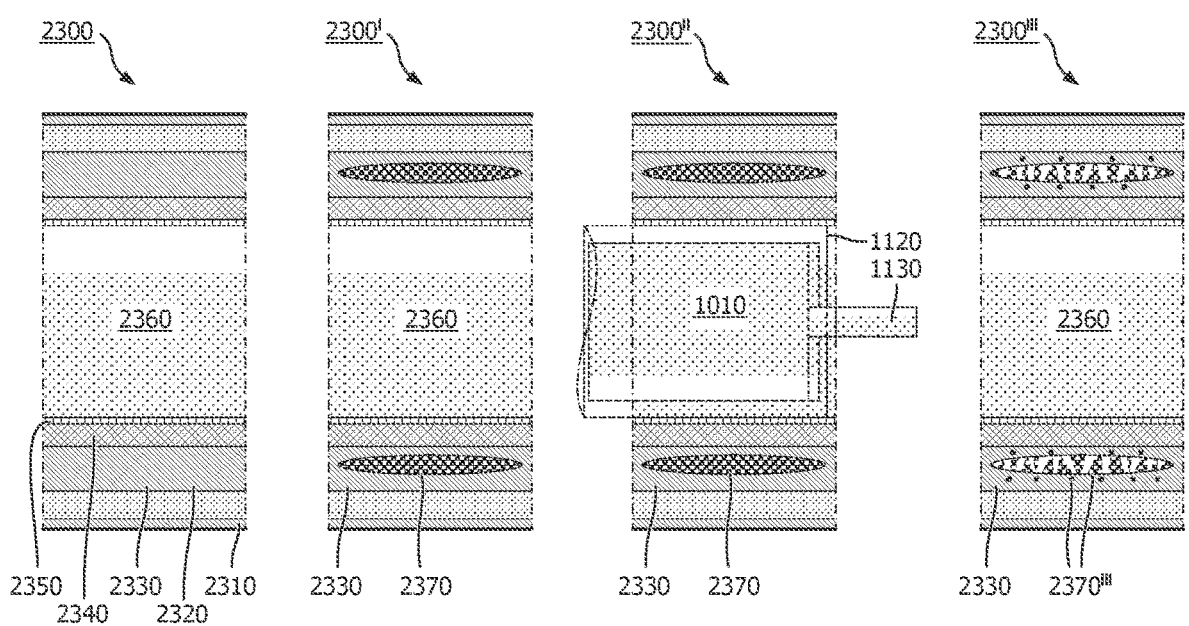

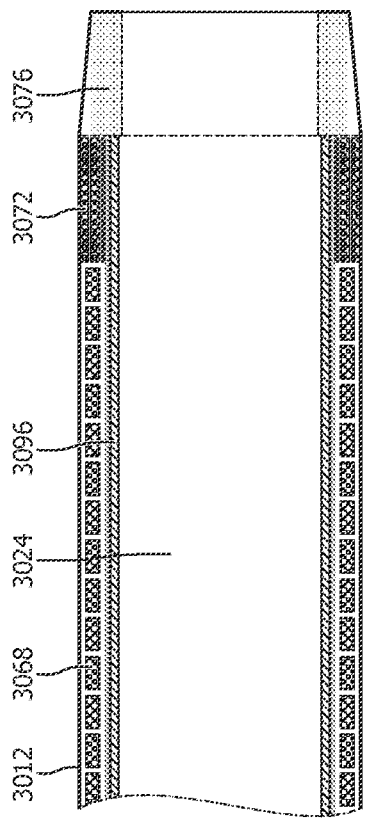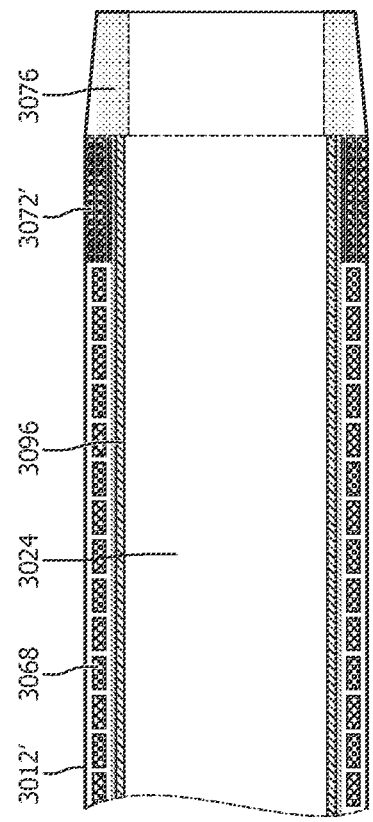

LASER-INDUCED PRESSURE WAVE EMITTING CATHETER SHEATH

CROSS REFERENCE TO RELATED APPLICATIONS

The present application is a continuation-in-part of commonly assigned, co-pending U.S. application Ser. No. 14/984,308, filed on Dec. 30, 2015 which is hereby incorporated herein by reference in its entirety for all that it teaches and for all purposes, which claims the benefit of and priority, under 35 U.S.C. .sctn.119(e), commonly assigned, U.S. Application Ser. No. 62/098,242, filed on Dec. 30, 2014 which is hereby incorporated herein by reference in its entirety for all that it teaches and for all purposes. U.S. application Ser. No. 14/984,308 also claims the benefit of and priority, under 35 U.S.C. .sctn.119(e), to commonly assigned, U.S. Application Ser. No. 62/209,691, filed on Aug. 25, 2015 which is hereby incorporated herein by reference in its entirety for all that it teaches and for all purposes. U.S. application Ser. No. 14/984,308 also claims the benefit of and priority, under 35 U.S.C. .sctn.119(e), to commonly assigned, U.S. Application Ser. No. 62/212,242, filed on Aug. 31, 2015 which is hereby incorporated herein by reference in its entirety for all that it teaches and for all purposes. U.S. application Ser. No. 14/984,308 also claims the benefit of and priority, under 35 U.S.C. .sctn.119(e), to commonly assigned, U.S. Application Ser. No. 62/248,753, filed on Oct. 30, 2015 which is hereby incorporated herein by reference in its entirety for all that it teaches and for all purposes. U.S. application Ser. No. 14/984,308 also claims the benefit of and priority, under 35 U.S.C. .sctn.119(e), to commonly assigned, U.S. Application Ser. No. 62/248,936, filed on Oct. 30, 2015 which is hereby incorporated herein by reference in its entirety for all that it teaches and for all purposes. U.S. application Ser. No. 14/984,308 also claims the benefit of and priority, under 35 U.S.C. .sctn.119(e), to commonly assigned, U.S. Application Ser. No. 62/264,725, filed on Dec. 8, 2015 which is hereby incorporated herein by reference in its entirety for all that it teaches and for all purposes. U.S. application Ser. No. 14/984,308 also claims the benefit of and priority, under 35 U.S.C. .sctn.119(e), to commonly assigned, U.S. Application Ser. No. 62/268,797, filed on Dec. 17, 2015 which is hereby incorporated herein by reference in its entirety for all that it teaches and for all purposes. The present application claims the benefit of and priority, under 35 U.S.C. .sctn.119(e), to commonly assigned, U.S. Application Ser. No. 62/366,409, filed on Jul. 25, 2016 which is hereby incorporated herein by reference in its entirety for all that it teaches and for all purposes. The present application claims the benefit of and priority, under 35 U.S.C. .sctn.119(e), to commonly assigned, U.S. Application Ser. No. 62/441,021, filed on Dec. 30, 2016 which is hereby incorporated herein by reference in its entirety for all that it teaches and for all purposes. The present application is related to commonly assigned, co-pending U.S. application Ser. No. 15/090,736, filed on Apr. 5, 2016 which is hereby incorporated herein by reference in its entirety for all that it teaches and for all purposes, which is a continuation of commonly assigned U.S. application Ser. No. 13/800,214, filed on Mar. 13, 2013, now U.S. Pat. No. 9,320,530, which is hereby incorporated herein by reference in its entirety for all that it teaches and for all purposes.

FIELD

The present disclosure relates generally to the use of medical devices for the treatment of vascular conditions. In particular, the present disclosure provides materials and methods for using laser-induced pressure waves to disrupt vascular blockages and to deliver therapeutic agents to the blockage area.

BACKGROUND

Arterial disease is a common disease that affects millions of Americans. Coronary artery disease (CAD) most often results from a condition known as atherosclerosis, which generally manifests as the accumulation of a waxy substance on the inside of a subject's coronary arteries. This substance, called plaque, is made of cholesterol, fatty compounds, calcium, and a blood-clotting material called fibrin. Similarly, peripheral artery disease (PAD) often results from the accumulation of plaque on the inside of a subject's peripheral arteries, such as the arteries in a patient's arms, hands, legs and/or feet.

As the plaque builds up in either coronary arteries, peripheral arteries and other arteries, the corresponding artery narrows and/or becomes stenotic, thereby making it more difficult for blood to flow through the arteries. As the size of the stenosis increases and the blockage worsens, blood flow slows and upon the formation of a total vascular occlusion, blood flow through the corresponding artery completely stops, which in turn may cause pain in the extremities and, in severe cases, gangrene, which may ultimately require amputation.

Balloon angioplasty and other transluminal medical treatments are well-known and have been proven efficacious in the treatment of stenotic lesions at the core of CAD and/or PAD, as long as the artery is only partially blocked and not totally blocked. In a typical angioplasty procedure to treat CAD, a catheter is inserted into the groin or arm of a subject and guided forward through the aorta and into the coronary arteries of the heart. The angioplasty catheter includes a balloon, which when placed within the partial occlusion, can be inflated, thereby dilating the obstruction or restriction and increasing the size of the diameter of the artery to provides more typical blood flow therethrough.

Over time, a vascular occlusion, particularly a total occlusion, may calcify and/or becomes fibrous, thereby decreasing the balloon's ability to dilate the vascular occlusion. Certain types of catheters, such as electrically-induced shockwave balloon catheters, may be used to break the calcified tissue. An electrically-induced shockwave balloon catheter may include a liquid filled balloon and a one or more pairs of electrodes within the balloon. Upon creating a discharge across the electrodes, plasma is produced, which results in the formation of one or more vapor bubbles. The vapor bubbles created within the balloon cause the balloon to expand and contract. The expansion and contraction of the balloon creates a hydraulic force that transfers energy to the vascular occlusion and/or to the walls of the vessel in an amount sufficient to disrupt intraluminal calcium as well as calcium within the tissue layer of the vasculature (for example, calcium deposits). In addition to producing vapor bubbles being upon the formation of plasma generated by the electrical reaction in the liquid, shockwaves are also produced. The shockwaves are transferred through the balloon and to the calcified vascular occlusion, and the shockwaves modify the calcified occlusion.

In the event a total stenotic occlusion forms, it may be difficult for the balloon to enter the stenosis. Additionally, if a total occlusion calcifies and/or become fibrous, thereby increasing the hardness of occlusion, it may become even more difficult, if not impossible, to penetrate the occlusion and insert a balloon catheter. For example, the proximal and/or distal ends of the occlusion may become calcified to the point that "caps" or "calcified caps" are created, such that even an electrically-induced shockwave balloon catheter may be unable to penetrate the calcified total occlusion because the balloon must be within and adjacent the occlusion in order to operate. And because the balloon within an electrically-induced shockwave balloon catheter is typically proximal the distal end of the electrically-induced shockwave balloon catheter, it is unable to be inserted into or through the calcified cap of the total occlusion.

SUMMARY

What is needed is a device that is capable of penetrating a calcified and/or fibrous vascular occlusion, particularly a calcified cap(s), and disrupting at least a portion of the vascular occlusion as the device penetrates and traverses the total occlusion. What is also needed is a device that is capable of delivering laser-induced pressure waves to the vascular occlusion in order to disrupt the calcified and/or fibrous portions without applying a hydraulic force thereto. These and other needs are addressed by the various aspects, embodiments, and configurations of the present disclosure.

The present disclosure provides a catheter comprising an outer sheath having a proximal end and a distal end, wherein the distal end comprises a tip, an inner sheath may include at least one lumen, a proximal end and a distal end, wherein the inner sheath is disposed radially within the outer sheath, wherein the distal end of the inner sheath may be disposed proximate the tip, thereby creating a cavity among the outer sheath, inner sheath, one or more emitters disposed within the inner sheath extending from a distal proximal portion of the inner sheath to the distal end of the inner sheath and into the cavity, wherein a proximal end of the one or more emitters is coupled to a laser generator, and at least one emitter is disposed within the cavity.

A catheter, wherein the catheter further comprises one or more liquid medium ports disposed about the sheath.

A catheter, wherein the outer sheath is capable of expanding and contracting in the axial direction.

A catheter, wherein the outer sheath is constructed from the group consisting of a polymer, polymer with a coil or embedded with braid, polymer with an embedded braid and fluorinated ethylene propylene or lubricious flouropolymer liner, laser cut hypotube, tricoil or bicoil or any combination of the foregoing.

A catheter wherein the catheter further comprises a shield axially disposed within the cavity between the distal end of the inner sheath and the tip.

A catheter, wherein the shield comprises a proximal end and a distal end, wherein the shield tapers from the proximal end to the distal end or the shield tapers from the distal end to the proximal end.

A catheter, wherein the tip comprises a proximal end and a distal end, wherein the tip has a solid construction along its longitudinal axis from its proximal end to its distal end.

A catheter, wherein the tip comprises an open construction at the distal end of the outer sheath.

A catheter, wherein the tip comprises a proximal end and a distal end, wherein the tip has a hollow construction along its longitudinal axis from its proximal end to its distal end.

A catheter, wherein the at least one emitter is configured to emit laser light energy at wavelengths of between about 300 nanometers to about 360 nanometers, at pulse durations between about 1 femtosecond to about 1 second, and at frequencies between about 1 pulse per second to about 5000 pulses per second.

A catheter, wherein the at least one emitter is configured to emit laser light energy at wavelengths of about 308 nanometers, at pulse durations between about 10 nanoseconds and about 200 nanoseconds, and at frequencies between about 1 pulse per second to about 100 pulses per second.

A catheter, wherein total energy output for the at least one emitter is between about 1 to 300 millijoules per millimeter squared (mJ/mm.sup.2).

A catheter, wherein the liquid medium is contrast medium or contrast solution.

A catheter, wherein the liquid medium is any one of iodine-containing contrast medium or gadolinium contrast medium.

A catheter, wherein the liquid medium is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 5000 pulses per second.

A catheter, wherein the at least one emitter is one or more concentric emitters.

A catheter, wherein the at least one emitter is two or more single-fiber emitters.

A catheter, wherein the at least one emitter is configured to translate within the outer sheath.

A catheter, wherein the tip comprises a distal end and a flexible membrane at its distal end.

A catheter, wherein the liquid medium is configured to absorb light energy, create a laser induced pressure wave and/or vapor bubbles and/or cavitation events to disrupt a vascular occlusion, modify the vascular surface to enhance drug absorption including but not limited to fracturing both intraluminal calcium and calcium deposits within the vasculature, and/or to deliver a drug to an area around a vascular occlusion. Liquid medium can include contrast medium, including for example, iodine-containing contrast medium or gadolinium contrast medium, as well as contrast solutions comprising dye(s) and/or particle(s).

A catheter, wherein the inner sheath further comprises a first guidewire lumen, and further comprising a sealable valve coupled to the outer sheath, the sealable valve having a second guidewire lumen and a seal, whereupon introducing a guidewire into the first guidewire lumen and the second guidewire lumen and introducing liquid medium to the cavity, the liquid medium actuates the seal within the valve and closes an opening between the valve and the guidewire.

A catheter, wherein the sealable valve further comprises an exterior wall and a flange disposed radially therein, wherein a gap exists between the exterior wall and the flange.

A catheter, wherein the sealable valve comprises a proximal portion and a distal portion, and wherein the flange is disposed toward the proximal portion of the sealable valve.

A catheter, wherein the proximal portion of the sealable valve is tubular.

A catheter, wherein the distal portion of the sealable valve is tapered radially inward from the exterior wall towards the second guidewire lumen.

A catheter, wherein the sealable valve further comprises openings within the exterior wall extending toward the proximal portion.

A catheter, wherein the flange is tapered radially inward towards the second guidewire lumen as the flange progresses from the distal portion toward the proximal portion.

The present disclosure also provides a method for treating an occlusion within the vasculature of a subject, the method comprising positioning a catheter within vasculature of a subject, the catheter comprising an outer sheath having a proximal end and a distal end, wherein the distal end comprises a tip, an inner sheath having at least one lumen, a proximal end and a distal end, wherein the inner sheath is disposed radially within the outer sheath, wherein the distal end of the inner sheath is disposed proximate the tip, thereby creating a cavity among the outer sheath, inner sheath and tip, a shield axially disposed within the cavity between the distal end of the inner sheath and the tip, one or more emitters disposed within distal end of the inner sheath and/or the cavity, wherein one or more of the emitters is coupled to a laser generator, wherein the one emitter is disposed within the cavity, and one or more liquid medium ports coupled to the at least one lumen, positioning the tip adjacent an occlusion within the vasculature, introducing a liquid medium into the cavity through the one or more liquid medium ports, activating the at least one emitter within the cavity to transmit pulses of light energy into the liquid medium, wherein transmitting the pulses of light energy from the emitter into the liquid medium generates at least one propagating laser-induced pressure waves that cause the tip to engage and disrupt at least a portion of the vascular occlusion.

A method for treating an occlusion within the vasculature of a subject, wherein the liquid medium is any one of iodine-containing contrast medium or gadolinium contrast medium.

The present disclosure provides a catheter system comprising: a sheath having a proximal end and a distal end and a lumen therein; a laser catheter comprising: a proximal end capable of coupling to a laser generator; a distal end; and at least one emitter coupled to the laser generator; wherein the catheter is disposed within the sheath, whereupon the distal end of the laser catheter being disposed proximate the distal end of the sheath, a cavity between the distal end of the laser catheter and the distal end of the sheath is created; a means for introducing a liquid medium into the cavity; a handle comprising: a base coupled to the proximal end of the sheath; and a drive mechanism translatably coupled to the base, the drive mechanism coupled to the laser catheter such that translation of the drive mechanism relative to the base causes translation of the laser catheter within the lumen of the sheath.

A catheter system, wherein the drive mechanism comprises: a control element movably coupled to the base; and a coupling translatably coupled to the base and driven by the control element, the coupling coupled to the laser catheter such that movement of the control element relative to the base causes translation of the laser catheter within the lumen of the sheath.

A catheter system, wherein the control element is rotatably coupled to the base, and rotation of the control element relative to the base causes translation of the laser catheter within the lumen of the sheath.

A catheter system, wherein the control element includes a first threaded surface, and the drive mechanism further includes a shaft that is translatable within the base and coupled to the coupling, the shaft including a second threaded surface, and the second threaded surface coupling to the first threaded surface such that rotation of the control element relative to the base causes translation of the shaft within the base and translation of the laser catheter within the lumen of the sheath.

A catheter system, wherein the handle further comprises a tube coupled to the base, the tube receiving the laser catheter, and wherein the shaft includes an inner lumen that translatably receives the tube as the shaft translates within the base.

A catheter system, wherein the drive mechanism further comprises a seal coupled to the shaft, the seal translatably engaging the tube.

A catheter system, wherein the tube is a hypotube.

A catheter system, wherein the base includes a first key feature, the shaft includes a second key feature that couples to the first key feature to inhibit rotation of the shaft relative to the base.

A catheter system, wherein the base includes an opening disposed within the control element, the second threaded surface extending through the opening to couple to the first threaded surface.

The present disclosure provides a handle for coupling to a sheath and a laser catheter, the handle comprising: a base configured to couple to a proximal end of the sheath; and a drive mechanism translatably coupled to the base, the drive mechanism configured to couple to the laser catheter such that translation of the drive mechanism relative to the base causes translation of the laser catheter within a lumen of the sheath.

A handle, wherein the drive mechanism comprises: a control element movably coupled to the base; and a coupling translatably coupled to the base and driven by the control element, the coupling being configured to couple to the laser catheter such that movement of the control element relative to the base causes translation of the laser catheter within the lumen of the sheath.

A handle, wherein the control element is rotatably coupled to the base, and rotation of the control element relative to the base causes translation of the laser catheter within the lumen of the sheath.

A handle, wherein the control element includes a first threaded surface, and the drive mechanism further includes a shaft that is translatable within the base and coupled to the coupling, the shaft including a second threaded surface, and the second threaded surface coupling to the first threaded surface such that rotation of the control element relative to the base causes translation of the shaft within the base and translation of the laser catheter within the lumen of the sheath.

A handle, wherein the handle further comprises a tube coupled to the base, the tube receiving the laser catheter, and wherein the shaft includes an passageway that translatably receives the tube as the shaft translates within the base.

A handle, wherein the drive mechanism further comprises a seal coupled to the shaft, the seal translatably engaging the tube.

A handle, wherein the tube is a hypotube.

A handle, wherein the base includes a first key feature, the shaft includes a second key feature that couples to the first key feature to inhibit rotation of the shaft relative to the base.

A handle, wherein the base includes an opening disposed within the control element, the second threaded surface extending through the opening to couple to the first threaded surface.

The present disclosure provides a catheter comprising: an outer sheath having a proximal end, a distal end and a porous attenuating member disposed adjacent the distal end, wherein the porous attenuating member comprises a plurality of openings; an inner sheath having a proximal end and a distal end, wherein the inner sheath is disposed radially within the outer sheath; and at least one emitter coupled to a laser generator, wherein the at least one emitter is disposed radially within the outer sheath such that the at least one emitter is disposed radially within the attenuating member.

A catheter, wherein the porous attenuating member is constructed to form a semi-rigid biocompatible structure.

A catheter, wherein the porous attenuating member is constructed to form a rigid biocompatible structure.

A catheter, wherein the outer sheath comprises a non-porous biocompatible layer.

A catheter, wherein the porous attenuating member is integrally disposed within the solid biocompatible layer.

A catheter, wherein the porous attenuating member is disposed on the exterior of the solid biocompatible layer.

A catheter, wherein the porous attenuating member is disposed on the interior of the solid biocompatible layer.

A catheter, wherein the porous attenuating member comprises a plurality of openings, wherein the plurality of openings comprise at least one of the following shapes: circle; oval; triangle; square; rectangle; helix; polygon; diamond; pentagon; hexagon; heptagon; octagon; nonagon; and decagon.

A catheter, wherein the liquid medium is contrast medium or contrast solution.

A catheter, wherein the liquid medium is any one of iodine-containing contrast medium or gadolinium contrast medium.

A catheter, wherein the liquid medium is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 500 pulses per second.

A catheter, wherein the at least one emitter is two or more concentric emitters.

A catheter, wherein the at least one emitter is two or more single-fiber emitters.

A catheter, wherein the at least one emitter is configured to translate within the outer sheath.

A catheter, wherein the distal end of the outer sheath comprises an open configuration.

A catheter, wherein the distal end of the outer sheath comprises a closed configuration.

The present disclosure provides a method for treating an occlusion within vasculature of a subject, the method comprising: introducing a catheter within vasculature of a subject, the catheter comprising: an outer sheath having a proximal end, a distal end and a porous attenuating member disposed adjacent the distal end, wherein the porous attenuating member comprises a plurality of openings; an inner sheath having a proximal end and a distal end, wherein the inner sheath is disposed radially within the outer sheath; and at least one emitter coupled to a laser generator, wherein the at least one emitter is disposed radially within the outer sheath; one or more liquid medium ports coupled to the at least one lumen; positioning the outer sheath at a location such that the porous attenuating member is adjacent an occlusion within the vasculature; positioning the at least one emitter the such that the at least one emitter is disposed radially within the porous attenuating member; introducing a liquid medium into the outer sheath; activating the at least one emitter to transmit pulses of light energy into the liquid medium; wherein transmitting the pulses of light energy from the emitter into the liquid medium generates at least one propagating laser-induced pressure waves that pass through the outer sheath and the porous attenuating member and disrupt at least a portion of the occlusion.

The present disclosure provides a kit comprising: an outer sheath having a proximal end, a distal end and a porous attenuating member disposed adjacent the distal end, wherein the porous attenuating member comprises a plurality of openings; and a laser catheter configured to be disposed within the porous attenuating member, the laser catheter comprising: an inner sheath having a proximal end and a distal end, wherein the inner sheath is configured to be disposed radially within the outer sheath; and at least one emitter coupled to a laser generator, wherein the at least one emitter is configured to be disposed radially within the outer sheath such that the at least one emitter is disposed radially within the porous attenuating member.

The present disclosure provides a method for treating an occlusion within vasculature of a subject, the method comprising: introducing an outer sheath within vasculature of a subject, wherein the outer sheath comprises a proximal end, a distal end and a porous attenuating member disposed adjacent the distal end, wherein the porous attenuating member comprises a plurality of openings; introducing a laser catheter within the vasculature of the subject, wherein the laser catheter is configured to be disposed within the porous attenuating member, wherein the laser catheter comprises an inner sheath having a proximal end and a distal end, wherein the inner sheath is configured to be disposed radially within the outer sheath; and at least one emitter coupled to a laser generator, wherein the at least one emitter is disposed radially within the outer sheath; one or more liquid medium ports coupled to the at least one lumen; positioning the outer sheath at a location such that the porous attenuating member is adjacent a portion of an occlusion within the vasculature; positioning the at least one emitter the such that the at least one emitter is disposed radially within the porous attenuating member; introducing a liquid medium into the outer sheath; activating the at least one emitter to transmit pulses of light energy into the liquid medium; wherein transmitting the pulses of light energy from the emitter into the liquid medium generates at least one propagating laser-induced pressure waves that pass through the outer sheath and the porous attenuating member and disrupt at least a portion of the occlusion.

A method, further comprising the step of re-positioning the outer sheath such that the attenuating member is adjacent another portion of the occlusion.

A method, further comprising the step of re-positioning the laser catheter within outer sheath.

A method, wherein the within the laser catheter is re-positioned within the attenuating member.

A method, further comprising the steps of removing the laser catheter from the vasculature and removing the outer sheath from the vasculature.

A method, further comprising the step of inserting a drug-coated balloon into the vasculature such that the drug-coated balloon is disposed adjacent to a remaining portion of the occlusion.

A method, further comprising the step of inflating the drug-coated balloon and applying a drug disposed on the drug-coated balloon to the remaining portion of the occlusion.

The present disclosure provides a catheter comprising: a sheath having a guidewire lumen, a proximal end, and a distal end; a plurality of emitters circumferentially arranged around or adjacent to the guidewire lumen, wherein each emitter emits laser light; and means for directing laser light emitted from the emitter towards the guidewire lumen or a guidewire within the guidewire lumen.

A catheter, wherein the means for directing laser light emitted from the emitter towards the guidewire lumen or a guidewire within the guidewire lumen comprises an outer band coupled to the distal end of the sheath, wherein the outer band comprises a distal end, and the emitter is disposed proximate the distal end of the outer band.

A catheter, wherein the emitter is directed at the guidewire lumen or a guidewire within the guidewire lumen.

A catheter, wherein the means for directing laser light emitted from the emitter towards the guidewire lumen or a guidewire comprises a cap coupled to the distal end of the sheath.

A catheter, wherein the cap comprises an interior side and an exterior side, wherein the interior side is tapered to direct laser-induced pressure wave and/or cavitation event towards the guidewire lumen or a guidewire within the guidewire lumen resulting in excitation and/or vibration of the guidewire.

A catheter wherein the emitter is disposed proximate the interior side of the cap.

A catheter, wherein the sheath is an inner sheath, and further comprising an outer sheath translatably receiving the inner sheath.

A catheter, wherein the outer sheath comprises a sleeve, and wherein the means for directing laser light emitted from the emitter towards the guidewire lumen or a guidewire within the guidewire lumen comprises an attenuating member of the outer sheath coupled to the sleeve.

A catheter, wherein the attenuating member comprises an inner surface, an outer surface, and a plurality of openings extending from the inner surface to the outer surface.

A catheter, wherein the attenuating member contains a plurality of openings which comprise at least one of the following shapes: circle; oval; triangle; square; rectangle; helix; polygon; diamond; pentagon; hexagon; heptagon; octagon; nonagon; and decagon.

The present disclosure provides a method for treating an occlusion within vasculature of a subject, the method comprising: positioning a catheter within the vasculature of the subject, the catheter comprising: a sheath having a guidewire lumen, a proximal end, and a distal end; a plurality of emitters circumferentially arranged around or adjacent to the guidewire lumen, wherein emitter is capable of emitting laser light; means for directing laser light emitted from the emitter towards the guidewire lumen or a guidewire within the guidewire lumen; positioning the distal end of the sheath adjacent the occlusion within the vasculature; delivering a liquid medium to the distal end of the sheath; activating the emitter to transmit pulses of light energy through the liquid medium; wherein transmitting the pulses of light energy from the emitter into the liquid medium generates a plurality of propagating laser-induced pressure waves that disrupt at least a portion of the occlusion; and wherein the means for directing laser light emitted from the emitter towards the guidewire lumen or a guidewire within the guidewire lumen induces vibrations within the guidewire.

A method, wherein the means for directing laser light emitted from the emitter towards the guidewire lumen or a guidewire within the guidewire lumen comprises an outer band coupled to the distal end of the sheath, wherein the outer band comprises a distal end, and the emitter is disposed proximate the distal end of the outer band.

A method, wherein the means for directing laser light emitted from the emitter towards the guidewire lumen or a guidewire within the guidewire lumen comprises an outer band coupled to the distal end of the sheath, wherein the outer band comprises a distal end, and the emitter is disposed proximate the distal end of the outer band.

A method, wherein the emitter is directed at the guidewire lumen or a guidewire in the guidewire lumen.

A method, wherein the means for directing laser light emitted from the emitter towards the guidewire lumen or a guidewire comprises a cap coupled to the distal end of the sheath.

A method, wherein the cap comprises an interior side and an exterior side, wherein the interior side is tapered to direct a laser-induced pressure wave and/or cavitation event towards the guidewire lumen or a guidewire within the guidewire lumen resulting in excitation and/or vibration of the guidewire.

A method, wherein the emitter is disposed proximate the interior side of the cap.

A method, wherein the sheath is an inner sheath, and wherein the catheter further comprises an outer sheath translatably receiving the inner sheath.

A method, wherein the outer sheath comprises a sleeve, and wherein the means for directing laser light emitted from the emitter towards the guidewire lumen or a guidewire within the guidewire lumen comprises a attenuating member of the outer sheath coupled to the sleeve.

A method, wherein the attenuating member comprises an inner surface, an outer surface, and a plurality of openings extending from the inner surface to the outer surface, and wherein transmitting the pulses of light energy from the emitter into the liquid medium generates a plurality of propagating laser-induced pressure waves that pass through the plurality of openings.

A method, wherein the attenuating member contains a plurality of openings which comprise at least one of the following shapes: circle; oval; triangle; square; rectangle; helix; polygon; diamond; pentagon; hexagon; heptagon; octagon; nonagon; and decagon.

The present disclosure provides a method for treating an occlusion within vasculature of a subject, the method comprising: positioning a catheter within the vasculature of the subject, the catheter comprising: a sheath having a guidewire lumen, a proximal end, and a distal end; a plurality of emitters circumferentially arranged around or adjacent to the guidewire lumen, wherein emitter is capable of emitting laser light; positioning the distal end of the sheath adjacent the occlusion within the vasculature; delivering a liquid medium to the distal end of the sheath; activating the emitter to transmit pulses of light energy through the liquid medium; wherein transmitting the pulses of light energy from the emitter into the liquid medium generates a plurality of propagating laser-induced pressure waves that disrupt at least a portion of the occlusion; and wherein the plurality of propagating laser induced pressure waves induce vibrations within the guidewire.

The present disclosure provides a method for treating an occlusion within vasculature of a subject, the method comprising: positioning a catheter within vasculature of a subject, the catheter comprising: an outer sheath having a proximal end and a distal end; a tip coupled to the distal end of the outer sheath; an inner sheath having a first guidewire lumen, a proximal end, and a distal end, wherein the inner sheath is disposed radially within the outer sheath, wherein the distal end of the inner sheath is disposed proximate the tip, thereby creating a cavity among the outer sheath, inner sheath and tip; a sealable valve coupled to the outer sheath, the sealable valve having a second guidewire lumen and a seal; one or more emitters disposed within the inner sheath extending from the proximal end of the inner sheath to the distal end of the inner sheath and into the cavity, wherein the one or more emitters is coupled to an energy source, such as a laser generator; wherein at least one emitter is disposed within the cavity; positioning the tip adjacent an occlusion within the vasculature by advancing the catheter along a guidewire, wherein the guidewire is received in the first guidewire lumen and the second guidewire lumen; introducing a liquid medium into the cavity, wherein the liquid medium actuates the seal within the valve and closes an opening between the valve and the guidewire; and; activating the at least one emitter within the cavity to transmit pulses of light energy into the liquid medium; wherein transmitting the pulses of light energy from the emitter into the liquid medium generates at least one propagating laser-induced pressure waves that cause the tip to engage and disrupt at least a portion of the vascular occlusion.

A method, wherein the sealable valve further comprises an exterior wall and a flange disposed radially therein, wherein a gap exists between the exterior wall and the flange, and wherein introducing the liquid medium into the cavity includes introducing the liquid medium to the gap to actuate the seal within the valve and close the opening between the valve and the guidewire.

A method, wherein the sealable valve further comprises openings within the exterior wall extending into the gap, and wherein introducing the liquid medium to the gap includes introducing the liquid medium to the gap via the openings.

A method, wherein the flange is tapered radially inward towards the second guidewire lumen as the flange progresses from a distal portion of the valve toward a proximal portion of the valve.

The present disclosure provides a catheter comprising a sheath having a proximal end and a distal end; a tip coupled to and forming a cavity at the distal end of the sheath; one or more emitters carried by the sheath and coupled to an energy source, such as a laser generator, wherein the at least one emitter is disposed within the cavity; and a light absorbing material coupled to at least part of the sheath and the tip and disposed such that light emitted from the at least one emitter intersects with the light absorbing material.

A catheter, wherein the light absorbing material is disposed within the cavity.

A catheter, wherein the light absorbing material is disposed outside of the cavity.

A catheter, wherein the light absorbing material is applied as a coating to a support structure located within the cavity.

The present disclosure provides a method for treating an occlusion within vasculature of a subject, the method comprising positioning a catheter within vasculature of a subject, the catheter comprising a sheath having a proximal end and a distal end; a tip coupled to and forming a cavity at the distal end of the sheath; one or more emitters carried by the sheath and disposed toward and/or in the cavity, wherein the one or more emitters is coupled to an energy source, such as a laser generator; a light absorbing material coupled to at least part of the sheath and the tip; positioning the tip adjacent an occlusion within the vasculature by advancing the catheter within the vasculature; and activating the at least one emitter to transmit a pulse of light energy such that the light energy intersects with at least a portion of the light absorbing material.

A method, further comprising delivering a liquid medium to the cavity.

A method, wherein the tip further comprises a flexible membrane carrying the light absorbing material, and activating the at least one emitter to transmit the pulse of light energy such that the light energy intersects with the at least a portion of the light absorbing material causes deflection of the flexible membrane.

The present disclosure provides a method for treating an occlusion within vasculature of a subject, the method comprising positioning a catheter within the vasculature of the subject, the catheter comprising a sheath having a proximal end and a distal end; at least one emitter carried by the sheath, wherein each emitter is capable of emitting laser light; positioning the distal end of the sheath adjacent the occlusion within the vasculature; delivering a gas-saturated liquid medium to the distal end of the sheath; activating the emitter to transmit pulses of light energy through the gas-saturated liquid medium; wherein transmitting the pulses of light energy from the emitter into the gas-saturated liquid medium generates at least one propagating laser-induced pressure wave that disrupts at least a portion of the occlusion.

A method, wherein the gas-saturated liquid medium is any one of iodine-containing contrast medium or gadolinium contrast medium.

A method, wherein the gas-saturated liquid medium comprises a super saturated liquid medium.

The present disclosure provides a method for treating an occlusion within vasculature of a subject, the method comprising: positioning a catheter within the vasculature of the subject, the catheter comprising: an outer sheath having a proximal end, a distal end, and a lumen therein; an inner sheath comprising: a proximal end capable of coupling to an energy source, such as a laser generator; a distal end opposite the proximal end; one or more optical fibers extending from the proximal end of the inner sheath to the distal end of the inner sheath; and at least one emitter coupled to the one or more optical fibers; positioning the distal end of the outer sheath adjacent the occlusion within the vasculature; positioning the distal end of the inner sheath proximally relative to the distal end of the outer sheath to create a cavity between the distal end of the inner sheath and the distal end of the outer sheath; delivering a liquid medium to the cavity; and activating the emitter to transmit pulses of light energy through the liquid medium; wherein transmitting the pulses of light energy from the emitter into the liquid medium generates at least one propagating laser-induced pressure waves that disrupt at least a portion of the occlusion.

A method, further comprising: repositioning the inner sheath within outer sheath after activating the emitter; and subsequently activating the emitter to transmit pulses of light energy through the liquid medium; wherein transmitting the pulses of light energy from the emitter into the liquid medium generates at least one propagating laser-induced pressure waves that disrupt at least a portion of the occlusion.

A method, further comprising traversing the entire occlusion with the inner sheath and the outer sheath after activating the emitter.

A method, wherein the inner sheath further comprises a guidewire lumen, wherein positioning the catheter within the vasculature of the subject comprises receiving a guidewire in the guidewire lumen and advancing the inner sheath and the outer sheath along the guidewire, and further comprising traversing the occlusion with the guidewire.

A method, further comprising traversing the occlusion with the inner sheath and without the outer sheath after activating the emitter.

A method, further comprising: inserting a drug-coated balloon into the vasculature, after activating the emitter, such that the drug-coated balloon is disposed adjacent a remaining portion of the occlusion; and inflating the drug-coated balloon and applying a drug disposed on the drug-coated balloon to the occlusion.

A catheter, kit and/or method, wherein the total energy output for the at least one emitter is between about 20 to about 1000 millijoules per millimeter squared (mJ/mm.sup.2).

A catheter, kit and/or method, wherein the at least one emitter is configured to emit laser light energy at wavelengths of between about 150 nanometers to about 400 nanometers, at pulse durations between about 1 femtosecond to about 1 second, and at frequencies between about 1 pulse per second to about 5000 pulses per second.

A catheter, kit and/or method, wherein the at least one emitter is configured to emit laser light energy at wavelengths of between about 400 nanometers to about 800 nanometers, at pulse durations between about 1 femtosecond to about 1 second, and at frequencies between about 1 pulse per second to about 5000 pulses per second.

A catheter, kit and/or method, wherein the at least one emitter is configured to emit laser light energy at wavelengths of between about 800 nanometers to about 3,000 nanometers, at pulse durations between about 1 femtosecond to about 1 second, and at frequencies between about 1 pulse per second to about 5000 pulses per second.

A catheter, kit and/or method, wherein the at least one emitter is configured to emit laser light energy at wavelengths of between about 3,000 nanometers to about 12,000 nanometers, at pulse durations between about 1 femtosecond to about 1 second, and at frequencies between about 1 pulse per second to about 5000 pulses per second.

A catheter, kit and/or method, wherein the at least one emitter is configured to emit laser light energy at wavelengths of between about 300 nanometers to about 360 nanometers, at pulse durations between about 1 femtosecond to about 1 second, and at frequencies between about 1 pulse per second to about 5000 pulses per second.

A catheter, kit and/or method, wherein the at least one emitter is configured to emit laser light energy at wavelengths of about 308 nanometers, at pulse durations between about 10 nanoseconds and about 200 nanoseconds, and at frequencies between about 1 pulse per second to about 100 pulses per second.

A catheter, kit and/or method, wherein the attenuating member is disposed on the exterior of the outer sheath.

A catheter, kit and/or method, wherein the attenuating member is disposed on the interior of the outer sheath.

A catheter, kit and/or method, wherein the attenuating member is disposed integral of the outer sheath.

A method for improving the compliance of a blood vessel within a subject, the method comprising locating a calcified portion in the media of the blood vessel of the subject, positioning a laser catheter within the vasculature of the subject, the catheter comprising a proximal end, a distal end, and at least one emitter disposed at the distal end, positioning a sheath over the laser catheter within the vasculature of the subject, wherein the sheath comprises a proximal end, a distal end and a attenuating member disposed adjacent the distal end, positioning the sheath within the vasculature such that the attenuating member is disposed adjacent a portion of the calcified portion, positioning the laser catheter within the vasculature such that the at least one emitter is positioned within the attenuating member and adjacent the portion of the calcified portion, introducing a liquid medium into the outer sheath and to the at least one emitter; activating the at least one emitter to transmit pulses of light energy into the liquid medium; emitting one or more pulses of light energy from the at least one emitter, wherein the one or more pulses of light energy reacts with the liquid medium and generates a plurality of propagating laser-induced pressure waves that disrupt the calcified portion of the media, thereby improving the compliance of the blood vessel.

A method further comprising the step of re-positioning the sheath such that the attenuating member is adjacent another calcified portion of the media.

A method further comprising the step of re-positioning the laser catheter within sheath.

A method, wherein the within the laser catheter is re-positioned within the attenuating member.

A method, further comprising the steps of removing the laser catheter from the vasculature and removing the outer sheath from the vasculature.

A method, wherein the at least one emitter is configured to emit laser light energy at wavelengths of between about 150 nanometers to about 400 nanometers, at pulse durations between about 1 femtosecond to about 1 second, and at frequencies between about 1 pulse per second to about 5000 pulses per second.

A method, wherein the at least one emitter is configured to emit laser light energy at wavelengths of between about 400 nanometers to about 800 nanometers, at pulse durations between about 1 femtosecond to about 1 second, and at frequencies between about 1 pulse per second to about 5000 pulses per second.

A method, wherein the at least one emitter is configured to emit laser light energy at wavelengths of between about 800 nanometers to about 3,000 nanometers, at pulse durations between about 1 femtosecond to about 1 second, and at frequencies between about 1 pulse per second to about 5000 pulses per second.

A method, wherein the at least one emitter is configured to emit laser light energy at wavelengths of between about 3,000 nanometers to about 12,000 nanometers, at pulse durations between about 1 femtosecond to about 1 second, and at frequencies between about 1 pulse per second to about 5000 pulses per second.

A method, wherein the at least one emitter is configured to emit laser light energy at wavelengths of between about 300 nanometers to about 360 nanometers, at pulse durations between about 1 femtosecond to about 1 second, and at frequencies between about 1 pulse per second to about 5000 pulses per second.

A method, wherein the at least one emitter is configured to emit laser light energy at wavelengths of about 308 nanometers, at pulse durations between about 10 nanoseconds and about 200 nanoseconds, and at frequencies between about 1 pulse per second to about 100 pulses per second.

A method, wherein total energy output for the at least one emitter is between about 1 to about 100 millijoules per millimeter squared (mJ/mm.sup.2).

A method, wherein total energy output for the at least one emitter is between about 30 to about 80 millijoules per millimeter squared (mJ/mm.sup.2).

A method, wherein the liquid medium is contrast medium or contrast solution.

A method, wherein the liquid medium is any one of iodine-containing contrast medium or gadolinium contrast medium.

A method, wherein the liquid medium is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

A method, wherein the at least one emitter is two or more concentric emitters.

A method, wherein the at least one emitter is two or more single-fiber emitters.

A method, wherein the attenuating member is constructed to form a semi-rigid biocompatible structure.

A method, wherein the attenuating member is constructed to form a rigid biocompatible structure.

A method, wherein the sheath comprises a non-porous biocompatible layer.

A method, wherein the attenuating member comprises an inner surface, an outer surface, and a plurality of openings extending from the inner surface to the outer surface.

A method, wherein the attenuating member contains a plurality of openings which comprise at least one of the following shapes: circle; oval; triangle; square; rectangle; helix; polygon; diamond; pentagon; hexagon; heptagon; octagon; nonagon; and decagon.

A method, wherein the attenuating member is integrally disposed within the sheath.

A method, wherein the attenuating member is disposed on the exterior of the sheath.

A method, wherein the attenuating member is disposed on the interior of the sheath.

A method, wherein the liquid medium is any one of iodine-containing contrast medium or gadolinium contrast medium.

A method, wherein the distal end of the sheath comprises an open configuration.

A method, wherein the distal end of the sheath comprises a closed configuration.

According to the present disclosure, after penetrating the calcified and/or fibrous total occlusion and disrupting at least a portion of the occlusion with the laser-induced pressure wave emitting catheter sheath, the method may also include delivering via a balloon catheter, one or more therapeutic agents, which is/are disposed on the balloon, wherein the therapeutic agents may comprise one or more oxidation-insensitive drugs in a polymer-free drug preparation, including one or more of taxanes, thalidomide, statins, corticoids, and lipophilic derivatives of corticoids. The therapeutic agents may also include one or more lipophilic antioxidants, such as nordihydroguaiaretic acid, resveratrol and propyl gallate in a polymer-free preparation. For example, U.S. application Ser. No. 13/628,608, which is a continuation of International Application No. PCT/EP2010/066754, filed Nov. 3, 2010, both of which are hereby incorporated herein by reference in their entireties for all that they teach and for all purposes, discloses a scoring or cutting balloon catheter providing improved adherence of therapeutic agents to the balloon catheter using a combination of an oxidation-insensitive drug and a lipophilic antioxidant.

Additionally, U.S. application Ser. No. 13/707,401, filed Dec. 6, 2012, and issued on Oct. 21, 2014, which is a divisional application of U.S. application Ser. No. 11/411,635, filed Apr. 26, 2006, and which claims priority to U.S. Provisional Application Ser. No. 60/680,450, filed May 11, 2005, all of which are hereby incorporated herein by reference in their entireties for all that they teach and for all purposes, discloses scoring elements of a balloon catheter coated with a polymer matrix to deliver hydrophobic and lipophilic drugs to regions within a thrombus or plaque.

Additionally, U.S. application Ser. No. 13/310,320, filed Dec. 2, 2011, and issued Oct. 22, 2013, which is a divisional application of U.S. application Ser. No. 12/712,134, filed Feb. 24, 2010, and issued Mar. 6, 2012, and U.S. application Ser. No. 12/726,101, filed Mar. 17, 2010, and issued Feb. 14, 2012, which is a continuation-in-part of U.S. application Ser. No. 12/712,134, filed Feb. 24, 2010, and issued Mar. 6, 2012, which is a continuation-in-part of U.S. application Ser. No. 12/558,420, filed Sep. 11, 2009, which is a continuation-in-part of U.S. application Ser. No. 12/210,344, filed Sep. 15, 2008, and issued Sep. 4, 2012, and U.S. application Ser. No. 14/149,862, filed Jan. 8, 2014, which is a continuation of U.S. application Ser. No. 13/560,538, filed Jun. 27, 2012, and issued Mar. 18, 2014, which is a divisional application of U.S. application Ser. No. 12/210,344, filed Sep. 15, 2008, and issued Sep. 4, 2012, all of which are hereby incorporated herein by reference in their entireties for all that they teach and for all purposes, disclose methods and devices for local delivery of water-soluble and water-insoluble therapeutic agents to the surface of normal and diseased body lumens.

Additionally, U.S. application Ser. No. 13/926,515, filed Jun. 25, 2013, which claims priority to U.S. Provisional Application Ser. No. 61/665,758, filed Jun. 28, 2012, both of which are hereby incorporated herein by reference in their entireties for all that they teach and for all purposes, disclose methods and devices for coating a medical device that includes a therapeutic agent dispersed in a polymer or oligomer matrix.

The present disclosure also provides a catheter system comprising a sheath having a proximal end and a distal end and a lumen therein, a laser catheter comprising, a proximal end, a distal end capable of coupling to an energy source, such as a laser generator, and at least one emitter disposed at the distal end of the laser catheter and coupled to an energy source, such as a laser generator, wherein the catheter is configured to be disposed within the sheath, whereupon the distal end of the laser catheter being disposed proximate the distal end of the sheath, a cavity between the distal end of the laser catheter and the distal end of the sheath is created, and a means for introducing a liquid medium into the cavity.

The present disclosure also provides A method for improving the compliance of a blood vessel within a subject, the method comprising locating a calcified portion in the media of the blood vessel of the subject, positioning a laser catheter within the vasculature of the subject, the catheter comprising a proximal end, a distal end, and at least one emitter disposed adjacent the distal end, positioning a sheath over the laser catheter within the vasculature of the subject, wherein the sheath comprises a proximal end, a distal end and an attenuating member disposed at or adjacent the distal end of the sheath, wherein the attenuating member comprises an open area between 40 percent and 60 percent, wherein the attenuating member is formed from at least one coil having between 75 and 125 wraps per inch, positioning the sheath within the vasculature such that the attenuating member is disposed adjacent a portion of the calcified portion in the media of the blood vessel, positioning the laser catheter within the vasculature such that the at least one emitter is positioned within the attenuating member and adjacent the portion of the calcified portion in the media of the blood vessel, introducing a liquid medium into the sheath and to the at least one emitter, and emitting a plurality of pulses of light energy from the at least one emitter into the liquid medium, wherein the plurality of pulses of light energy react with the liquid medium and generate a plurality of propagating laser-induced pressure waves that disrupt the calcified portion of media, thereby improving the compliance of the blood vessel.

A method, wherein the at least one coil comprises a flat wire.

A method, wherein the flat wire comprises a height between 0.0005 and 0.002 inches and a width of between 0.002 and 0.010 inches.

A method, wherein the flat wire comprises a height of about 0.001 inches and a width of about 0.005 inches.

A method, wherein a spacing between each wrap of flat wire in the coil is between 0.003 and 0.008 inches.

A method, wherein the coil has between 90 and 100 wraps per inch.

A method, wherein the coil has about 95 wraps per inch.

A method, wherein the sheath comprises a tip and a lumen, wherein the lumen comprises a first internal diameter and a second internal diameter proximate the tip, wherein the first internal diameter is smaller than the second internal diameter.

A method, wherein laser catheter has an outer diameter that is about equal to the first inner diameter of the tip.

A method, wherein a first difference between the outer diameter of the laser catheter and the first inner diameter of the tip is about 0.0005 inches.

A method, wherein a second difference between the outer diameter of the laser catheter and the second inner diameter of the sheath is about 0.0025 inches.

A method, wherein the sheath comprises a tip having a proximal end and a distal end, wherein the tip tapers from the proximal end to the distal end.

The present disclosure also provides a method for performing an atherectomy within a subject having a vasculature occlusion within the subject's vasculature, the method comprising inserting a guidewire through a vascular occlusion within the vasculature, introducing a laser catheter into the vasculature and over the guidewire, wherein the laser catheter comprises at least one emitter, ablating at least a portion of the vascular occlusion with the laser catheter, introducing a sheath into the vasculature and over the laser catheter, wherein the sheath comprises a distal portion and an attenuating member disposed at or adjacent the distal portion of the sheath, wherein the attenuating member comprises an open area between 40 percent and 60 percent, wherein the attenuating member is formed from at least one coil having between 75 and 125 wraps per inch, positioning the sheath within the vasculature such that the attenuating member is disposed radially adjacent a calcified portion within the vasculature, positioning the laser catheter within the vasculature such that the at least one emitter is positioned within the attenuating member and radially adjacent the calcified portion, introducing a liquid medium into the sheath and to the at least one emitter; and emitting a plurality of pulses of light energy from the at least one emitter into the liquid medium, wherein the plurality of pulses of light energy react with the liquid medium and generate a plurality of propagating laser-induced pressure waves that disrupt the calcified portion.

A method further comprising extending the laser catheter distally of the sheath and ablating another portion of a second vascular occlusion, positioning the sheath within the vasculature such that the attenuating member is disposed radially adjacent a second calcified portion of the second vascular occlusion, positioning the laser catheter within the vasculature such that the at least one emitter is positioned within the attenuating member and radially adjacent the second calcified portion, introducing a liquid medium into the sheath and to the at least one emitter, and emitting a plurality of pulses of light energy from the at least one emitter into the liquid medium, wherein the plurality of pulses of light energy react with the liquid medium and generate a plurality of propagating laser-induced pressure waves that disrupt the second calcified portion.

The present disclosure also provides a catheter system comprising a laser catheter comprising a proximal end, a distal end, and at least one emitter disposed adjacent the distal end, a sheath configured to be disposed over the laser catheter and configured to receive a liquid medium, the sheath comprising a proximal end, a distal end, and an attenuating member disposed at or adjacent the distal end of the sheath, wherein the attenuating member comprises an open area between 40 percent and 60 percent, wherein the attenuating member is formed from at least one coil having between 75 and 125 wraps per inch.

A system, wherein the at least one coil comprises a flat wire.

A system, wherein the flat wire comprises a height between 0.0005 and 0.002 inches and a width of between 0.002 and 0.010 inches.

A system, wherein a spacing between each wrap of flat wire in the coil is between 0.003 and 0.008 inches.

A system, wherein the at least one coil has between 90 and 100 wraps per inch.

A system, wherein the sheath further comprises an inner liner, an outer jacket; and an intermediate layer disposed concentrically between the inner liner and the outer jacket.

A system, wherein the braided structure is integrally disposed within the inner liner or the outer jacket.

A system, wherein the braided structure is integrally disposed within the inner liner.

A system, wherein the braided structure is integrally disposed within the outer jacket.

A system, wherein the braided structure is integrally disposed within the outer jacket and the inner liner.

The present disclosure also provides a catheter system comprising a laser catheter comprising a proximal end, a distal end, and at least one emitter disposed adjacent the distal end, a sheath configured to be disposed over the laser catheter and configured to receive a liquid medium, the sheath comprising a proximal end, a distal end, and an attenuating member disposed at or adjacent the distal end of the sheath, wherein the attenuating member comprises a braided structure having a braid density between 40 and 80 picks per inch.

A system, wherein the braided structure has an open area between 55 percent and 75 percent.

A system, wherein the braided structure has between 12 and 20 carriers.

A system, wherein the sheath further comprises an inner liner, an outer jacket, and an intermediate layer disposed concentrically between the inner liner and the outer jacket.

A system, wherein the braided structure is integrally disposed within the inner liner or the outer jacket.

A system, wherein the braided structure is integrally disposed within the inner liner.

A system, wherein the braided structure is integrally disposed within the outer jacket.

A system, wherein the braided structure is integrally disposed within the outer jacket and the inner liner.

As used herein, "at least one," "one or more," and "and/or" are open-ended expressions that are both conjunctive and disjunctive in operation. For example, each of the expressions "at least one of A, B and C," "at least one of A, B, or C," "one or more of A. B, and C," "one or more of A, B, or C," and "A, B, and/or C" means A alone, B alone. C alone, A and B together, A and C together. B and C together, or A, B and C together. When each one of A, B, and C in the above expressions refers to an element, such as X, Y, and Z, or class of elements, such as X.sub.1-X.sub.n, Y.sub.1-Y.sub.m, and Z.sub.1-Z.sub.0, the phrase is intended to refer to a single element selected from X, Y, and Z, a combination of elements selected from the same class (for example, X.sub.1 and X.sub.2) as well as a combination of elements selected from two or more classes (for example, Y.sub.1 and Z.sub.0).

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "about" when used in conjunction with a numeric value shall mean plus and/or minus ten percent (10%) of that numeric value, unless otherwise specifically mentioned herein.

The term "attenuating member" as used herein is any component which alters a cavitation event, and/or vapor bubble. An example of an attenuating member is an element which minimally affects the laser induced pressure wave, yet alters the cavitation event and/or the vapor bubble. An example of an attenuating member is a porous attenuating member. The attenuating member, however, does not need to be porous and may include a solid configuration.

The term "catheter" as used herein generally refers to a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter). In some uses a catheter may contain a lumen along part or all of its length to allow the introduction of other catheters or guidewires. An example of a catheter is a sheath.

The term "balloon catheter" as used herein generally refers to the various types of catheters which carry a balloon for containing fluids. Balloon catheters may also be of a wide variety of inner structure, such as different lumen design, of which there are at least three basic types: triple lumen, dual lumen and co-axial lumen. All varieties of internal structure and design variation are meant to be included by use of the term "balloon catheter" herein. In some uses, balloon catheters can be used to perform angioplasty.

The term "cavitation event" as used herein describes the rapid fluid movement that leads to collapse of a vapor bubble to its smallest radius. In some cases, a cavitation event may include the generation of a pressure wave.

The terms "coupler" or "fiber optic coupler" refers to the optical fiber device with one or more input fibers or emitters and one or several output fibers or emitters. Fiber couplers are commonly special optical fiber devices with one or more input fibers or emitters for coupling these fibers or emitters to an energy source. The energy source can be another optical energy carrying fiber or emitter which is coupled to one or more additional fibers or emitters.

The term "emitter" as used herein refers to a fiber or an optical component (including any portion thereof, such as the end of a fiber) that emits light from a distal end of device, such as a catheter, towards a desired target. In some uses, this target can be tissue, or an absorptive media, such as contrast fluid. An emitter can be the output end of any device that transports light from an optical energy source to a target or treatment area. These optical energy transport devices can include glass or fused silica fiber optics, plastic fiber optics, air or gas light guides, and liquid light guides. As described herein, an emitter or emitters can be used to emit light of any wavelength. An emitter or emitters can emit light, including but not limited to, laser light, white light, visible light, infrared light, and ultraviolet light.

According to the present disclosure, the catheter contains at least one emitter, which may comprise glass or fused silica fiber optics, plastic fiber optics, air or gas light guides, and liquid light guides. Examples of a liquid light guide, or a catheter that contain a liquid light guide can be seen in U.S. application Ser. No. 11/923,488, filed Oct. 24, 2007 and U.S. application Ser. No. 12/254,254, filed Oct. 20, 2008, both of which are hereby incorporated herein by reference in their entireties for all that they teach and for all purposes.

The term "flexible structure" as used herein shall mean a structure that is able to bend or otherwise conform to the shape of the vasculature as it passes therethrough. The term "radial flexible structure" shall include a flexible structure that is also able to expand and/or contract in the radial direction upon a laser induced pressure wave passing therethrough.

A "laser emitter" as used herein refers to an end portion of a fiber or an optical component that emits laser light from a distal end of the catheter towards a desired target. In some uses, this target can be tissue, or an absorptive media, such as contrast fluid.

The term "laser-induced pressure wave" as used herein is a pressure wave caused by a reaction between laser light and an absorptive material. The laser-induced pressure wave may be generated in a gas, liquid (e.g., saline that may or may not include a contrast medium) or solid.

The term "means" as used herein shall be given its broadest possible interpretation in accordance with 35 U.S.C. .sctn.112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

The term an "optical fiber" (or laser active fibre) as used herein refers to a flexible, transparent fiber made of an optically transmissive material, such as glass (silica) or plastic, which functions as a waveguide, or "light pipe", to transmit light between the two ends of the fiber.

The term "porous attenuating member" as used herein shall mean an attenuating member constructed of a rigid member or semi-rigid member having openings therein. Examples of a rigid member and a semi-rigid member include a member constructed of coils, braids, laser-cut tubing, reinforced polymer extrusions, patterned plastics, metals and ceramics. Specific materials used to construct such rigid member and a semi-rigid member may include nitinol (which is a nickel-titanium alloy), stainless steel, titanium, silver, aluminum, cobalt, chromium, pebax, silicone, urethane, polyethylene and derivatives, nylons, polytetrafluoroethylene and derivatives, polyethylene terephthalate, polypropylene, poly(ether ether ketone), hydroxyapatite, alumina, tricalcium phosphate, silicates or other biocompatible metals, ceramics or polymers. Possible configurations for the porous attenuating member include, but are not limited to, spiral cuts, interrupted spiral cut, honeycomb, lattice structures as found commonly in vascular stents, slots, offset slots, helices, slits that are either longitudinal, radial, circumferential, or a combination thereof, openings that are shaped cutouts. The scope of this disclosure also encompasses the "porous attenuating member" being constructed of a flexible structure and/or a radial flexible structure, although it may be preferable for the attenuating to be constructed of a rigid member or semi-rigid member.

The term "rigid structure" as used herein shall mean a structure that is able to bend or otherwise conform to the shape of the vasculature as it passes therethrough but is substantially unable to expand and/or contract in the radial direction upon a laser induced pressure wave passing therethrough.

The term "semi-rigid structure" as used herein shall mean a structure that is partly rigid with an additional degree of flexibility as it passes through the vasculature but is substantially unable to expand and/or contract in the radial direction upon a laser induced pressure wave passing therethrough.

The term "sheath" as used herein generally refers to a tube that can be inserted into a body cavity duct, lumen, or vessel, such as the vasculature system that allows for the introduction of catheters and the introduction of fluid along its length. An example of a catheter that can be introduced into a sheath is a laser catheter. An example of fluid that can be introduced into a sheath is an absorptive fluid such as contrast. The sheath can have a closed end or an open end. Because the sheath is a tube that can be inserted into a body cavity, duct, lumen, or vessel, such as the vasculature system, the sheath may also be considered a catheter. Accordingly, a catheter, such as a laser catheter, can be introduced into another catheter.

The term "therapeutic agent" as used herein generally refers to any known or hereafter discovered pharmacologically active agent that provides therapy to a subject through the alleviation of one or more of the subject's physiological symptoms. A therapeutic agent may be a compound that occurs in nature, a chemically modified naturally occurring compound, or a compound that is chemically synthesized. The agent will typically be chosen from the generally recognized classes of pharmacologically active agents, including, but not necessarily limited to, the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; anti spasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; restenosis inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

The term "vapor bubble" as used herein is a gaseous cavity created within a liquid.

The terms "vasculature" and "vascular" as used herein refer to any part of the circulatory system of a subject, including peripheral and non-peripheral arteries and veins. Vasculature can be comprised of materials such as nucleic acids, amino acids, carbohydrates, polysaccharides, lipids fibrous tissue, calcium deposits, remnants of dead cells, cellular debris and the like.

The term "vascular occlusion" or "occlusion" refers to buildup of fats, lipids, fibrin, fibro-calcific plaque, thrombus and other atherosclerotic tissue within the lumen or within the intima of an artery that either narrows or completely obstructs the inner lumen the artery thereby restricting or blocking normal blood flow through the artery segment. The occlusion may be partially or totally occlude the vasculature. Accordingly, the term "vascular occlusion" or "occlusion" shall include both a total occlusion and a partial occlusion. Alternatively, a vascular occlusion or occlusion may also be referred to as a vascular obstruction (or obstruction) or a vascular restriction (or restriction). A vascular obstruction may, therefore, be referred to as a total obstruction or a partial obstruction, and a vascular restriction may be referred to as a total restriction or a partial restriction.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 2A is a schematic view of a distal portion of the laser induced pressure wave emitting catheter sheath of FIG. 1, according to one embodiment of the present disclosure;

FIG. 2B is an elevation view of an embodiment of the distal portion of the laser induced pressure wave emitting catheter, according to one embodiment of the present disclosure;

FIG. 2C is a cross-sectional view (through plane C in FIG. 2B) of the distal portion of the laser induced pressure wave emitting catheter;

FIG. 2B' is an elevation view of an embodiment of the distal portion of the laser induced pressure wave emitting catheter, according to one embodiment of the present disclosure;

FIG. 2C' is a cross-sectional view (through plane C in FIG. 2B') of the distal portion of the laser induced pressure wave emitting catheter, according to one embodiment of the present disclosure;

FIG. 3 is a cross-sectional view of the distal portion of the laser induced pressure wave emitting catheter, according to one embodiment of the present disclosure;

FIG. 4 is a cross-sectional view of the distal portion of the laser induced pressure wave emitting catheter, according to one embodiment of the present disclosure;

FIG. 11C is a perspective view of a kit within the vasculature of a patient, wherein the kit includes a laser catheter radially disposed within a sheath and over a guidewire, according to one embodiment of the present disclosure, wherein the sheath is located proximally of a vascular occlusion, and the laser catheter and guidewire have penetrated the vascular occlusion;

FIG. 11D is a perspective view of a kit within the vasculature of a patient, wherein the kit includes a laser catheter radially disposed within a sheath and over a guidewire, according to one embodiment of the present disclosure, wherein the kit and guidewire have penetrated the vascular occlusion;

FIG. 14A is an elevation view of a kit that includes a laser catheter radially disposed within a handle and a sheath and over a guidewire, according to one embodiment of the present disclosure;

FIG. 14B is a detail elevation view of the laser catheter and the handle of FIG. 14A at a proximal end of the handle;

FIG. 15A is a perspective view of the handle of FIG. 14A, wherein several external components are partially transparent to illustrate internal components, and a shaft of the handle is shown in a proximal position;

FIG. 15B is another perspective view of the handle of FIG. 14A, wherein several external components are partially transparent to illustrate internal components, and the shaft is shown in the proximal position;

FIG. 15E is an elevation view of the handle of FIG. 14A, wherein several external components are partially transparent to illustrate internal components, and the shaft is shown in a distal position;

FIG. 15F is a cross-sectional view of the handle of FIG. 14A, wherein the shaft is shown in the proximal position;

FIG. 15J is another detail exploded view of the handle of FIG. 14A;

FIG. 20 is a representative cross-sectional view of the distal end of a catheter, according to one embodiment of the present disclosure.

FIG. 20' is a representative cross-sectional view of the distal end of the catheter illustrated in FIG. 20, according to an alternate embodiment of the present disclosure.

FIG. 20" is a representative cross-sectional view of the distal end of the catheter illustrated in FIG. 20, according to another alternate embodiment of the present disclosure.

FIG. 20''' is a representative cross-sectional view of the distal end of the catheter illustrated in FIG. 20, according to yet another alternate embodiment of the present disclosure.

FIG. 25A is reduced version of the cross-sectional view of the arterial wall in FIG. 25.

FIG. 26A is a longitudinal-sectional view of a healthy arterial wall taken along a direction parallel to the longitudinal axis of the arterial wall.

FIG. 26B is a longitudinal-sectional view of an arterial wall taken along a direction parallel to the longitudinal axis of the arterial wall, wherein the arterial wall includes fat and/or lipids.

FIG. 26C is a longitudinal-sectional view of an arterial wall taken along a direction parallel to the longitudinal axis of the arterial wall, wherein the arterial wall includes plaque and calcium in the intima.

FIG. 26D is a longitudinal-sectional view of an arterial wall taken along a direction parallel to the longitudinal axis of the arterial wall, wherein the arterial wall includes calcified plaque and lipids in the intima.

FIG. 26E is a longitudinal-sectional view of an arterial wall taken along a direction parallel to the longitudinal axis of the arterial wall, wherein the arterial wall has ruptured.

FIG. 26F is a longitudinal-sectional view of an arterial wall taken along a direction parallel to the longitudinal axis of the arterial wall, wherein the artery includes an occlusion.

FIG. 26G is a longitudinal-sectional view of an arterial wall taken along a direction parallel to the longitudinal axis of the arterial wall with a laser catheter removing the occlusion depicted in FIG. 21F.

FIG. 26H' is a longitudinal-sectional view of an arterial wall taken along a direction parallel to the longitudinal axis of the arterial wall with a sheath and laser catheter located adjacent the remaining portion of the vascular occlusion depicted in FIG. 26G, wherein the end of the laser catheter, particularly its emitter(s), is disposed within and proximally of the most distal end of the sheath.

FIGS. 27A and 27B are a method of removing restriction vascular occlusion and treating the remainder of the vascular occlusion within the intima with a sheath and laser catheter.

FIG. 28A is a longitudinal-sectional view of a healthy arterial wall taken along a direction parallel to the longitudinal axis of the arterial wall similar to the arterial wall depicted in FIG. 26A.

FIG. 28B is a longitudinal-sectional view of an arterial wall taken along a direction parallel to the longitudinal axis of the arterial wall with calcification of the media portion of the blood vessel.

FIG. 28C is a longitudinal-sectional view of an arterial wall taken along a direction parallel to the longitudinal axis of the arterial wall with a sheath and laser catheter located adjacent the portion of the arterial wall that includes the calcified media portion of the blood vessel.

FIG. 30B' is an enlarged longitudinal sectional view of the distal portions of the laser catheter assembly and outer sheath assembly depicted in FIG. 30A, wherein the laser catheter assembly is disposed within the outer sheath and the distal end of the laser catheter assembly is proximal of the distal end of the outer sheath assembly.

FIG. 31C is an enlarged longitudinal sectional view of the distal portion of the outer sheath assembly within line 31C-31C of FIG. 31B.

FIG. 31C' is an alternative embodiment of an enlarged longitudinal sectional view of the distal portion of the outer sheath assembly depicted in FIG. 31B.

DETAILED DESCRIPTION

The present disclosure relates generally to the use of medical devices for the treatment of vascular conditions. In particular, the present disclosure provides materials and methods for using laser-induced pressure waves to disrupt vascular blockages and to deliver therapeutic agents to the blockage area.

Figure 1:
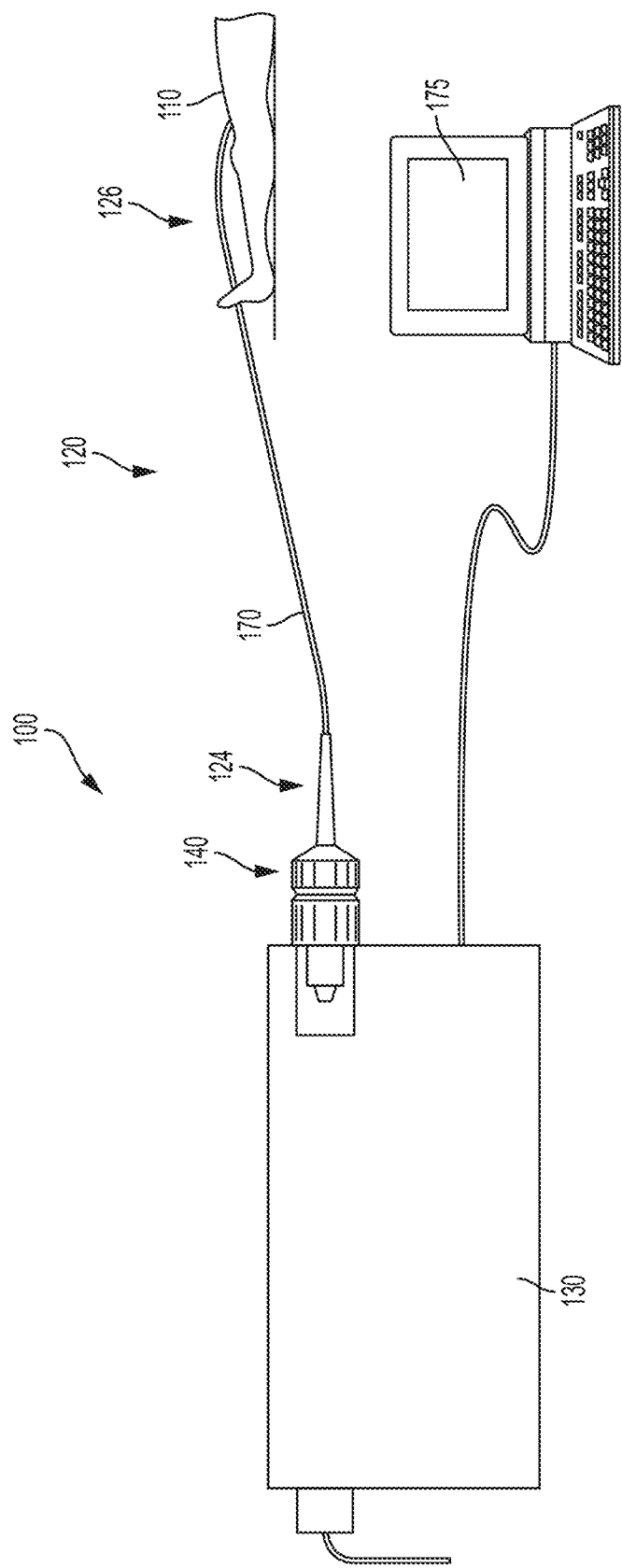
FIG. 1 illustrates an exemplary ablation system, including a laser generator and a laser induced pressure wave emitting catheter sheath.
Figure 2D:
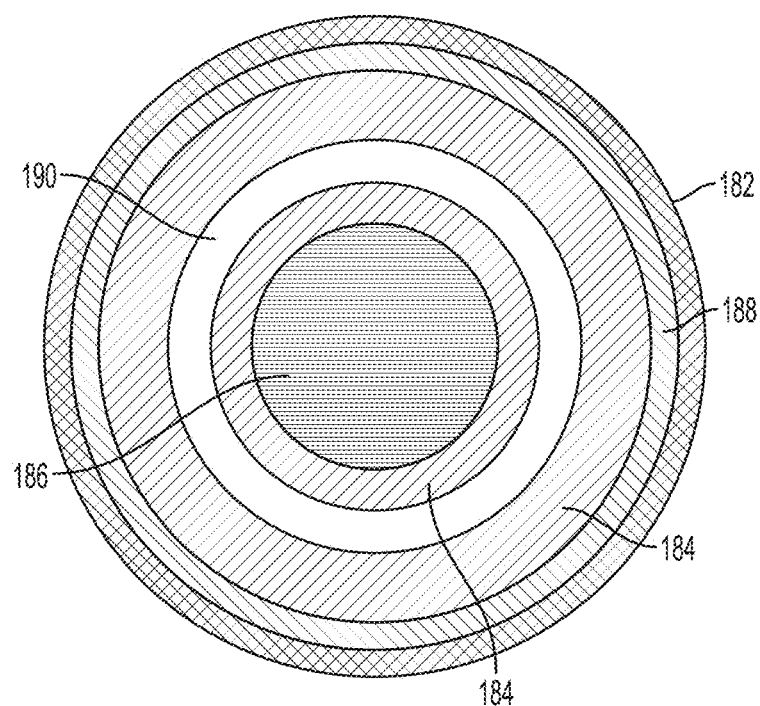
FIG. 2D is a cross-sectional view (through plane D in FIG. 2C) of the distal portion of the laser induced pressure wave emitting catheter, according to one embodiment of the present disclosure.

Referring to FIG. 1, there is depicted an exemplary ablation system 100 of the present disclosure. Ablation system 100 includes a laser apparatus 130 coupled to a laser controller 175. Controller 175 includes one or more computing devices programmed to control laser 130. Controller 175 may be internal or external to laser apparatus 130, such as a laser generator. Laser apparatus 130 may include an excimer laser or another suitable laser. In some embodiments, laser 130 produces light in the ultraviolet frequency range. In one embodiment, laser 130 produces optical energy in pulses.

Laser 130 is connected with the proximal end of a laser energy delivery system 120, illustratively a laser catheter 170 via coupler 140. Laser catheter 170 includes one or more optical energy transport devices which receive laser energy from laser 130 and transports the received laser energy from a first, proximal end 124 of laser energy catheter 170 towards a second, distal end 126 of laser catheter 170. The distal end of catheter 170 may be inserted into a vessel or tissue of a human body 110. In some embodiments, system 100 employs a plurality of light guides as the optical energy transport devices, such as optical fibers, that guide laser light from laser 130 through catheter 170 toward a target area in human body 110.

Exemplary laser catheter devices or assemblies may include laser catheters and/or laser sheaths. Examples of laser catheters or laser sheath are sold by The Spectranetics Corporation under the tradenames ELCA™ and Turbo Elite™ (each of which is used for coronary intervention or peripheral intervention, respectively, such as recanalizing occluded arteries, changing lesion morphology, and facilitating stent placement) and SLSII™ and GlideLight™ (which is used for surgically implanted lead removal). The working (distal) end of a laser catheter typically has a plurality of laser emitters that emit energy and ablate the targeted tissue. The opposite (proximal) end of a laser catheter typically has a fiber optic coupler 140 and an optional strain-relief member 124. The fiber optic coupler 140 connects to a laser system or generator 130. One such example of a laser system is the CVX-300 Excimer Laser System, which is also sold by the Spectranetics Corporation.

The laser controller 175 of FIG. 1 includes a non-transitory computer-readable medium (for example, memory 204) that includes instructions that, when executed, cause one or more processors 200 to control laser 130 and/or other components of ablation system 100. Controller 175 includes one or more input devices 206 to receive input from an operator. Exemplary input devices include keys, buttons, touch screens, dials, switches, mouse, and trackballs which providing user control of laser 130. Controller 175 further includes one or more output devices to provide feedback or information to an operator. Exemplary output devices include a display, lights, audio devices which provide user feedback or information.

A laser source of laser 130 is operatively coupled to laser controller 175. Laser source is operative to generate a laser signal or beam and provide the laser signal through a fiber optic bundle of catheter 170 to the human. Fiber optic bundle serves as delivery devices for delivering the laser signal to the target area of the human body 110.

FIG. 1 depicts the catheter 170 entering the leg, preferably through the femoral artery, of the human body. As discussed above, it may be desirable to treat either CAD or PAD. After entering the femoral artery, it the catheter 170 is intended to treat CAD, the catheter 170 will be directed through the patient's vasculature system and to the coronary arteries. Alternatively, if the catheter 170 is intended to treat PAD, the catheter 170 will be directed through the patient's vasculature system and to the peripheral arteries, such as the vasculature below the knee, particularly the vasculature in the patient's legs and/or feet. Unlike balloon catheters, the catheter 170 of the present disclosure is able to more easily navigate and enter smaller sized vasculature because the overall diameter of the sheath is smaller in comparison to balloon catheters, thereby allowing the catheter 170 of the present disclosure more easily treat PAD. That is, the increased size of a balloon of an electrically-induced shockwave balloon catheter and/or a typical dilation balloon catheter (in comparison to the catheter 170 of the present disclosure) may prevent or increase the difficulty of the balloon-type catheter from entering, penetrating and/or treating the peripheral vasculature, such the vasculature below the knee in the legs and/or feet.

Referring to FIGS. 2A, 2B, 2C and 2D, there is depicted an embodiment of the catheter 170 of the present disclosure. The catheter 170 of the present disclosure may include an outer sheath 182, an inner sheath 184, one or more optical fibers 186, and a tip 180. The outer sheath 182, inner sheath 184, and one or more optical fibers 186 generally span the length of the catheter 170, and each have a proximal end and a distal end. The inner sheath 184 is disposed concentrically and/or radially within the outer sheath 182, and the one or more optical fibers 186 are disposed concentrically and/or radially within the inner sheath 184.

As depicted in FIG. 2C, at the distal end 126 of the catheter 170, the distal end of the outer sheath 182 is directly coupled to the tip 180. The inner sheath 184 and the one or more optical fibers 186 are not directly coupled to the tip 180. Rather, the inner sheath 184 and the one or more optical fibers 186 are disposed proximate the tip 180, thereby forming a cavity among the outer sheath 182, the inner sheath 184, one or more optical fibers 186, and the tip 180.

The inner sheath 184, which is constructed of a biocompatible polymer has one or more lumens 190, which are used to deliver a liquid medium to the cavity, thereby partially or completely filling the cavity with the liquid medium. The liquid medium is introduced to the catheter 170 through one or more liquid medium ports (not shown) in fluid communication with the one or more lumens 190 within the inner sheath 184 and disposed about the outer sheath 182. The liquid medium ports may also serve as a means for removing the liquid medium from the catheter 170.

The liquid medium is configured to absorb light energy and thereby produce laser-induced pressure waves in the liquid medium. The laser-induced pressure wave compresses the fluid surrounding its origin, thereby generating a vapor bubble. As the laser-induced pressure wave propagates away from its origin, the fluid surrounding the vapor bubble displaces inwardly, collapsing the vapor bubble and creating a cavitation event. The vapor bubble and subsequent cavitation event(s) are byproducts of the laser-induced pressure wave. And the subsequent cavitation event(s) produce additional resultant pressure waves that are transmitted to the tip 180 and/or the outer sheath 182 to disrupt a vascular occlusion.

Liquid medium can include contrast medium, including for example, iodine-containing contrast medium or gadolinium contrast medium, as well as contrast solutions comprising dye(s) and/or particle(s). Additionally, any liquid medium can be used, as long as the liquid medium is coupled with a light source, such as emitters coupled to the one or more optical fibers, which emits light at a suitable wavelength such that the liquid absorbs the light, produces laser-induced pressure waves, vapor bubbles, and cavitation events that produce additional resultant pressure waves. In some cases, the liquid medium can be contrast medium (for example, iodine-containing contrast medium or gadolinium contrast medium) and/or the liquid medium can be a contrast solution comprising a biocompatible fluid (for example, saline) in which a contrast dye(s) or particle(s) have been mixed at various concentrations.

As mentioned above, one or more optical fibers 186 are disposed within the inner sheath 184 extending from a proximal portion of the inner sheath 184 to the distal end of the inner sheath 184 and into the cavity. The proximal end of the one or more optical fibers is coupled to the laser generator 130. The distal end(s) of the one or more optical fibers 186 are proximate, at, or distal the distal end of the inner sheath 184. Again, one or more emitters are disposed at the distal end of the one or more optical fibers 186. The emitter(s) are in direct contact with the liquid medium, such that when laser light energy is emitted from the emitter(s), the liquid medium absorbs the emitted light, which in turn produces laser-induced pressure waves and generates vapor bubbles and cavitation events that produce additional pressure waves.

To treat a subject having a vascular occlusion, the tip 180 of the catheter 170 is positioned adjacent to the vascular occlusion. When the laser system 130 is activated, light energy travels through one or more optical fibers until the light energy is released from the emitter. As the liquid medium absorbs the light energy, laser-induced pressure waves are produced. Additionally, the liquid medium rapidly displaces outwards and inwards, creating vapor bubbles. The energy produced by the laser-induced pressure waves is captured within the cavity and converted to mechanical energy via moving the tip 180 and/or transferred to the vascular occlusion through the tip 180. The transfer of the energy produced by the laser-induced pressure waves to the vascular occlusion is sufficient to disrupt vascular occlusion, particularly the calcified and/or fibrous (for example, calcium deposits) portions of a total occlusion. It is desirable for the mechanical energy created at the tip 180 by the laser-induced pressure waves and resulting fluid displacement to be transferred to the occlusion. Accordingly, when the energy produced by the laser-induced pressure waves is captured within the cavity, it is desirable for the forces generated by the laser-induced pressure waves to propagate longitudinally, including in a forward (that is, parallel with the vessel) direction, thereby increasing the tip's ability to disrupt, destroy and/or penetrate the vascular occlusion. That is, as the laser-induced pressure waves are produced, the tip 180 of the catheter rapidly moves (translates) forwards and backwards towards and away from, respectively, the occlusion. Pressure waves produced in this manner can also be used to increase vessel compliance prior to performing another procedure, such as a traditional balloon angioplasty or drug eluting balloon treatment.

In order to facilitate the direction in which the forces that are produced by the laser-induced pressure waves translate into the movement of the tip 180 in a forward/backward longitudinal direction, the outer sheath 182 is not only flexible, but the outer sheath 182 also has the ability to expand and contract in a longitudinal direction. One example of such an outer sheath 182 includes a slotted or laser-cut hypotube constructed of a biocompatible material, such as stainless steel, or a biocompatible polymer. The hypotube has spring-like characteristics, which allow it to expand and contract in a longitudinal direction. Specifically, the slotted or laser cut pattern in the hypotube allows it to expand and contract. Another example of the outer sheath 182 may include of one or more spirally wound wires, thereby creating a coiled sheath, which also has the ability to expand and contract in a longitudinal direction.

In order to further facilitate the movement of the tip 180 in a longitudinal direction, it may be desirable to include a shield 188 disposed axially between the distal end of the inner sheath 184 and the proximal end of the tip 180, and disposed radially between the one or more optical fibers 186 and the outer sheath 182. As illustrated in FIG. 2C, the shield 188, which is depicted as a generally cylindrical tube, may increase the laser-induced pressure waves' resistance in the radial direction, thereby reducing the ability of the laser-induced pressure waves to travel radially towards the outer sheath 182 and may concentrate the energy produced by the laser-induced pressure waves in the longitudinal direction. The configuration of the cylindrically-shaped shield 188 may allow for a reduced resistance in the longitudinal direction, in comparison to the radial direction, thereby potentially increasing the energy produced by the laser-induced pressure waves in the longitudinal direction and increasing the tip's ability to translate in a forward/backward direction. The cylindrically-shaped shield 188 may also be configured such that its diameter is greater at its proximal end in comparison to its distal end, thereby potentially concentrating the laser-induced pressure waves towards the center of the tip 180. Or the cylindrically-shaped shield 188 may be configured such that its diameter is less its proximal end in comparison to its distal end, thereby potentially concentrating the laser-induced pressure waves towards the center of the tip 180.

The tip 180 illustrated in FIGS. 2B & 2C has a closed configuration. However, the present disclosure contemplates that the tip can also have an open configuration. Additionally, the tip 180 illustrated in FIGS. 2B & 2C is a separate component from the distal end 126 of laser catheter 170 and is coupled to the distal end 126. However, the present disclosure contemplates that the tip can also be integral with the distal end 126 of the laser catheter 170. The tip 180 illustrated in FIGS. 2B & 2C is generally tapered from a larger diameter to a smaller diameter as the tip progresses distally. Additionally, the shape of the tip 180 shown in FIGS. 2B & 2C is generally conical. Furthermore, the tip 180 has a completely solid configuration, but it may be also be partially solid. It is desirable for the tip to be constructed of a biocompatible material, such as stainless steel or a biopolymer.

Similar to the tip 180 illustrated in FIGS. 2B & 2C, the tip 180' in FIGS. 2B' & 2C' has a completely solid configuration, but the tip 180' in FIGS. 2B' & 2C' may alternatively have a partially solid configuration. Unlike the tip 180 illustrated in FIGS. 2B & 2C, the tip 180' in FIGS. 2B' & 2C' may have a generally convex, spherical shape. Although the present disclosure only depicts a generally conically-shaped tip 180 in FIGS. 2B & 2C and a generally spherically-shaped tip 180' in FIGS. 2B' & 2C', the tip may have alternative shapes, such as a flat shape, concave shape, triangular shape, a pyramid shape, chisel, etc.

Referring to FIG. 3, there is depicted an alternative embodiment of the catheter of the present disclosure. Similar to the tip 180' in FIGS. 2B' & 2C', the tip 380 in FIG. 3 has a generally spherical shaped. However, unlike the tip 180' in FIGS. 2B' & 2C', which has a solid configuration, the tip 380 in FIG. 3 has a hollow or shell-type configuration. Also, the tip 280 in this embodiment, as well as the other embodiments, may be press fit and/or welded to the outer sheath 182".

The embodiments of the catheter depicted in FIGS. 2B & 2C and FIGS. 2B' & 2C' and FIG. 3 include a shield 188. However, it may not be necessary to include a shield within the catheter. For example, FIG. 4 illustrates an embodiment of the catheter 170 in which the shield is omitted from the distal tip of the catheter. As depicted in this figure, in the event that a shield is omitted, it may be desirable for the outer sheath 182''' to include a solid portion between the distal end of the inner sheath 184''' and the proximal end of the tip 480 in order to create a non-porous cavity.

Figure 5:
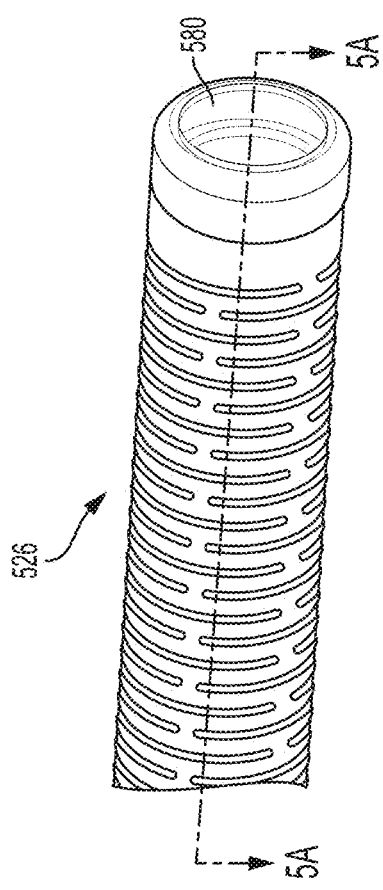
FIG. 5 is a perspective view of an embodiment of the distal portion of the laser induced pressure wave emitting catheter, according to one embodiment of the present disclosure.
Figure 5A:
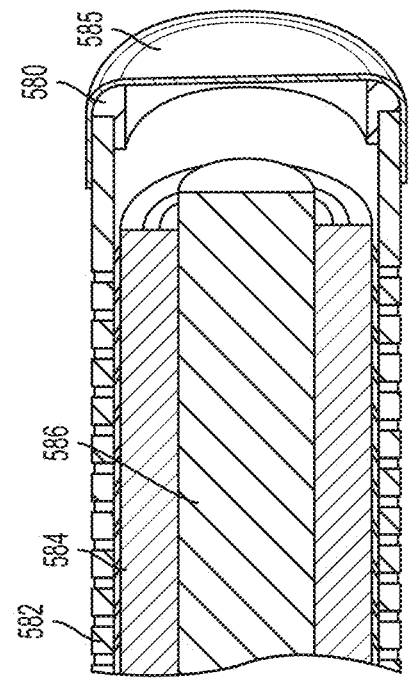
FIG. 5A is a cross-sectional view (through plane A in FIG. 5) of the distal portion of the laser induced pressure wave emitting catheter, according to one embodiment of the present disclosure.
Figure 5A:
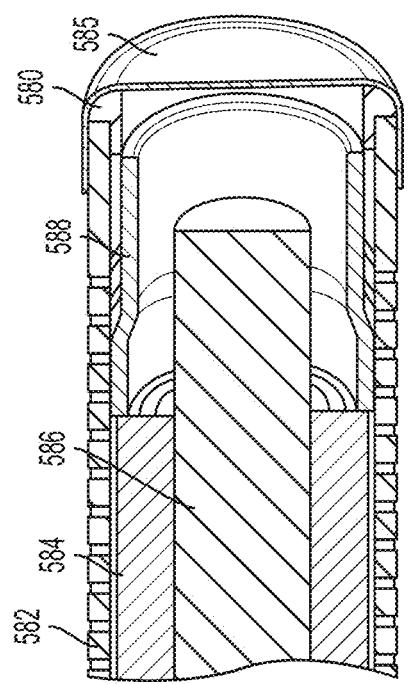

Referring to FIGS. 5, 5A and 5A', the distal end 526 of the catheter may include a tip 580 that comprises a non-metallic component in lieu of a metallic (for example, stainless steel) solid or hollow construction. Referring to FIG. 5A, the catheter includes an outer sheath 582, an inner sheath 584 disposed concentrically and/or radially within the outer sheath 582, and one or more optical fibers 586 disposed concentrically and/or radially within the inner sheath 584. The distal end of the outer sheath 582 is directly coupled (via a press fit and/or a weld) to the tip 580. The inner sheath 584 and the one or more optical fibers 586 are not directly coupled to the tip 580. Rather, the inner sheath 584 and the one or more optical fibers 586 are disposed proximate the tip 580, thereby forming a cavity among the outer sheath 582, the inner sheath 584, one or more optical fibers 586, and the tip 580.

Continuing to refer to FIG. 5A, the catheter may include a shield 588 disposed axially between the distal end of the inner sheath 584 and the proximal end of the tip 580, and disposed radially between the one or more optical fibers 586 and the outer sheath 582. As illustrated in FIG. 5A, the shield 588, which is depicted as a generally cylindrical tube, increases the laser-induced pressure waves' resistance in the radial direction, thereby reducing the ability of the laser-induced pressure waves to travel radially towards the outer sheath 582. The configuration of the cylindrically-shaped shield 588 allows for a reduced resistance in the longitudinal direction, in comparison to the radial direction, thereby increasing the tip's ability to translate in a forward/backward direction. The cylindrically-shaped shield 588 may also be configured such that its diameter is greater (or less) at its proximal end in comparison to its distal end, thereby potentially tapering in either the proximal or distal direction and concentrating the laser-induced pressure waves towards the center of the tip 580. The shield 588 may also serve to create a sealed cavity at the distal end of the catheter, thereby preventing the leakage of the liquid medium through the outer sheath 582 because a portion of the shield overlaps with a portion of the outer sheath 582 that may be porous. Referring to FIG. 5A', if the shield is omitted, it may be desirable for the outer sheath 582 to include a solid or non-porous sheath portion between the distal end of the inner sheath 584 and the proximal end of the tip 580 in order to create a non-porous cavity.

The inner sheath also includes one or more lumens for passage of liquid medium into the cavity. The distal end(s) of the one or more optical fibers 586 are proximate, at, or distal the distal end of the inner sheath 584. Again, one or more emitters are disposed at the distal end of the one or more optical fibers 586. The emitter(s) are in direct contact with the liquid medium, such that when laser light energy is emitted from the emitter(s), the liquid medium absorbs the emitted light, which in turn produces laser-induced pressure waves and generates pressure waves and/or vapor bubbles that produce additional pressure waves and/or one or more cavitation events.

As depicted in FIGS. 5A and 5A', the tip 580 has a circular construction, thereby creating a collar for the distal end of the outer sheath 582. The tip 580 also includes a flexible membrane 585 at its distal end. For example, the membrane 585 may be constructed of Mylar and be adhesively bonded to the distal end of the tip 580 in an orientation perpendicular to the longitudinal axis. In addition the membrane may be compliant in order to form against and engage the shape of the calcified cap, total occlusion or lesion.

To treat a subject having a vascular occlusion, the distal end of the catheter, particularly the tip 580 is positioned adjacent to the vascular occlusion with the membrane adjacent the vascular occlusion. The liquid medium is delivered to the cavity from the one more lumens within the inner sheath 584 through one or more liquid medium ports or between the outer sheath and the inner sheath or laser catheter. When the laser system 130 is activated, light energy travels through one or more optical fibers until the light energy is released from the emitter(s) at the end of the one or more optical fibers. As the liquid medium absorbs the light energy, a lase-induced pressure wave forms, the liquid medium rapidly displaces outward and then inwardly, thereby creating a vapor bubble. The energy produced by the laser-induced pressure wave and vapor bubble is captured within the closed system provided by the cavity and transferred to the vascular occlusion through the flexible membrane 585 of the tip 580. The transfer of the energy produced by the laser-induced pressure waves to the vascular occlusion is sufficient to disrupt calcium deposits and/or fibrous tissue within the vascular occlusion. The forces generated by the laser-induced pressure waves can propagate longitudinally forward (that is, parallel to the vessel). Laser-induced pressure waves produced in this manner can also be used to increase vessel compliance prior to performing another procedure, such as a traditional balloon angioplasty.

Figure 6:
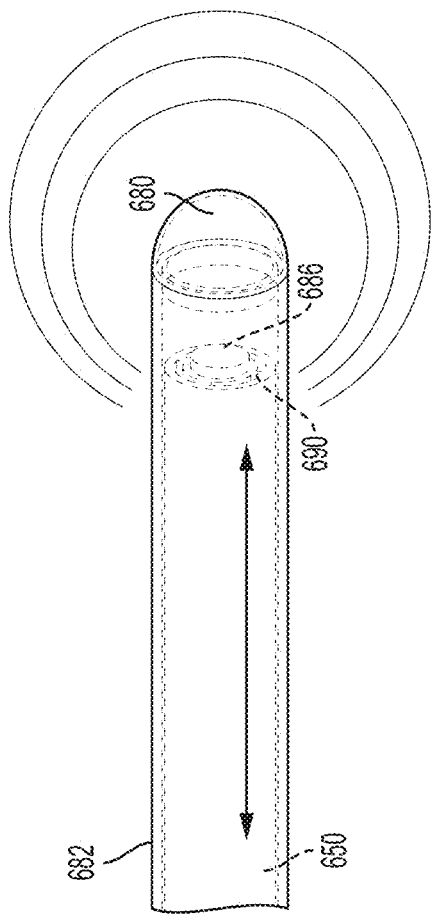
FIG. 6 is a partially transparent elevation view of the distal portion of a laser catheter disposed at one location within the distal portion of a catheter sheath.
Figure 6A:
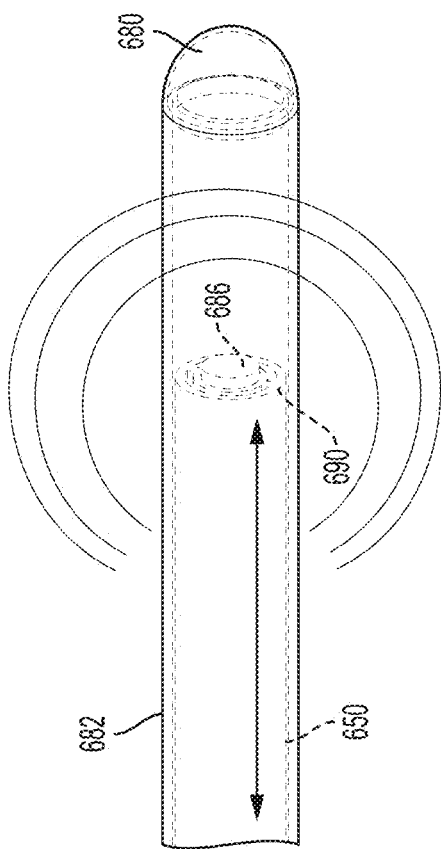
FIG. 6A is a partially transparent elevation view of the distal portion of the laser catheter disposed at an alternative location within the distal portion of the catheter sheath, in comparison to the position of the laser catheter in FIG. 6.

The embodiments of the catheters discussed hereinabove with respect to FIGS. 1-5 are integral catheters, such that the optical fiber(s) are integrated within the design of a single catheter. The present disclosure, however, also encompasses a two-piece catheter system or kit. Referring to FIGS. 6 and 6A, the catheter system may include a laser catheter 650 and a tubular sheath 682 having a lumen therein and/or therethrough and configured to surround the laser catheter 650. Depending upon whether the tubular sheath 682 has an open or closed distal end, the tubular sheath 682 may be coupled to a tip 680. A traditional laser catheter 650, including one or more optical fibers 686, can be inserted within the lumen, thereby allowing a clinician to translate the laser catheter 650 within sheath 682 along the longitudinal axis of the sheath in a forward (distal) and backwards (proximal) direction. For the purposes of this disclosure, the laser catheter 650 may include one or more one more lumens 690 to deliver the liquid medium from the one or more liquid medium ports. When the laser system 130 is activated, light energy travels through one or more optical fibers until the light energy is released from the emitter(s) at the end of the one or more optical fibers. As the liquid medium absorbs the light energy, a laser-induced pressure wave forms, the liquid medium rapidly displaces outward then inward, thereby creating a vapor bubble. The energy produced by the laser-induced pressure wave and vapor bubble is captured within the closed system provided by the cavity and transferred to the vascular occlusion through the walls of the sheath 682 and/or the tip 680. The transfer of the energy produced by the laser-induced pressure waves to the vascular occlusion is sufficient to disrupt calcium deposits and/or fibrous tissue within the vascular occlusion. Depending upon the location of the emitter(s) within lumen of the sheath 682, a smaller or larger cavity is created among the distal end of the laser catheter 650, the tip 680, and the sheath 682. It may desirable for the distal end of the laser catheter 650 to be disposed proximal of the tip 680 or translated inside of the outer sheath to create a cavity with which the forces generated by the laser induced pressure wave can propagate radially from multiple axial positions along the longitudinal axis of the outer sheath.

Depending upon the location of the emitter(s) within lumen of the sheath 682, the forces generated by the laser-induced pressure waves may propagate radially, including in forward (that is, parallel to the vessel), upward (that is, perpendicular to the vessel), and backward (that is, proximally) directions. As depicted in FIG. 6, when the laser catheter 650 is disposed proximate the tip 680, the laser-induced pressure waves may propagate radially from the sheath 650 and forward (that is, parallel to the vessel) from the tip. As depicted in FIG. 6A, upon the laser catheter 650 translating proximally along the longitudinal axis of the lumen within the sheath 682 in in comparison to the position of the laser catheter 650 in FIG. 6, the laser-induced pressure waves may propagate in a direction radially from the sheath 650, forward (that is, parallel to the vessel), upward (that is, perpendicular to the vessel), and/or backward (that is, proximally). Accordingly, after the tip 680 of the sheath 682 destroys the calcified and/or fibrous tissue within the vascular occlusion, the sheath 682 may penetrate and cross the occlusion, and the laser catheter 650 can slide in proximal and/or distal direction to destroy additional portions of the occlusion.

Figure 6B:
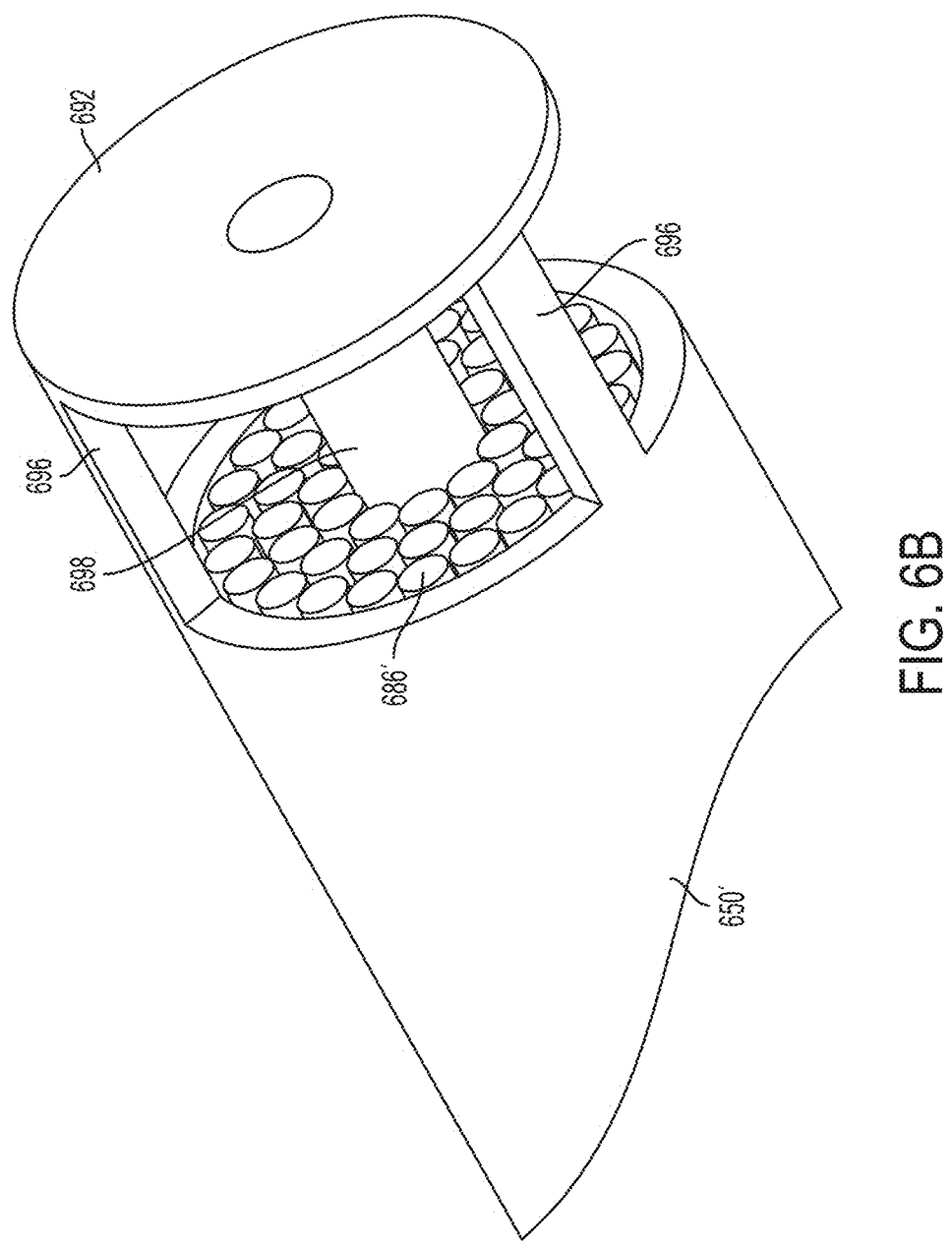
FIG. 6B is an enlarged partial perspective view of the distal portion of an alternative laser catheter including a deflector coupled to the distal end of the laser catheter.

Referring to FIG. 6B, the laser catheter 650' may also include a deflector 692 attached to its distal end via at least one, and possibly a plurality of, support member(s) 696, 698. The purpose of the deflector is to direct the laser-induced pressure wave generated by the interaction between the liquid medium and the emitters from one or more optical fibers 686' within the liquid medium in a particular direction. In this figure, the deflector 692 is positioned along the longitudinal axis of the laser catheter 650', but the shape of the deflector 692 is oriented in a radial direction that is perpendicular to longitudinal axis of the laser catheter 650'. Accordingly, as the laser-induced pressure waves are produced from the interaction between the liquid medium and the laser light energy emitted from the emitters, the deflector 692 may direct the laser-induced pressure waves in a radial direction, such as 360 degrees about the circumference of the laser catheter 650' and/or sheath 682. The deflector 692 may be constructed of a non-metallic material or a metallic material, such as stainless steel. The deflector 692 may also have a solid or porous construction. Regardless of the construction of the deflector 692, the deflector 692 shall direct the laser-induced pressure waves in a particular direction that is in an advantageous direction, such as toward the vascular occlusion, which may be on the side of the sheath 682.

Figure 7:
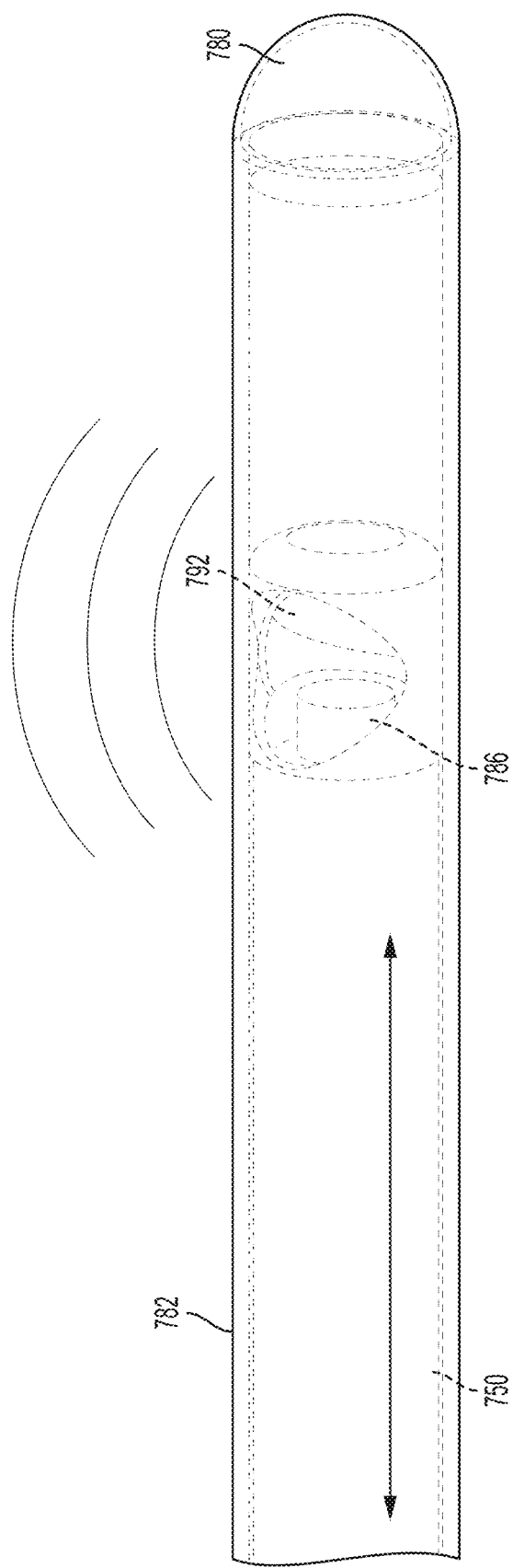
FIG. 7 is a perspective view of a laser catheter including a shield or deflector as the distal end thereof, according to one embodiment of the present disclosure, wherein the laser catheter is disposed at one location within the distal portion of a catheter sheath.

Various shapes and configurations of deflectors are envisioned. For example, referring to FIG. 7, the laser catheter 750 may include a deflector 792 disposed distally from the one or more optical fibers 786 of the laser catheter 750, may be configured to direct the laser-induced pressure waves in a radial direction less than 360 degrees (for example, 5 degrees, 10 degrees, 15 degrees, . . . , 30 degrees 45 degrees, . . . , 60 degrees, . . . , 75 degrees, . . . , 90 degrees, . . . , 105 degrees, 120 degrees, . . . , 135 degrees, . . . , 150 degrees . . . , 165 degrees, . . . , 180 degrees, etc.) about the circumference of the laser catheter 750 and/or sheath 782. For example, the deflector 792 may have a solid construction with an opening facing a particular direction. And the shape and size of the opening within the deflector may dictate the direction that the laser-induced pressure waves may travel. As depicted in FIG. 7, the laser catheter 750 may translate axially within the sheath 782 along the longitudinal axis of the laser catheter 750 and/or sheath 782. The present disclosure also contemplates that the laser catheter 750 may rotate within the sheath 782 about the longitudinal axis of the laser catheter 750 and/or sheath 782, thereby directing not only directing the laser-induced pressure waves along a longitudinal direction but also about a radial direction.

The transfer of the energy produced by the creating a laser-induced pressure wave to the vascular occlusion and/or to the walls of the vessel is sufficient to disrupt intraluminal calcium as well as calcium within the tissue of the blood vessel, vascular occlusion (for example, calcium deposits). The forces generated by the laser-induced pressure wave can propagate radially, including in forward (that is, parallel to the vessel), upward (that is, perpendicular to the vessel), and backward (that is, proximally) directions. Laser-induced pressure waves produced in this manner can also be used to increase vessel compliance prior to performing another procedure, such as a traditional balloon angioplasty, drug-eluting balloon angioplasty and/or stent placement. That is, the laser-induced pressure wave disruption of the intraluminal calcium and/or calcium within the tissue of the blood vessel and the vascular occlusion, can improve the vasculature's ability to absorb drugs, particularly when such drugs are applied with a drug eluting balloon.

Referring again to FIGS. 6 and 6A, the catheter system includes the laser catheter 650 disposed within the sheath 682 and proximate the tip 680, thereby allowing the laser-induced pressure waves to propagate radially from the sheath 650 and forward (that is, parallel to the vessel) from the tip. In order to ensure that the laser catheter 650 is proximate the tip 680 to create a cavity between the distal end of the laser catheter 650, the sheath 682 and the tip 680, the laser catheter 650 and/or the sheath 682 may include stops and/or matingly engageable springs and/or recesses to maintain the laser catheter 650 at the desirable distance proximate the tip 680. The stops and/or matingly engageable springs and/or recesses shall also be configured to allow the clinician to easily disengage the laser catheter 650 from the sheath 682 so the laser catheter 650 may translate within the sheath 682.

Figure 8:
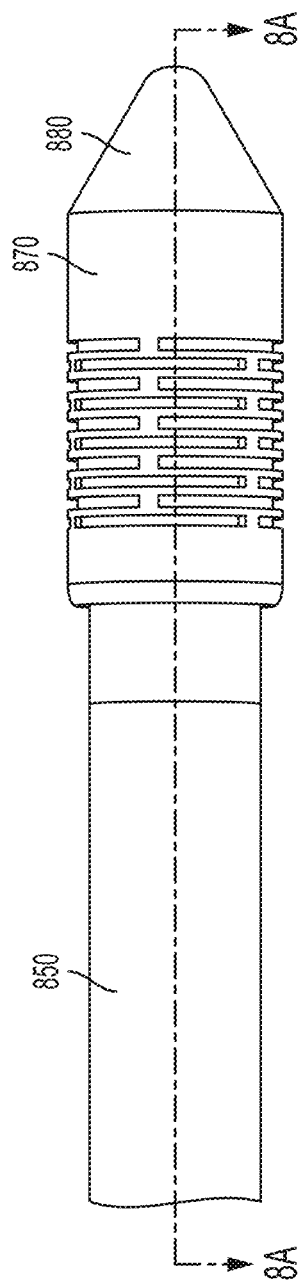
FIG. 8 is an elevation view of a removable tip for an ablation catheter, according to one embodiment of the present disclosure.
Figure 8A:
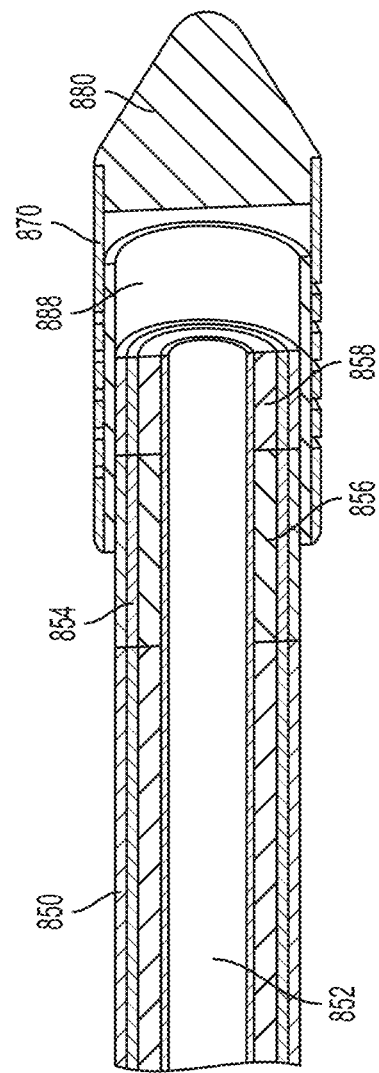
FIG. 8A is a cross-sectional view (through plane A in FIG. 8) of a removable tip for an ablation catheter.

Referring to FIGS. 8 and 8A, if it is not desirable to slide the laser catheter within the sheath, then the laser system may include laser catheter 850 that is engageable with and removable from a cap 870. The cap 870 may include a relatively short sheath attached to a tip 880 and an optional shield 888. Similar to the embodiment in FIGS. 6 and 6A, the embodiment in FIGS. 8 and 8A may include matingly engageable springs and/or recesses that are configured to allow the clinician to easily engage and disengage the laser catheter 850 from the cap 870.

The laser catheter 850 may include one or more layers of optical fibers 854 arranged circumferentially around or adjacent to an optional inner lumen, which may be used to insert a guidewire and/or the liquid medium. Or the laser catheter 850 may include one or more additional lumens to serve independent purposes. Again, the proximal end of the laser catheter is coupled to a laser generator. The one or more layers of optical fibers 854 are housed in a flexible tubular catheter and terminate at the distal emitter at the distal tip 856 of the laser catheter 850. The liquid medium travels through the lumen 852 until being introduced from one or more liquid medium ports (not shown) into the cavity. The emitter is in direct contact with the liquid medium such that when laser light energy is emitted from the proximal emitter, the liquid medium absorbs the emitted light, which in turn generates a laser-induced pressure wave and/or vapor bubbles that produce additional pressure waves, thereby converting the laser-induced pressure waves to mechanical energy via moving the tip 880 and/or transferring the pressure to the vascular occlusion through the tip 880.

Figure 9:
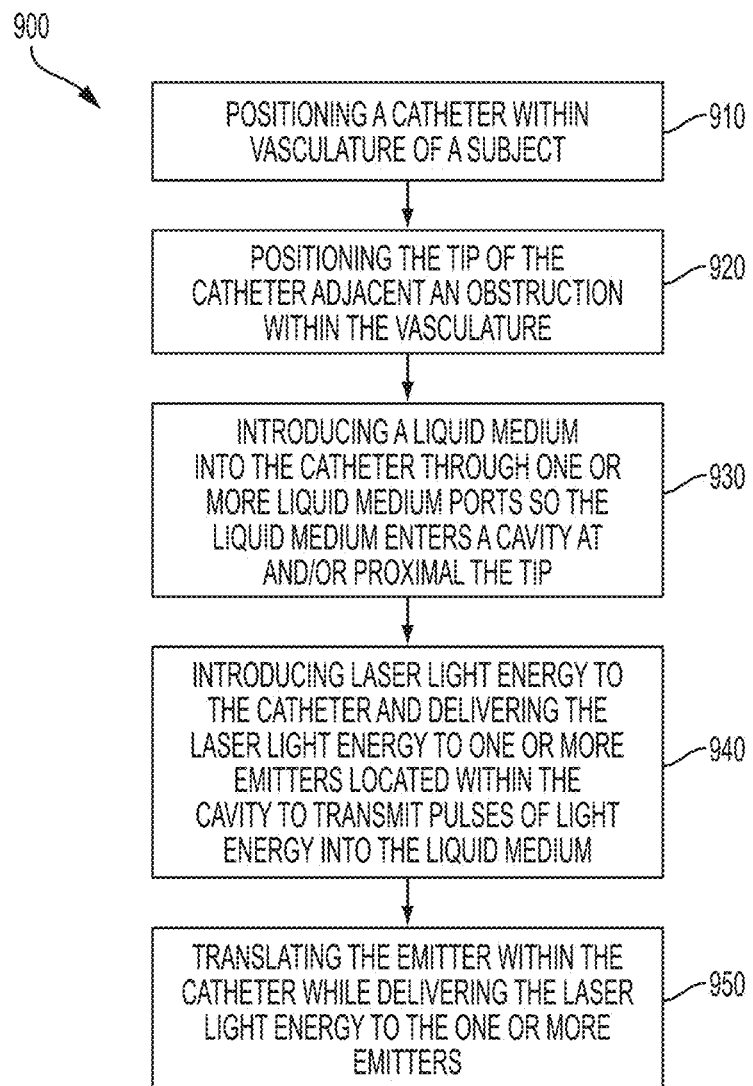
FIG. 9 is a representative flow diagram of a method of treating a subject using a catheter, according to one embodiment of the present disclosure.

Referring to the flow chart in FIG. 9, the present disclosure includes a method 900 for treating a subject with a vascular occlusion using embodiments of the catheter assemblies and systems described herein. Although it is not illustrated in FIG. 9, it may be desirable to treat at least a portion of the vascular occlusion in the vessel of the subject prior to performing the method set forth in FIG. 9. Such treatment may include, for example, mechanically cutting and/or ablating (via application of laser light energy, microwave energy, radiofrequency energy, or the like) at least a portion of the vascular occlusion. The method 900 in FIG. 9 begins at block 910 by positioning an embodiment of a catheter assembly or system described herein within the vasculature of a subject. At block 920, the distal tip of the catheter assembly or system is positioned adjacent the occlusion within the vasculature (for example, by advancing the distal tip through the vasculature). At block 930, a liquid medium, such as any of the liquid mediums described herein, is introduced to cavity at and/or proximal the distal tip of the catheter assembly or system (for example, introduced via a space between an outer sheath and a laser catheter carried within the sheath). At block 940, laser light energy is delivered to one or more emitters (for example, optical fibers) located within the cavity to transmit pulses of light energy into the liquid medium. As described herein, transmission of pulses of light energy into the liquid medium creates a laser-induced pressure wave and/or vapor bubbles and additional resultant pressure waves to disrupt the vascular occlusion. At block 950, the catheter (and the emitters) may be translated relative to the sheath while laser light energy is delivered to one or more emitters and the liquid medium. The catheter (and the emitters) or the entire catheter assembly can be repositioned within the vasculature. The method 900 also includes ending the procedure when the desired therapeutic outcome is obtained, or repeating any of blocks 910 through 960 as may be necessary to treat a subject having a vascular occlusion. Furthermore, although it is not illustrated in FIG. 9, after performing the method 900 it may be desirable to use a drug eluting (coated) balloon (DEB or DCB) catheter to deliver drugs to the remnants of the vascular occlusion. Disrupting the vascular occlusion with the laser-induced pressure waves prior to utilizing a DEB may increase the effectiveness of the drugs being applied to the vascular occlusion because the laser-induced pressure waves disrupt the intraluminal calcium as well as calcium within the tissue (e.g., calcium deposits and/or medial calcium) of the blood vessel, vascular obstructions or restrictions, thereby creating a pathway for the drug to enter the intraluminal and tissue portions of the vasculature and/or vascular occlusion.

Figure 10:
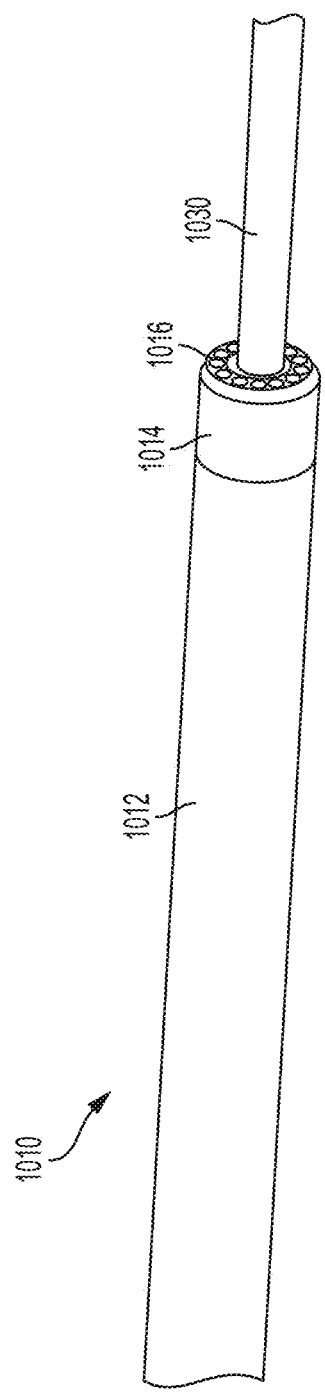
FIG. 10 is a perspective view of a laser catheter and a guidewire, according to one embodiment of the present disclosure.

Referring to FIG. 10, there is depicted a laser catheter 1010 and a guidewire 1020 extending through the lumen of the catheter 1010. The laser catheter 1010 includes one or more layers of a plurality of optical fibers 1016 surrounding a lumen extending therethrough, and a sheath 1012 surrounds the layer(s) of optical fibers 1016. The distal end of the laser catheter 1010 may include a metal band 1014, which improves the strength of the distal end and provides a radiopaque marker. Examples of laser catheters 1010 or laser sheaths are sold by The Spectranetics Corporation under the tradenames ELCA™ and Turbo Elite™ (each of which is used for coronary intervention or catheterization such as recanalizing occluded arteries, changing lesion morphology, and facilitating stent placement) and SLSIL™ and GlideLight™ (which is used for surgically implanted lead removal). Again, as illustrated in FIG. 10, the working (distal) end of a laser catheter typically has a plurality of laser emitters that emit energy and ablate the targeted tissue. The opposite (proximal) end of a laser catheter, which is not shown, typically has a fiber optic coupler that connects to a laser system or generator. One such example of a laser system is the CVX-300 Excimer Laser System, which is also sold by The Spectranetics Corporation.

Figure 11A:
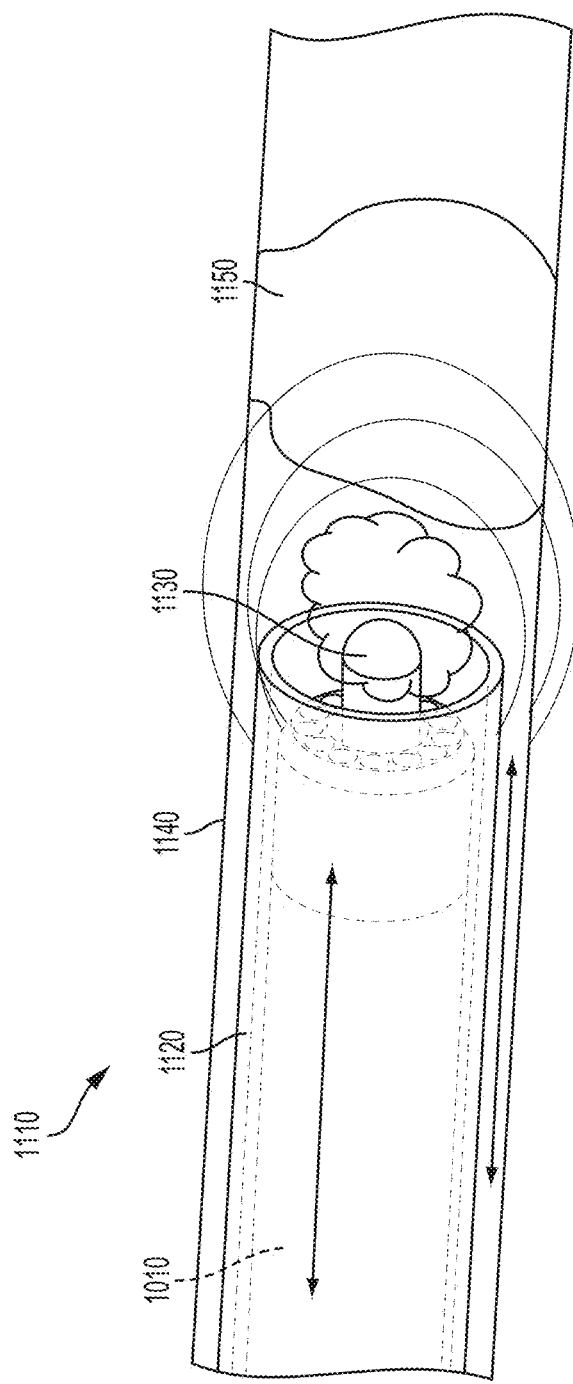
FIG. 11A is a perspective view of a kit within the vasculature of a patient, wherein the kit includes a laser catheter radially disposed within a sheath and over a guidewire, according to one embodiment of the present disclosure, wherein the kit and guidewire are located proximally of a vascular occlusion.

Again, the present disclosure envisions a two-piece catheter system or kit. Referring to FIG. 11A, the system 1110 may include a laser catheter 1010 radially disposed within a sheath 1140. The system may optionally include a guidewire 1130 disposed within a lumen of the laser catheter 1010. As discussed above, a liquid medium is introduced into the sheath 1120 distal to the laser catheter 1010, particularly distal to the optical fibers/emitters of the laser catheter 1010 such that when the laser is activated, the liquid absorbs the light and creates laser-induced pressure waves and/or vapor bubbles and additional resultant pressure waves and/or cavitation events. Although the liquid is not shown in this figure, the liquid may be introduced through a lumen in the laser catheter 1010, a lumen in the sheath 1120 and/or the lumen or space between the laser catheter 1010 and the sheath 1120. Regardless of which of these locations is used, one or more liquid medium ports located at or toward the proximal end of the catheter system will be also be used.

Figure 12:
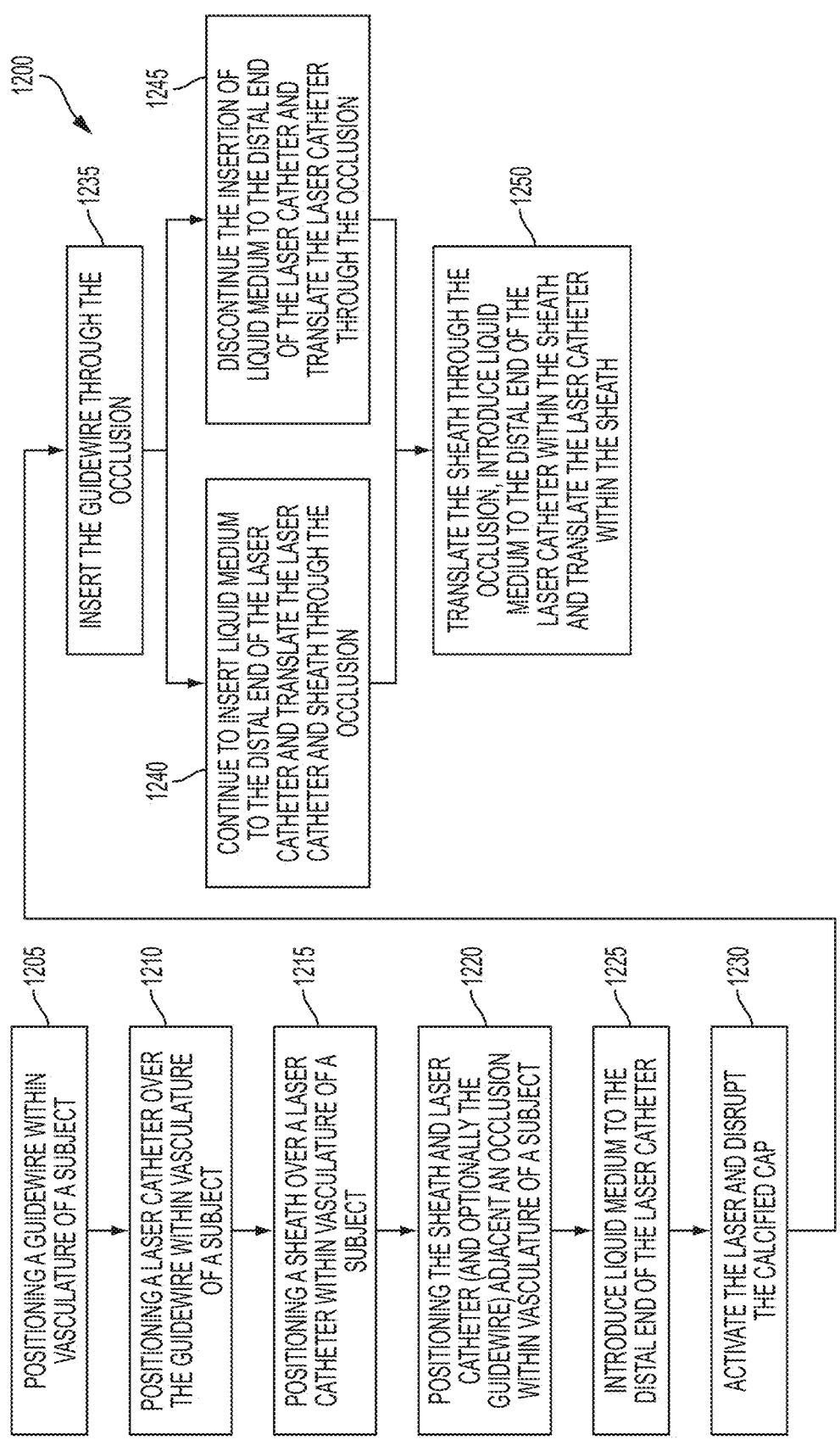
FIG. 12 is a representative flow diagram of a method of treating a subject using a laser catheter and sheath, according to one embodiment of the present disclosure.

Referring to FIG. 12, there is depicted a representative flow diagram of a method 1200 of removing restriction vascular occlusion using a laser catheter 1010 to ablate a portion of the vascular occlusion, and/or using the laser catheter 1010 in conjunction with the sheath 1120 to create laser-induced pressure waves in the presence of a liquid medium and disrupt a portion of the vascular occlusion. The method 1200 may include the step 1205 of positioning a guidewire 1130 within the vasculature 1140 of a subject, the step 1210 of positioning a laser catheter 1010 over the guidewire 1130 within the vasculature 1215, the step of positioning a sheath 1120 over the laser catheter 1010 within the vasculature and the step 1220 of positioning the sheath 1120 and laser catheter 1010 (and optionally the guidewire 1130) adjacent restriction vascular occlusion 1150 within the vasculature 1140 of a subject. Referring again to FIG. 11A, positioning the sheath 1120 and laser catheter 1010 adjacent the vascular occlusion 1150 creates a cavity for the liquid medium to collect distally of the laser catheter 1010, particularly distally of the emitters/optical fibers of the laser catheter 1010.

FIG. 11A depicts the distal end of the laser catheter 1010 proximal of the distal end of the sheath 1120. However, it is envisioned that the distal end of the laser catheter 1010 may be disposed at or distally of the distal end of the sheath 1120, as long as there is liquid medium between the emitters/optical fibers of the laser catheter 1010 and the vascular occlusion 1150. The axial locations of the laser catheter 1010 and the sheath 1120 may be adjusted by translating either or both components with respect to one another. In order to visualize the respective locations of the laser catheter 1010 and the sheath 1120 under fluoroscopy, the laser catheter 1010 and the sheath 1120 may include radiopaque markers at any corresponding locations along their lengths.

Figure 11B:
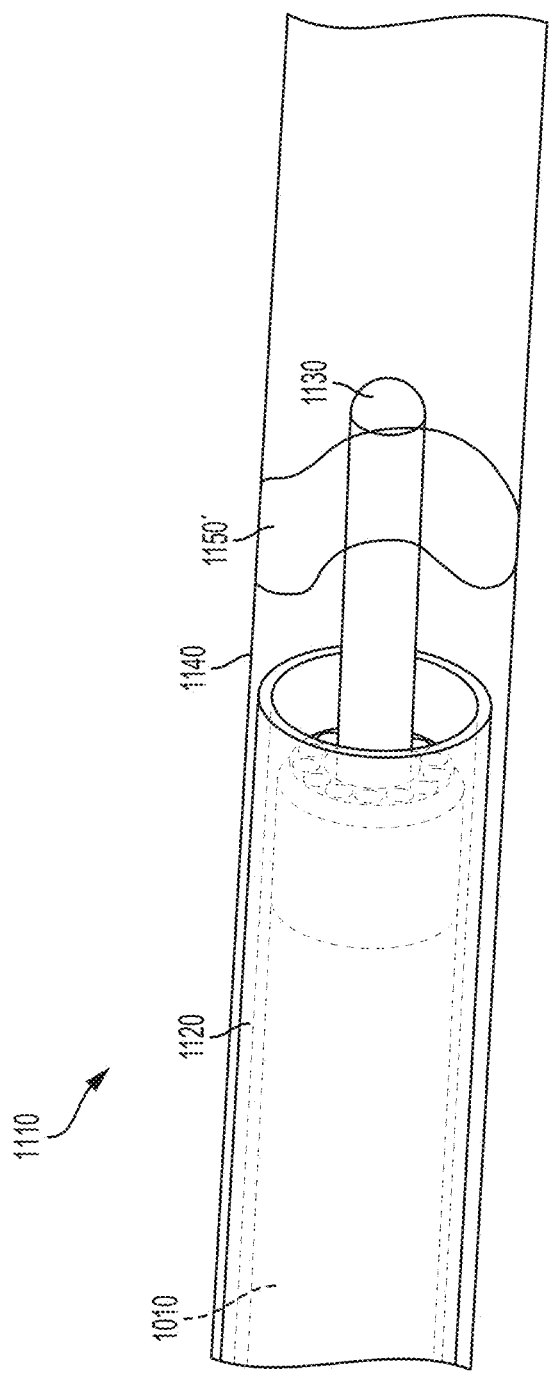
FIG. 11B is a perspective view of a kit within the vasculature of a patient, wherein the kit includes a laser catheter radially disposed within a sheath and over a guidewire, according to one embodiment of the present disclosure, wherein the kit is located proximally of a vascular occlusion, and the guidewire has penetrated the vascular occlusion.

Continuing to refer to FIG. 11A, once the sheath 1120 and laser catheter 1010 are disposed adjacent the vascular occlusion 1150, the liquid medium may be introduced to the distal end of the laser catheter as set forth in step 1225 of FIG. 12. Continuing to refer to FIG. 12, step 1230 includes activating the laser to create laser-induced pressure waves in the presence of the liquid medium and disrupting a portion of the vascular occlusion, particularly the calcified cap of the vascular occlusion. The laser catheter 1010 and sheath 1120 may be used to traverse the entire vascular occlusion 1150, as set forth in step 1240 of FIG. 12 (and optionally step 1235 of FIG. 12), or only disrupt a portion of the vascular occlusion 1150. If the laser catheter 1010 and sheath 1120 are only used to disrupt a portion of the vascular occlusion 1150, then the guidewire 1130 may penetrate and traverse the vascular occlusion 1150. For example, FIG. 11B depicts the guidewire 1130 penetrating and traversing the vascular occlusion 1150.

Referring to FIG. 11C, assuming that the laser catheter 1010 and sheath 1120 are only used to disrupt a portion of the vascular occlusion 1150', the laser catheter 1120 may be used to traverse the vascular occlusion 1150 without the sheath 1120. Referring to step 1245 of FIG. 12, the insertion of the liquid medium may be discontinued and the laser catheter 1010 may be used to ablate the vascular occlusion as the laser catheter 1150 passes over the guidewire 1130 through the vascular occlusion 1150' while the sheath 1120 remains proximal of the vascular occlusion.

Once the entire vascular occlusion has been traversed by the laser catheter 1010, the opening created by the laser catheter 1010 should be large enough to translate the sheath 1120 distally and through the vascular occlusion. At this point, both the distal end of the sheath 1120 and the distal end of the laser catheter 1010 should be distal of the vascular occlusion. At this point, referring to FIG. 11D, the laser catheter 1010 is able to translate proximally while the sheath 1120 remains stationary within the vascular occlusion. Upon introducing the liquid medium into the sheath 1120 in front of the laser catheter 1010, the laser may be activated, thereby creating laser-induced pressure waves in the presence of the liquid medium. At least a portion of the laser-induced pressure waves are directed radially, and as the laser catheter 1010 translates proximally within the sheath 1120, the laser-induced pressure waves transmit through the sheath 1120 thereby disrupting the remainder of the vascular occlusion 1150'.

To ensure that the majority of the remainder of the vascular occlusion 1150''' is disrupted, and if desired, disrupt the intraluminal calcium and/or calcium within the tissue layers (e.g., medial layer) of the blood vessel, and the vascular occlusion, the laser catheter 1010 may be repeatedly translated distally and proximally within the sheath 1120. As discussed above, disruption of the intraluminal layer and/or tissue layers (e.g., medial layer) of the blood vessel and the vascular occlusion, can improve the vasculatures ability to absorb drugs, particularly when such drugs are applied with a drug eluting balloon. Also, it is contemplated that prior to, during and/or after any step in the process outlined in FIG. 12, the laser catheter 1010 may be used individually to ablate a portion of the vascular occlusion, or the laser catheter 1010 may be used in conjunction with the sheath 1120.

Figure 13:
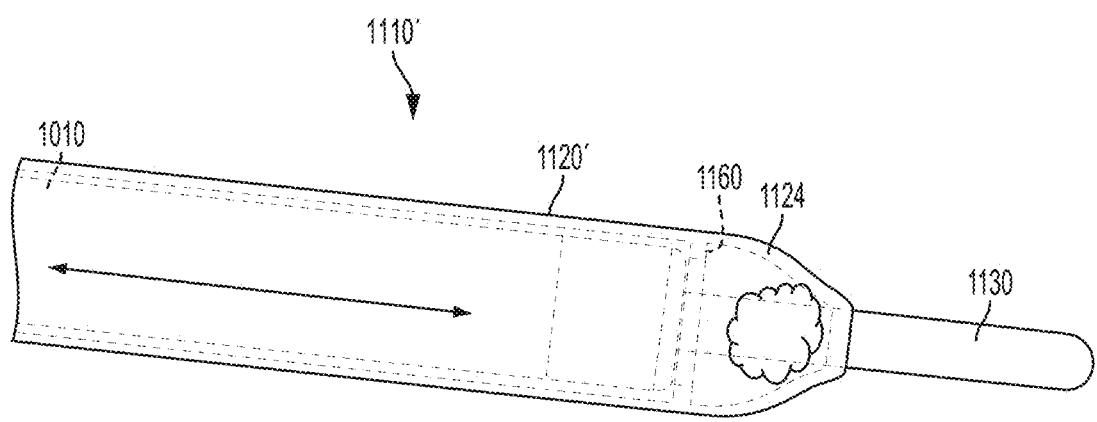
FIG. 13 is an elevation view of a kit that includes a laser catheter radially disposed within a sheath and over a guidewire, according to one embodiment of the present disclosure.

FIGS. 11A-11D illustrate the catheter system as having a sheath 1120 with an open distal end or tip 1124. Referring to FIG. 13, the sheath 1120' may have a tip 1124 that is fully or partially closed. For example, if it is desirable to have a guidewire 1130 pass through the laser catheter 1010 and the sheath 1120', the tip 1124 will only be partially closed, but if it is not necessary to utilize a guidewire, then the tip 1124 may be fully closed.

Similar to FIGS. 11A-11D, the laser catheter 1010 may translate distally and/or proximally within the sheath 1120'. In order to ensure that a cavity remains between the distal end of the laser catheter 1010 and the proximal end of the tip of the sheath 1120', the sheath 1120' may include one or more internal stops 1160. The shape of the tip 1124 may be configured similar to the tips 180 illustrated and described with respect to FIGS. 2-6 such that the catheter system 1110', including the laser catheter 1010 tip 1124, is configured such that the energy produced by the laser-induced pressure waves is captured within the cavity and the forces generated by the laser-induced pressure waves propagate longitudinally, including in a forward (that is, parallel with the vessel) direction, thereby increasing the tip's ability to disrupt, destroy and/or penetrate the vascular occlusion.

Referring to FIGS. 14A and 14B, a laser catheter system 1410 generally includes a laser catheter 1412, a guidewire 1414, a sheath 1416, and a handle 1418 that translatably couples the laser catheter 1412 to the sheath 1416. The laser catheter 1412, the guidewire 1414, and the sheath 1416 may be similar to, for example, the components of the two-piece catheter systems or kits described herein. As a specific example, the laser catheter 1412, the guidewire 1414, and the sheath 1416 may be similar to the components described above in connection with FIGS. 11A-11D. The laser catheter 1412 is disposed within a lumen of the sheath 1416 and the handle 1418, and the laser catheter 1412 includes a proximal coupling 1420 for coupling to the handle 1418. The guidewire 1414 is disposed within a lumen of the laser catheter 1412. The sheath 1416 includes a proximal coupling 1422 for coupling to the handle 1418.

A liquid medium is introduced into the sheath 1416 distal to the laser catheter 1412, particularly distal to the optical fibers/emitters of the laser catheter 1412 such that when the laser is activated, the liquid absorbs the light and creates laser-induced pressure waves and/or vapor bubbles and resultant pressure waves. The liquid is introduced via the lumen or space between the laser catheter 1412 and the sheath 1416, which in turn receives the liquid from a proximal port 1424 coupled to the sheath 1416.

Referring now to FIGS. 14A, 14B, 15A-15G, the handle 1418 generally includes a base 1426 that couples to the sheath 1416 and a drive mechanism 1428 that couples to the laser catheter 1412. As described in further detail below, a portion of the drive mechanism 1428 is translatably coupled to the base 1426 to facilitate translating the laser catheter 1412 within the lumen of the sheath 1416 (for example, to the various positions shown in FIGS. 11A-11D). The drive mechanism 1428 may be translated to a proximal position relative to the base 1426 (see FIGS. 15A-15C), a distal position relative to the base 1426 (sec FIGS. 15E and 15F), and an infinite number of intermediate positions therebetween (see FIGS. 15D and 15G). As a result, the laser catheter 1412 may be translated to corresponding positions relative to the sheath 1416.

Figure 16A:
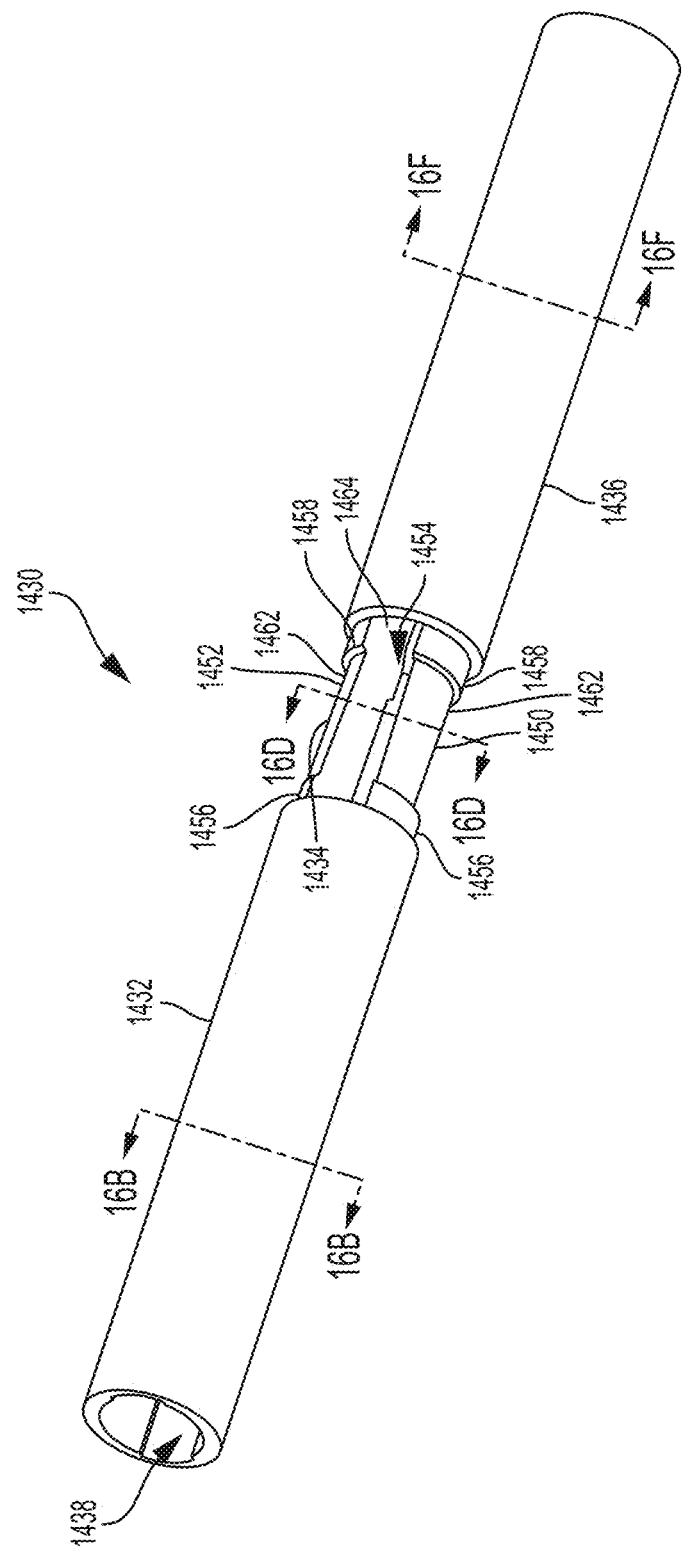
FIG. 16A is a perspective view of a frame of the handle of FIG. 14A.
Figure 16B:
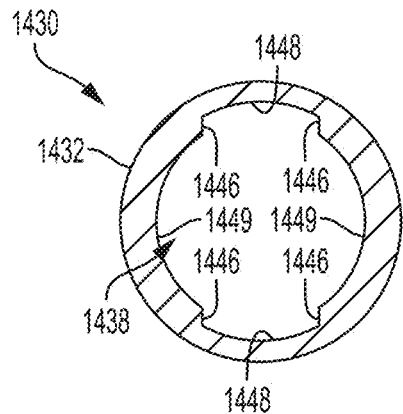
FIG. 16B is an elevation cross-sectional view of the frame along line 16B-16B of FIG. 16A.
Figure 16C:
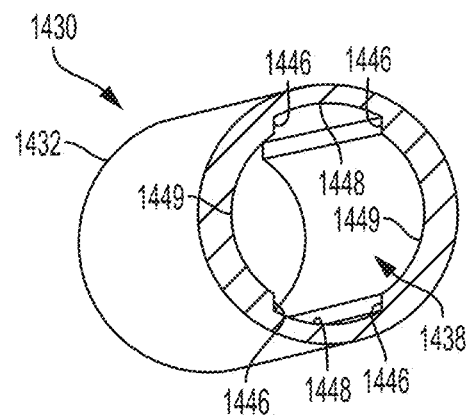
FIG. 16C is a perspective cross-sectional view of the frame along line 16B-16B of FIG. 16A.
Figure 16D:
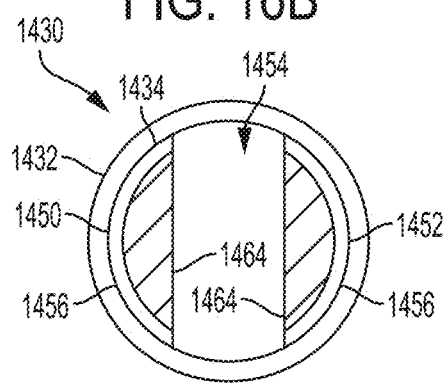
FIG. 16D is an elevation cross-sectional view of the frame along line 16D-16D of FIG. 16A.
Figure 16E:
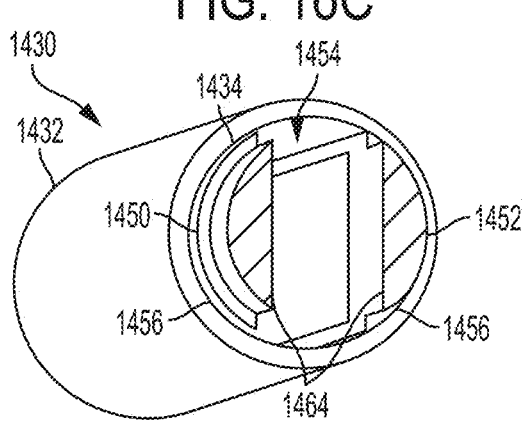
FIG. 16E is a perspective cross-sectional view of the frame along line 16D-16D of FIG. 16A.
Figure 16F:
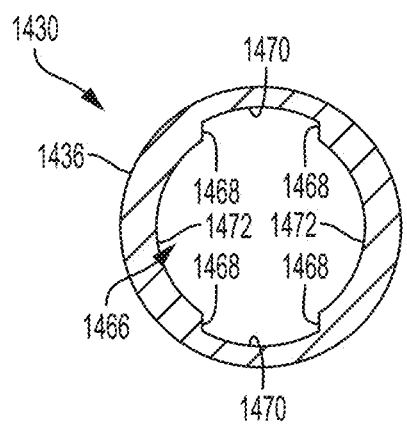
FIG. 16F is an elevation cross-sectional view of the frame along line 16F-16F of FIG. 16A.
Figure 16G:
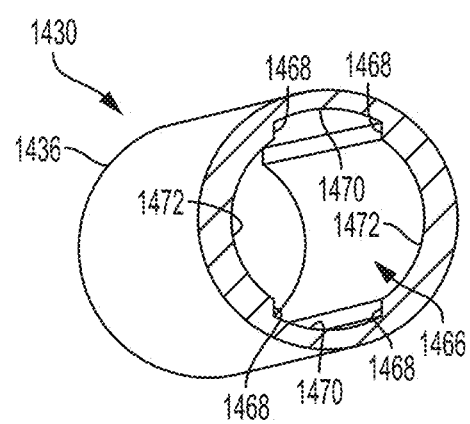
FIG. 16G is a perspective cross-sectional view of the frame along line 16F-16F of FIG. 16A.
Figure 17:
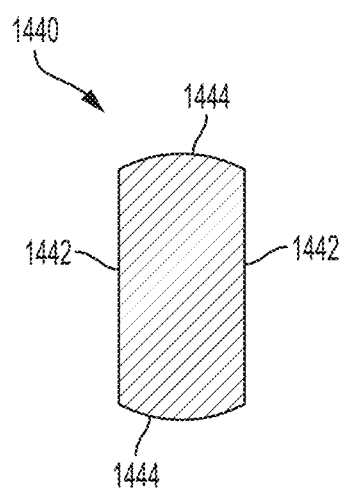
FIG. 17 is an elevation cross-sectional view of the shaft of the handle of FIG. 14A.

Referring now to FIGS. 14A-17, the base 1426 includes an elongated, hollow frame 1430 that movably couples to the drive mechanism 1428. The frame 1430 includes a proximal portion 1432, an intermediate portion 1434, and a distal portion 1436. The proximal portion 1432 defines a proximal passageway 1438 for translatably receiving a shaft 1440 of the drive mechanism 1428 therein. Referring specifically to FIGS. 16B, 16C, and 17, the proximal passageway 1438 may include a first key feature that, by coupling to a second key feature of the shaft 1440, inhibits rotation of the shaft 1440 relative to the frame 1430. For example, the second key feature of the shaft 1440 may be a non-circular cross-sectional area, and the first key feature of the proximal passageway 1438 may be a cross-sectional area that is approximately identical (that is, permitting sufficient clearance to permit relative longitudinal translation, but inhibit relative rotation and transverse translation) to the cross-sectional area of the shaft 1440, or a cross-sectional area that is approximately identical to a portion of the cross-sectional area of the shaft 1440. As a more specific example and as shown in FIGS. 16B, 16C, and 17, the shaft 1440 includes rectangle-like cross-sectional shape, with two opposing flat side surfaces 1442 and two opposing arcuate side surfaces 1444. The proximal passageway 1438 includes a cross-sectional area that is approximately identical to a portion of the cross-sectional area of the shaft 1440. Specifically, the proximal passageway 1438 is defined by four opposing flat side surfaces 1446 and two opposing arcuate side surfaces 1448. The flat side surfaces 1446 and the arcuate side surfaces 1448 engage the flat side surfaces 1442 and the arcuate side surfaces 1444 of the shaft 1440, respectively, to permit relative longitudinal translation, but inhibit relative rotation and transverse translation of the shaft 1440 relative to the frame 1430. In the present example, the proximal passageway 1438 is also defined by two additional opposing arcuate side surfaces 1449 that extend between the flat side surfaces 1446. The arcuate side surfaces 1449 are disposed apart from the shaft 1440 to reduce sliding friction between the shaft 1440 and the frame 1430.

Referring specifically to FIGS. 16A, 16D, and 16E, the intermediate portion 1434 of the frame 1430 includes a first bearing portion 1450, a second bearing portion 1452, and an opening 1454 extending therebetween and aligned with the proximal passageway 1438. Each of the first and second bearing portions 1450, 1452 includes first and second bearing surfaces 1456, 1458. The first and second bearing surfaces 1456, 1458 rotatably support a control element 1460 of the drive mechanism 1428. Each of the first and second bearing portions 1450, 1452 also includes a clearance surface 1462 between the bearing surfaces 1456, 1458. The clearance surface 1462 is also disposed radially inwardly relative to the bearing surfaces 1456, 1458. The clearance surface 1462, together with the opening 1454, facilitates driving engagement of the control element 1460 with the shaft 1440, as described in further detail below. Within the opening 1454, each of the first and second bearing portions 1450, 1452 includes a guide surface 1464. The guide surface 1464s translatably couple to the shaft 1440 and inhibit the shaft 1440 from rotating within the frame 1430.

Figure 15C:
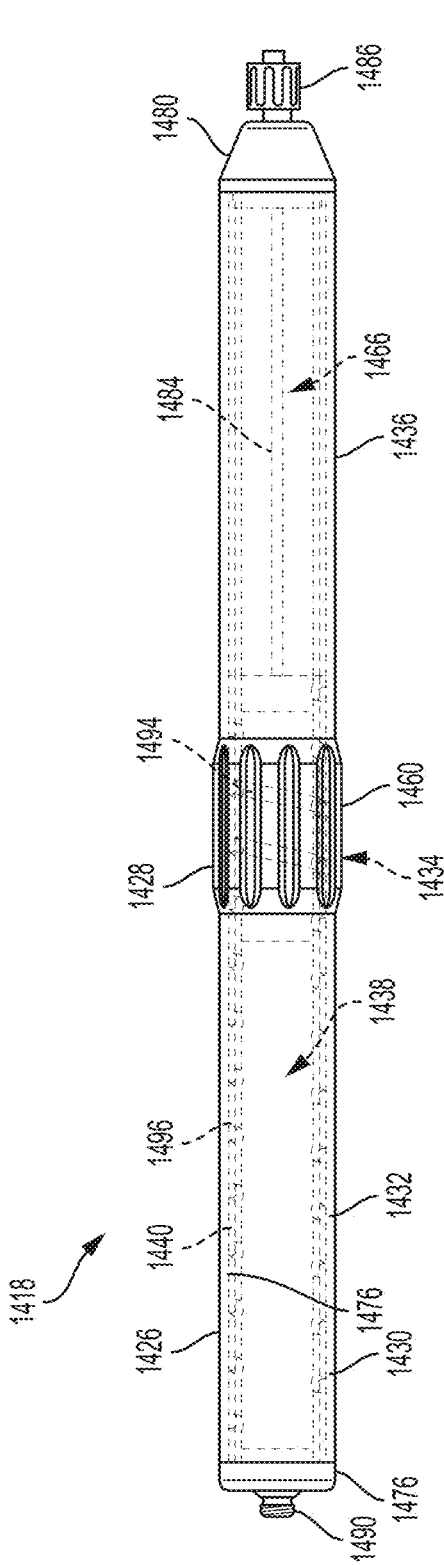
FIG. 15C is an elevation view of the handle of FIG. 14A, wherein several external components are partially transparent to illustrate internal components, and the shaft is shown in the proximal position.
Figure 15D:
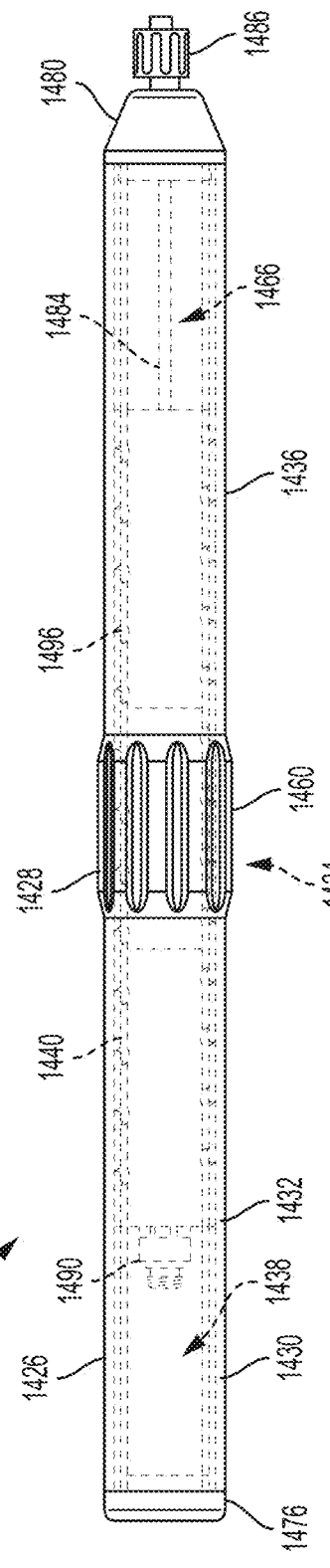
FIG. 15D is an elevation view of the handle of FIG. 14A, wherein several external components are partially transparent to illustrate internal components, and the shaft is shown in an intermediate position.
Figure 15G:
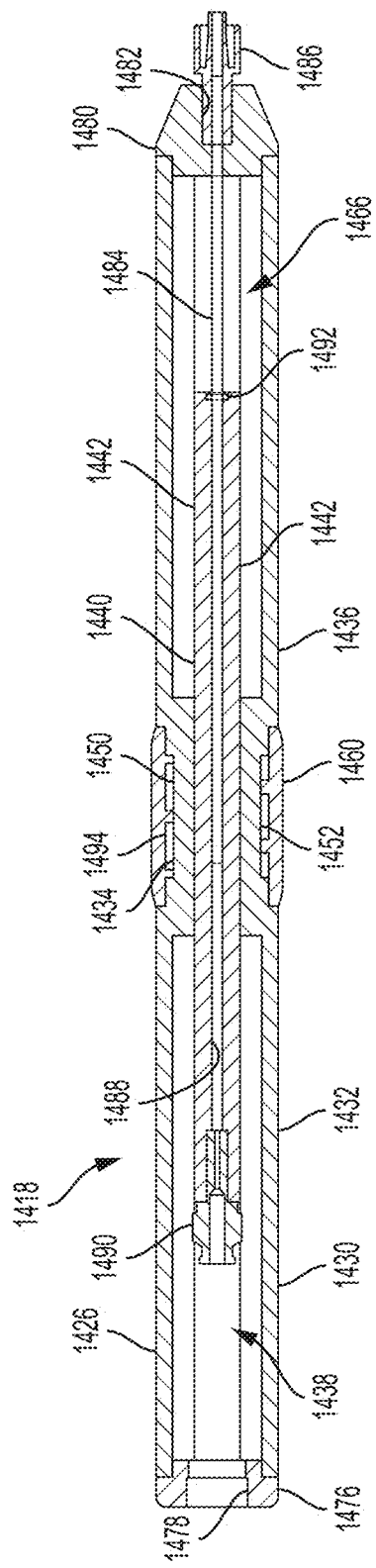
FIG. 15G is a cross-sectional view of the handle of FIG. 14A, wherein the shaft is shown in an intermediate position.
Figure 15H:
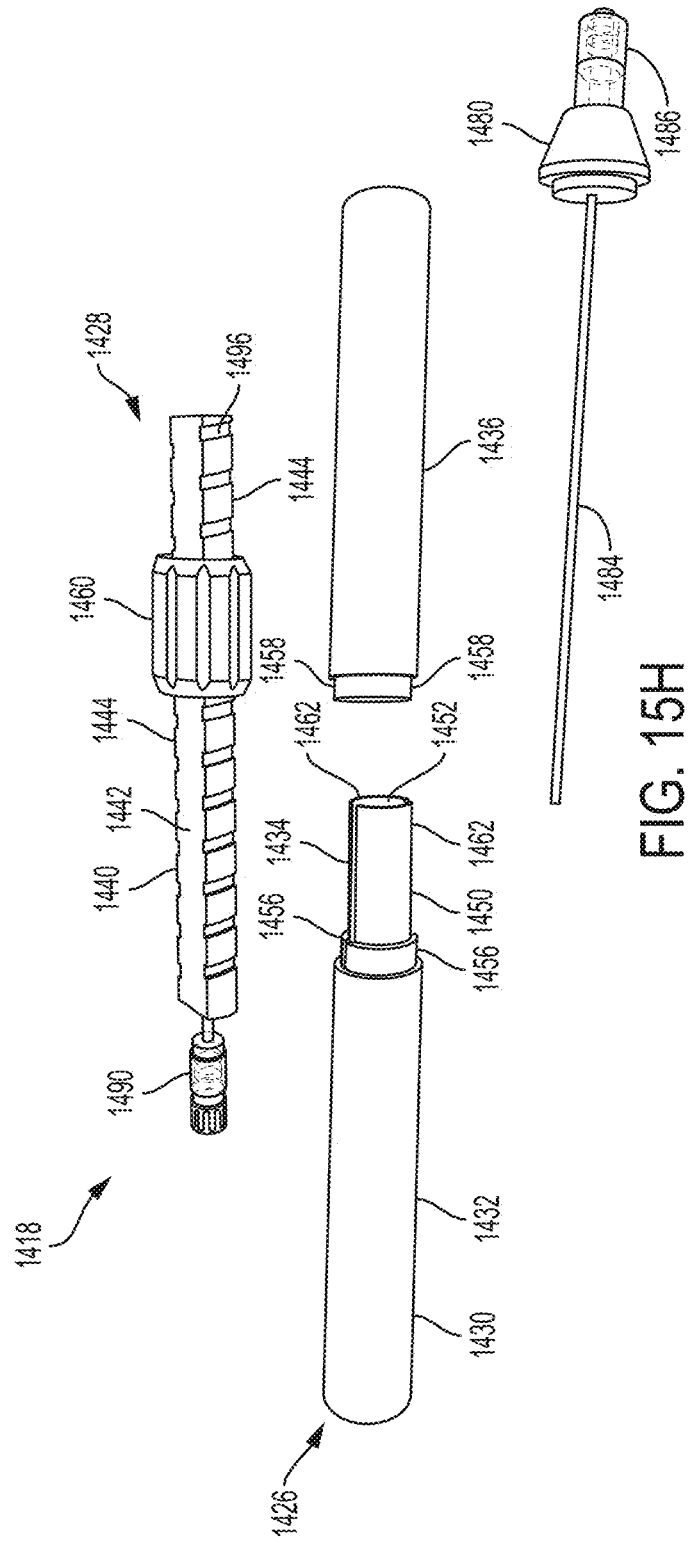
FIG. 15H is an exploded view of the handle of FIG. 14A.
Figure 15I:
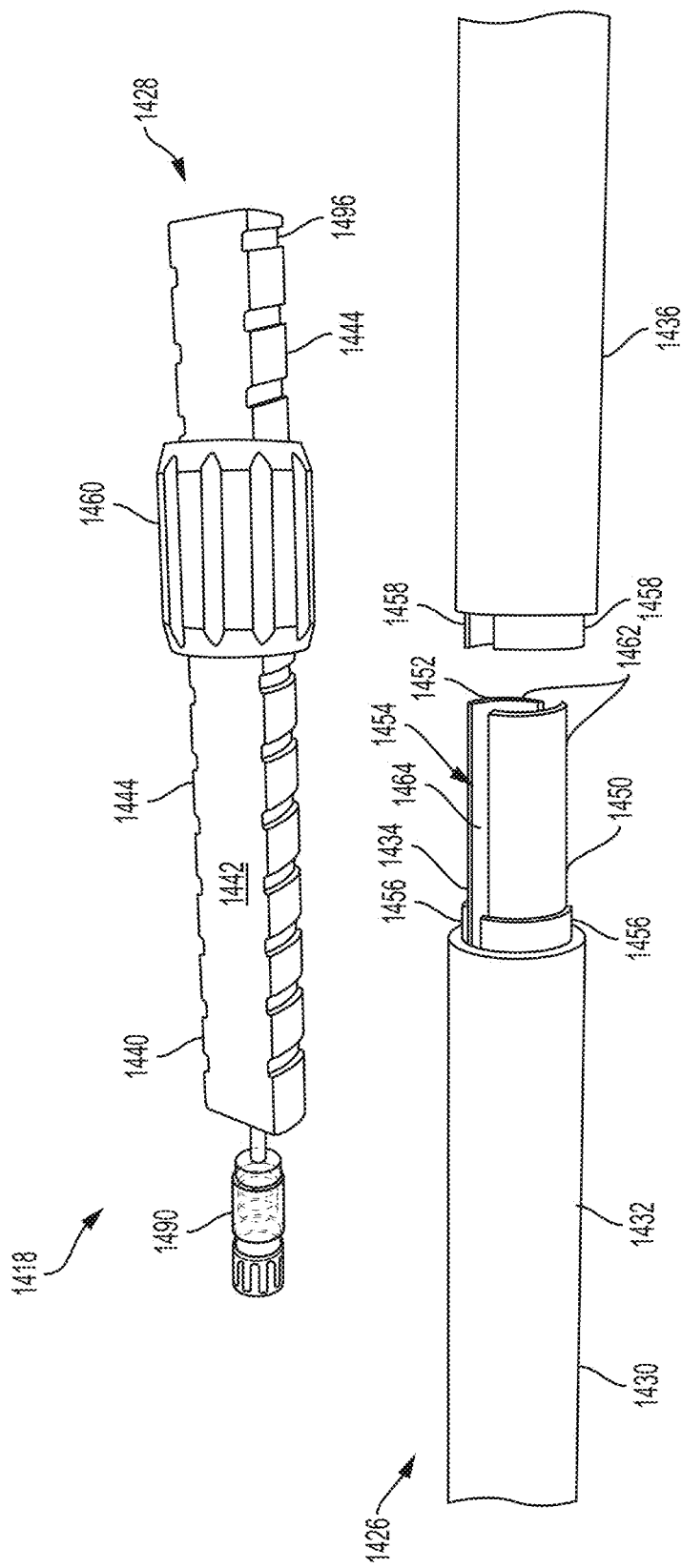
FIG. 15I is a detail exploded view of the handle of FIG. 14A.

Referring briefly to FIGS. 15H-15J, to facilitate assembly of the base 1426, each clearance surface 1462 may be monolithically coupled with the first bearing surface 1456, 1458. After positioning the shaft 1440 within the frame 1430 and the control element 1460 over the first bearing surface 1456, 1458 and the clearance surface 1462, each clearance surface 1462 may couple to the second bearing surface 1456, 1458 via, for example, press fit, one or more adhesives, snap connectors (not shown), or the like.

Referring to FIGS. 16A, 16F, and 16G, the distal portion 1436 of the frame 1430 may be similar to the proximal portion 1432 of the frame 1430. That is, the distal portion 1436 defines a distal passageway 1466 aligned with the opening 1454 for translatably receiving the shaft 1440. Referring specifically to FIGS. 16F, 16G, and 17 and in a similar manner to the proximal passageway 1438, the distal passageway 1466 may include a first key feature that, by coupling to the second key feature of the shaft 1440, inhibits rotation of the shaft 1440 relative to the frame 1430. For example, the second key feature of the shaft 1440 may be a non-circular cross-sectional area, and the first key feature of the distal passageway 1466 may be a cross-sectional area that is approximately identical to the cross-sectional area of the shaft 1440, or a cross-sectional area that is approximately identical to a portion of the cross-sectional area of the shaft 1440. In accordance with the specific example described above and as shown in FIGS. 16F, 16G, and 17, the distal passageway 1466 includes a cross-sectional area that is approximately identical to a portion of the cross-sectional area of the shaft 1440. Specifically, the distal passageway 1466 is defined by four opposing flat side surfaces 1468 and two opposing arcuate side surfaces 1470. The flat side surfaces 1468 and the arcuate side surfaces 1470 engage the flat side surfaces 1442 and the arcuate side surfaces 1444 of the shaft 1440, respectively, to permit relative longitudinal translation, but inhibit relative rotation and transverse translation of the shaft 1440 relative to the frame 1430. In the present example, the distal passageway 1466 is also defined by two additional opposing arcuate side surfaces 1472 that extend between the flat side surfaces 1468. The arcuate side surfaces 1472 are disposed apart from the shaft 1440 to reduce sliding friction between the shaft 1440 and the frame 1430.

Referring again to FIGS. 14A-16G, at its proximal end, the frame 1430 couples to a proximal cover 1476 (for example, via press fit, one or more adhesives, or the like). The proximal cover 1476 includes a proximal aperture 1478 (see FIGS. 15F and 15G) for permitting the laser catheter 1412 to extend into the frame 1430. At its distal end, the frame 1430 couples to a distal cover 1480 (for example, via press fit, one or more adhesives, or the like). The distal cover 1480 includes a distal aperture 1482 (see FIGS. 15F and 15G) for permitting the laser catheter 1412 to extend out of the frame 1430 and into the sheath 1416. The distal aperture 1482 press-fittingly receives a tube 1484 (for example, a hypotube 1484) that extends into the shaft 1440 and receives the laser catheter 1412. The distal aperture 1482 also press-fittingly receives a distal coupling 1486 that detachably and sealingly couples to the proximal coupling 1422 of the sheath 1416.

Referring now to FIGS. 14A and 15A-15J, the drive mechanism 1428 generally includes the shaft 1440 and the control element 1460. Referring specifically to FIGS. 15F-15J, the shaft 1440 includes a shaft 1440 passageway 1488 for permitting the laser catheter 1412 to extend through the shaft 1440 and for receiving the tube 1484. The shaft 1440 passageway 1488 press-fittingly receives a proximal coupling 1490 that detachably and sealingly couples to the proximal coupling 1420 of the laser catheter 1412. As such, movement of the control element 1460 relative to the base 1426 causes the shaft 1440 to translate within the base 1426, the laser catheter 1412 thereby translates within the lumen of the sheath 1416.

The shaft 1440 passageway 1488 also receives a seal 1492, for example, an O-ring that translatably engages the outer surface of the tube 1484. As such, the seal 1492 inhibits the liquid in the shaft 1440 passageway 1488 (received from the sheath 1416 via the distal coupling 1486 and the hypotube 1484) from exiting the shaft 1440 by flowing between the shaft 1440 and the tube 1484.

As described briefly above, the control element 1460 is rotatably supported by the frame 1430. The control element 1460 includes a first engagement feature that couples to a second engagement feature of the shaft 1440 such that rotation of the control element 1460 relative to the base 1426 causes translation of the shaft 1440 relative the base 1426 (and translation of the laser catheter 1412 within the lumen of the sheath 1416). For example and as shown in the Figures, the first engagement feature may be a first threaded surface 1494 within the control element 1460, and the second engagement feature may be a second threaded surface 1496 formed on the arcuate side surfaces 1444 of the shaft 1440. Stated differently, the shaft 1440 may include a second, interrupted threaded surface that extends from the opening 1454 in the frame 1430 to engage the first threaded surface 1494 of the control element 1460. In any case, rotation of the control element 1460 and the first threaded surface 1494, together with the shaft 1440 being rotatably fixed within the frame 1430, causes translation of the second threaded surface 1496 and the shaft 1440 relative to the frame 1430 (and translation of the laser catheter 1412 within the lumen of the sheath 1416).

Laser-induced pressure waves generally have different characteristics in comparison to ultrasound. Ultrasound typically consists of periodic oscillations with limited band-width. Laser-induced pressure waves are single, mainly positive pressure pulses that are followed by comparatively small tensile wave components. Ultrasound applies an alternating high frequency load to tissue, with a frequency range of several megahertz, and can thus lead to heating, tissue tears and cavitation at high amplitudes. The effect of laser-induced pressure waves in comparison, however, largely involves radially directed energy, as described above, enabling the treatment of deep tissue as well as adjacent tissue with enhanced sensitivity.

The ability of the catheter of the present disclosure to generate laser-induced pressure waves for treating a vascular occlusion in a subject involves the suitable coupling of the light system and the liquid medium. Any wavelength of light can be used, including but not limited to, laser light, visible light, ultraviolet light and infrared light, as long as the light being emitted is coupled with a liquid medium capable of absorbing the light and producing laser-induced pressure waves. Additionally, any liquid medium can be used, as long as the liquid medium is coupled with a light source that emits light at a suitable wavelength such that the liquid absorbs the light and creates laser-induced pressure waves and/or vapor bubbles. In some cases, the liquid medium can be contrast medium (for example, iodine-containing contrast medium or gadolinium contrast medium) and/or the liquid medium can be a contrast solution comprising a biocompatible fluid (for example, saline) in which a contrast dye(s) or particle(s) have been mixed at various concentrations.

The force amplitude generated by the laser-induced pressure waves depends in part on the degree of absorption of the light energy by the liquid medium as well as total energy deposited by the light source. Generally, the greater the absorption of the light energy by the liquid medium 160, the greater the force generated by the laser-induced pressure waves. Also, the greater the amount of the light energy delivered to the liquid medium 160, the greater the force generated by the laser-induced pressure waves. For example, an excimer laser typically emits laser light at a wavelength of about 308 nanometers at pulse durations between about 120 nanoseconds and about 140 nanoseconds, at frequencies between about 25 pulses per second to about 80 pulses per second, and with a total energy output between about 1 to about 100 millijoules. In some cases, however, total energy output of a laser light system can range from greater than 0 to about 300 mJ. When emitted within contrast medium, such as iodine-containing contrast medium or gadolinium contrast medium, there will be a very high degree of absorption by the contrast medium, thus creating laser-induced pressure waves with sufficient force to treat a vascular occlusion in a subject.

Light energy can be emitted at any suitable wavelength capable of generating laser-induced pressure waves. Light energy can be emitted between about 1 nanometer and about 1 millimeter. In some cases, light can be emitted from about 10 nanometers to about 5000 nanometers. In some cases, light can be emitted from about 100 nanometers to about 1000 nanometers. In some cases, light can be emitted from about 250 nanometers to about 750 nanometers. In some cases, light can be emitted from about 300 nanometers to about 600 nanometers. In still other cases, light can be emitted from about 300 nanometers to about 350 nanometers.

Light energy can be emitted at any suitable pulse duration capable of generating laser-induced pressure waves. In some cases, light can be emitted at pulse durations between about 1 femtosecond to about 1 second. In some cases, light can be emitted at pulse durations between about 10 nanoseconds to about 500 nanoseconds. In some cases, light can be emitted at pulse durations between about 100 nanoseconds to about 150 nanoseconds. In still other cases, light can be emitted at pulse durations between about 120 nanoseconds and about 140 nanoseconds.

Light energy can be emitted at any suitable pulse repetition frequency (PRF), or pulses per second, capable of generating vapor bubbles and producing resultant pressure waves that propagate through the surrounding vasculature. In some cases, light can be pulsed at a frequency of between about 1 pulse to about 5000 pulses per second. In some cases, light can be pulsed at a frequency of between about 10 pulses to about 2500 pulses per second. In some cases, light can be pulsed at a frequency of between about 10 pulses to about 1500 pulses per second. In some cases, light can be pulsed at a frequency of between about 100 pulses to about 1000 pulses per second. In other cases, light can be pulsed at a frequency of between about 50 pulses to about 500 pulses per second. In other cases, light can be pulsed at a frequency of between about 50 pulses to about 150 pulses per second. In other cases, light can be pulsed at a frequency of between about 50 pulses to about 100 pulses per second. In still other cases, light can be pulsed at a frequency of between about 25 pulses to about 80 pulses per second.

The total number of pulses administered during a particular treatment period depends on a variety of factors, including patient characteristics, the type of condition being treated, and the specific characteristics of the vascular occlusion, as one of ordinary skill in the art would readily appreciate based on the present disclosure. In some cases, the total number of pulses administered during a treatment period can range from a single pulse to any number of pulses generated in a 10 second treatment period, a 15 second treatment period, a 20 second treatment period, a 25 second treatment period, a 30 second treatment period, up to a 1 minute treatment period. Treatment periods can be repeated depending on the extent of the vascular occlusion remaining after initial treatment.

For example, a generator and/or one or more emitters may be configured to emit laser light energy at wavelengths of between about 150 nanometers to about 400 nanometers, at pulse durations between about 1 femtosecond to about 1 second, and at frequencies between about 1 pulse per second to about 5000 pulses per second. In some cases, the generator and/or the emitter(s) may be configured to emit laser light energy at wavelengths of between about 400 nanometers to about 800 nanometers, at pulse durations between about 1 femtosecond to about 1 second, and at frequencies between about 1 pulse per second to about 5000 pulses per second. In other cases, the generator and/or the emitter(s) may be configured to emit laser light energy at wavelengths of between about 800 nanometers to about 3,000 nanometers, at pulse durations between about 1 femtosecond to about 1 second, and at frequencies between about 1 pulse per second to about 5000 pulses per second. In other cases, the generator and/or the emitter(s) may be configured to emit laser light energy at wavelengths of between about 3,000 nanometers to about 12,000 nanometers, at pulse durations between about 1 femtosecond to about 1 second, and at frequencies between about 1 pulse per second to about 5000 pulses per second. In other cases, the generator and/or the emitter(s) may be configured to emit laser light energy at wavelengths of between about 300 nanometers to about 360 nanometers, at pulse durations between about 1 femtosecond to about 1 second, and at frequencies between about 1 pulse per second to about 5000 pulses per second.

The degree of force generated by the laser-induced pressure waves can be modulated by using lasers that produces laser light energy at different wavelengths and at different pulse durations, as would be appreciated by one of ordinary skill in the art based on the present disclosure. For example, different degrees of force may be required to break apart a vascular occlusion, as compared to the degree of force required to deliver a therapeutic agent to vascular tissue. In some embodiments, a laser having a holmium source, referred a Holmium laser, can emit laser light energy at a wavelength of about 2,100 nanometers (nm) and can be coupled with various light absorbing materials, including an aqueous or saline-based medium, to treat a vascular occlusion in a subject.

Several other additional sources of laser light energy can be paired with corresponding light absorbing materials to generate laser-induced pressure waves to treat a vascular occlusion. For example, YAG crystal lasers can produce wavelengths of infrared light, which is highly absorptive in aqueous solutions. Aqueous solutions can be used as light absorbing material or medium to generate laser-induced pressure waves. Aqueous solutions include, but are not limited to, saline, dextrose, radio-opaque contrast, lactated ringer's, and electrolyte solutions. In some cases, YAG wavelengths can be doubled to generate visible spectrum light of 532 nm wavelength. Materials or medium capable of absorbing light of this wavelength include, but are not limited to, gold nanospheres, nitrite solutions, potassium permanganate solutions, copper salts, aluminum solutions, aluminon, ammonia salts, and dyes such as hemotoxylin and propidium iodide. Light absorbing materials such as these can be part of a solution, such as an aqueous solution as described above, and/or they can be applied as coatings on various surfaces within a device.

In some embodiments, a Holmium YAG laser can emit laser light energy at a wavelength of about 2,120 nm and can be coupled with various light absorbing materials, including an aqueous or saline-based medium, to treat a vascular occlusion in a subject. In some embodiments, a thulium laser, such as a Thulium YAG laser, can emit laser light energy at a wavelength of about 2,013 nm and can be coupled with various light absorbing materials, including an aqueous or saline-based medium, to treat a vascular occlusion in a subject. In some embodiments, a thulium laser, such as a Thulium Fiber laser, can emit laser light energy at a wavelength of about 1,908 nm and can be coupled with various light absorbing materials, including an aqueous or saline-based medium, to treat a vascular occlusion in a subject. In some embodiments, an Nd-YAG laser can emit laser light energy at a wavelength of about 1,064 nm and can be coupled with various light absorbing materials to treat a vascular occlusion in a subject. In some embodiments, a doubled YAG laser can emit laser light energy at a wavelength of about 532 nm and can be coupled with various light absorbing materials to treat a vascular occlusion in a subject. In some embodiments, an alternative band YAG laser can emit laser light energy at a wavelength of about 1,319 nm and can be coupled with various light absorbing materials to treat a vascular occlusion in a subject. In still other embodiments, an Er-YAG laser can emit laser light energy at a wavelength of about 2,940 nm and can be coupled with various light absorbing materials to treat a vascular occlusion in a subject.

Carbon dioxide ($CO_2$) lasers can emit infrared light that is highly absorptive in aqueous solutions. $CO_2$ lasers are common surgical lasers and are highly absorptive in tissues due to their high water content. Light absorbing materials that can be coupled with $CO_2$ lasers that emit infrared light, such as light emitted at a 10.6 micron wavelength, to generate laser-induced pressure waves include, but are not limited to, aqueous solutions such as saline, dextrose, radio-opaque contrast, lactated ringer's, and electrolyte solutions.

Nitrogen lasers can be used to produce low frequency, high energy laser pulses. Nitrogen lasers can emit light in the UV spectrum can emit laser light energy at a wavelength of about 337 nm and can be coupled with various light absorbing materials to generate laser-induced pressure waves, including but not limited to, radio-opaque contrast as well as metals and oxides such as aluminum, silver, gold, copper, nickel, cerium, zinc, titanium, and dyes such as hydroxycoumarin and aminocoumarin.

Other medically useful lasers that can be used to generate a laser-induced pressure wave to treat a vascular occlusion include Ti-Sapphire lasers, which can emit laser light energy at wavelengths of about 800 nm; Ruby lasers, which can emit laser light energy at wavelengths of about 694 nm; and Alexandrite lasers, which can emit laser light energy at about 755 nm. These medical lasers emit laser light energy in the near infrared light spectrum, and can be used for laser-induced pressure wave generation. Light absorbing material or medium that can be coupled with these laser include, but are not limited to, dyes and colorants which could be used in solution, suspension, or coating on another material or surface within a device. Various materials capable of absorbing laser light energy in these wavelengths include aqueous copper, copper salts, and cupric sulfate, and materials such as fluorophores that are used in fluorescent microscopy (for example, methylene blue).

Dye lasers can also be used to generate laser-induced pressure waves to treat a vascular occlusion. In some cases, dye lasers can be tuned to output a specific wavelength of light in the visible spectrum, which can allow for the optimization of the laser for a certain light absorbing material, as an alternative or in addition to, using a material which is highly absorptive of a specific wavelength of light. In this way, the light absorbing material can be any of the previously mentioned materials, as well as dyes, colorants, and visible light chromophores.

For certain applications, it may be desirable to increase the amount and/or the size of vapor bubbles produced along with a laser-induced pressure wave that is generated by emitting laser light energy into a corresponding light absorbing liquid medium. For example, when entering smaller diameter sized blood vessels, the size of the catheter may be limited. In some cases, the force that vapor bubbles exert on tissue (for example, a vascular occlusion) may be proportional to the size of the individual vapor bubbles created, as the bubbles expand and contract after laser light energy is emitted into liquid medium and a pressure wave is generated. That is, the strength of the initial laser-induced pressure wave and/or the size of the vapor bubble may be limited with the use of a non-gas saturated liquid medium. One manner by which the size of individual vapor bubbles can be increased (for example, to impart greater amount of force on a particular tissue) is to saturate the liquid medium with gaseous substances so that the gas within the liquid medium exhibits a higher vapor pressure as compared to that of the liquid medium without such gas. Suitable gaseous substances that may be used to create gas-saturated liquid medium include, but are not limited to, ambient air, carbon dioxide, iodine gas, oxygen, nitrogen, compressed air, nitrous oxide, and combinations of these.

The higher vapor pressure of the gaseous substance added to the liquid medium will cause the gaseous substance to return to a gaseous state faster (under smaller pressure fluctuations) than the liquid medium. In other words, less pressure is required to cause the saturated gaseous substances to come out of solution, resulting in the creation of larger vapor bubbles, and concomitantly, a greater amount of force. In some cases, the use of gas-saturated liquid medium allows for the use of laser light energy at decreased intensities, or decreased pulses or pulse durations, without any accompanying decrease in the overall force generated by the vapor bubbles (as each vapor bubble is larger). This can enhance both the safety and efficacy of the procedure being performed.

The gaseous substances can be imparted to the liquid medium through various means, including under pressure, through mechanical agitation, and/or by bubbling the gas into the liquid medium. In some cases, gas-saturated liquid medium can be prepared prior to a procedure and then delivered to the distal end of a catheter prior to performing the procedure. Additionally or alternatively, gaseous substances can be delivered into that liquid medium that is already present in the catheter.

The gases and/or gaseous substances may be dissolved and quantified by the amount of gases present in a 1 kg of the liquid medium. The maximum amount of gas that will dissolve in the liquid medium is dependent on the solubility of the particular gas in that liquid medium, the pressure, and the temperature as described by Henry's law of gas solubility. For example, carbon dioxide may be dissolved into water at a concentration of 1.25 g/kg of water or less at 30 degrees C. under atmospheric pressure. And upon dissolving carbon dioxide into water or saline, an overall concentration between 0.25-3.5 $g/kgH_2O$ is produced. The concentrations of other dissolved gases in a kilogram of liquid medium ranges from 1 mg-1 g/kg for iodine, 5-80 mg/kg for oxygen, 5-40 mg/kg for nitrogen, 5-500 mg/kg for room air, and 0.1-4 g/kg for nitrous oxide.

The gases and/or gaseous substances may be dissolved in quantities above the theoretical limit, which is known as super saturation. The theoretical limit is described by Henry's law as mentioned previously. By dissolving the gases under increased pressure or decreased temperature and then returning it to normal atmospheric conditions, it is possible to dissolve a larger quantity of gas then is possible at atmospheric conditions. For example, 2.5 g of carbon dioxide may be dissolved into 30 degrees C. water under 2 atm of pressure, and then returned to atmospheric pressure. For any dissolved gas, the saturation percentage is defined by the concentration of gas over the theoretical maximum concentration. For any of the previously mentioned gases in a supersaturated solution, the saturation percentage can range from 100-300 percent.

The use of a gas saturated liquid medium or super saturated liquid medium may also increase the initial laser-induced pressure wave caused by the interaction of the laser light and the liquid medium. That is, the gas saturated liquid medium or super saturated liquid medium may contain larger potential energy, which when activated by the laser light, may create a larger initial laser-induced pressure wave in comparison to a laser-induced pressure wave created by the interaction of laser light and a non-gas saturated liquid medium.

Additionally or alternatively, methods of the present disclosure also include activating at least one proximal laser emitter enclosed within the sheath assembly to send pulses of laser light energy through the liquid medium and propagating laser-induced pressure waves to assist in stent deployment. Pressure waves generated from vapor bubbles can assist in seating or expanding the stent to its full diameter as part of a medical procedure.

As discussed above, activating one or more emitters and transmitting pulses of light energy into the liquid medium produces vapor bubbles. Upon emitting light from an emitter, such as a laser catheter, within a sheath that contains an absorptive liquid medium, the vapor bubbles may be produced within the interior of the sheath and/or exterior to the sheath. Assuming that the vapor bubbles are created on the interior of the sheath, it may be desirable to limit some or all of the potential expansion of the relevant portion of the sheath caused by the vapor bubbles. That is, it may be desirable to reduce or prevent the sheath's ability to expand and contract upon creation of the vapor bubbles therein so as to reduce or prevent the sheath from applying a hydraulic force or pressure to the vascular occlusion and/or to the walls of the vessel. Also, assuming that the vapor bubbles are created on exterior of the sheath within the vessel wall, it may be desirable to reduce and/or prevent the formation of such vapor bubbles so as to reduce or prevent the cavitation event and the formation of the vapor bubbles themselves from applying a hydraulic force or pressure to the vascular occlusion and/or to the walls of the vessel.

Figure 18:
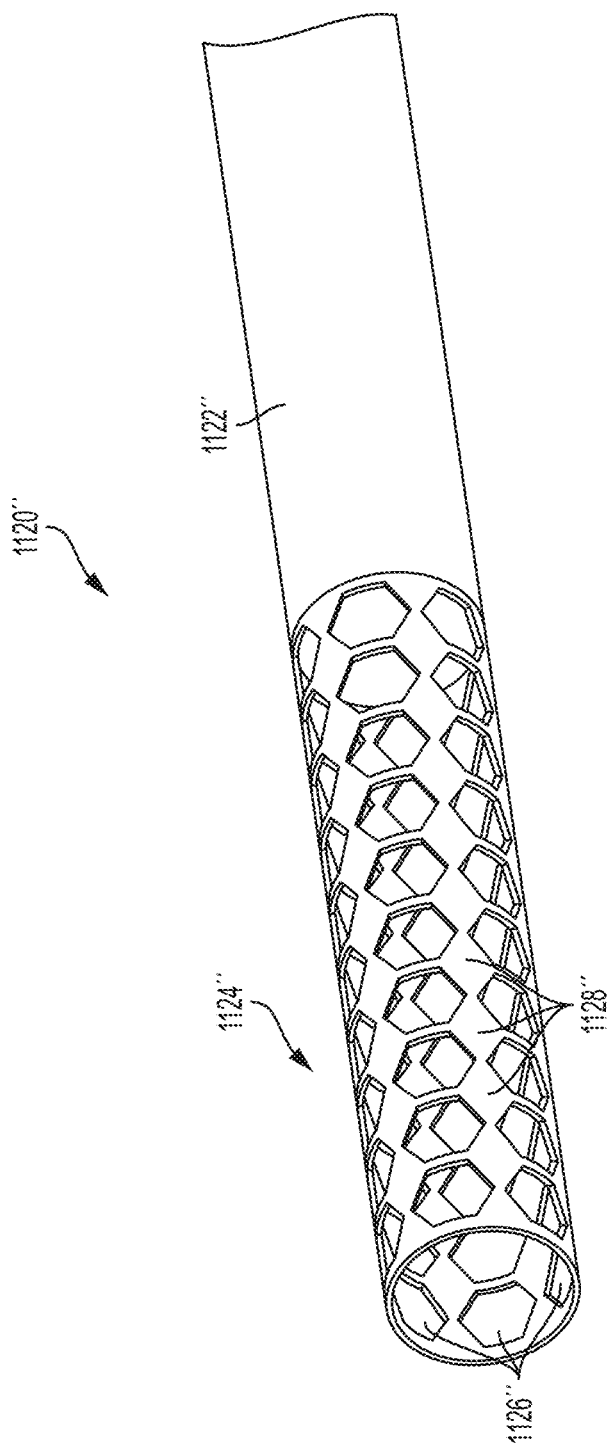
FIG. 18 is a perspective view of an outer sheath comprising a attenuating member, according to one embodiment of the present disclosure.

Referring to FIG. 18, there is depicted a perspective view of biocompatible sheath 1120" that can be used in conjunction with a laser catheter or any of the earlier embodiments to perform a method of treating a subject, such as removing or treating a vascular occlusion. The sheath 1120" may include a sleeve or jacket 1122" and an attenuating member 1124". FIG. 18 illustrates the attenuating member 1124" as being exposed and coupled to the distal end of the sleeve 1122" via an adhesive. The attenuating member 1124", however, can alternatively be integrally disposed within the sleeve 1122", disposed on the exterior of the sleeve 1122" and/or disposed on the interior of the sleeve 1122". Additionally, if the attenuating member 1124" is coupled to the distal end of the sleeve 1122" or the attenuating member 1124" is integrally disposed within the sleeve 1122" or disposed on the interior of the sleeve 1122", the entire attenuating member 1124" may be covered (unexposed) by the sleeve 1122", the entire attenuating member 1124" may be exposed, or a portion (for example, distal portion) of the attenuating member 1124" may be exposed and another portion (for example, proximal portion) may be covered.

FIG. 18 also illustrates the attenuating member 1124" as being disposed at the distal end of the sheath 1120". The attenuating member 1124", however, may alternatively and/or or additionally as be disposed at the proximal end of the sheath 1120", the central portion of the sheath 1120", any location or multiple locations between the proximal end and distal end of the sheath 1120", or in the entire length or substantially the entire length of the sheath 1120".

The attenuating member 1124" has two purposes. One purpose is to reinforce the sleeve 1122" and/or the sheath 1120", and the other purpose is to reduce the size or prevent the likelihood formation of vapor bubbles exterior of the attenuating member 1124", the sleeve 1122" and/or the sheath 1120". Regarding the reinforcing the sleeve 1122", coupling the attenuating member 1124" with the sleeve 1122" may reduce or prevent the sheath's ability to expand and contract upon creation of the vapor bubbles therein so as to reduce or prevent the sleeve 1122" from applying a hydraulic force or pressure to the vascular occlusion and/or to the walls of the vessel. Reinforcing the sleeve 1122" may minimize and/or prevent the sleeve from bulging, splitting, or delaminating (in the event the sleeve comprises multiple layers), as well as minimize and/or prevent a hole from forming within the sleeve. In the event of one or more occurrences, the difficulty of subsequent translation of the sleeve through the patient's vasculature and/or translation relative to the laser catheter may be increased.

Both the attenuating member 1124" and the sleeve 1122" are constructed of biocompatible materials. Coupling the attenuating member 1124" with the sleeve 1122" forms a rigid or semi-rigid structure within the sheath 1120" such that it applies a small hydraulic force or it does not apply a hydraulic force to the vascular occlusion and/or to the walls of the vessel upon formation of vapor bubbles therein. It may be desirable that the majority or only force(s) applied to the vascular occlusion and/or to the walls of the vessel are a result of the laser-induced pressure waves that pass through the 1120", thereby allowing more precise control over the laser-induced pressure waves.

Regarding the other purpose of the attenuating member 1124", which is to reduce or prevent the formation of vapor bubbles exterior of the attenuating member 1124", the sleeve 1122" and/or the sheath 1120" and continuing to refer to FIG. 18, the openings 1126" within the attenuating member 1124" may prevent the formation and propagation of vapor bubbles on the sheath 1120". The openings 1126" not only allow the laser-induced pressure waves to pass therethrough, but the quantity and size of the openings 1126", particularly with respect to the remainder of the structural mass (or portions thereof 1128") of the sleeve 1122", may also limit the size of the vapor bubbles that can form on the exterior of the sheath 1120". The relationship between the open area and the closed area (or the ratio of the open area to the overall area) within the attenuating member 1124" should be such that a sufficient amount of the laser-induced pressure waves pass through the attenuating member 1124". And the size of the openings 1126" should allow the laser-induced pressure waves to pass therethrough, while also limiting the size of the vapor bubbles that can form on the exterior of the sheath 1120". Accordingly, it may be desirable for the ratio of the open area to the overall area of the attenuating member 1124" to be between 1 percent-99 percent, including any increment therebetween such as 2 percent, 3 percent, 4 percent, 5 percent, 6 percent, 7 percent, 8 percent, 9 percent, 10 percent, . . . , 15 percent . . . 20 percent, . . . , 25 percent, . . . , 30 percent, . . . , 35 percent, . . . , 40 percent, . . . 45 percent, . . . 50 percent, . . . 55 percent, . . . , 60 percent, . . . 65 percent, . . . , 70 percent, . . . 75 percent, . . . , 80 percent, . . . 85 percent, . . . 90 percent, 91 percent, 92 percent, 93 percent, 94 percent, 95 percent, 96 percent, 97 percent, and 98 percent. It may also be desirable for the ratio of the open area to the overall area of the attenuating member 1124" to be within a particular range such as between 5 percent to 95 percent, 10 percent to 90 percent, 15 percent to 85 percent, 20 percent to 80 percent, 25 percent to 75 percent, 30 percent to 70 percent, 35 percent to 65 percent, 40 percent to 60 percent, and 45 percent to 55 percent. Additionally, for any of the above listed ratios it may be desirable for each opening to have a particular size, such as between 10 microns to 10,000 microns (1 millimeter), including any increment therebetween such as 10 microns 12.5 microns 15 microns, 17.5 microns, . . . 20 microns, . . . 30 microns, . . . 40 microns, . . . 50 microns, . . . 75 microns, . . . 100 microns, . . . , 125 microns, . . . , 150 microns, 175 microns, . . . , 200 microns, . . . , 300 microns, . . . , 400 microns, . . . , 500 microns, . . . , 600 microns 700 microns, 800 microns 900 microns 1000 microns, . . . , 2000 microns, . . . , 3000 microns, . . . , 4000 microns, . . . 5000 microns, . . . 6000 microns, . . . , 7000 microns, . . . , 8000 microns, . . . , 9000 microns, . . . , 9100 microns, . . . , 9200 microns, . . . , 9300 microns, . . . , 9400 microns, . . . , 9500 microns, 9600 microns, . . . , 9700 microns, . . . , 9800 microns, . . . , 9900 microns, . . . , and 10,000 microns. It may also be desirable for the size openings 1126" within the attenuating member 1124" to be within a particular range such as between 1000 to 9000 microns, 2000 to 8000 microns, 3000 to 7000 microns. 4000 to 6000 microns, and 4500 to 5500 microns.

The attenuating member's ability to reduce or prevent the formation of vapor bubbles exterior of the attenuating member 1124", the sleeve 1122" and/or the sheath 1120" potentially reduces the existence and/or the size of the vapor bubbles formed on the exterior of the attenuating member 1124", the sleeve 1122" and/or the sheath 1120", which in turn reduces the likelihood that vapor bubbles will be created and expand and contract between the attenuating member 1124", the sleeve 1122" and/or the sheath 1120" and the vasculature wall. And reducing or preventing expansion and contraction of vapor bubbles between the sleeve 1122", and/or the sheath 1120", and the vasculature wall prevent or reduce the likelihood that a hydraulic force or pressure will be applied to the vascular occlusion and/or to the walls of the vessel, thereby preventing and/or minimizing potential damage to the vasculature itself.

Regarding the attenuating member's ability to reinforce the sleeve 1122" and/or the sheath 1120", the attenuating member 1124" may reduce or prevent the sleeve's ability and/or the sheath's ability to expand and contract upon creation of the vapor bubbles therein. Reducing the sleeve's ability and/or the sheath's ability to expand and contract upon the formation of vapor bubbles therein, reduces or prevents the sleeve 1122" and/or the sheath 1120" from applying a hydraulic force or pressure to the vascular occlusion, restriction and/or to the walls of the vessel.

Figure 18A:
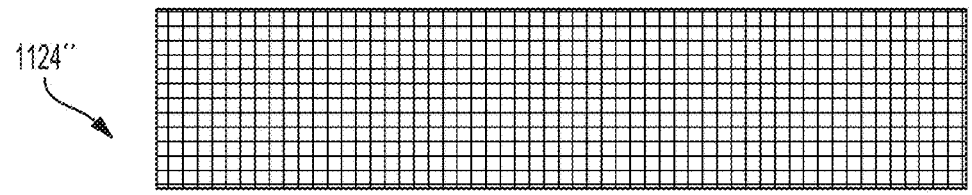
FIG. 18A is a side elevation view of an attenuating member comprising a plurality of square-shaped openings, according to one embodiment of the present disclosure.
Figure 18B:
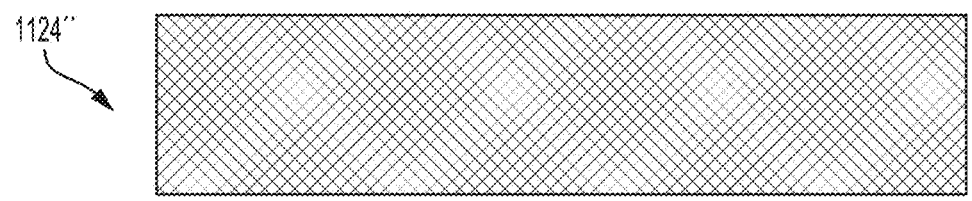
FIG. 18B is a side elevation view of an attenuating member comprising a plurality of diamond-shaped openings, according to one embodiment of the present disclosure.
Figure 18C:
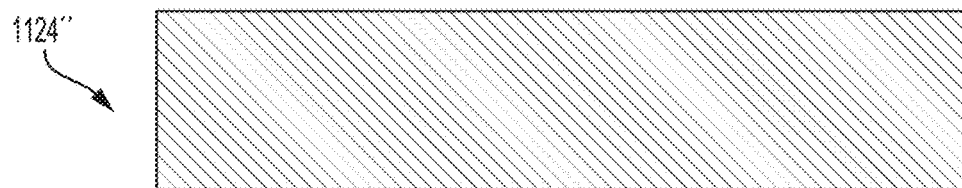
FIG. 18C is a side elevation view of an attenuating member comprising a plurality of openings formed by a helical structure wound in a particular direction, according to one embodiment of the present disclosure.
Figure 18D:
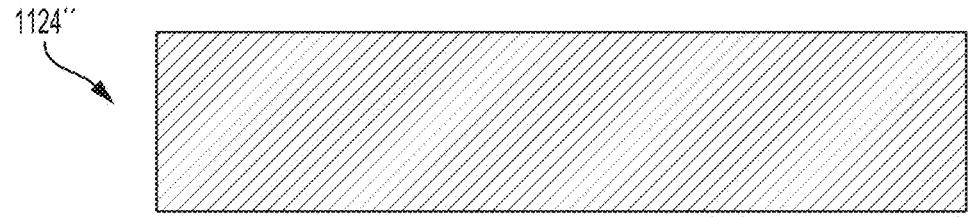
FIG. 18D is a side elevation view of an attenuating member comprising a plurality of openings formed by a helical structure wound in a particular direction, according to one embodiment of the present disclosure.
Figure 18E:
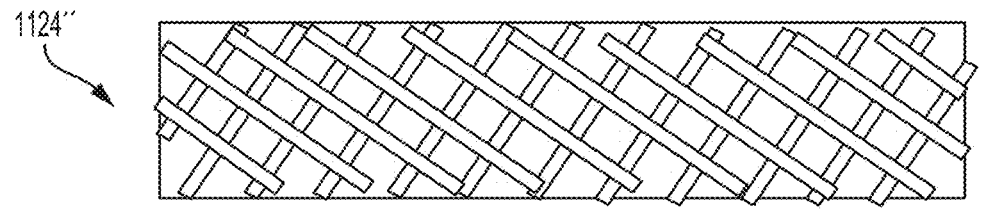
FIG. 18E is a side elevation view of an attenuating member comprising a plurality of openings formed by a helical wound ribbons, according to one embodiment of the present disclosure.
Figure 18F:
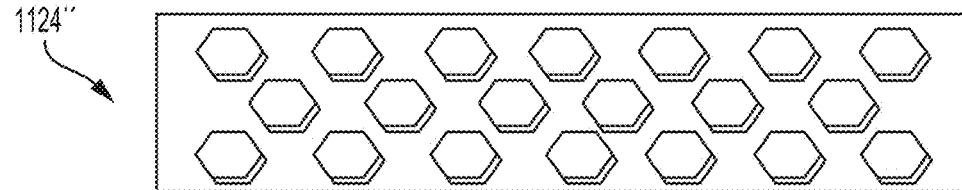
FIG. 18F is a side elevation view of an attenuating member comprising a plurality of hexagon-shaped openings, according to one embodiment of the present disclosure.

The openings 1126" in the attenuating member 1124" depicted in FIG. 18 are shown as hexagons, which are disposed around the circumference of the attenuating member 1124", as well as along its length. Although the openings 1126" in the attenuating member 1124" are illustrated as hexagons, the openings may have an alternate shape, such as a circle, oval, triangle, square, rectangle, helix, polygon, diamond, pentagon, heptagon, octagon, nonagon, and decagon. For example, FIG. 18A illustrates a side view of a attenuating member 1124" comprising a plurality of square-shaped openings; FIG. 18B is a side view of a attenuating member 1124" comprising a plurality of diamond-shaped openings, FIG. 18C is a side view of a attenuating member 1124" comprising a plurality of openings formed by a helical structure wound in a particular direction (for example, clockwise or left to right) while FIG. 18D is a side view of a attenuating member 1124" comprising a plurality of openings formed by a helical structure wound in an alternate direction (for example, counter-clockwise or right to left). Additionally, the two helically formed attenuating members 1124" may be combined to form the attenuating member 1124" depicted in FIG. 18E. The attenuating member 1124" depicted in FIG. 18E is similar to the attenuating member 1124" depicted in FIG. 18B, but the attenuating member 1124" depicted in FIG. 18B is braided and the attenuating member 1124" depicted in FIG. 18E is wound or formed by one or two hypotubes. Additionally, the structural mass (or portions thereof) of the attenuating member 1124" depicted in FIG. 18E is larger than the structural mass (or portions thereof 1128") of the attenuating member 1124" depicted in FIG. 18B because braided materials are generally smaller in size. Referring to FIG. 18F, the structural mass (or portions thereof) of the attenuating member 1124" are substantial in comparison to the size of the hexagonal openings.

Figure 19:
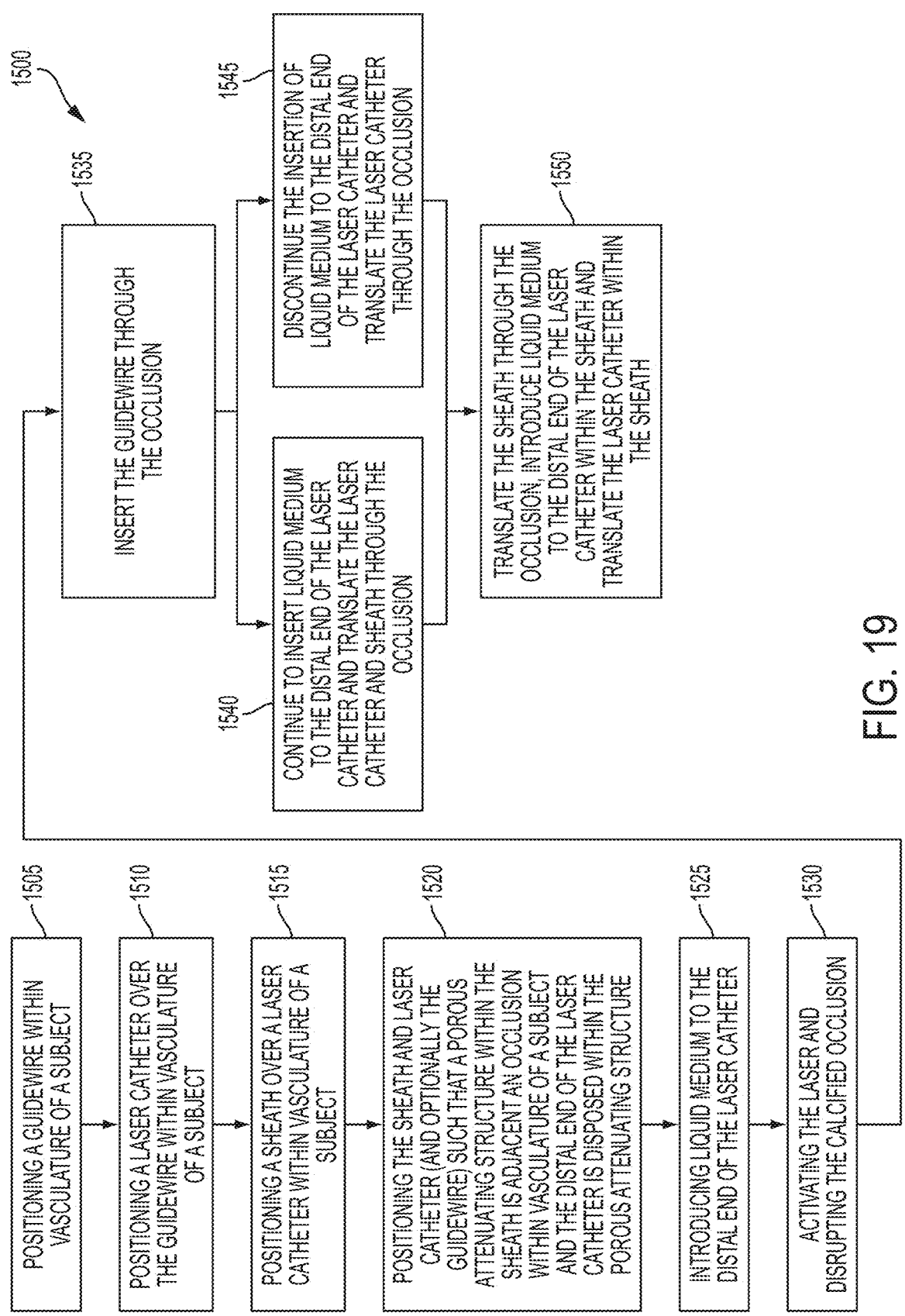
FIG. 19 is a representative flow diagram of a method of treating a subject using a laser catheter and sheath, according to one embodiment of the present disclosure.

Referring to FIG. 19, there is depicted a representative flow diagram of a method 1500 of treating a subject using a laser catheter 1010 (depicted in FIG. 10) and the sheath 1120" (depicted in FIG. 18), and/or using the laser catheter 1010 in conjunction with the sheath 1120 to ablate a vascular occlusion and/or create laser-induced pressure waves in the presence of a liquid medium and disrupt a portion of the vascular occlusion as depicted in FIGS. 11A-11D. The method 1500 may include the step 1505 of positioning a guidewire 1130 within the vasculature 1140 of a subject, the step 1510 of positioning a laser catheter 1010 over the guidewire 1130 within the vasculature 1515, the step of positioning a sheath 1120 over the laser catheter 1010 within the vasculature and the step 1520 of positioning the sheath 1120 and laser catheter 1010 (and optionally the guidewire 1130) adjacent an vascular occlusion 1150 within the vasculature 1140 of a subject. Referring again to FIG. 11A, positioning the sheath 1120 and laser catheter 1010 adjacent the vascular occlusion 1150 creates a cavity for the liquid medium to collect distally of the laser catheter 1010, particularly distally of the emitters/optical fibers of the laser catheter 1010.

FIG. 11A depicts the distal end of the laser catheter 1010 proximal of the distal end of the sheath 1120. However, it is envisioned that the distal end of the laser catheter 1010 may be disposed at or distally of the distal end of the sheath 1120, as long as there is liquid medium between the emitters/optical fibers of the laser catheter 1010 and the vascular occlusion 1150. The axial locations of the laser catheter 1010 and the sheath 1120 may be adjusted by translating either or both components with respect to one another. In order to visualize the respective locations of the laser catheter 1010 and the sheath 1120 under fluoroscopy, the laser catheter 1010 and the sheath 1120 may include radiopaque markers at any corresponding locations along their lengths.

Continuing to refer to FIG. 11A, once the sheath 1120 and laser catheter 1010 are disposed adjacent the vascular occlusion 1150, the liquid medium may be introduced to the distal end of the laser catheter as set forth in step 1525 of FIG. 19. Continuing to refer to FIG. 19, step 1530 includes activating the laser to create laser-induced pressure waves in the presence of the liquid medium and disrupting a portion of the vascular occlusion, particularly the calcified cap of the vascular occlusion. The laser catheter 1010 and sheath 1120 may be used to traverse the entire vascular occlusion 1150, as set forth in step 1540 of FIG. 19 (and optionally step 1535 of FIG. 19), or only disrupt a portion of the vascular occlusion 1150. If the laser catheter 1010 and sheath 1120 are only used to disrupt a portion of the vascular occlusion 1150, then the guidewire 1130 may penetrate and traverse the vascular occlusion 1150. For example, FIG. 11B depicts the guidewire 1130 penetrating and traversing the vascular occlusion 1150.

Referring to FIG. 11C, assuming that the laser catheter 1010 and sheath 1120 are only used to disrupt a portion of the vascular occlusion 1150', the laser catheter 1120 may be used to traverse the vascular occlusion 1150 without the sheath 1120. Referring to step 1545 of FIG. 19, the insertion of the liquid medium may be discontinued and the laser catheter 1010 may be used to ablate vascular occlusion as the laser catheter 1150 passes over the guidewire 1130 through the vascular occlusion 1150' while the sheath 1120 remains proximal of the vascular occlusion.

Referring to step 1550 of FIG. 19 and once the entire vascular occlusion has been traversed by the laser catheter 1010, the opening created by the laser catheter 1010 should be large enough to translate the sheath 1120 distally and through the vascular occlusion. At this point, both the distal end of the sheath 1120 and the distal end of the laser catheter 1010 should be distally of the vascular occlusion. At this point, referring to FIG. 11D, the laser catheter 1010 is able to translate proximally while the sheath 1120 remains stationary within the vascular occlusion. Upon introducing the liquid medium into the sheath 1120 in front of the laser catheter 1010, the laser may be activated, thereby creating laser-induced pressure waves in the presence of the liquid medium. At least a portion of the laser-induced pressure waves are directed radially, and as the laser catheter 1010 translates proximally within the sheath 1120, the laser-induced pressure waves transmit through the sheath 1120 and/or the sheath 1120 itself expands and contracts, thereby disrupting the remainder of the vascular occlusion 1150'".

To ensure that the majority of the remainder of the vascular occlusion 1150'" is disrupted, and if desired, disrupt the intraluminal layer and/or the tissues of the blood vessel and the vascular occlusion, the laser catheter 1010 may be repeatedly translated distally and proximally within the sheath 1120. As discussed above, disruption of the intraluminal layer and/or tissues of the blood vessel and the vascular occlusion, can improve the vasculature's ability to absorb drugs, particularly when such drugs are applied with a drug eluting balloon. Also, it is contemplated that prior to, during and/or after any step in the process outlined in FIG. 19, the laser catheter 1010 may be used individually to ablate a portion of the vascular occlusion, or the laser catheter 1010 may be used in conjunction with the sheath 1120.

As discussed above, transmitting pulses of light energy from an emitter into a liquid medium creates laser-induced pressure waves and/or vapor bubbles and cavitation events resulting in additional pressure waves that disrupt at least a portion of a vascular occlusion. The catheter may include a guidewire lumen through which a guidewire can pass and cross the vascular occlusion. It may also be desirable to excite and vibrate the guidewire to increase the guidewire's ability to pierce and cross the vascular occlusion. Accordingly, the present disclosure also contemplates directing the laser light energy emitted by the emitter into the liquid medium in a direction which causes the liquid medium to propagate pressure waves toward the guidewire lumen and/or guidewire such that the pressure waves excite and vibrate the guidewire.

Referring to FIG. 20, there is depicted a cross-sectional view of the distal end of system 1610 including a laser catheter 1612 radially disposed within a sheath 1614. As shown, the distal end of the catheter 1612 includes one or more layers of optical fibers 1616 arranged circumferentially around an inner guidewire lumen 1618 that receives a guidewire 1620. The inner layer of optical fibers 1616 extends to the distal tip 1626 of the catheter 1612 and terminates at the distal emitter 1622 within the catheter 1612. The liquid medium may be introduced distal to the catheter 1612 through a lumen in the catheter 1612 (for example, the guidewire lumen 1618), a lumen in the sheath 1614 (not shown), and/or the lumen or space between the laser catheter 1612 and the sheath 1614.

Continuing to refer to FIG. 20, in addition to having a plurality of optical fibers 1616 and a guidewire lumen 1618, the catheter 1612 may also include an outer band 1624 that surrounds the distal tip 1626, thereby increasing the strength and rigidity of the distal tip 1626. As mentioned above, the present disclosure contemplates directing the laser light energy emitted by the emitter 1622 into the liquid medium in a direction which causes the liquid medium to propagate pressure waves toward the guidewire lumen 1618 and/or the guidewire 1620 such that the pressure waves excite and vibrate the guidewire 1620. A means for directing laser light emitted from the emitter 1622 towards the guidewire lumen 1618 or the guidewire 1620 includes disposing the emitter 1622 proximate the distal tip 1626 of the catheter 1612 and/or proximate the distal end of the outer band 1624 such that the emitter 1622 is recessed from the distal tip 1626 of the catheter 1612 and/or proximate the distal end of the outer band 1624 along the longitudinal axis of the catheter 1612. By recessing the emitter 1622 from the distal tip 1626 of the catheter 1612 and/or proximate the distal end of the outer band 1624, the pressure waves may be directed toward the guidewire lumen 1618 and/or the guidewire 1620.

An additional means for directing laser light emitted from the emitter 1622 towards the guidewire lumen 1618 and/or the guidewire 1620 includes directing the emitter 1622 toward the guidewire lumen 1618 or the guidewire 1620. For example, as discussed above, the term "emitter" as used herein may refer to an end portion of a fiber or an optical component that emits light from a distal end thereof. The emitter 1622 is directed towards the guidewire lumen 1618 and/or the guidewire 1620 because the optical fiber is tapered in a manner that the light emitted therefrom is directed radially inward towards the guidewire lumen 1618 and/or the guidewire 1620. As illustrated in FIG. 20, the guidewire lumen 1618 and/or guidewire 1620 may extend longitudinally distal of the emitter 1622. Accordingly, as the laser light is emitted from the emitter 1622, the light interacts with the liquid medium, and the liquid medium absorbs the light energy, thereby creating laser-induced pressure waves and/or vapor bubbles and additional resultant pressure waves that cause the guidewire lumen 1618 and/or guidewire 1620 to excite and/or vibrate.

Referring to FIG. 20', there is depicted an alternate embodiment of the present disclosure, particularly an alternate embodiment of a means for directing laser light emitted from the emitter 1622 towards the guidewire lumen 1618 and/or the guidewire 1620. Similar to the embodiment discussed above with respect to FIG. 20, the system 1610' in FIG. 20' includes a catheter 1612' having a plurality of optical fibers 1616, a guidewire lumen 1618, and an outer band 1624 that surrounds the distal tip 1626. This embodiment also includes a cap 1628 having a guidewire lumen 1630 extending therethrough.

The cap 1628 can be either removably coupled to the catheter 1612', particularly removably coupled to the outer band 1624, or the cap 1628 can be permanently affixed to the catheter 1612', particularly permanently affixed to the outer band 1624. The cap 1628 includes a proximal (for example, interior) side 1632 and a distal (for example, exterior) side 1634. The interior side 1632 is tapered such that a cavity 1636 forms between the distal end of the catheter 1612' and the interior side 1632 of the cap 1628, thereby allowing the liquid medium to enter and collect within the cavity 1636. Although FIG. 20' is depicted as having a catheter 1612' with a flush distal end and a tapered, recessed cap 1628 to create the cavity 1636 between the catheter 1612' and the cap 1628 for the liquid medium to collect, the present disclosure also contemplates having a catheter with a recessed distal end, as depicted in FIG. 20, that could be used in conjunction with a cap 1628 having a flush or recessed interior side 1632 to create a cavity for the liquid medium to collect. Accordingly, as the laser light is emitted from the emitter 1622, the light interacts with the liquid medium within the cavity, and the liquid medium absorbs the light energy, thereby creating laser-induced pressure waves and/or vapor bubbles and additional resultant pressure waves that cause the guidewire lumen 1618 and/or guidewire 1620 to excite and/or vibrate.

The sheath 1614 may be, for example, any of the sheaths described herein. In some embodiments, the sheath 1614 may be the sheath 1140 shown in FIGS. 11A-11D, and the catheter 1612 or 1612' may be translatably carried therein. Referring now to FIGS. 20" and 20'", systems 1610" and 1610'" include laser catheters 1612 and 1612', respectively. The systems 1610" and 1610" also include a sheath 1614' that translatably carries the catheters 1612 and 1612', respectively. The sheath 1614' may be the sheath 1120" shown in FIGS. 18-18E. That is, the sheath 1614' includes a sleeve or jacket 1122" and an attenuating member 1124", which may be any of the attenuating members described herein.

The attenuating member 1124" has multiple purposes, as follows: (1) reinforcing the sleeve 1122" and/or the sheath 1614'; (2) reducing or preventing the formation of vapor bubbles exterior of the attenuating member 1124", the sleeve 1122" and/or the sheath 1614'; (3) redirecting at least a portion of the pressure waves toward the guidewire lumen 1618 and/or guidewire 1620 to excite and/or vibrate the guidewire 1620. Accordingly, the attenuating member 1124" acts as (1) a means for reinforcing the sleeve 1122" and/or the sheath 1614'; (2) a means for reducing or preventing the formation of vapor bubbles exterior of the attenuating member 1124", the sleeve 1122" and/or the sheath 1614'; (3) a means for redirecting at least a portion of the pressure waves toward the guidewire lumen 1618 and/or guidewire 1620 to excite and/or vibrate the guidewire 1620.

Further details regarding the first and second purposes of the attenuating member 1124" are described in connection with FIG. 18. Regarding the ability of the attenuating member 1124" to redirect at least a portion of the pressure waves toward the guidewire lumen 1618 and/or guidewire 1620 to excite and/or vibrate the guidewire 1620, the pressure waves or portion of the pressure wave(s) that do not pass through the attenuating member 1124" may be redirected by the attenuating member 1124" toward the guidewire lumen 1618 and/or guidewire 1620 to excite and/or vibrate the guidewire 1620. The sizes of the openings 1126" of the attenuating member 1124" (see FIG. 18) may be selected to control the amplitude or direction of the pressure waves that are reflected toward the guidewire lumen 1618, guidewire 1620 and/or targeted tissue.

Also, similar to the discussion included above with respect to FIG. 18 the attenuating member 1124" depicted in FIGS. 20" and 20' is shown at the distal end of the sheath 1614'. The attenuating member 1124", however, may alternatively and/or additionally as be disposed at the proximal end of the sheath 1614', the central portion of the sheath 1614', any location or multiple locations between the proximal end and distal end of the sheath 1614', or in the entire length or substantially the entire length of the sheath 1614'. Therefore, as the catheter 1612 or 1612' translates within the sheath 1614', the guidewire 1620 will continue to excite and/or vibrate.

Figure 21:
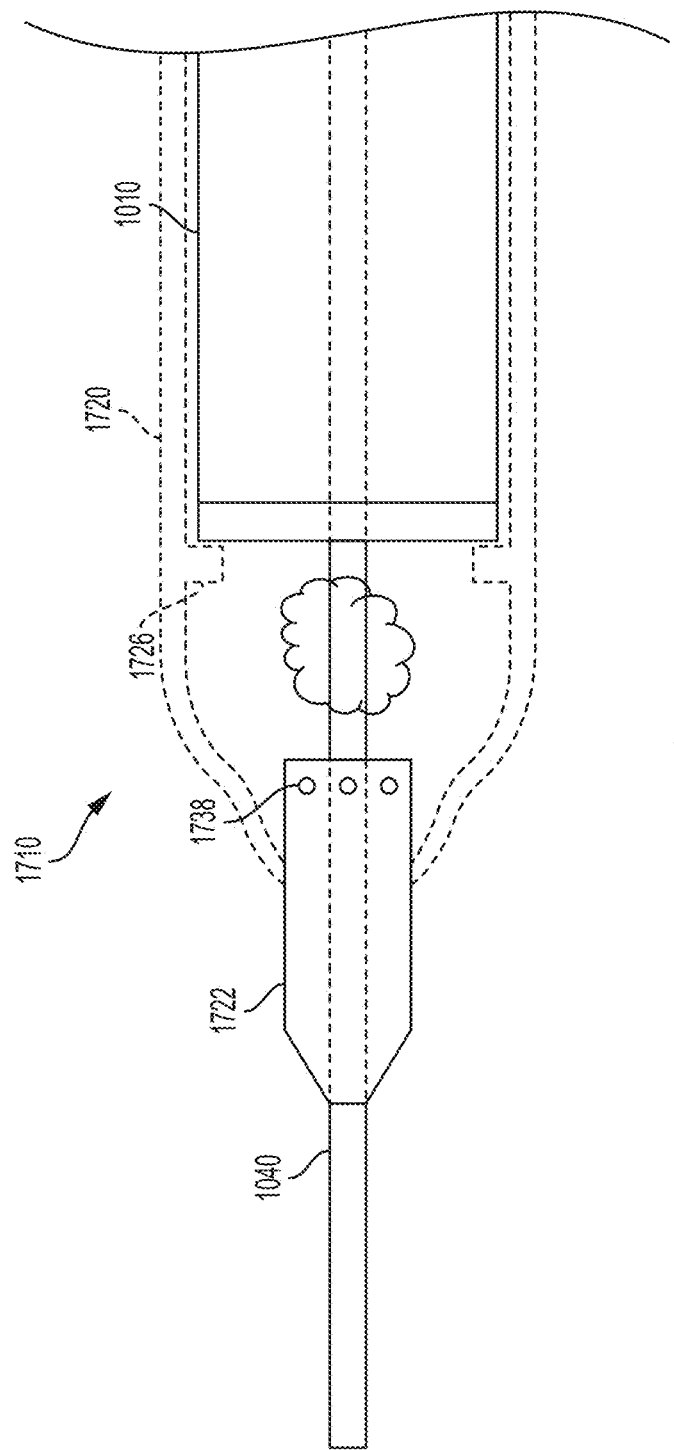
FIG. 21 is a representative side view of a catheter system including a laser catheter and a sheath having a sealable valve, according to an embodiment of the present disclosure.
Figure 22:
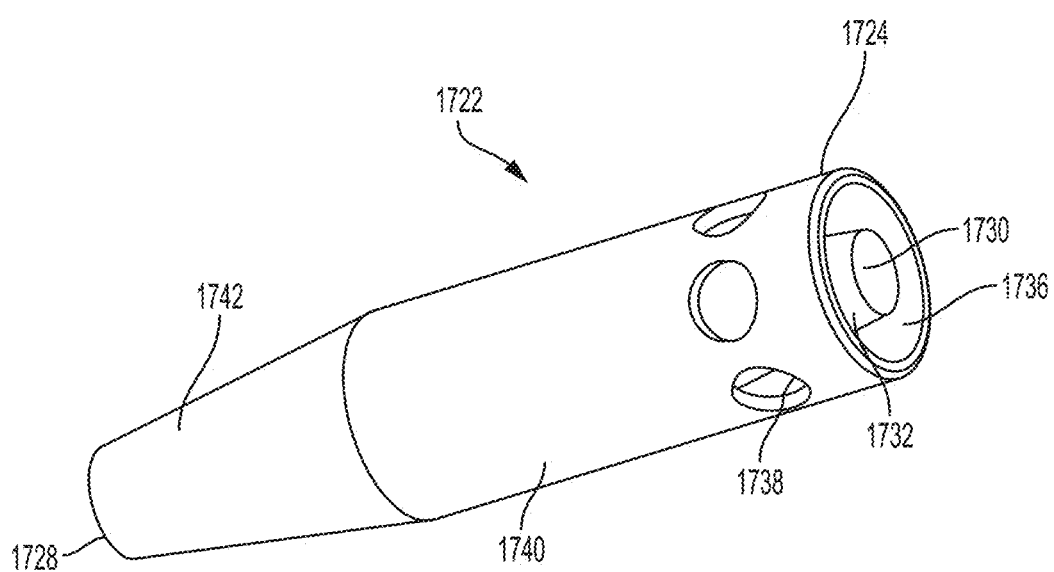
FIG. 22 is an enlarged representative perspective view of the sealable valve of the catheter system depicted in FIG. 21.

As described above, for example, with reference to FIG. 13, catheter systems according to embodiments of the present disclosure may have distal tips that are fully or partially closed. In some of these embodiments, it may be desirable to seal the sheath with the guidewire upon introduction of the liquid medium to the closed distal tip. FIGS. 21-22B illustrate a catheter system 1710 according to such an embodiment. That is, the catheter system 1710 includes a sheath 1720 (which is hidden in FIG. 21 to illustrate internal components of the catheter system 1710) that has a partially-closed tip 1722. The sheath 1720 carries a laser catheter, such as the laser catheter 1010 described herein, and the laser catheter 1010 may translate distally and/or proximally within the sheath 1720. As shown in FIG. 21, the sheath 1720 may taper proceeding distally toward the tip 1722. Alternatively, the sheath 1720 may include a flat surface that receives the tip 1722. As another alternative, the tip 1722 may have a similar size to the lumen of the sheath 1720 and be press-fittingly received in the lumen. In order to ensure that a cavity remains between the distal end of the laser catheter 1010 and the proximal end 1724 of the tip 1722 of the sheath 1720, the sheath 1720 may include one or more internal stops 1726. The shape of the tip 1722 may be configured similar to the tips 180 illustrated and described with respect to FIGS. 2-6 such that the catheter system 1710, including the laser catheter tip 1722, is configured such that the energy produced by the pressure waves is captured within the cavity and the forces generated by the pressure waves propagate longitudinally, including in a forward (that is, parallel with the vessel) direction, thereby increasing the tip's ability to disrupt, destroy and/or penetrate the vascular occlusion.

The tip 1722 includes the proximal end 1724, a distal end 1728, and a lumen 1730 extending therethrough from its proximal end 1724 to its distal end 1728. The tip 1722 also includes a valve that seals the intersection of the tip 1722 and the guidewire 1040 as the guidewire 1040 passes through the guidewire lumen 1730. One example of a valve is that which is depicted in FIGS. 22-22B which illustrate a flange 1732 that is disposed at and/or toward the proximal end 1724 of the tip 1722.

Figure 22A:
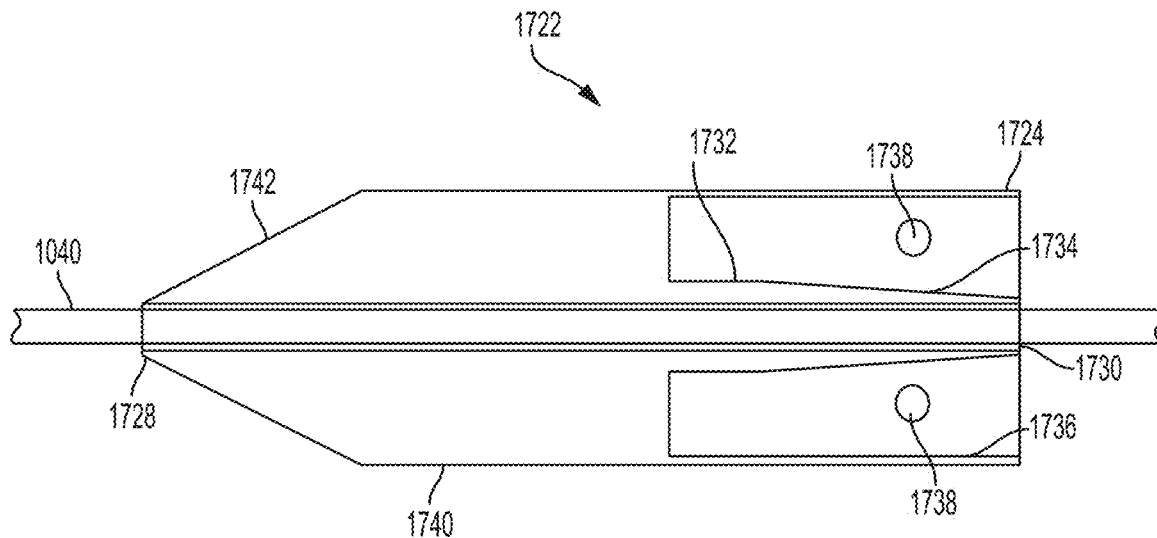
FIG. 22A is an enlarged representative cross-sectional side view of the sealable valve of the catheter system depicted in FIG. 21 in an unsealed configuration with respect to a guidewire.
Figure 22B:
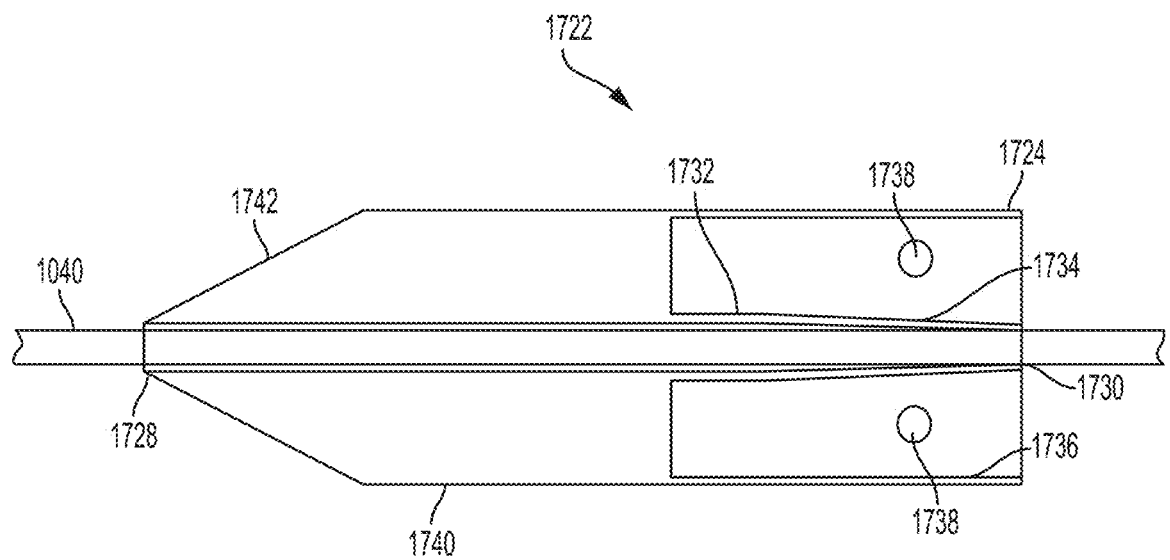
FIG. 22B is an enlarged representative cross-sectional side view of the sealable valve of the catheter system depicted in FIG. 21 in a sealed configuration with respect to a guidewire.

Referring back to FIGS. 21-22B, upon introducing the guidewire 1040 through the lumen 1730 of the laser catheter 1010 and into the guidewire lumen 1730 of the tip 1722, the guidewire 1040 and tip 1722 are slidably coupled such that the tip 1722 can slide over the guidewire 1040 (or the guidewire 1040 can slide through a lumen 1730 of the tip 1722), as depicted in FIG. 22A. As illustrated in this figure, there is a gap (or opening) caused by the guidewire lumen 1730 between the flange 1732 and the guidewire 1040. If the gap is maintained during introduction of the liquid medium into the distal end of the catheter system 1710 (via, for example, the opening or gap between the laser catheter 1010 and the sheath 1720), the liquid medium would travel through the guidewire lumen 1730 and into the patient's vasculature, which may be undesirable. The flange 1732, which may include a tapered portion 1734 that tapers from the tip's distal end 1728 toward its proximal end 1724, is configured to radially collapse upon introduction of the liquid medium into the distal end of the catheter system 1710 due to the increased fluid pressure on the flange 1732. The increased fluid pressure on the flange 1732 actuates the flange 1732 and moves it radially inward toward the guidewire lumen 1730 such that the gap between flange 1732 and the guidewire 1040 closes, thereby creating a seal between the between flange 1732 and the guidewire 1040, as depicted in FIG. 22B. The reduced thickness of the tapered portion 1734 of the flange 1732 as the flange 1732 tapers radially inward towards the guidewire lumen 1730 as the flange 1732 progresses from the distal end 1728 toward the proximal end 1724 increases the flange's ability to flex upon exposure to the pressure created upon introduction of the liquid medium. Upon removal of the liquid medium from the distal end of the catheter system 1710, the pressure within the catheter system 1710, the pressure on the flange 1732 decreases, and the flange 1732 naturally retracts to its original position as depicted in FIG. 22A, thereby reestablishing the gap between the tip 1722 and the guidewire 1040 so that the two components may slide with respect to one another. Accordingly, the flange 1732 acts as sealable valve within the tip 1722, and the flange 1732 is actuated with the introduction and removal of the liquid medium into and from the distal end of the catheter system 1710.

Although the tapered portion 1734 illustrated in FIGS. 22A and 22B tapers from the tip's distal end 1728 toward its proximal end 1724, the direction of the taper may be reversed such that the tapered portion 1734 tapers from the tip's proximal end 1724 toward its distal end 1728. Additionally, the flange 1732 may taper towards any portion along its length such that a portion of the flange 1732 is thinner at one or more locations along its length in comparison to other locations along its length. Accordingly, upon an increased fluid pressure being imparted on the flange 1732, thinner portion of the flange 1732 actuates and moves radially inward toward the guidewire lumen 1730 such that the gap between flange 1732 and the guidewire 1040 closes, thereby creating a seal between the between flange 1732 and the guidewire 1040.

The tip 1722 may be constructed from any type of compressible or compliant biopolymers, such as silicones or flouro-polymers, compliant adhesives, etc. The configuration of the tip 1722 depicted in these figures includes an exterior wall 1736 and the flange 1732 disposed radially therein, to create a gap therebetween for the liquid medium to enter and actuate the flange 1732. The flange 1732 is also depicted as being disposed toward the proximal end 1724 of the tip 1722, which itself is depicted as tubular, and its distal end 1728 has an inward taper that tapers distally from the exterior wall 1736 towards the guidewire lumen 1730. Although the tip 1722 is depicted as including particular components and shapes, the present disclosure shall include other shapes and components known to one of skill in the art. Moreover, the tip 1722 may alternatively include a self-sealing tube constructed of any type of compressible or compliant biopolymers, such as silicones or flouro-polymers, compliant adhesives, etc. For example, the tip 1722 may include a tube that has a lumen 1730 passing therethrough such that upon insertion of a guidewire, the lumen expands, and upon removable of the guidewire, the lumen contracts, thereby appearing as a slit.

Continuing to refer to FIGS. 21-22B, the tip 1722 may include one or more openings 1738 through its exterior wall 1736. The openings 1738 allow the liquid medium to reach the flange 1732 not only from the gap between the flange 1732 and the exterior wall 1736 at the proximal end 1724 of the tip 1722 but also at a location distal the proximal end 1724 of the tip 1722. Allowing the liquid medium to reach the flange 1732 at or toward its distal portion, potentially increases the likelihood and effectiveness of actuating the flange 1732. Although the tip 1722 is illustrated as having a tubular section 1740 from its proximal end 1724 and a tapered section 1742 from the end of its tubular section 1740 toward the tip's distal end 1728, the scope of this disclosure shall include other shapes for the tip 1722.

As discussed herein, as the laser light is emitted from the emitter(s), the light interacts with the liquid medium, and the liquid medium absorbs the light energy, thereby creating vapor bubbles within the catheter system 1710. The openings 1738 within the tip 1722 may reduce the size of the bubble formed within the catheter system 1710 and/or reduce the likelihood that the bubble will expand toward the distal end of the catheter system 1710.

In some embodiments, the devices and methods of the present disclosure can also be used deliver laser-induced pressure waves to ablate a vascular occlusion using a substantially solid light absorbing material instead of liquid medium. In some circumstances, pairing a laser that emits a specific wavelength of light with a light absorbing material designed to absorb light at that wavelength can significantly increase the energy efficiency of the resultant laser-induced pressure waves produced by the reaction. The use of such pairings can ultimately reduce the energy input required to treat a vascular occlusion, which can increase the safety of the procedure and reduce costs. For example, the catheters according to embodiments of the present disclosure can be filled with air or a substantially inert liquid medium (for example, saline) instead of contrast medium, which can significantly reduce the amount and size of vapor bubbles produced along with the laser-induced pressure waves. Because the laser-induced pressure waves can propagate outside of the catheter to ablate a vascular occlusion, it can be advantageous in some circumstances to reduce (for example, by filling the catheter with saline) or eliminate (for example, by filling the catheter with air or inert gas) the production of vapor bubbles. In other cases, liquid medium delivered to the distal end of the catheter can be pre-treated to remove the amount of gas dissolved in it using methods known to one of ordinary skill in the art based on the present disclosure, as this can also reduce the amount of vapor bubbles generated along with the laser-induced pressure waves.

Suitable light absorbing material can be any agent capable of absorbing light energy and producing a laser-induced pressure wave. For example, the light absorbing material can contain an aromatic hydrocarbon with iodine bonded to it, such as iodinated x-ray contrasts. Low osmolar, non-ionic, iodinated, and radio-opaque contrasts are also suitable light absorbing materials that can be used to produce laser-induced pressure waves. Other light absorbing materials include, but are not limited to, iodinated contrasts such as Diatrizoic acid, Metrizoic acid, Iodamide, Iotalamic acid, Ioxitalamic acid, Ioglicic acid, Acetrizoic acid, Iocarmic acid, Methiodal, Diodone, Metrizamide, Iohexol, Ioxaglic acid, Iopamidol, Iopromide, Iotrolan, Ioversol, Iopentol, Iodixanol, Iomeprol, Iobitridol, Ioxilan, Iodoxamic acid, Iotroxic acid, Ioglycamic acid, Adipiodone, Iobenzamic acid, Iopanoic acid, Iocetamic acid, Sodium iopodate, Tyropanoic acid, Calcium iopodate, Iopydol, Propyliodone, Iofendylate, Lipiodol, non-iodinated contrasts such as Barium sulfate, MRI contrast agents such as Gadobenic acid, Gadobutrol, Gadodiamide, Gadofosveset, Gadolinium, Gadopentetic acid, Gadoteric acid, Gadoteridol, Gadoversetamide, Gadoxetic acid, Ferric ammonium citrate, Mangafodipir, Ferumoxsil, and Ferristene Iron oxide nanoparticles, Perflubron, Glucose and other carbohydrates, Albumen and other proteins, Nitroglycerin or other vasodilators, Hydrocarbons such as Oils, Alcohols, or other organic functional groups (Amines, Alkanes, Carboxyl, and the like), blood/tissue products such as Platelet Rich Plasma (PRP), packed red cells, plasma, platelet, fat, Charcoal, biocompatible materials such as stainless steel, biopolymers, and bioceramics, or other pharmacological agents which contain a combination of aromatic carbon rings and functional groups such as Salicylic acid, Acetylsalicylic acid, Methyl salicylate, Mesalazine, Aspirin, Acetaminophen, Ibuprofen, Clopidogrel, or other pharmacological and/or biological agents which may be compatible with the medical procedures described herein.

Suitable light absorbing material can also include those materials capable of absorbing wavelengths in the UV spectrum. For example, light absorbing materials can include, but are not limited to, PABA, Padimate 0, Phenylbenzimidazole sulfonic acid, Cinoxate, Dioxybenzone, Oxybenzone, Homosalate, Menthyl anthranilate, Octocrylene, Octyl methoxycinnamate, Octyl salicylate, Sulisobenzone, Trolamine salicylate, Avobenzone, Ecamsule, 4-Methylbenzylidene camphor, Tinosorb M, Tinosorb S, Tinosorb A2B, Neo Heliopan AP, Mexoryl XL, Benzophenone-9, Uvinul T 150, Uvinul A Plus, Uvasorb HEB, Parsol SLX, or Amiloxate, Silicon and its various atomic structures, Cadmium telluride, Copper indium gallium selenide, Gallium arsenide, Ruthenium metalorganic dye, Polyphenylene vinylene, Copper phthaloncyanine, Carbon fullerenes and derivatives, Carbon compounds such as Graphite, Graphene, Diamond, Charcoal, Titanium and oxides, Nickel and oxides, Gold, Silver, Zinc and oxides, Tin and oxides, Aluminum and oxides, or alloys or ceramics of the preceding metals.

Light absorbing material may be combined with various other compounds to facilitate their attachment to a substrate. For example, light absorbing materials may be combined with various compounds (for example, solubilizing agents) that aid in the generation of a solution or mixture comprising the light absorbing material, which can be used to coat the substrate. In some embodiments, a biodegradable and biocompatible hydrophobic polymer may be used as a light absorbing material. For example, the biodegradable and biocompatible hydrophobic polymer may be poly(glycerol sebacate acrylate) (PGSA), or variations and combinations thereof, which can be crosslinked using ultraviolet light. Ultraviolet light may be emitted from the distal end of a catheter, which may be disposed within or outside of a sheath, to activate the PGSA, for example.

Other light absorbing material can also include agents having adhesive-like properties, and in some cases, the light absorbing properties of these agents can be in addition to, or independent of, their use as adhesives. For example, light absorbing materials can include, but are not limited to, cyanoacrylates, bovine serum albumin (BSA)-glutaraldehyde, fibrin sealants, gelatin matrix thrombin, gelatin sponge, oxidized cellulose, collagen sponge, collagen fleece, recombinant factor VIIa, and the like. In some embodiments, the light absorbing material may comprise hydrophobic functional groups, such as hexanoyl (Hx; C6), palmitoyl (Pam; C16), stearoyl (Ste; C18), and oleoyl (Ole; C18 unsaturated) groups, so as to resist being washed out or disengaged from their substrate in predominately aqueous environments (for example, vascular tissue). Such light absorbing materials can include, but are not limited to, 10Ole-disuccinimidyl tartrate, 10Ste-disuccinimidyl, and variations and combinations thereof.

Light absorbing material can be configured to exhibit high absorption of light energy from an emitter. Light energy can be emitted at any suitable wavelength capable of generating laser-induced pressure waves. Light energy can be emitted between about 1 nanometer and about 1 millimeter. In some cases, light can be emitted from about 10 nanometers to about 5000 nanometers. In some cases, light can be emitted from about 100 nanometers to about 1000 nanometers. In some cases, light can be emitted from about 250 nanometers to about 750 nanometers. In some cases, light can be emitted from about 300 nanometers to about 600 nanometers. In still other cases, light can be emitted from about 300 nanometers to about 350 nanometers.

In general, the light absorbing material can be located anywhere within a catheter, so long as it generally intersects with the path of light emitted from the optical fibers. In some embodiments, the light absorbing material may be substantially solid (for example, stable in a generally solid state, such as metals and metal alloys). Substantially solid light absorbing material can be used to construct various portions of the components of the catheter, and/or substantially solid light absorbing material can be used to construct a separate structure that is independent of another catheter component.

In some embodiments, the light absorbing material can be applied to a separate supporting structure (that is, a support structure that is not predominately made of light absorbing material, or a support structure that is not being used as a light absorbing material) and used to generate laser-induced pressure waves using the devices and methods of the present disclosure. In some embodiments, the light absorbing materials are stable only in liquid, gel, or semi-liquid forms. In these embodiments, the light absorbing material can be included as part of a formulation or coating that is suitable for application to a support structure, such as impregnated in hydrogel or other solid support matrix. In some embodiments, the light absorbing materials can be part of a formulation or coating containing other agents that facilitate their placement on and/or adherence to a support structure. For example, solid absorbing materials can be formulated with coating agents, thickening agents, adhesive agents, and/or other pharmaceutical or biological agents that are suitable for use with the devices and methods of the present disclosure.

Figure 23:
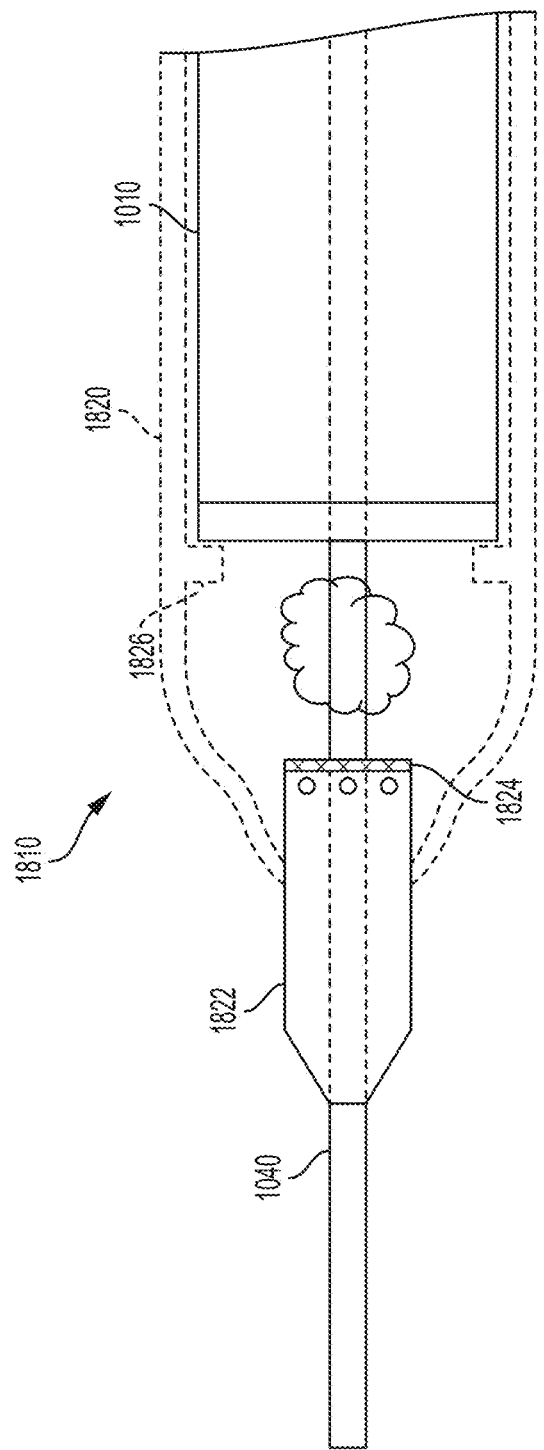
FIG. 23 is a representative side view of a catheter system including a laser catheter, a sheath having a sealable valve, and a light absorbing material support structure, according to an embodiment of the present disclosure.

Referring to FIG. 23, the distal end of a catheter system 1810 including a light absorbing material according to an embodiment of the present disclosure is illustrated. The catheter system 1810 is similar to the catheter system 1710. That is, the catheter system 1810 includes a sheath 1820 (which is hidden in FIG. 23 to illustrate internal components of the catheter system 1810) that has a partially-closed tip 1822. The sheath 1820 carries a laser catheter, such as the laser catheter 1010 described herein, and the laser catheter 1010 may translate distally and/or proximally within the sheath 1820. As shown in FIG. 23, the sheath 1820 may taper proceeding distally toward the tip 1822. Alternatively, the sheath 1820 may include a flat surface that receives the tip 1822. As another alternative, the tip 1822 may have a similar size to the lumen of the sheath 1820 and be press-fittingly received in the lumen. In order to ensure that a cavity remains between the distal end of the laser catheter 1010 and the proximal end of the tip 1822 of the sheath 1820, the sheath 1820 may include one or more internal stops 1826. The shape of the tip 1822 may be configured similar to the tips 180 illustrated and described with respect to FIGS. 2-6 such that the catheter system 1810, including the laser catheter tip 1822, is configured such that the energy produced by the laser-induced pressure waves is captured within the cavity and the forces generated by the laser-induced pressure waves propagate longitudinally, including in a forward (that is, parallel with the vessel) direction, thereby increasing the tip's ability to disrupt, destroy and/or penetrate the vascular occlusion.

The tip 1822 may include the same features and structures as the tip 1722. In addition, the tip 1822 includes a light absorbing material support structure 1824. The light absorbing material support structure 1824 acts as a substrate for the application of light absorbing material, which may be any of the light absorbing materials described herein. Light absorbing material can be applied as a coating, as described herein, on the proximal end of the tip 1822 within the cavity of the catheter system 1810, and light absorbing material support structure 1824 can be positioned such that it generally intersects with the path of the light emitted from the distal end of the laser catheter 1010.

In some embodiments, the light absorbing material can be applied to various surfaces within the catheter system 1810 itself instead of being applied to a support structure. For example, the light absorbing material can be applied as a coating to the inner surface of the catheter system 1810 or portions thereof (such as the inner surface of the sheath 1820). The laser light emitted from the distal end of the laser catheter 1010 can be directed upward and/or outward such that it can react with the light absorbing material to generate a laser-induced pressure wave, without the need for an additional support structure.

Figure 24:
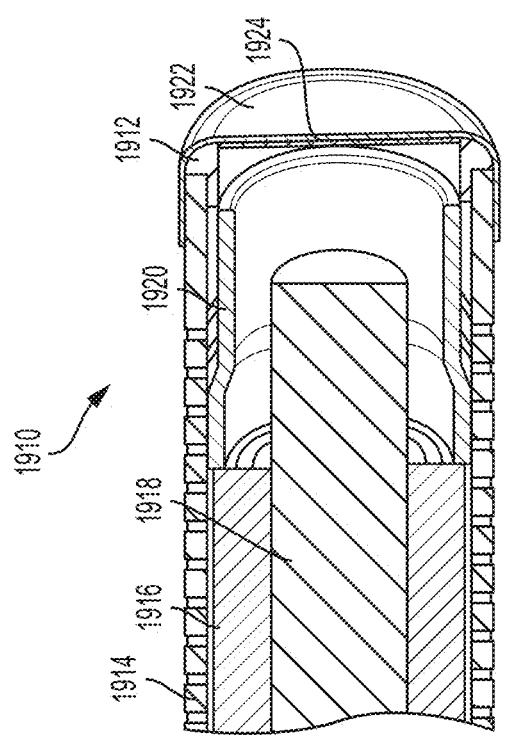
FIG. 24 is a cross-sectional view of a distal portion of a catheter system including a light absorbing material support structure, according to one embodiment of the present disclosure.

Referring to FIG. 24, the distal end of a catheter 1910 including a light absorbing material according to an embodiment of the present disclosure is illustrated. The catheter 1910 is similar to the catheter illustrated in FIG. 5A. That is, the catheter 1910 includes a distal end having a tip 1912 that comprises a non-metallic component in lieu of a metallic (for example, stainless steel) solid or hollow construction. The catheter 1910 includes an outer sheath 1914, an inner sheath 1916 disposed concentrically and/or radially within the outer sheath 1914, and one or more optical fibers 1918 disposed concentrically and/or radially within the inner sheath 1916. The distal end of the outer sheath 1914 is directly coupled (via a press fit and/or a weld) to the tip 1912. The inner sheath 1916 and the one or more optical fibers 1918 are not directly coupled to the tip 1912. Rather, the inner sheath 1916 and the one or more optical fibers 1918 are disposed proximate the tip 1912, thereby forming a cavity among the outer sheath 1914, the inner sheath 1916, one or more optical fibers 1918, and the tip 1912.

The catheter 1910 may include a shield 1920 disposed axially between the distal end of the inner sheath 1916 and the proximal end of the tip 1912, and disposed radially between the one or more optical fibers 1918 and the outer sheath 1914. The shield 1920, which is depicted as a generally cylindrical tube, increases the laser-induced pressure waves' resistance in the radial direction, thereby reducing the ability of the laser-induced pressure waves to travel radially towards the outer sheath 1914. The configuration of the cylindrically-shaped shield 1920 allows for a reduced resistance in the longitudinal direction, in comparison to the radial direction, thereby increasing the tip's ability to translate in a forward/backward direction. The cylindrically-shaped shield 1920 may also be configured such that its diameter is greater (or less) at its proximal end in comparison to its distal end, thereby potentially tapering in either the proximal or distal direction and concentrating the laser-induced pressure waves towards the center of the tip 1912. The shield 1920 may also serve to create a sealed cavity at the distal end of the catheter 1910, thereby preventing the leakage of the liquid medium through the outer sheath 1914 because a portion of the shield overlaps with a portion of the outer sheath 1914 that may be porous.

The inner sheath also includes one or more lumens for passage of liquid medium into the cavity. The distal end(s) of the one or more optical fibers 1918 are proximate, at, or distal the distal end of the inner sheath 1916. Again, one or more emitters are disposed at the distal end of the one or more optical fibers 1918. The emitter(s) are in direct contact with the liquid medium, such that when laser light energy is emitted from the emitter(s), the liquid medium absorbs the emitted light, which in turn produces laser-induced pressure waves and generates vapor bubbles and/or cavitation events that produce additional pressure waves.

The tip 1912 has a circular construction, thereby creating a collar for the distal end of the outer sheath 1914. The tip 1912 also includes a flexible membrane 1922 at its distal end. For example, the membrane 1922 may be constructed of Mylar and be adhesively bonded to the distal end of the tip 1912 in an orientation perpendicular to the longitudinal axis. In addition the membrane may be compliant in order to deflect and engage the shape of the calcified cap, total occlusion or lesion. In some embodiments, the membrane 1922 may be constructed of an elastic or hyperelastic material (for example, nitinol).

The membrane 1922 carries a light absorbing material support structure 1924 within the cavity. The light absorbing material support structure 1924 acts as a substrate for the application of light absorbing material, which may be any of the light absorbing materials described herein. In other embodiments, the light absorbing material support structure 1924 could be carried by the membrane 1922 outside of the cavity, or light absorbing material can be applied as a coating, as described herein, on the membrane 1922 (with the cavity or outside of the cavity). In any case, the light absorbing material can be positioned such that it generally intersects with the path of the light emitted from the distal end of the optical fiber(s) 1918. In some embodiments and as shown in FIG. 24, the light absorbing material support structure 1924 may cover the entire membrane 1922 within the cavity. In other embodiments, the light absorbing material support structure 1924 may partially cover the membrane 1922 within the cavity. In these embodiments, the position and/or size of the light absorbing material support structure 1924 on the membrane 1922 may affect the location of vapor bubble formation and collapse, which in turn may affect the deflected shape of the membrane 1922. In some embodiments, the light absorbing material can be applied to various surfaces other within the catheter 1910 instead of being applied to a support structure. For example, the light absorbing material can be applied as a coating to the inner surface of the shield 1920 or portions thereof.

To treat a subject having a vascular occlusion, the distal end of the catheter 1910, particularly the tip 1912 is positioned adjacent to the vascular occlusion with the membrane 1922 adjacent the vascular occlusion. The liquid medium may be delivered to the cavity from the one more lumens within the inner sheath 1916 through one or more liquid medium ports or between the outer sheath and the inner sheath or laser catheter 1910. When the laser system is activated, light energy travels through one or more optical fibers until the light energy is released from the emitter(s) at the end of the one or more optical fibers. As the light absorbing material and the liquid medium absorb the light energy, a laser-induced pressure wave forms, the liquid medium rapidly displaces outward and inward, creating a vapor bubble. The energy produced by the laser-induced pressure wave and vapor bubble is captured within the closed system provided by the cavity and transferred to the vascular occlusion through the flexible membrane 1922. The transfer of the energy produced by the laser-induced pressure waves to the vascular occlusion is sufficient to disrupt calcium deposits and/or fibrous tissue within the vascular occlusion. The forces generated by the laser induced pressure waves can propagate longitudinally in forward (that is, parallel to the vessel). Pressure waves produced in this manner can also be used to increase vessel compliance prior to performing another procedure, such as a traditional balloon angioplasty.

Figure 25:
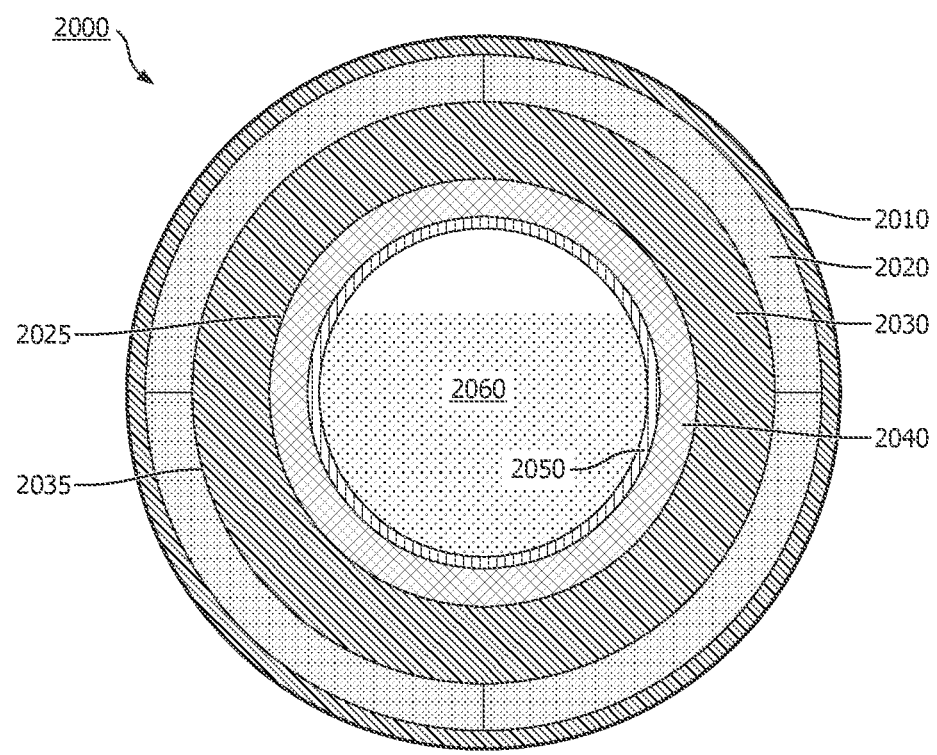
FIG. 25 is a cross-sectional view of an arterial wall taken along a direction perpendicular to the longitudinal axis of the arterial wall.

As discussed above with respect to FIGS. 12 and 19, the present disclosure discusses using a laser catheter to ablate 1010 at least a portion of the vascular occlusion or restriction in the vessel of the subject prior to using the combination of the laser catheter 1010 (depicted in FIG. 10) and a sheath 1120 (depicted in FIG. 18) to create laser-induced pressure waves in the presence of a liquid medium and disrupt a portion of the vascular occlusion. FIGS. 25-26F are included to illustrate the formation of a vascular occlusion within the vasculature of a subject that is treated with the laser catheter 1010 and the sheath 1120. Referring to FIG. 25, there is depicted a cross-sectional view of a healthy arterial wall 2000 taken along a direction perpendicular to the longitudinal axis of the arterial wall. A healthy arterial wall 2000, or vascular wall, typically includes an outer layer referred to as the "adventitia" or "adventicia" which is shown in FIG. 25 as layer 2020. There may be additional layers, such as layer 2010 of the arterial wall 2000, on the outside of the adventitia. A healthy arterial wall 2000 also includes a middle or central layer referred to as the media 2030. The media 2030 is located radially inward of and adjacent to the inner portion of the adventitia 2020. The media 2030 has a layers of smooth muscle cells and layers of elastin fiber that allows the artery to expand and contract. A healthy arterial wall 2000 also includes an inner layer referred to as the intima 2040. The intima 2040 is located radially inward of and adjacent to the media 2030. A healthy arterial wall 2000 also includes an endothelium layer 2050, which is located on the inner most surface of the intima 2040 and creates the boundary for the passageway (or inner lumen) 2060.

As mentioned above, the media 2030 is located radially inward of and adjacent to the inner portion of the adventitia 2020. Specifically, an external elastic membrane, commonly referred to as the external elastic lamina, 2035 separates the media 2030 from the adventitia 2020. As also mentioned above, the intima 2040 is located radially inward of and adjacent to the inner portion of the media 2030. An internal elastic membrane 2025, commonly referred to as the internal elastic lamina, separates the intima 2040 from the media 2030.

Referring to FIG. 25A, there is depicted a smaller version of the structure of the healthy arterial wall 2000 depicted in FIG. 25. Also, FIG. 26A is a longitudinal-sectional view of the healthy arterial wall 2000 taken along a direction parallel to the longitudinal axis of the arterial wall. Specifically, FIG. 26A is a longitudinal-sectional view of the structure of the healthy arterial wall 2000 taken along line B-B of FIG. 25A.

Referring to FIG. 26B, over time, fat and/or lipids 2070' may start to collect and/or deposit in the intima 2040' of the arterial wall 2000' as a result of buildup of fat and lipids in the blood. This disease process is commonly referred to as atherosclerosis and occurs in the arteries of the body including the coronary and peripheral arteries. It is this collection of fat and/or lipids 2070' in the intima 2040' that will lead to the formation of a vascular occlusion that can reduce or completely obstruct blood flow in the passageway 2060'. Over time this buildup of fat and lipids 2070' becomes a heterogeneous mix 2065" (commonly referred to as plaque) of many constituents including but not limited to fats, lipids, fibrin, fibro-calcific plaque, calcium crystals, thrombus, etc. For example, a portion of the fat and/or lipids 2070' may turn into plaque 2065" and even become calcified, which is depicted as 2055" in FIG. 26C. As the fat and/or lipids 2070" collect, turn into plaque 2065" and/or become calcified 2055", the intima 2040" starts to inflame and expand, thereby decreasing the cross-sectional area of the passageway 2060".

Referring to FIG. 26D, as atherosclerotic disease progresses, and the condition of the arterial wall 2000''' is left untreated, the plaque 2065''' continue to collect, and the intima 2040''' continues to expand and decrease the cross-sectional area of the passageway 2060'. However, upon the intima 2040' {hacek over ( )} of the arterial wall 2000'{hacek over ( )} reaching its limit to expand further, the intima 2040'{hacek over ( )} and the endothelium can rupture 2058'{(hacek over ( )} and release the plaque contents previously contained in the thickened lipids and enlarged intima white blood cells into the passageway 2060'{hacek over ( )}, as depicted in FIG. 26E. Platelets and fibrin collect within the passageway 2060{hacek over ( )} of the arterial wall 2000{hacek over ( )} to try and repair the rupture, and in doing so form a vascular occlusion 2080{hacek over ( )}, which may have calcified portions 2085{hacek over ( )}, as depicted in FIG. 26F. This figure also illustrates that formation of the vascular occlusion 2080{hacek over ( )} further decreases the size of the passageway 2060{hacek over ( )} and in some instances fully obstructs flow.

Figures 26H, 26I:
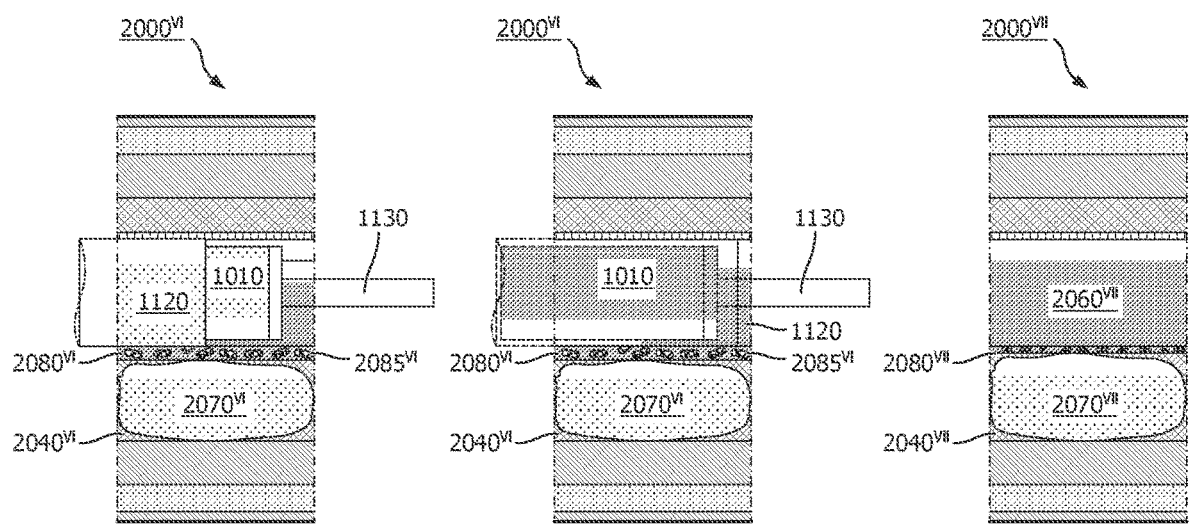
FIG. 26H is a longitudinal-sectional view of an arterial wall taken along a direction parallel to the longitudinal axis of the arterial wall with a sheath and laser catheter located adjacent the remaining portion of the vascular occlusion depicted in FIG. 26G, wherein the end of the laser catheter, particularly its emitter(s) is disposed distally of the most distal end of the sheath.
FIG. 26I is a longitudinal-sectional view of an arterial wall taken along a direction parallel to the longitudinal axis of the arterial wall after utilizing a sheath and laser catheter illustrated in FIG. 26H and or FIG. 26H'.

Referring to FIG. 26D and FIGS. 26G and 2611, a laser catheter 1010 may be used to debulk or remove plaque buildup contained behind the intima 2065''' or within the vascular occlusion 2080{hacek over ( )} or a portion thereof from the passageway of the arterial wall 2000{hacek over ( )}. After debulking the plaque buildup or the occlusive disease, the combination of the laser catheter 1010 and the sheath 1120 of the present disclosure may be used to treat the remaining portion of the plaque buildup 2065''' or the vascular occlusion 2080{hacek over ( )}', particularly by disrupting the calcified portions 2085 {hacek over ( )}" as depicted in FIG. 26H and/or FIG. 26H' by creating laser-induced pressure waves as described previously, to treat the condition of the arterial wall 2000{hacek over ( )}" as depicted in FIG. 26I.

FIG. 26I illustrates the arterial wall 2000{hacek over ( )}" with an enlarged passageway 2060{hacek over ( )}", the majority of the plaque 2065''' or vascular occlusion 2080{hacek over ( )}" removed, and the calcification of the remaining portion of the vascular occlusion, along with the calcification of the intima 2040{hacek over ( )}", fractured or modified making it more amenable to dilation at lower atmospheric pressures. FIGS. 25, 25A and 26A-211 use similar numeric values, but the different figures include different indicators, such as' and {hacek over ( )} and combinations thereof, for the numeric values due to the changes occurring within the arterial wall as the vascular occlusion is formed and treated, which is progressively illustrated from one figure to the next. For purposes of brevity, certain layers of the arterial wall 2000 are omitted from the discussion of particular figures, and numeric values of certain items of the arterial wall 2000 are omitted from the particular figures. Nevertheless, one should consider the layers of the arterial wall 2000, and the formations therein, to have the same numeric values even if omitted from FIGS. 25, 25A and 26A-26I.

Figure 27B:
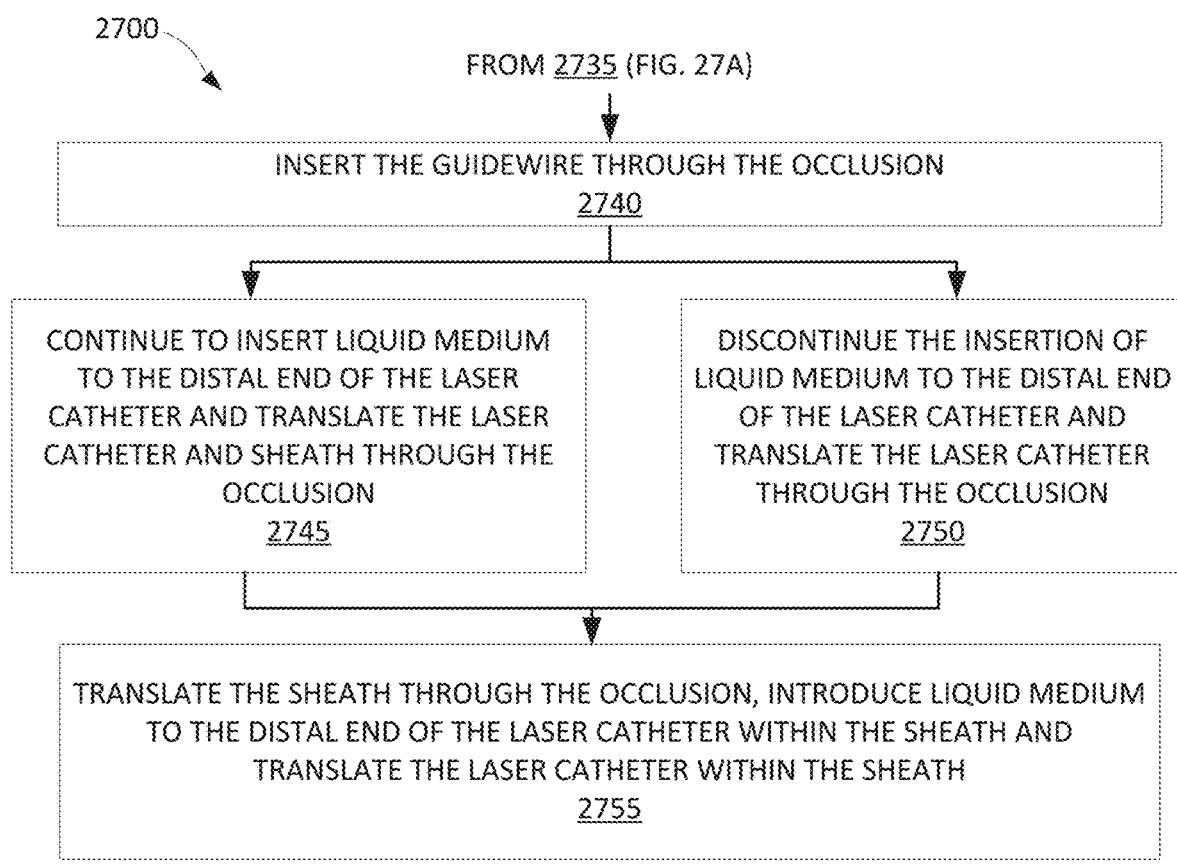

Referring to FIGS. 27A and 27B, there is a method 2700 of removing plaque buildup or occlusive disease by performing an atherectomy procedure and treating the remainder of the vascular occlusion within the intima using a laser catheter 1010 (depicted in FIG. 10) in conjunction with the sheath 1120 (depicted in FIG. 18) to create laser-induced pressure waves in the presence of a liquid medium and disrupt a portion of the vascular occlusion. This method 2700 may be used to treat coronary arteries and/or peripheral arteries including but not limited to arteries of the vasculature of the legs, the renal arteries, subclavian arteries, etc.

The method 2700 in FIGS. 27A and 27B includes locating a vascular occlusion in the vessel of a subject at step 2705. The next step 2710, which is optional, includes locating a guidewire at the vascular occlusion and/or inserting a guidewire through the vascular occlusion or through the passageway past the vascular occlusion. Step 2715 includes performing an atherectomy procedure to remove the plaque or vascular occlusion or a portion thereof. One type of atherectomy device is an ablation catheter, such as a laser ablation catheter 1010 discussed herein, which is capable of ablating at least a portion of the vascular occlusion as depicted in FIG. 26G. Other types of ablation catheters include radiofrequency ablation catheters, microwave ablation catheters, and cryoablation catheters. Atherectomy devices other than ablation catheters, such as mechanical atherectomy devices, may also be used to remove the vascular occlusion.

After the vascular occlusion (or a portion thereof) is removed from the vasculature, step 2720 may then be performed. Step 2720 includes positioning a sheath 1120 of the present disclosure over a laser catheter 1010 within vasculature of a subject, as depicted in FIG. 26H, followed by step 2725, which includes positioning the sheath 1120 and laser catheter 1010 adjacent the vascular occlusion, as depicted in FIG. 26H'. For example, if a clinician uses a catheter 1010, which has a guidewire lumen, and a sheath 1120, the catheter 1010 may be slid over the guidewire 1130 and into the vasculature, and the sheath 1120 is subsequently slid over the catheter 1010, which is then coupled to the sheath 1120. Step 2725 also includes is positioning the sheath 1120 and laser catheter 1010 adjacent to the vascular occlusion (or remainder thereof). The axial locations of the laser catheter 1010 and the sheath 1120 may be adjusted be translating either or both components with respect to one another. Particularly, the sheath 1120 may be translated from the position depicted in FIG. 26H, which illustrates the laser catheter 1010 extending beyond the distal end of the sheath 1120, to the axial locations of the laser catheter 1010 and the sheath 1120 depicted in FIG. 26H', wherein the emitters of the laser catheter 1010 are within the attenuating member of the sheath 1120 and axially aligned with both the attenuating member and the remainder of the vascular occlusion, and the corresponding portions of the sheath and attenuating member are adjacent the vascular occlusion (or remainder thereof).

Once the sheath 1120 and laser catheter 1010 are disposed adjacent the vascular occlusion, such that the emitters and the attenuating member are axially aligned adjacent the vascular occlusion as depicted in FIG. 26H', the liquid medium may be introduced to the distal end of the laser catheter as set forth in step 2730 of FIGS. 27A and 27B. Continuing to refer to FIGS. 27A and 27B, step 2735 includes activating an energy source, such as a laser, to create laser-induced pressure waves in the presence of the liquid medium and disrupting a portion of the vascular occlusion. The laser catheter 1010 and sheath 1120 may be used to traverse the entire vascular occlusion or only disrupt a portion of the vascular occlusion. This is, the laser catheter 1010 and sheath 1120 may move axially with respect to another (between the positions shown in FIG. 26H and FIG. 26H') and/or together, while emitting laser-induced pressure waves to disrupt a portion of the vascular occlusion. If the laser catheter 1010 and sheath 1120 are used to disrupt a portion of the vascular occlusion, then the guidewire 1130 may penetrate and traverse the vascular occlusion as set forth in step 2740.

Activating at least one energy source coupled to at least one emitter of the laser catheter, which is surrounded by the sheath 1120, to emit and send pulses of laser light energy into and/or to react with the liquid medium to produce propagating laser-induced pressure waves and disrupt a remaining portion of the vascular occlusion. Disrupting the remaining portion of the vascular occlusion, particularly any calcified portions within the vascular occlusion, produces cracks in the calcified portions and/or reduces the size of the calcified portions because the laser-induced pressure waves disrupt the calcified portions, thereby cracking the calcified portions and/or fragmenting the size of the calcified particles such that the contiguous area is reduced. In some cases, the method 2700 may include an additional step (not shown) of activating at least one energy source coupled to at least one emitter enclosed within the sheath to emit and send pulses of laser light energy into and/or to react with the liquid medium to produce propagating laser-induced pressure waves to deliver a therapeutic agent from the sheath to a remaining portion of the vascular occlusion and/or the vascular tissue near the obstruction or restriction.

One of the benefits of the present disclosure is that the catheter 1010 and sheath 1120 depicted in FIG. 26H and FIG. 26H' may optionally include an attenuating member, such as the attenuating member depicted in the sheath 1120 of FIG. 18 above. The attenuating member 1124, or the alternatives illustrated in FIGS. 18A-18F, may reduce or prevent the formation of vapor bubbles on the exterior of the attenuating member and/or the sheath 1120 and/or reinforces the sheath such as to minimize or prevent sheath expansion. Reinforcing the sheath and/or reducing or preventing the formation of vapor bubbles on the exterior of the attenuating member (or sheath) reduces or prevents the outward and inward fluid displacement from dilating the arterial wall while simultaneously allowing the laser-induced pressure wave to penetrate the arterial wall and disrupt calcified portions in the vascular occlusion and/or intima. That is, incorporating an attenuating member, reinforces the sheath, reduces or preventing the formation of vapor bubbles on the exterior of the attenuating member, potentially inhibits displacement of the soft tissue within the arterial wall and possibly reduces or prevents delamination of the layers of the arterial wall.

Referring again to FIGS. 27A and 27B, after performing step 2735 (and possibly 2740), step 2745 may be performed. Step 2745 includes the continued insertion of the liquid medium into the gap between the combination of the laser catheter 1010 and the sheath 1120, thereby continuing to disrupt the vascular occlusion with laser-induced pressure waves, while the laser catheter 1010 remains within the sheath 1120 proximal its distal end. Alternatively, the insertion of the liquid medium may be discontinued and the laser catheter 1010 may be used to ablate vascular occlusion as the laser catheter 1010 passes over the guidewire 1130 through the vascular occlusion while the sheath 1120 remains proximal of the vascular occlusion as set forth in step 2750. That is, introduction of the liquid medium between the laser catheter 1010 and the sheath 1120 may be terminated, and the laser catheter 1010 may extend beyond the distal end of the sheath 1120 so that the laser catheter 1010 can perform additional atherectomy. After the additional atherectomy procedure is performed, the distal end of the laser catheter 1010 may return to a position within the distal end of the sheath 1120, and the liquid medium may again be supplied to the distal end of the laser catheter 1010 within the sheath 1120, thereby once more creating laser-induced pressure waves to disrupt the remainder of the vascular occlusion recently ablated by the laser catheter.

To ensure that the majority of the remainder of the vascular occlusion is disrupted, and if desired, disrupt the intraluminal layer and/or tissues of the blood vessel and the vascular occlusion, the laser catheter 1010 may be repeatedly translated distally and proximally within the sheath 1120, as in step 2745 and/or step 2755. As discussed above, disruption of the intraluminal layer and/or tissues of the blood vessel and the vascular occlusion, can improve the vasculature's ability to absorb drugs, particularly when such drugs are applied with a drug eluting balloon. Also, it is contemplated that prior to, during and/or after any step in the process outlined in FIG. 19, the laser catheter 1010 may be used individually to ablate a portion of the vascular occlusion, or the laser catheter 1010 may be used in conjunction with the sheath 1120.

As discussed above, transmitting pulses of light energy from an emitter into a liquid medium creates laser-induced pressure waves and/or vapor bubbles and additional resultant pressure waves that disrupt at least a portion of a vascular occlusion. The catheter may include a guidewire lumen through which a guidewire can pass and cross the vascular occlusion. It may also be desirable to excite and vibrate the guidewire to increase the guidewire's ability to pierce and cross the vascular occlusion. Accordingly, the present disclosure also contemplates directing the laser light energy emitted by the emitter into the liquid medium in a direction which causes the liquid medium to propagate laser-induced pressure waves toward the guidewire lumen and/or guidewire such that the laser-induced pressure waves excite and vibrate the guidewire.

Although the method illustrated in FIGS. 27A and 27B depicts steps 2705 through 2755 of method 2700 as being performed serially, any or all of the steps within the method 2700 may in any order and/or in parallel with any of the other steps. For example, certain steps can be performed without performing other steps. Upon completing step 2735 and/or step 2740, the combined laser catheter and sheath can optionally be repositioned within the vasculature and adjacent another portion thereof. Similarly, upon completing step 2735 and/or step 2740, the emitter(s) can optionally be repositioned within the sheath. The sheath can be repositioned within the vasculature and/or the emitter(s) can be repositioned within the sheath. The method 2900 also includes ending the procedure when the desired therapeutic outcome is obtained, or repeating any of steps 2905 through 2945 as may be necessary to treat a subject having a vascular occlusion.

Furthermore, a drug eluting (coated) balloon (DEB or DCB) catheter may be used to deliver drugs to the remnants of the vascular occlusion. Disrupting the remaining portion of the vascular occlusion with the laser-induced pressure waves prior to utilizing a DEB may increase the effectiveness of the drugs being applied to the vascular occlusion because the laser-induced pressure waves disrupt calcium formed in the intima layer, as well as in tissues within the blood vessel, thereby creating a pathway for the drug to enter the intima and tissues within the blood vessel and/or vascular occlusion.

The present disclosure also contemplates using the laser-induced sheath with conventional angioplasty balloons, as well as with DEBs. For example, a surgical procedure may include performing an atherectomy with a laser catheter, using the sheath in combination with the laser catheter to treat the calcified portions of the vasculature as set forth in FIGS. 27A and 27B above, and then inserting an angioplasty balloon (or DEB) into the vasculature adjacent the relevant portion of the vasculature and expanding the angioplasty balloon to dilate the relevant portion of the vasculature.

As discussed above, the laser-induced pressure waves created by the laser catheter and sheath of the present disclosure not only disrupt a vascular occlusion and/or calcium in the intima layer, the laser-induced pressure waves created by the catheter of the present disclosure can also disrupt calcification of the tissues within the vessel wall(s) That is, the laser-induced pressure waves may be used to fracture or modify calcified tissue regardless of whether the vasculature includes an occlusion. For example, patients with medial artery calcification, which is also known as Monckeberg's sclerosis, could potentially benefit from being treated with the catheter of the present disclosure.

Referring to FIG. 28A, there is depicted a healthy arterial wall 2300 similar to the arterial wall depicted in FIG. 26A. For example, reference numerals 2010, 2020, 2030, 2040, 2050 and 2060 of FIG. 26A correspond to reference numerals 2310, 2320, 2330, 2340, 2350 and 2360 of FIG. 28A. That is, reference numerals 2310 and 2320 are the externa, reference numeral 2330 is the media, reference numeral 2340 is the intima, reference numeral 2350 is the endothelium, and reference numeral 2360 is the passageway.

Referring to FIG. 28B, there is depicted is a cross-sectional view of an arterial wall 2300' that includes calcium deposits 2370 formed in the media 2330. The calcium deposits begin as crystal aggregates and typically aggregate along the elastin fibrin layers within the media. As Monckeberg's sclerosis (commonly referred to as medial calcification) progresses, multiple layers of calcium can form that involve up to the full circumference of the vessel. The calcium can also extend radially into the adventitia and intima layers. Monckeberg's sclerosis (medial calcification) is caused by a recruitment of calcium by the smooth muscle cells and is attributed but not limited to common comorbidities found in patients suffering from vascular disease including diabetics, kidney disease patients and other metabolic or hormonal imbalances. The media 2330 includes smooth muscle cells and elastin fiber, which allow the artery to expand and contract. Upon formation of calcium deposits 2370, however, the artery's ability to expand and contract is reduced. That is, formation of calcium deposits 2370 in the media 2330 reduces the compliance of the artery 2300', which in turn potentially reduces the amount of blood flow through such arteries and can potentially negatively affect other health conditions, such as diabetes. This condition can occur with atherosclerotic disease as described previously or be an isolated condition without the narrowing of the lumen of the artery.

The combined catheter 1010 and sheath 1120 of the present disclosure are able to create laser-induced pressure waves, which fracture or disrupt the calcium deposits 2370 in the media 2330 of the arterial wall 2300'' as shown in FIG. 28C, thereby increasing the compliance of the arterial wall 2300'' and blood flow therethrough while minimizing or preventing dilation of the arterial wall. That is, one of the benefits of the present disclosure is that the sheath depicted in FIG. 28C, may optionally include an attenuating member, such as the attenuating member 1124 depicted in FIG. 18 above. The attenuating member 1124, or the alternatives illustrated in FIGS. 18A-18F, may reduce or prevent the formation of vapor bubbles on the exterior of the attenuating member and/or reinforce the sheath such as to minimize or prevent its expansion. Reinforcing the sheath and/or reducing or preventing the formation of vapor bubbles on the exterior of the attenuating member reduces or prevents outward and inward fluid displacement from expanding and contracting the arterial wall while simultaneously allowing the laser-induced pressure wave to penetrate the arterial wall and disrupt calcium deposits in the tissue (e.g., media) and/or tissue layers (e.g., media layer) of the blood vessel.

FIGS. 28A-28D use similar numeric values, but the different figures include different indicators, such as ' and {hacek over ( )} and combinations thereof, for the numeric values due to the changes occurring within the arterial wall as the calcium is formed and treated, which is progressively illustrated from one figure to the next. For purposes of brevity, certain layers of the arterial wall 2300 are omitted from the discussion of particular figures, and numeric values of certain items of the arterial wall 2300 are omitted from the particular figures. Nevertheless, one should consider the layers of the arterial wall 2300, and the formations therein, to have the same numeric values even if omitted from FIGS. 28A-28D.

Figure 29:
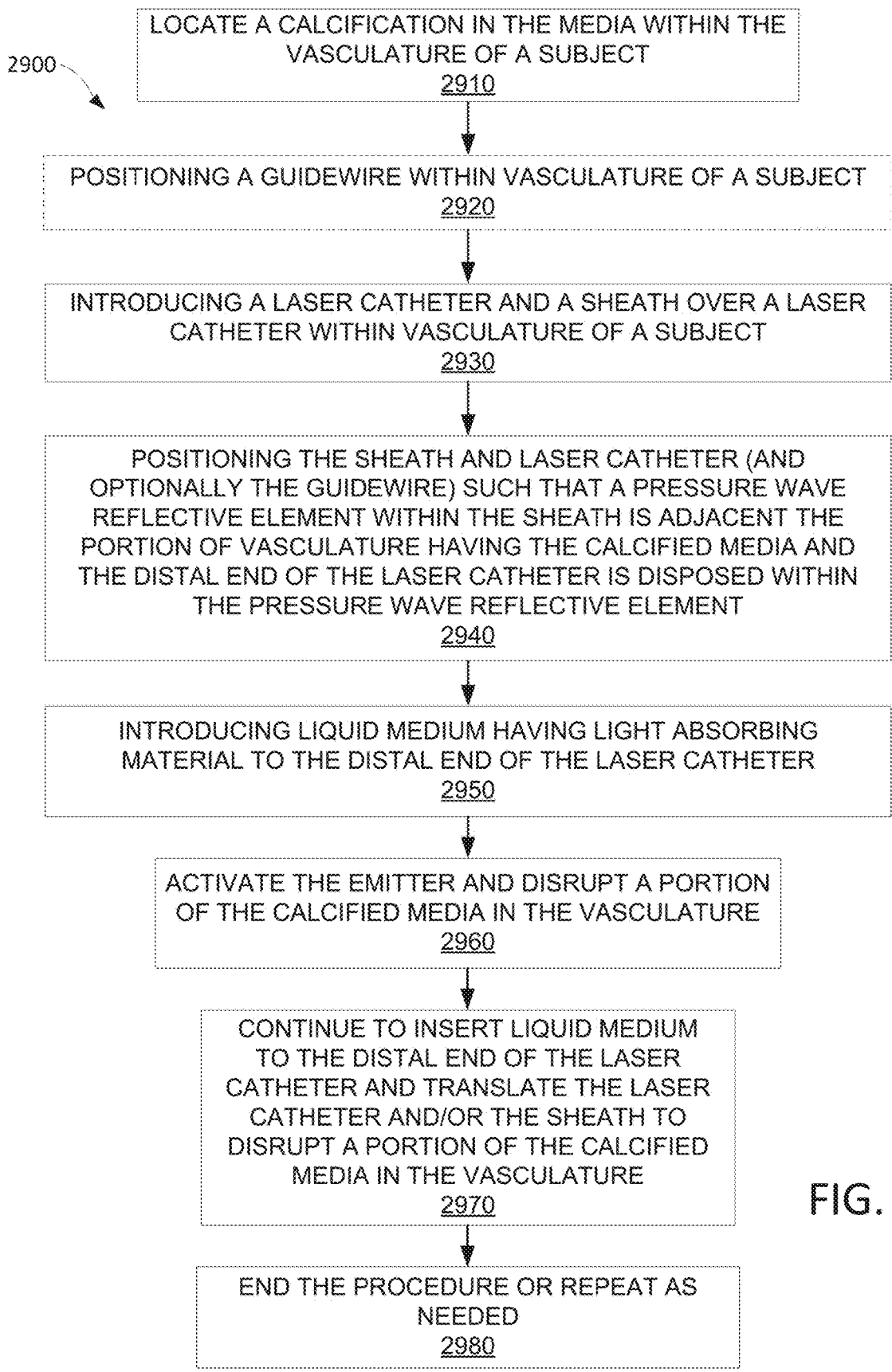
FIG. 29 is a method of using a sheath and laser catheter to treat the calcified media portion of the blood vessel.

Referring to FIG. 29, there is depicted a method 2900 of using a catheter to generate laser-induced pressure waves to treat the calcium deposits in the tissue (e.g., media) and/or tissue layers (e.g., media layer) of the blood vessel by disrupting the calcium deposits to increase vasculature compliance, thereby increasing blood flow therethrough. This method 2900 may be used to treat calcium deposits in the tissue(s) of coronary arteries and/or peripheral arteries. The method 2900 in FIG. 29 includes locating a calcification of the tissue (e.g., media) and/or tissue layers (e.g., media layer) within the vasculature of a subject at step 2910. The next step 2920, which is optional, includes positioning a guidewire within the vasculature of a subject.

After locating the calcified portion(s) of the tissue (e.g., media) and/or tissue layers (e.g., media layer) within the vasculature, step 2930 may then be performed. Step 2930 includes introducing to the vasculature a laser catheter of the present disclosure and a sheath of the present disclosure over the laser catheter. Step 2940 includes positioning within the vasculature the sheath and the laser catheter (and optionally the guidewire) such that an attenuating member within the sheath is adjacent the portion of vasculature having the calcification, and the distal end of the laser catheter is disposed within the attenuating member adjacent the vasculature that includes the calcified portion(s). For example, if a clinician uses a laser catheter 1010 described herein, which has a guidewire lumen, the laser catheter may be slid over the guidewire and into the vasculature such that the emitter(s) of the laser catheter are positioned adjacent to the vasculature that has the calcification. A sheath 1120 of the present disclosure is then slid over the laser catheter 1010 to a position within the vasculature such that the attenuating member is adjacent the vasculature that includes the calcified portion(s). Accordingly, the emitter will be disposed within the portion of the sheath comprising the attenuating member.

The method 2900 also includes step 2950, which comprises introducing the liquid medium (for example, contrast medium) having light absorbing material to the distal end of the laser catheter, wherein the laser catheter is disposed within the sheath, and preferably within the portion of the sheath comprising the attenuating member. At step 2960, the emitters on the laser catheter are activated, thereby initiating the formation of laser-induced pressure waves a portion of which at least pass through the sheath, including the attenuating member, thereby disrupting the calcium in the vasculature. That is, the laser-induced pressure waves crack the calcified portion(s) and/or break the calcified portions of the tissue (e.g., media) and/or tissue layers (e.g., media layer) into smaller particles. Disrupting the calcified portion(s) within the tissue(s) of the blood vessel cracks the calcified portion(s) because the laser-induced pressure waves are absorbed by the calcified portions, thereby increasing the arterial wall's compliance, which in turn leads to improved blood flow and positive implications for other health conditions.

Step 2970 of method 2900 may include continuing to insert liquid medium to the distal end of the laser catheter and axially translate the laser catheter and/or the sheath to disrupt a portion of the calcified tissues of the blood vessel in the same portion or other portions of the vasculature. And any of the steps of method 2900 may be repeated until a sufficient amount of calcium is disrupted and the arterial wall's compliance is satisfactorily increased, as set forth in step 2980.

Additionally, although it is not disclosed in FIG. 29, in some cases, the method 2900 may include the step of activating at least one energy source coupled to at least one emitter enclosed within the sheath to emit and send pulses of laser light energy into and/or to react with the liquid medium to produce propagating laser-induced pressure waves to deliver a therapeutic agent from the exterior of the sheath to through the cracks in the calcified portions through the cracks in the calcified portions and/or through (or to) potentially.

Figure 30:
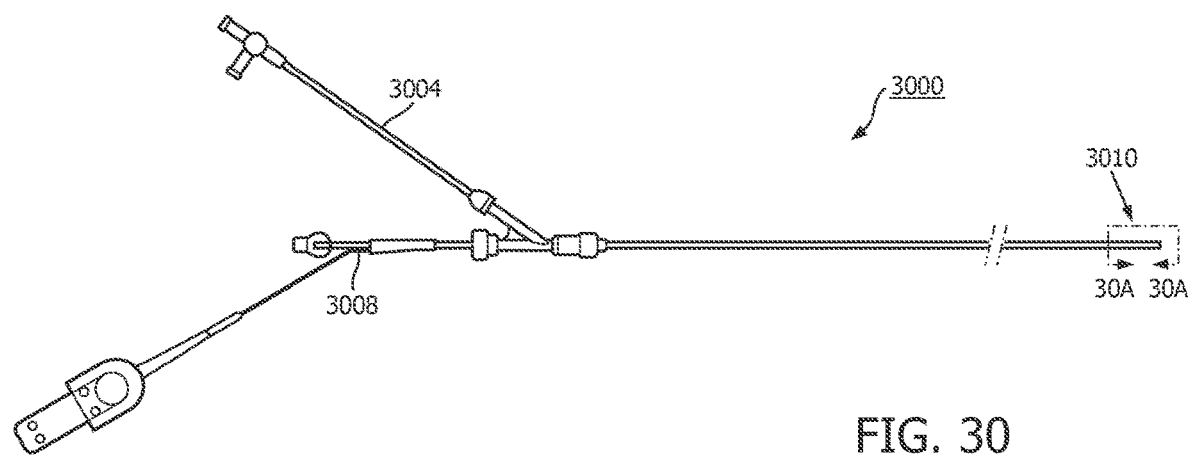
FIG. 30 is a kit that includes a laser catheter assembly and an outer sheath assembly.

Referring to FIG. 30, there is depicted a kit 3000 that includes a laser catheter assembly 3008 and a sheath assembly 3004. Sheath assembly 3004 may also be referred to as outer sheath assembly 3004 due to its disposition with respect to the laser catheter assembly 3008. FIG. 31 depicts the sheath assembly 3004 shown in FIG. 30, and FIG. 32 depicts the laser catheter assembly 3008 shown in FIG. 30. The sheath assembly 3004 may include a proximal end portion, a distal end portion 3040 and a sheath 3012 having a working length of about between 50 cm and 200 cm, including 140 cm, and a lumen 3024 extending between such ends. The sheath 3012 may also be referred to as the outer sheath 3012 due to its disposition with respect to the laser catheter assembly 3008. The distal end portion 3040 is shown in further detail in FIG. 31A. The proximal end of the sheath assembly 3004 may include a bifurcate 3016 (or Y connector) that is coupled to the sheath 3012 by a luer fitting 3020. The bifurcate 3016 may comprise a tube 3028 extending in one direction (e.g., an axial direction) and another tube 3032 that extends in a direction offset from tube 3028. The tube 3028 may have an opening 3024 through which a guidewire (not shown) may enter the proximal end of the sheath assembly 3004. The tube 3028 may also comprise a hemostasis valve at or adjacent the opening 3024. The guidewire is capable of extending from the proximal end of the sheath assembly 3004 to the distal end of the sheath assembly 3004 through a lumen therein. The tube 3032 may include a stopcock 3036 through which the liquid medium may enter the sheath assembly 3004.

Figure 31A:
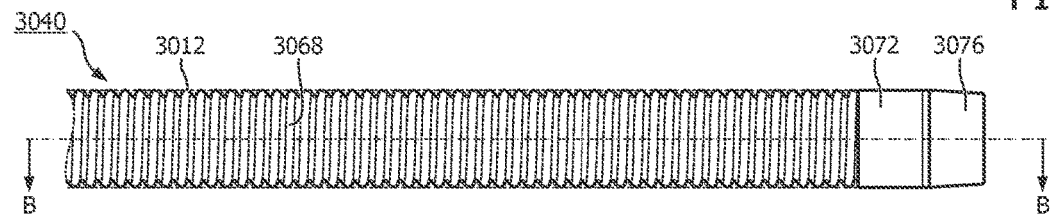
FIG. 31A is an enlarged view of the distal portion of the outer sheath assembly within line 31A-31A of FIG. 31, wherein a portion of the outer sheath assembly is illustrated in a translucent material for purposes of clarifying the figure.
Figure 31B:
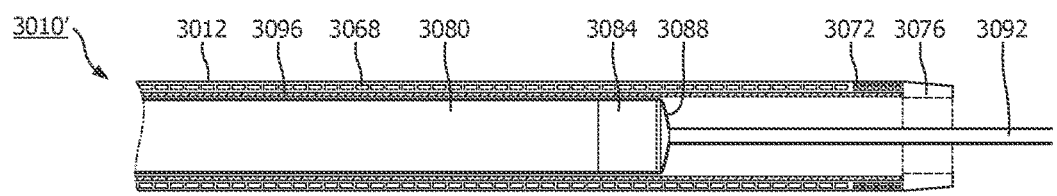
FIG. 31B is an enlarged longitudinal sectional view of the distal portion of the outer sheath assembly depicted in FIG. 31A taken along line B-B.
Figure 32B:
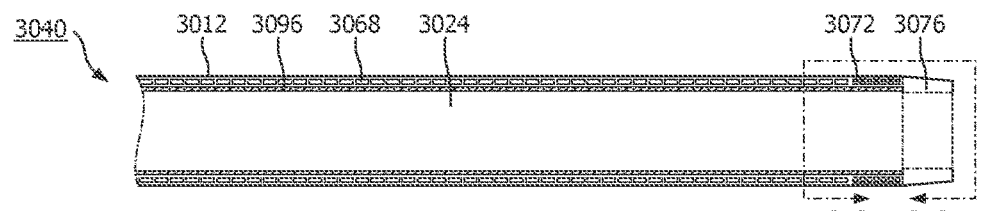
FIG. 32 is the laser catheter assembly depicted in FIG. 30.
Figure 31:
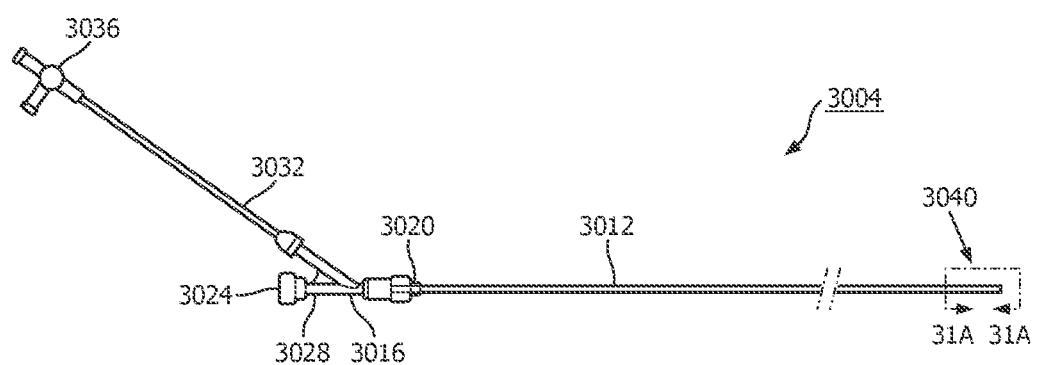
FIG. 31 is the outer sheath assembly depicted in FIG. 30.

Referring to FIG. 31A, FIGS. 31B, 31C and 31C' there are depicted enlarged views of distal end portion 3040 of the sheath assembly 3004 having a lumen 3024 there though. The distal end portion 3040 of the sheath assembly 3004 may comprise a sheath 3012 (or outer jacket), an inner liner 3096 radially or concentrically disposed within the sheath 3012, an outer band 3072 disposed about the distal end of the sheath 3012 (FIG. 31C), and a tapered tip 3076 disposed distally of the outer hand 3072. The outer band 3072' may alternatively be disposed integrally within the distal end of the sheath 3012' such that the outer sheath (or jacket) 3012' covers the (FIG. 31C') outer band 3072'. The distal end portion 3040 of the sheath 3012 may also have an attenuating member formed therein. The attenuating member may be included within the entire length of the sheath 3012 or only at the distal end portion 3040. Assuming that the length of the sheath 3012 is 140 centimeters, the distal end portion 3040 that includes the attenuating member may be between 0.010 and 10.0 centimeters in length, which represents between 0.05 and 20.0 percent of the length of the sheath 3012.

Figure 38:
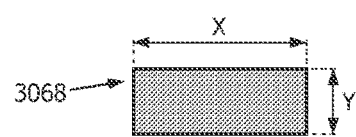
FIG. 38 is an enlarged view of a flat wire disposed within one or more embodiments of the outer sheath assembly.

The attenuating member may include a coil or coils 3068 integrally formed from flat wire within the sheath 3012. An example of the flat wire is shown in FIG. 38, wherein the cross-sectional width (X) of the flat wire is 0.005 inches, and the cross-sectional height (Y) of the flat wire is 0.001 inches. The flat wire may be constructed of stainless steel, such as 304 stainless steel, or other type of metal or metal alloy. Additionally, it may be preferable for the flat wire to be constructed with alternative dimensions, such as a cross-sectional width (X) of between 0.001 and 0.010 inches and a cross-sectional height (Y) of between 0.0005 and 0.015 inches. Alternatively, it may be preferable to use a round wire having a diameter between 0.0005 and 0.015 inches in lieu of a flat wire.

As discussed herein, it may be desirable for the ratio of the open area for the attenuating member in comparison to the overall area of the attenuating member to be within a certain range, such as between 30 percent to 70 percent, and possibly between 40 percent and 60 percent, and more possibly between 45 percent and 55 percent, such as 45, 46, 47, 48, 49, 50, 51, 52, 53, 54 or 55 percent. Although round wire may be used to create the coil(s) 3068, using flat wire to construct the coil(s) 3068 may provide the attenuating member with an overall thinner longitudinal cross-sectional profile while decreasing the amount of open area per wrap of the wire because the height of the flat wire may be smaller than the width of the flat wire. The width of the flat wire provides the desired ratio of open area for the attenuating member in comparison to the overall area of the attenuating member, while the height of the material increases the coil(s) strength to withstand the laser-induced pressure wave without breaking. In other words, a smaller longitudinal cross-sectional profile reduces the overall diameter of the sheath assembly, thereby allowing the kit to enter smaller sized vasculature, while maintaining sufficient strength and rigidity to absorb and attenuate the laser-induced pressure wave.

There are three factors in determining the percentage of open area in the attenuating member: (1) the width of the flat wire (or diameter of the round wire); (2) the number of wraps of the wire; and (3) the gap between each wrap of wire. Once two of these factors are determined for a desired percentage of open area in the attenuating member, the third factor can be solved. In order to maintain a certain percentage of open area in the attenuating member, there is an inverse relationship between the number of wraps and the width of the flat wire (or diameter of the round wire). That is, for a certain percentage of open area in the attenuating member, the necessary wraps per inch decreases with a wire having a larger width, and the necessary wraps per inch increases with a wire having a smaller width. Additionally, there is also an inverse relationship between the number of wraps per inch and the gap between the wire wraps. That is, for a certain percentage of open area in the attenuating member using a predetermined wire size, the wraps per inch increases with a smaller gap between the wire(s). Moreover, there is a direct relationship between the size of the gap between the wire and the amount of open area in the attenuating member. That is, for a given wire width, the greater the gap between each winding, the larger the open area in the attenuating member, and the smaller the gap between each winding, the smaller the open area in the attenuating member.

For example, assuming that the attenuating member is constructed of 0.005 inch wide by 0.001 tall inch flat wire with a desired open area between 30 percent and 70 percent, the attenuating member may include between about 75 and 125 wraps (or revolutions) per inch. Specifically, a gap of about 0.008 inches between each wrap of 0.005 inch wide flat wire produces an open area of about 61.5 percent, and a gap of about 0.003 inches between each wrap of 0.005 inch wide flat wire produces an open area of about 37.5 percent. Additionally, a gap of about 0.005 inches between each wrap of 0.005 inch wide flat wire produces an open area of about 50 percent. The attenuating member, therefore, may be constructed from the flat wire such that the attenuating member includes between 75 and 125 wraps (or revolutions) per inch of the flat wire, between 80 and 120 wraps per inch of the flat wire, between 85 and 115 wraps per inch of the flat wire, between 90 and 110 wraps per inch of the flat wire depending upon the amount of open area within the attenuating member, the size (i.e., width) of the wire and the gap between each wrap of the wire. As such, it may also be preferable for the attenuating member to include about 75, 80, 85, 90, 95, 100, 105, 110, 115, 120 or 125 wraps per inch of the flat wire, wherein the flat wire is wound such that the width (X) of the flat wire is parallel with the longitudinal axis of the sheath 3012, and the height (Y) of the flat wire is perpendicular with the longitudinal axis of the sheath 3012. Additionally, if it desirable for the attenuating member to have a desired open area between 30 percent and 70 percent using a 0.004 inch wide flat wire, the gap between windings may be between, 0.0017 and 0.0093 inches respectively. These are examples, which shall not limit the scope of this disclosure because it may be desirable to have a flat wire with dimensions of 0.0002 to 0.010 inches wide and 0.0005 to 0.002 inches high, as well as round wire having a diameter between 0.0005 to 0.010 inches. For these ranges of wire size, the gap between the wire winding(s) and the wraps per length (inch) can be adjusted accordingly to produce the desired open area in the attenuating member.

Upon forming the sheath 3012 with the internally disposed attenuating member, the sheath 3012 may have an inner diameter between 0.010 and 0.200 inches and an outer diameter of about 0.014 inches such that the wall thickness of the sheath 3012 is between 0.002 and 0.015 inches. The sheath 3012 may be constructed of a polymeric material, such as Nylon-12. As mentioned above, distal end portion 3040 may also include an inner liner 3096 radially or concentrically disposed within the sheath 3012. The inner liner 3096 may be constructed of a polymer such as a polyimide having a thickness between 0.0005 and 0.010 inches, such as 0.0005, 0.0006, 0.0007, 0.0008, 0.0009, 0.001, 0.0015, 0.002, 0.00025, 0.003, 0.0035, 0.004, 0.0045, 0.005, 0.0055, 0.006, 0.0065, 0.007, 0.0075, 0.008, 0.0085, 0.0090, 0.0095 and 0.010 inches.

Again, the distal end portion 3040 of the sheath assembly 3004 may comprise an outer band 3072, which may also be referred to as a marker band, disposed about the distal end of the sheath 3012 and a tapered tip 3076 disposed distally of the outer band 3072. The outer band 3072 may be constructed of a highly radiopaque material, such as platinum iridium alloy or polymers doped with radiopaque materials such as barium sulfate, bismuth subcarbonate, bismuth trioxide, or tungsten. The tapered tip 3076 may be constructed of the same material as the sheath 3012 or an alternative material, such as pebax, polysulfone, HDPE, LDPE, UHMWPE, polypropylene, polyolefins, carbothane, polyurethane, Suralyn, ionomers, Estane, EPTFE, PTFE, or FEP. The tapered tip 3076 may, therefore, be formed integrally with the sheath 3012 or as a separate component. The circumference of the tapered tip 3076 may taper radially inward from its proximal end to its distal end between 1 degree and 10 degrees, such as 1, 2, 3, 4, 5, 6, 7, 8, 9 or 10 degrees.

It may also be preferable for the inner diameter of the tapered tip 3076 to be slightly less than the inner diameter of the inner liner 3096 of the sheath 3012, particularly if the inner liner 3096 is omitted from the distal end 3040 of the sheath assembly 3004. For example, it may be preferable for the tapered tip 3076 to seal the interface between the sheath assembly 3004 and the laser catheter assembly 3008 such that the escape of the liquid medium at the distal end of the kit 3000 is minimized or reduced. If a 5 French sized laser catheter 3080 of the laser catheter assembly 3008 has an outer diameter of about 0.056 inches, then it may be preferable for the inner diameter of the tapered tip 3076 to be about 0.057 inches, thereby leaving a radial distance or gap of about 0.0005 inches between the laser catheter 3080 and the tapered tip 3076. For the purposes of this disclosure about 0.0005 inches means 0.0001 to 0.001 inches. Additionally, if a 6 French sized laser catheter 3080 of the laser catheter assembly 3008 has an outer diameter of about 0.069 inches, then it may be preferable for the inner diameter of the tapered tip 3076 to be about 0.070 inches, thereby leaving a distance or gap of about 0.0005 inches between the laser catheter 3080 and the tapered tip 3076. Although the embodiments described above includes a gap of about 0.0005 inches between the laser catheter 3080 and the tapered tip 3076, such gap may be between 0 and 0.002 inches and still perform a sufficient seal.

The gap between the laser catheter 3080 and the inner liner 3096 (of the sheath 3012) will preferably be greater than the gap between the laser catheter 3080 and tapered tip 3076, thereby allowing the liquid medium to enter such gap between the laser catheter 3080 and the inner liner 3096. For example, for a 5 French sized laser catheter 3080 of the laser catheter assembly 3008 having an outer diameter of about 0.056 inches, it may be preferable for the inner diameter of the inner liner 3096 to be about 0.0615 inches, thereby leaving a radial distance or gap of about 0.00275 inches between the laser catheter 3080 and the inner liner 3096, which is about five times the gap between the gap between the laser catheter 3080 and the tapered tip 3076. For a 6 French sized laser catheter 3080 of the laser catheter assembly 3008 having an outer diameter of about 0.069 inches, it may be preferable for the inner diameter of the inner liner 3096 to be about 0.0745 inches, thereby leaving a distance or gap of about 0.00275 inches between the laser catheter 3080 and the inner liner 3096, which is about five times the gap between the gap between the laser catheter 3080 and the tapered tip 3076. Accordingly, the diameter of the lumen in the inner liner 3096 is greater than the diameter of the lumen in the tapered tip 3076. Although the embodiments described above includes a radial gap of about 0.00275 inches between the laser catheter 3080 and the inner liner 3096, such radial gap may be between about 0.001 and 0.010 inches and still provide a sufficient amount of liquid medium to enter the radial gap and create the desired pressure wave upon exposure to the laser light energy.

Figure 32A:
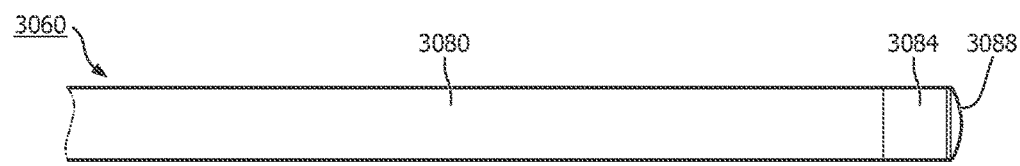
FIG. 32A is an enlarged view of a distal portion of the laser catheter assembly within line 32A-32A of FIG. 32.
Figure 32:
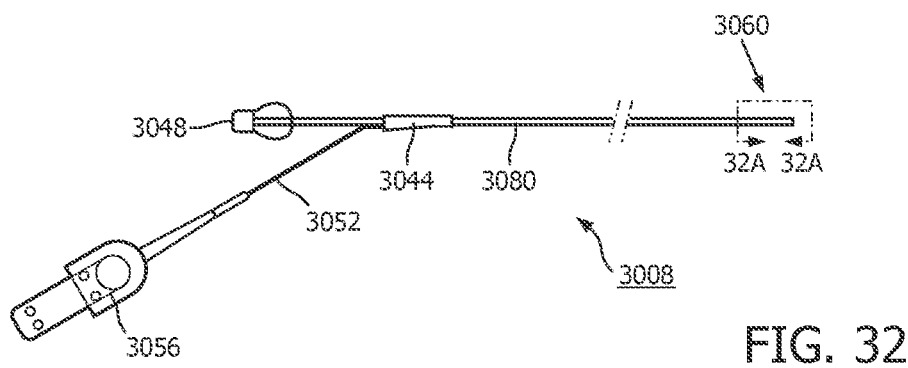

Referring to FIG. 32 and FIG. 32A, there is depicted the laser catheter assembly 3008 shown in FIG. 30. An example of the laser catheter assembly 3008 is the Turbo-Elite™ laser atherectomy catheter produced by The Spectranetics Corporation. The laser catheter assembly 3008 may include a laser catheter 3080, a bifurcate 3044, a luer adapter 3048, another sheath 3052 and a coupler 3056. Coupler 3056 is coupled to a laser system, such as the CVX-300 Excimer Laser System, which is also produced by The Spectranetics Corporation. The sheath 3052 is coupled to the coupler 3056, and sheath 3052 encapsulates the fiber optic bundle, which passes through the bifurcate 3044 and the laser catheter 3080. The coupler 3056 is configured to encapsulate or incorporate the fiber optic bundle. The bifurcate 3044 may be coupled to the proximal end of the sheath 3080. Additionally, luer adapter 3048 may also be coupled to the proximal end of the bifurcate 3044, thereby providing an entry point to for a guidewire to enter into and pass through the laser catheter assembly 3008. The distal portion 3060 of the laser catheter assembly 3008 may include a radiopaque outer band 3084 and emitters 3088 disposed distally of the radiopaque outer band 3084, wherein the emitters 3088 are the distal ends of the optical fibers or coupled to the optical fibers.

Figure 33:
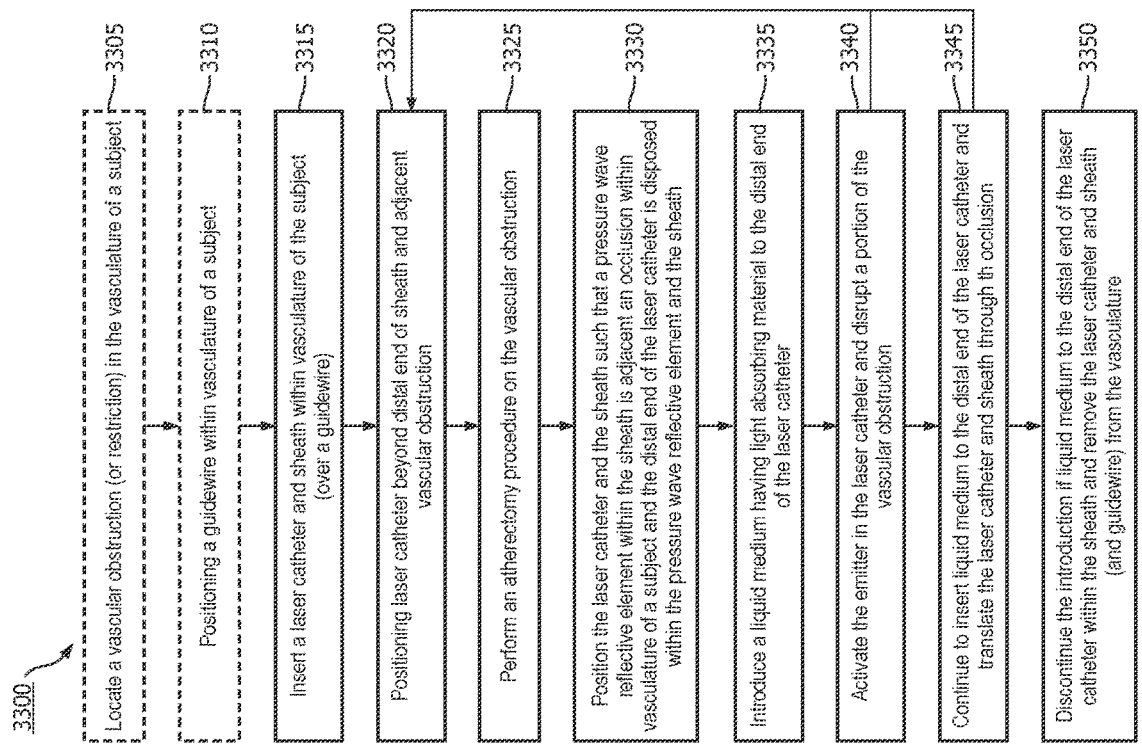
FIG. 33 is a flow chart illustrating the steps of a method of using a kit that includes a laser catheter assembly and an outer sheath assembly.

Referring to FIG. 33, there is depicted a flow chart illustrating the steps of a method 3300 of using, for example, the kit 3000 (depicted in FIG. 30) that includes the laser catheter assembly 3008 (depicted in FIG. 32) and the sheath assembly 3004 (depicted in FIG. 31) to remove plaque buildup or occlusive disease by performing an atherectomy procedure and treating the remainder of the vascular occlusion within the intima using the laser catheter assembly 3008 in conjunction with the sheath assembly 3004 to create laser-induced pressure waves in the presence of a liquid medium and disrupt a portion of the vascular occlusion. This method 3300 may be used to treat coronary arteries and/or peripheral arteries including but not limited to arteries of the vasculature of the legs, the renal arteries, subclavian arteries, etc. The method 3300 in FIG. 33 includes locating a vascular occlusion in the vasculature (or blood vessel) of a subject at step 3305. The next step 3310, which is optional, includes locating the guidewire 3092 at the vascular occlusion and/or inserting the guidewire 3082 through the vascular occlusion or through the passageway past the vascular occlusion. Step 3315 includes inserting an atherectomy device over the guidewire 3092 and into the patient's vasculature. One type of atherectomy device is an ablation catheter, such as the laser catheter assembly 3008 discussed herein, which is capable of ablating at least a portion of the vascular occlusion. Other types of ablation catheters include radiofrequency ablation catheters, microwave ablation catheters, and cryoablation catheters. Atherectomy devices other than ablation catheters, such as mechanical atherectomy devices, may also be used to remove the vascular occlusion. Assuming that the laser catheter assembly 3008 is used as the atherectomy device, the sheath assembly 3004 may also be introduced to the patient's vasculature either simultaneously with the laser catheter assembly 3008 or sequentially, such as prior to or after introducing the laser catheter assembly 3008 into the patient's vasculature.

Figure 30A:
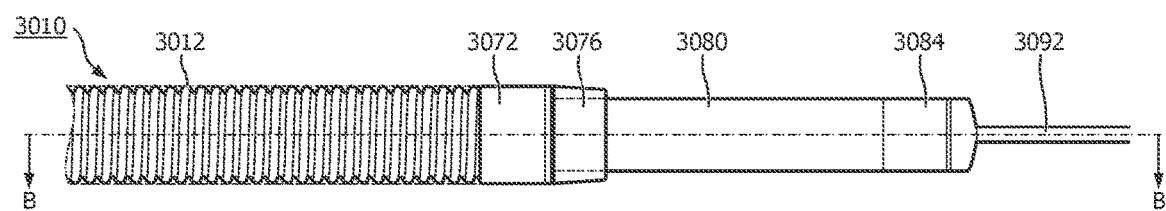
FIG. 30A is an enlarged view of the distal portions of the laser catheter assembly and an outer sheath assembly within line 30A-30A of FIG. 30, wherein the laser catheter assembly extends beyond the distal end of the outer sheath assembly, and wherein a portion of the outer sheath assembly is illustrated in a translucent material for purposes of clarifying the figure.

Once the laser catheter assembly 3008 and the sheath assembly 3004, particularly the laser catheter 3080 and the sheath 3012, respectively, are located within the patient's vasculature, the laser catheter 3080 is positioned beyond the distal end of the sheath 3012 and adjacent the vascular occlusion at step 3320. The clinician using the kit 3000 will be able to determine that the laser catheter assembly 3008, particularly the emitters 3088 is positioned beyond the distal end 3040 of the sheath assembly 3004 and adjacent the vascular occlusion because the radiopaque outer band 3084 of the laser catheter 3080 will be illustrated under fluoroscopy as being distal of the outer band 3072 of the sheath assembly 3004, as illustrated in FIG. 30A. At this point, step 3325 may be initiated by activating the emitters 3088, such as supplying laser light energy thereto, and ablating the vascular occlusion (or a portion thereof), as illustrated in FIG. 26G, FIG. 26H and/or FIG. 26H', wherein the laser catheter assembly 3008 and the sheath assembly 3004 replace the sheath 1120 and the catheter 1010, respectively, in FIG. 26G, FIG. 26H and/or FIG. 26H'.

After the vascular occlusion (or a portion thereof) is removed from the vasculature, step 3330 may then be performed. Step 3330 includes positioning the sheath assembly 3004 over the laser catheter assembly 3008, particularly the sheath 3012 over the laser catheter 3080, within vasculature of a subject and adjacent the vascular occlusion similar to the way in which the sheath 1120 and the catheter 1010 are situated in FIG. 26H'. The axial locations of the laser catheter 3080 and the sheath 3012 may be adjusted by translating either or both components with respect to one another hack and forth between the positions illustrated in FIG. 26H and FIG. 2611' or any position(s) therebetween. For purposes of clarification, FIGS. 30A and 30B correspond to how the laser catheter assembly 3040 and the sheath assembly 3004, particularly the laser catheter 3080 and the sheath 3012, of those figures would be oriented in the vasculature if the catheter 1010 and sheath 1120 of FIG. 26H, and FIG. 30B' corresponds to how the laser catheter 3080 and the sheath 3012 of that figure would be oriented in the vasculature, if the catheter 1010 and sheath 1120 of FIG. 26H' would be replaced with the laser catheter 3080 and the sheath 3012. Particularly, the axial locations of the laser catheter 3080 and the outer sheath 3008 may be axially aligned such that the emitters 3088 are within the attenuating member 3068 of the sheath 3012, and the corresponding portions of the sheath 3012 and attenuating member 3068 are adjacent the vascular occlusion (or remainder thereof). That is, step 3330 includes positioning the sheath 3012 over a laser catheter 3080 within the vasculature of a subject and adjacent the vascular occlusion such that distal end 3060 of the laser catheter assembly 3008, including its emitters 3088, are within the distal end 3040 of the sheath assembly 3008 such that the emitters 3088 are within the attenuating member 3068 of the sheath assembly 3004, and the outer band 3084 of the laser catheter assembly 3008 is proximal of the radiopaque outer band 3072 of the sheath assembly 3004, as depicted if FIG. 30B' (and FIG. 26H').

Once the distal portions 3040, 3060 of the sheath assembly 3004 and laser catheter assembly 3008 are disposed adjacent the vascular occlusion, such that the emitters 3088 and the attenuating member 3068 are axially aligned adjacent the vascular occlusion, the liquid medium may be introduced to the distal end 3060 of the laser catheter assembly 3008 as set forth in step 3335 of FIG. 33. The liquid medium may be introduced to the kit 3000 through the tube 3032 and/or stopcock 3036 at the proximal end of the sheath assembly 3004. Continuing to refer to FIG. 33, step 3340 includes activating an energy source, such as a laser, to create laser-induced pressure waves in the presence of the liquid medium and disrupting a portion of the vascular occlusion. The distal ends 3040, 3060 of the laser catheter assembly 3008 and the sheath assembly 3004 may be used to traverse the entire vascular occlusion or only disrupt a portion of the vascular occlusion. That is, the laser catheter assembly 3008 and the sheath assembly 3004, particularly their respective distal portions 3040, 3060 may move axially with respect to another and/or together, while emitting laser-induced pressure waves to disrupt a portion of the vascular occlusion. While activating the emitters 3088, it may be desirable to translate the laser catheter assembly 3008 within the sheath assembly 3004 while the sheath assembly 3004 remains stationary, as the liquid medium continues to be introduced to the distal end 3010 of the kit 3000. For example, it may be desirable to retract the laser catheter assembly 3008 within the sheath assembly 3004 by axially moving the laser catheter assembly 3008 within the sheath assembly 3004 in a proximal direction at a rate of between 0.5 mm/second and 5 mm/second, particularly at a rate of less than or equal to 4.5, 4.0, 3.5, 3.0, 2.5, 2.0, 1.5 or 1 mm/second. In addition to moving the laser catheter assembly 3008 within the sheath assembly 3004 in a proximal direction, the laser catheter assembly 3008 may move in a distal direction within the sheath assembly 3004 while maintaining the emitters 3088 proximal of the distal end 3040 of the sheath assembly 3008. For the purposes of clarification, during emitter activation, as well as proximal and distal movement of the sheath assembly 3008 to disrupt the calcium, the emitters 3088 are within the distal end 3040 of the sheath assembly 3008 such that the emitters 3088 are within the attenuating member 3068 of the sheath assembly 3004, and the outer band 3084 of the laser catheter assembly 3008 is proximal of the radiopaque outer band 3072 of the sheath assembly 3004.

During disruption of the calcium, it may be desirable to adjust the settings of the laser system to which the laser catheter assembly 3008 is coupled such that the emitters 3088 produce a fluence between 30 and 80 mJ/mm.sup.2, more preferably between 40 and 70 mJ/mm.sup.2, and even more preferably at a fluence of 45, 50, 55, 60 mJ/mm.sup.2. It may also be desirable for the repetition rate of the laser to be between 25 hertz and 80 hertz, including 25, 30, 35, 40, 45, 50, 55, 60, 65, 70, 75 and 80 hertz. It may also be desirable for the pulse width of the laser to be between 125 nanoseconds and 200 nanoseconds, including 125, 130, 135, 140, 145, 150, 155, 160, 165, 170, 175, 180, 185, 190, 195 and 200 nanoseconds. As also discussed herein, the wavelength of the laser light energy and that emitted by the emitters may include a variety of wavelengths, including a wavelength of between about 150 nanometers to about 400 nanometers such as 308 nanometers.

Figure 30B:
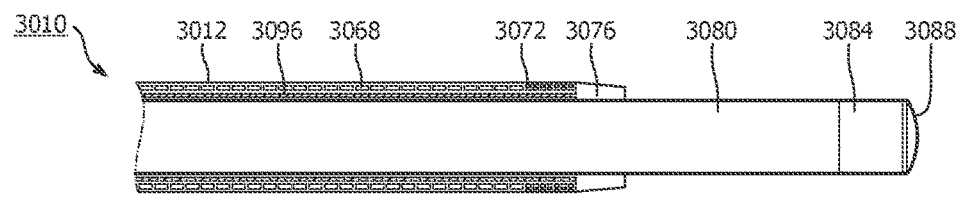
FIG. 30B is an enlarged longitudinal sectional view of the distal portions of the laser catheter assembly and outer sheath assembly depicted in FIG. 30A taken along line B-B, wherein the laser catheter assembly is disposed within the outer sheath assembly and extends beyond the distal end of the outer sheath assembly.

If the laser catheter assembly 3008 and the sheath assembly 3004 are continued to be used to disrupt a portion of the vascular occlusion, then laser catheter assembly 3008 and sheath assembly 3004 are used as set forth in step 2740. If, however, the clinician wishes to discontinue using the laser catheter assembly 3008 and the sheath assembly 3004 to disrupt a portion of the vascular occlusion and use the laser catheter assembly 3008 to perform additional ablation, then the clinician repeats step 3320 (as well as the additional subsequent steps), as depicted in FIG. 33, and the distal portion 3060 of laser catheter assembly 3008 is again extended beyond the distal portion 3040 of the sheath assembly 3004, as illustrated in FIGS. 30A and 30B (and FIG. 26G, FIG. 26H and/or FIG. 26H'). Upon satisfactory ablation and disruption of the vascular occlusion by repeating steps 3320 to 3340 or 3345, activation of the emitters and introduction of the liquid medium to the kit 3000 is discontinued and the kit is removed from the patient's vasculature.

As discussed above, transmitting pulses of light energy from an emitter into a liquid medium creates laser-induced pressure waves and/or vapor bubbles and additional resultant pressure waves that disrupt at least a portion of a vascular occlusion. The catheter may include a guidewire lumen through which a guidewire can pass and cross the vascular occlusion. It may also be desirable to excite and vibrate the guidewire to increase the guidewire's ability to pierce and cross the vascular occlusion. Accordingly, the present disclosure also contemplates directing the laser light energy emitted by the emitter into the liquid medium in a direction which causes the liquid medium to propagate laser-induced pressure waves toward the guidewire lumen and/or guidewire such that the laser-induced pressure waves excite and vibrate the guidewire.

Although the method illustrated in FIG. 33 depicts steps 3305 through 3350 of method 3300 as being performed serially, any or all of the steps within the method 3300 may in any order and/or in parallel with any of the other steps. For example, certain steps can be performed without performing other steps. Upon completing step 3335 and/or step 3340, the combined laser catheter and sheath can optionally be repositioned within the vasculature and adjacent another portion thereof. Similarly, upon completing step 3335 and/or step 3340, the emitter(s) can optionally be repositioned within the sheath. The sheath can be repositioned within the vasculature and/or the emitter(s) can be repositioned within the sheath.

Similar to how the laser catheter assembly 3008 and the sheath assembly 3004 of FIGS. 30-32 can replace the catheter 1010 and sheath 1120 shown in FIGS. 26G, 26H and FIG. 26H' to perform the method of FIG. 33, which is similar to the method of FIGS. 27A and 27B, to perform an atherectomy followed by disruption of the remaining portion of the vasculature occlusion, the laser catheter assembly 3008 and the sheath assembly 3004 of FIGS. 30-32, particularly the laser catheter 3080 and the sheath 3012, respectively, can replace the catheter 1010 and sheath 1120 shown in FIG. 28C to perform the method of FIG. 33, which is similar to the method of FIGS. 27A and 27B, to perform the method of depicted in FIG. 29. As set forth above, FIG. 29 illustrates a method using a kit 3000 to generate laser-induced pressure waves to treat the calcium deposits in the tissue (e.g., media) and/or tissue layers (e.g., media layer) of the blood vessel by disrupting the calcium deposits to increase vasculature compliance, thereby increasing blood flow therethrough.

Figure 34A:
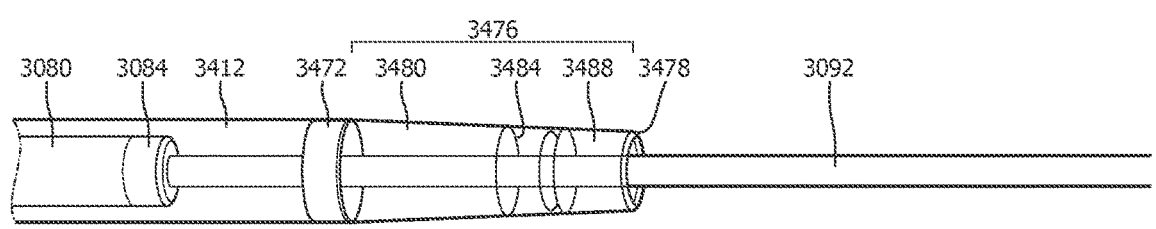
FIG. 34A is an enlarged view of a distal portion of another kit that includes a laser catheter assembly and an alternative embodiment of the outer sheath assembly, wherein the laser catheter assembly is disposed within the outer sheath assembly and proximal of the distal end of the outer sheath assembly.
Figure 34B:
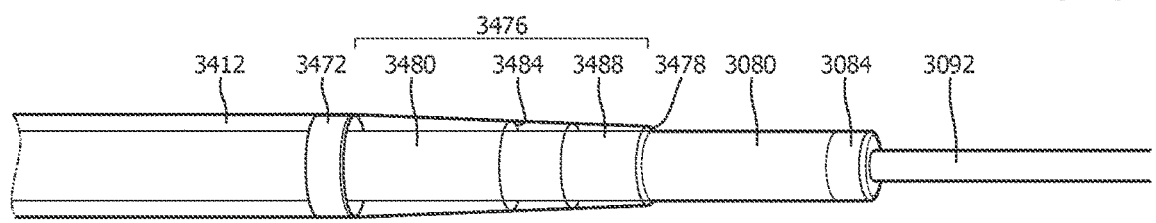
FIG. 34B is an enlarged view of a distal portion of the kit in FIG. 34A, wherein the laser catheter assembly is disposed within the outer sheath and extends beyond the distal end of the outer sheath assembly.

Referring to FIGS. 34A and 34B, there are depicted enlarged views of a distal portion of another kit that includes a the distal portion of the laser catheter assembly 3008 and an alternative embodiment of the distal portion sheath assembly 3004 in comparison to the sheath assembly 3004 in FIGS. 30-31. Similar to the distal portion of the sheath assembly 3004 in FIGS. 30-31, which comprises a sheath 3012 (or outer jacket) with an attenuating member formed therein, an inner liner 3096 radially or concentrically disposed within the sheath 3012, an outer band 3072 disposed about the distal end of the sheath 3012, and a tapered tip 3076 disposed distally of the outer hand 3072, the distal end portion of the sheath assembly depicted in FIGS. 34A and 34B, may also have a sheath 3412 (or outer jacket) with an attenuating member (not shown) formed therein, an inner liner (not shown) radially or concentrically disposed within the sheath 3412, an outer hand 3472 disposed about the distal end of the sheath 3412, and a tapered tip 3476 disposed distally of the outer band 3472. The tapered tip 3476 may have multiple sections, such as a proximal section 3480, an intermediate section 3484 and a distal section 3488. The length of some or all of the sections may the same or different. For example, in FIGS. 34A and 34B, the length of the proximal section 3480 is longer than both the intermediate section 3484 and the distal section 3488, but the intermediate section 3484 is shorter than the distal section 3488. Additionally, some or all of the sections may be tapered. For example, in FIGS. 34A and 34B, the proximal section 3480 is tapered radially inward from its proximal end to its distal end, the intermediate section 3484 is tapered and the distal section 3488 is not tapered. The sections may be tapered between 1 degree and 10 degrees, such as 1, 2, 3, 4, 5, 6, 7, 8, 9 or 10 degrees. The internal diameter of sections may be the same or different, but it is be preferable for the inner diameter of the distal section 3488 of the tapered tip 3476 to be the smallest and similar to the size of the internal diameter of the tapered tip 3076 in FIGS. 30 and 31. For example, in FIGS. 34A and 34B, the proximal section 3480 has the largest internal diameter, the intermediate section 3484 has the next largest diameter and the internal diameter of the distal section 3488 is equal to or less than the internal diameter of the intermediate section 3484.

Depending upon the length of the tapered tip 3476, it may be preferable for the distal end of the distal section 3488 to also include a radiopaque marker 3478, similar to outer band 3472. Including radiopaque outer band 3472 at or proximate the proximal section 3480 of the tapered tip 3476 and a radiopaque marker at the distal end of the distal section 3488 allows a clinician to know whether the distal end of the laser catheter assembly 3008, particularly the outer band 3084 and the emitters 3088 are proximal to both the tapered tip 3476, within the tapered tip 3476 or distal of the tapered tip 3476. This may be particularly helpful when a clinician is alternating between translating the laser catheter beyond and within the outer sheath, such as switching between performing an atherectomy procedure and activating the emitters to disrupt a portion of the occlusion or calcium within vasculature.

Figure 35:
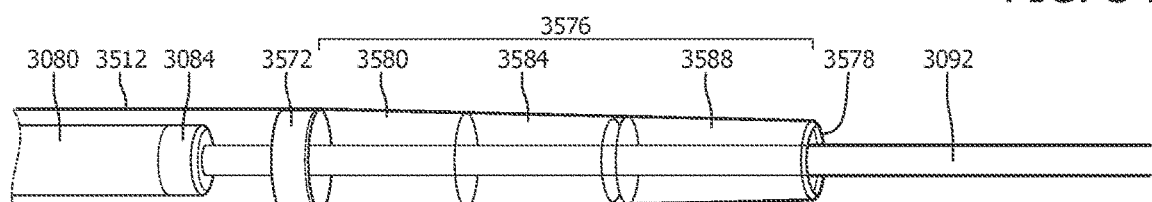
FIG. 35 is an enlarged view of a distal portion of another kit that includes a laser catheter assembly and an alternative embodiment of the outer sheath assembly, wherein the laser catheter assembly is disposed within the outer sheath and proximal of the distal end of the outer sheath assembly.

As mentioned above, the length of some or all of the sections of the tapered tip may be the same or different. For example, FIG. 35 is an enlarged view of a distal portion of another kit that includes a laser catheter assembly 3008 and an alternative embodiment of the sheath assembly, wherein the sheath assembly has an outer sheath 3512 and a tapered tip 3576 comprising a proximal section 3580, an intermediate section 3584 and a distal section 3588 of about equal lengths, thereby increasing the overall length of the tapered tip 3576 in comparison to the overall length of the tapered tip 3476 in FIGS. 34A and 34B. Similar to outer sheath in FIGS. 34A and 34B, the outer sheath in FIG. 35 also includes a radiopaque outer band 3572 at or proximate the proximal section 3580 of the tapered tip 3576 and a radiopaque marker 3578 at the distal end of the distal section 3588 of the tapered tip 3576.

Figure 36A:
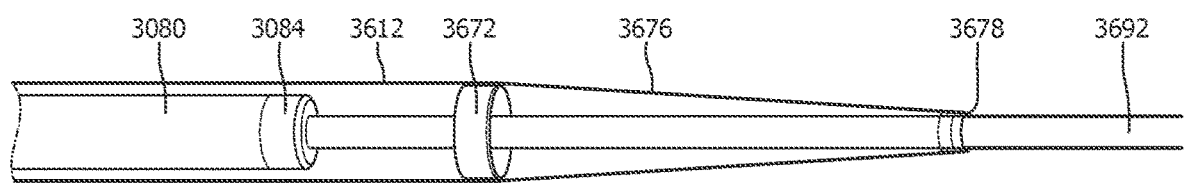
FIG. 36A is an enlarged view of a distal portion of another kit that includes a laser catheter assembly and an alternative embodiment of the outer sheath assembly, wherein the laser catheter assembly is disposed within the outer sheath assembly and proximal of the distal end of the outer sheath assembly.
Figure 36B:
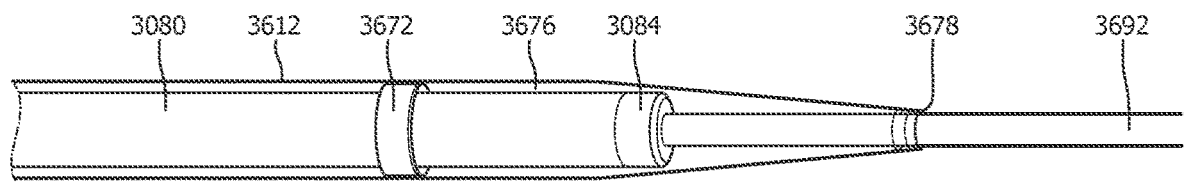
FIG. 36B is an enlarged view of a distal portion of the kit in FIG. 36A, wherein the laser catheter assembly is disposed within the outer sheath assembly in a position further distally than that in FIG. 36A but proximal of the distal end of the outer sheath assembly.

Referring to FIGS. 36A and 36B, there are depicted enlarged views of a distal portion of a kit that includes a laser catheter assembly 3008 and an alternative embodiment of the distal portion of the sheath assembly, wherein the sheath assembly has an outer sheath 3612 and a convex-shaped tapered tip 3676 disposed distally of the outer sheath 3612. As shown in these figures, the convex-shaped tapered tip 3676 has an increasing varying pitch angle from its proximal end to its distal end. The outer sheath 3612 also may also have a radiopaque outer band 3672 at the proximal end of the tapered tip 3676 and a radiopaque marker 3678 at the distal end of the tapered tip 3676. FIG. 36A depicts the distal end and emitter(s) of the laser catheter assembly 3008 is a position proximal the tapered tip 3676 and the radiopaque outer band 3672. FIG. 36B depicts the distal end and emitter(s) of the laser catheter assembly 3008 is a position distally of the proximal end of the tapered tip 3676 and proximal the distal end of the tapered tip 3676, such that the distal end and emitter(s) of the laser catheter assembly 3008 are radially aligned within tapering portion of the tapered tip 3676. The material from which the tapered tip 3676 is constructed may include a non-expandable or radially expandable material to allow for the inner diameter of the tapered tip 3676 to expand as the laser catheter assembly 3008 translates distally into the tapered tip 3676. The material of the tapered tip 3676 may be sufficiently flexible so that the radially expandable material allows the inner diameter of the tapered tip 3676 to expand to a diameter that allows the distal end and emitter(s) of the laser catheter assembly 3008 to extend beyond the distal end of the tapered tip 3676, while simultaneously sealing the interface between the laser catheter and outer sheath, thereby minimizing or preventing the escape or leakage of any liquid medium therebetween.

Figure 37A:
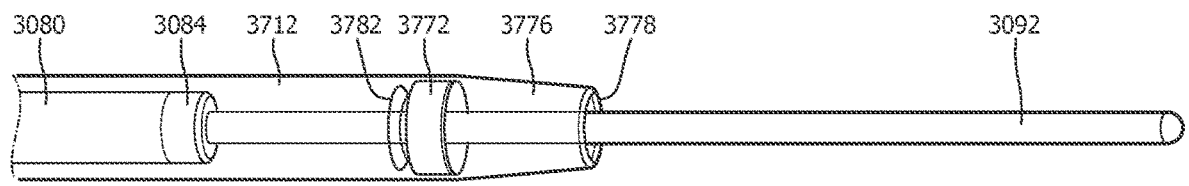
FIG. 37A is an enlarged view of a distal portion of another kit that includes a laser catheter assembly and an alternative embodiment of the outer sheath assembly, wherein the laser catheter assembly is disposed within the outer sheath and proximal of the distal end of the outer sheath assembly.
Figure 37B:
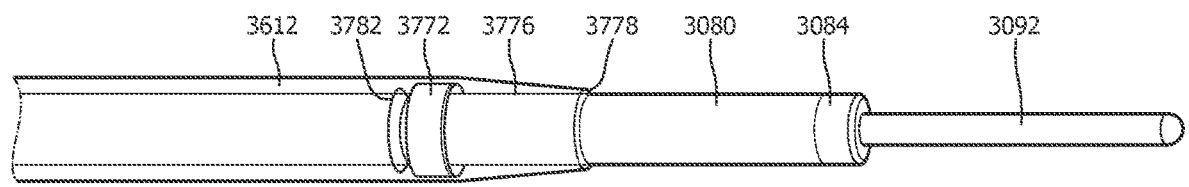
FIG. 37B is an enlarged view of a distal portion of the kit in FIG. 37A, wherein the laser catheter assembly is disposed within the outer sheath assembly and extends beyond the distal end of the outer sheath assembly.

Referring to FIGS. 37A and 37B, there is depicted is an enlarged view of a distal portion of another kit that includes a laser catheter assembly 3008 and an alternative embodiment of the outer sheath 3712. Rather than having a tapered distal tip as shown in FIGS. 34, 35 and 36, the tip 3776 in FIGS. 37A and 37B may be the same size at its proximal end and distal end and have a constant outer diameter and inner diameter along the length of the tip 3776. The inner diameter of the tip 3776 is a size that cooperates to seal the interface between the tip 3776 of the sheath assembly and the laser catheter assembly 3008 as the distal portions thereof.

Figure 39:
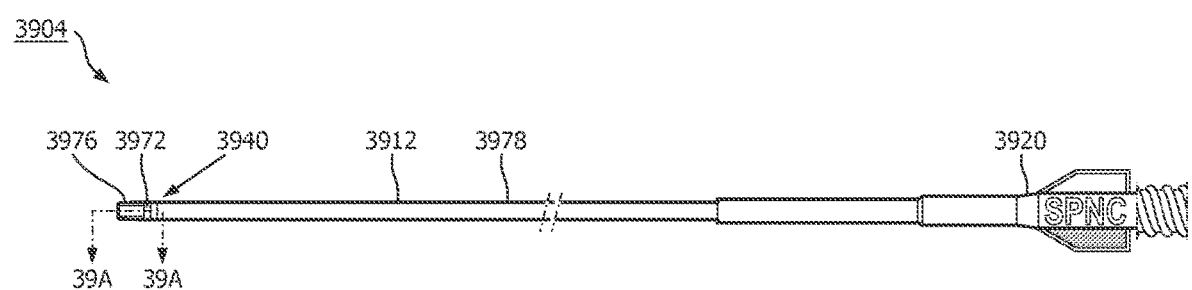
FIG. 39 is an outer sheath for a kit that also includes a laser catheter assembly.
Figure 39A:
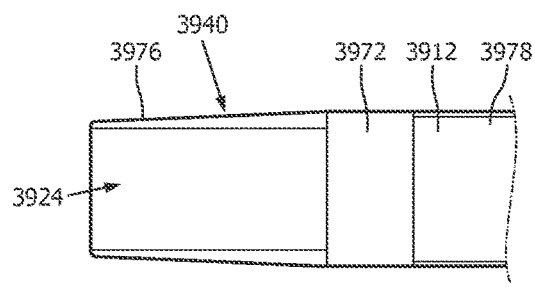
FIG. 39A is an enlarged longitudinal sectional view of a distal portion of the outer sheath along line 39A-39A of FIG. 39.

Referring to FIGS. 39 and 39A, there is depicted an outer sheath assembly 3904 for a kit (not shown) that further includes a bifurcate (such as the bifurcate or Y connector 3016) and a laser catheter assembly (such as the laser catheter assembly 3008). The sheath assembly 3904 may include a luer fitting 3920 at a proximal end portion for detachably coupling to the bifurcate. The sheath assembly 3904 may further include a distal end portion 3940 and an outer sheath 3912 having a working length of about between 50 cm and 200 cm, including 140 cm, and a lumen 3924 extending between such ends. The outer sheath 3912 of FIGS. 39, 39A and 40 may be used in alternative to outer sheath 3012 in FIGS. 30 and 31 discussed hereinabove.

Figure 40:
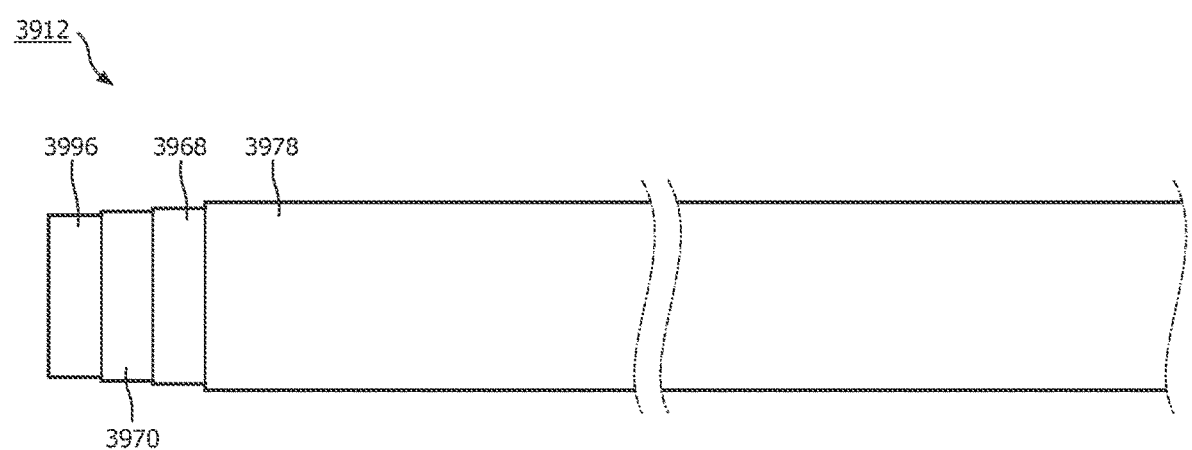
FIG. 40 is an enlarged partially exploded view illustrating various layers of the outer sheath of FIG. 39.

Referring now to FIGS. 39A and 40, there are depicted an enlarged view of the distal end portion 3940 of the sheath assembly 3904 and a partially exploded view illustrating various layers of the sheath 3912, respectively. The distal end portion 3940 of the sheath assembly 3904 may include a tapered tip 3976, an outer band 3972 disposed proximally from the tapered tip 3976 and disposed about the distal end of the sheath 3912, and the distal end of the sheath 3912.

The tapered tip 3976 may be constructed of various materials, such as pebax, polysulfone, high-density polyethylene (HDPE), low-density polyethylene (LDPE), ultra-high-molecular-weight polyethylene (UHMWPE), polypropylene, polyolefins, carbothane, polyurethane, Suralyn, ionomers, Estane, expanded polytetrafluoroethylene (EPTFE), polytetrafluoroethylene (PTFE), or fluorinated ethylene propylene (FEP). The tapered tip 3976 may be formed integrally with the sheath 3912 or as a separate component. The circumference of the tapered tip 3976 may taper radially inward from its proximal end to its distal end between 1 degree and 10 degrees, such as 1, 2, 3, 4, 5, 6, 7, 8, 9 or 10 degrees. It may be preferable for the tapered tip 3976 to have an inner diameter that facilitates sealing the interface between the sheath assembly 3904 and the laser catheter assembly such that the escape of the liquid medium at the distal end of the kit is minimized or reduced. If a 6

French sized laser catheter of the laser catheter assembly has an outer diameter of about 0.069 inches, then it may be preferable for the inner diameter of the tapered tip 3976 to be about 0.058 inches. If a 7 French sized laser catheter of the laser catheter assembly is to be used, it may be preferable for the inner diameter of the tapered tip 3976 to be about 0.071 inches. If an 8 French sized laser catheter of the laser catheter assembly is to be used, it may be preferable for the inner diameter of the tapered tip 3976 to be about 0.082 inches.

The outer band 3972, which may also be referred to as a marker band, may be constructed of a highly radiopaque material, such as platinum iridium alloy or polymers doped with radiopaque materials such as barium sulfate, bismuth subcarbonate, bismuth trioxide, or tungsten.

Referring specifically to FIG. 40, the sheath 3912 includes an outer jacket 3978 that covers the outer band 3972 (not shown). The sheath 3912 further includes an attenuating member 3968 radially or concentrically disposed within the outer band 3972, an intermediate layer 3970 radially or concentrically disposed within the attenuating member 3968, and an inner liner 3996 radially or concentrically disposed within the intermediate layer 3970. Proximally from the outer band 3972, the sheath 3912 includes a similar structure. Specifically, the attenuating member 3968 is radially or concentrically disposed within the outer jacket 3978, the intermediate layer 3970 is radially or concentrically disposed within the attenuating member 3968, and the inner liner 3996 is radially or concentrically disposed within the intermediate layer 3970. In some embodiments, the attenuating member 3968 is only present at the distal end portion 3940. Assuming that the length of the sheath 3912 is 140 centimeters, the distal end portion 3940 that includes the attenuating member 3968 may be between 0.010 and 10.0 centimeters in length, which represents between 0.05 and 20.0 percent of the length of the sheath 3912.

The outer jacket 3978 may be constructed of various materials, such as pebax, polysulfone, HDPE, LDPE. UHMWPE, polypropylene, polyolefins, carbothane, polyurethane, Suralyn, ionomers, Estane, EPTFE, PTFE, or FEP. If a 6 French sized laser catheter of the laser catheter assembly is to be used, the outer jacket 3978 may provide the sheath 3912 with an outer diameter between 0.058 and 0.098 inches, such as 0.058, 0.062, 0.066, 0.070, 0.074, 0.078, 0.082, 0.086, 0.090, 0.094, and 0.098 inches. If a 7 French sized laser catheter of the laser catheter assembly is to be used, the outer jacket 3978 may provide the sheath 3912 with an outer diameter between 0.071 and 0.111 inches, such as 0.071, 0.075, 0.079, 0.083, 0.087, 0.091, 0.095, 0.099, 0.103, 0.107, and 0.111 inches. If an 8 French sized laser catheter of the laser catheter assembly is to be used, the outer jacket 3978 may provide the sheath 3912 with an outer diameter between 0.082 and 0.122 inches, such as 0.082, 0.086, 0.090, 0.094, 0.098, 0.102, 0.106, 0.110, 0.114, 0.118, and 0.122 inches. The outer jacket 3978 may have a wall thickness between 0.0015 and 0.0035 inches, such as 0.0015, 0.0017, 0.0019, 0.0021, 0.0023, 0.0025, 0.0027, 0.0029, 0.0031, 0.0033, and 0.0035.

The attenuating member 3968 is a braided structure 3968. The braided structure 3968 may include between 4 and 28 carriers and more particularly between 12 and 20 carriers, such as 12, 13, 14, 15, 16, 17, 18, 19, or 20 carriers. Each carrier may include between 1 and 10 wires, such as 1, 2, 3, 4, 5, 6, 7, 8, 9, and 10 wires. Each wire may have a cross-sectional height between 0.0005 and 0.005, such as 0.0005, 0.0007, 0.0009, 0.001, 0.002, 0.003, 0.004, and 0.005. Each wire may be a flat wire having a cross-sectional width between 0.0005 and 0.003, such as 0.0005, 0.0007, 0.0009, 0.001, 0.002, and 0.003. Each wire may be constructed of stainless steel, such as 304 stainless steel, or other type of metal or metal alloy. The braided structure 3968 may have a braid density between 20 and 100 picks per inch (PPI) and particularly between 40 and 80 PPI, such as 40, 44, 48, 52, 56, 60, 64, 68, 72, 76, and 80 PPI. The relationship between the open area and the closed area (or the ratio of the open area to the overall area) within the braided structure 3968 should be such that a sufficient amount of laser-induced pressure waves pass through the braided structure 3968, and the open area should allow the laser-induced pressure waves to pass therethrough, while also limiting the size of the vapor bubbles that can form on the exterior of the sheath 3912. The braided structure 3968 may have an open area between 45 percent and 85 percent, and possibly between 55 percent and 75 percent, such as 55, 56, 57, 58, 59, 60, 61, 62, 63, 64, 65, 66, 67, 68, 69, 70, 71, 72, 73, 74, or 75 percent. The open area of the braided structure depends on the braid density, the number of carriers in the braided structure 3968, the number of wires in each carrier, and the dimensions of the wires.

The intermediate layer 3970 may be constructed of various materials, such as pebax, polysulfone, HDPE, LDPE, UHMWPE, polypropylene, polyolefins, carbothane, polyurethane, Suralyn, ionomers, Estane, EPTFE, PTFE, or FEP. The intermediate layer 3970 may have a wall thickness between 0.0005 and 0.0025 inches, such as 0.0005, 0.0007, 0.0009, 0.0011, 0.0013, 0.0015, 0.0017, 0.0019, 0.0021, 0.0023, and 0.0025.

The inner liner 3996 may be constructed of various materials, such as a polyamide or a fluoropolymer, specifically Neoflon FEP NP-101 available from Daikin America. If a 6 French sized laser catheter of the laser catheter assembly is to be used, the inner liner 3996 may provide the sheath 3912 with an inner diameter between 0.040 and 0.080 inches, such as 0.044, 0.048, 0.052, 0.056, 0.060, 0.064, 0.068, 0.072, 0.076 and 0.080 inches. If a 7 French sized laser catheter of the laser catheter assembly is to be used, the inner liner 3996 may provide the sheath 3912 with an inner diameter between 0.053 and 0.093 inches, such as 0.053, 0.057, 0.061, 0.065, 0.069, 0.073, 0.077, 0.081, 0.085, 0.089, and 0.093 inches. If an 8 French sized laser catheter of the laser catheter assembly is to be used, the inner liner 3996 may provide the sheath 3912 with an inner diameter between 0.064 and 0.104 inches, such as 0.064, 0.068, 0.072, 0.076, 0.080, 0.084, 0.088, 0.092, 0.096, 0.100, and 0.104 inches. The inner liner 3996 may have a wall thickness between 0.0005 and 0.0025 inches, such as 0.0005, 0.0007, 0.0009, 0.0011, 0.0013, 0.0015, 0.0017, 0.0019, 0.0021, 0.0023, and 0.0025.

Kits including the sheath assembly 3904 can be used to perform any of the methods described herein. In some embodiments, the sheath assembly 3904 is capable of resisting damage for a duration of at least 1, 2, 3, 4 or 5 minutes (or any duration therebetween) when laser pulses are emitted by a laser catheter during performance of such methods. More specifically, the sheath 3904 is capable of resisting damage when using Spectranetics 1.4, 1.7, and 2.0 Turbo-Elite™ and 2.0 Turbo-Power™ laser catheters to emit laser pulses at 60 fluence and 25 Hz into a contrast medium of fifty percent (50%) Optiray 320 contrast with saline, infused to the sheath 3904 at 5 mL/min. To facilitate this capability, one or both of the outer jacket 3978 and the intermediate layer 3970 may be integrally formed with the braided structure 3968 (that is, formed in manner that causes one or both of the outer jacket 3978 and the intermediate layer 3970 to occupy at least some of the open area of the braided structure). For example, the inner liner 3996 may be extruded, the intermediate layer 3970 may be over-extruded on the inner liner 3996, the braided structure 3968 may be positioned over the intermediate layer 3970, and the outer jacket 3978 may be over-extruded on the braided structure 3968. The sheath 3912 is laminated, coupled to the luer fitting 3020, and the outer jacket 3978 may be stripped at the distal end of the sheath 3912.

In comparison to conventional unreinforced and/or reinforced sheaths, such as in comparison to sheath assemblies that include various or multiple laminated layers or sheath assemblies using other manufacturing processes, the sheath assembly 3904 disclosed and discussed herein with respect to FIGS. 39-41 is susceptible to less damage when used in conjunction with a laser catheter and laser pulses are emitted into a contrast medium within such sheath assemblies over short or extended durations, particularly durations in which continues emission of laser pulses occurs for more than 20 seconds, 40 seconds, 1 minute and/or 2 minutes. Minimizing and/or preventing the sleeve from such potential damage, such as bulging, splitting, or delaminating (in the event the sleeve comprises multiple layers), forming a whole within the sleeve, in turn, reduces the possibility of a surgeon experiencing increased difficulty while translating the sleeve through the patient's vasculature and/or translation relative to the laser catheter.

Although a large portion of this disclosure includes a discussion of laser ablation catheters used in conjunction with a sheath assembly to perform CAD and PAD procedures, other the laser ablation catheter and sheath assembly may be used to perform other types of medical and/or surgical procedures. Laser catheters typically transmit laser energy through optical fibers housed in a relatively flexible tubular catheter inserted into a body lumen, such as a blood vessel, ureter, fallopian tube, cerebral artery and the like to remove obstructions or restrictions in the lumen. Catheters used for laser angioplasty and other procedures may have a central passageway or tube which receives a guide wire inserted into the body lumen (for example, vascular system) prior to catheter introduction. The guide wire facilitates the advancement and placement of the catheter to the selected portion(s) of the body lumen for laser ablation of tissue.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, for example, for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A catheter system comprising:
   a laser catheter comprising a proximal end, a distal end, and at least one emitter disposed adjacent the distal end, wherein the at least one emitter is configured to produce pressure waves;
   a sheath configured to be disposed over the laser catheter and configured to receive a liquid medium, the sheath comprising an outer jacket having a proximal end, a distal end, and an attenuating member disposed within the outer jacket of the sheath at or adjacent the distal end of the sheath, wherein the attenuating member comprises a coil having an area that encompasses a plurality of windings separated by a plurality of gaps, wherein the plurality of gaps between the windings collectively create an open area representing at least thirty percent of the area of the coil to thereby permit at least some of the pressure waves produced by the at least one emitter to pass through the gaps in the coil.

2. The catheter system of claim 1, wherein the coil comprises a flat wire having a height that is smaller than a width, wherein the coil is wound so that the height of the flat wire is aligned radially with the sheath and the length of the flat wire is aligned longitudinally with the sheath.

3. The catheter system of claim 2, wherein the height is between 0.0005 and 0.002 inches and the width is between 0.002 and 0.010 inches.

4. The catheter system of claim 2, wherein a spacing between each wrap of flat wire in the coil is between 0.003 and 0.008 inches.

5. The catheter system of claim 1, wherein the at least one coil has between 90 and 100 wraps per inch.

6. The catheter system of claim 1, wherein the sheath further comprises:
   an inner liner; and
   an intermediate layer disposed concentrically between the inner liner and the outer jacket.

7. The catheter system of claim 6, wherein the at least one coil is integrally disposed within the inner liner or the outer jacket.

8. The catheter system of claim 7, wherein the at least one coil is integrally disposed within the inner liner.

9. The catheter system of claim 8, wherein the at least one coil is integrally disposed within the outer jacket.

10. The catheter system of claim 9, wherein the braided structure is integrally disposed within the outer jacket and the inner liner.

11. The catheter system of claim 6, wherein the at least one coil is integrally disposed within the inner liner or the outer jacket, and wherein the at least one coil extends only through the distal end of the sheath.

12. The catheter system of claim 1 wherein the coil extends only through the distal end of the sheath.

13. The catheter system of claim 1 wherein the at least one coil has between 75 and 125 wraps per inch.

14. The catheter system of claim 1 wherein the open area represents between forty and sixty percent of the area of the coil.

* * * * *